US007951931B2

(12) United States Patent
Rouleau et al.

(10) Patent No.: US 7,951,931 B2
(45) Date of Patent: *May 31, 2011

(54) NUCLEIC ACID ENCODING SODIUM CHANNEL SCN3A ALPHA SUBUNITS

(75) Inventors: Guy A. Rouleau, Montréal (CA);
Ronald G. Lafrenière, Verdun (CA);
Daniel Rochefort, Laval (CA)

(73) Assignee: McGill University, Montreal (CA)

( * ) Notice: Subject to any disclaimer, the term of this patent is extended or adjusted under 35 U.S.C. 154(b) by 0 days.
This patent is subject to a terminal disclaimer.

(21) Appl. No.: 12/364,166

(22) Filed: Feb. 2, 2009

(65) Prior Publication Data

US 2009/0148855 A1 Jun. 11, 2009

Related U.S. Application Data

(60) Continuation of application No. 10/664,422, filed on Sep. 17, 2003, now Pat. No. 7,485,449, which is a division of application No. 09/718,355, filed on Nov. 24, 2000, now abandoned.

(60) Provisional application No. 60/167,623, filed on Nov. 26, 1999.

(51) Int. Cl.
| | |
|---|---|
| *C07H 21/00* | (2006.01) |
| *C12N 15/00* | (2006.01) |
| *C12N 15/09* | (2006.01) |
| *C12N 15/12* | (2006.01) |
| *C12N 5/16* | (2006.01) |
| *C12N 1/15* | (2006.01) |
| *C12N 1/21* | (2006.01) |

(52) U.S. Cl. .......... 536/23.5; 536/24.31; 435/320.1; 435/325; 435/252.3; 435/254.2

(58) Field of Classification Search .......... None
See application file for complete search history.

(56) References Cited

U.S. PATENT DOCUMENTS

| | | | |
|---|---|---|---|
| 5,223,409 A | 6/1993 | Ladner et al. | |
| 5,482,845 A | 1/1996 | Soares et al. | |
| 5,871,940 A | 2/1999 | Hall et al. | |
| 6,030,810 A | 2/2000 | Delgado et al. | |
| 6,110,672 A | 8/2000 | Mandel et al. | |
| 6,673,549 B1 | 1/2004 | Furness et al. | |
| 7,078,515 B2 | 7/2006 | Wallace et al. | |
| 7,485,449 B2 | 2/2009 | Rouleau et al. | |
| 7,528,093 B2 | 5/2009 | Rouleau et al. | |
| 7,655,460 B2 | 2/2010 | Rouleau et al. | |
| 2002/0076780 A1 | 6/2002 | Turner et al. | |
| 2004/0096885 A1* | 5/2004 | Rouleau et al. .......... | 435/6 |

FOREIGN PATENT DOCUMENTS

| | | |
|---|---|---|
| WO | WO 96/14077 | 5/1996 |
| WO | WO 97/01577 | 1/1997 |
| WO | WO 99/21875 | 8/1999 |

OTHER PUBLICATIONS

Kayano 1988 (FEBS Letters 228:187-194).*
Suzuki 1988 (FEBS Letters 228:195-200).*
Christoph Lossin, "A catalog of SCN1A variants", Brain & Development, 31:114-130 (2009).
Meisler and Kearney, "Sodium channel mutations in epilepsy and other neurological disorders", The Journal of Clinical Investigation, 115(8):2010-2017 (2005).
Barnard et al., "Molecular biology of the GABA(A) receptor: the receptor/channel superfamily", TINS, 10(12):502-509, 1987.
Cho et al., "An Unnatural Biopolymer," Science, 261:1303-1305, 1993.
Cossette et al., "Functional characterization of the D188V mutation in neuronal voltage-gated sodium channel causing generalized epilepsy with febrile seizures plus (GEFS).", Epilepsy Research 52:107-117, 2003.
Current Protocols in Molecular Biology (1989-1996), pp. 6.0.3-6.0.5, 6.1.1-6.1.4, 6.3.1-6.3.6, and 6.5.1-6.5.2.
Davila, HM, "Molecular and Functional Diversity of Voltage-Gated Calcium Channels", Annals New York Academy of Sciences, pp. 102-117 Apr. 1999—vol. 868.
Geibel et al., "Establishment of Cell-Free Electrophysiology for Ion Transporters: Application for Pharmacological Profiling", Journal of Biomolecular Screening 2006:262-268.
Goldin, "Diversity of Mammalian Voltage-Gated Sodium Channels," Annals of the New York Academy of Sciences, 868:38-50, 1999.
Harvald, "Hereditary Factors Elucidated by Twin Studies". 1965.
Kohlhardt, M, "Different temperature sensitivity of cardiac Na+ channels in cell-attached and cell-free conditions", Am J Physiol. Oct. 1990;259(4 Pt 1):C599-604.
Kohlhardt, M, "Gating Properties of Cardiac Na + Channels in Cell-Free Conditions", J. Membrane Biol. 122, 11-21 (1991).
Raymond et al., "Expression of Alternatively Spliced Sodium Channel alpha-Subunit Genes—Unique Splicing Patterns are Observed in Dorsal Root Ganglia", Journal of Biological Chemistry, 279(44):46234-46241, 2004.
Rudy, "Introduction: Molecular Diversity of Ion Channels and Cell Function," Annals of the New York Academy of Sciences, 868:1-12, 1999.
Sequence alignment for NCBI Accession No. X03638, mailed Oct. 11, 2006.
Sequence alignment for US 6,110,672 sequence 14.
Ahmed et al., Proc. Nadl. Acad. Sci. USA 89:8220-8224, 1992.
Alberts et al., Molecular Biology of the Cell, 3rd Edition, pp. 98-104, 1994.

(Continued)

*Primary Examiner* — Daniel E Kolker
(74) *Attorney, Agent, or Firm* — Goudreau Gage Dubuc; Charles Goyer

(57) ABSTRACT

The present invention relates to epilepsy. More particularly, the present invention relates to idiopathic generalized epilepsy (IGE) and to the identification of three genes mapping to chromosome 2, which show mutations in patients with epilepsy. The invention further relates to nucleic acid sequences, and protein sequences of these loci (SCNA) and to the use thereof to assess, diagnose, prognose or treat epilepsy, to predict an epileptic individual's response to medication and to identify agents which modulate the function of the SCNA. The invention also provides screening assays using SCN1A, SCN2A and/or SCN3A which can identify compounds which have therapeutic benefit for epilepsy and related neurological disorders.

14 Claims, 21 Drawing Sheets

OTHER PUBLICATIONS

Andermann, E., Raven Press, New York, pp. 355-374, 1982.
Anderson et al., In Vitro, 20:856-858, 1984.
Annals of the New York Academy of Sciences 1999, Table of Contents for vol. 868, Aug. 9, 2006.
Annegers et al., Raven Press, New York, pp. 151-159, 1982.
Avanzini et al., Prog. Nat, Epileptogenenesis (Epilepsy Res. Suppl.), 12:53-61, 1996.
Baker et al., Cell Prolif., 28:1-15, 1995.
Barker et al., Neurosci. Lett., 47:313-318, 1984.
Bar-Sagi et al., J. Biol. Chem., 260:4740-4744, 1985.
Baulac et al., Am. J. Hum. Genet., 65:1078-1085, 1999.
Baunoch et al., Biotechniques, 12:412-417, 1992.
Berkovic et al., Ann. Neural., 43:435-445, 1998.
Biervert et al., Science, 279:403-406, 1998.
Birch et al., Drug Discovery Today, 9:410-418, 2004.
Bu et al., Genomics, 21:222-228, 1994.
Cardell et al., Agnew. Chem. Int. Ed. Engl., 33:2061-2063, 1994.
Charlier et al., Nat. Genet, 18:53-55, 1998.
Cheviron et al., Cell Prolif., 29:437-446, 1996.
Chia et al., Exp. Cell Res., 244:340-348, 1998.
Clare et al., Drug Discovery Today, 5:506-520, 2000.
Corey et al., Neurology, 41:1433-1436, 1991.
Commission on classification and terminology of the international league against epilepsy, Epilepsia, 30:389-399, 1989.
Cull et al., Proc. NAtl. Acad. Sci. USA, 89:1865-1869, 1992.
"Decision of a Delegate of the Commissioner of Patents", issued in Australian Patent Appln. No. 18465/01, Jan. 29, 2007.
Denyer et al., Drug Discovery Today, 3:323-332, 1998.
Dewitt et al., Proc. Natl. Acad. Sci. USA, 90:6909-6913, 1993.
Elliot et al., Oncogene, 18:3564-3573, 1999.
Elmslie et al., Hum. Mol. Genet., 6:1329-1334, 1997.
Engel et al., Epilepsy: A Comprehensive Textbook, Lippincott-Raven, Philadelphia, 1:1-7, 1997.
Erb et al., Proc. Natl. Acad. Sci., USA, 91:11422-11426, 1994.
Escayg et al., Nat. Genet., 24:343-345, 2000.
Fodor et al., Nature, 364:555-556, 1993.
Gallop et al., J. Med. Chem., 37:1233-1251, 1994.
GenBank AF035685, sequence from Aug. 10, 1998, printed Apr. 28, 2008.
GenBank AAC29514, sequence from Aug. 10, 1998, printed Apr. 28, 2008.
"Gene Characterization", Stratagene Catalog, pp. 66, 1991.
Gonzalez et al., Drug Discovery Today, 4:431-439, 1999.
Gonzalez et al., Cell. Mol. Biol., 44:1117-1127, 1998.
Greenberg et al., Am. J. Med. Genet., 31:185-192, 1988.
Guipponi et al., Hum. Mol. Genet., 6:473-477, 1997.
Gyapay et al., Nat. Genet., 7:246-339, 1994.
Hamill et al., Pflügers Archiv, 391:85-100, 1981.
Hartshorne et al., J. Biol. Chem., 259:1667-1675, 1984.
Honig et al., Journal of Molecular Biology, 293:283-293, 1999.
Hu et al., Journ. Pharmacology Experimental Therapeutics, 290:28-37, 1999.
Kawai et al., Oncogene, 18:3471-3480, 1999.
Kienle et al., Biosensors and Bioelectronics, 12:779-786, 1997.
Komada et al., Genes & Dev., 13:1475-1485, 1999.
Lam et al., Nature, 354:82-84, 1991.
Lam, K.S., Anti-Cancer Drug Design, 12:145-167, 1997.
Lanthrop et al., Am. J. Genet., 36:460-465, 1984.
Lennox et al., Little Brown, pp. 532-574, 1960.
Leppert et al., Nature, 337:647-648, 1989.
Lewis et al., Am J. Hum. Genet., 53:670-675, 1993.
Liu et al., Cell. Signal., 11:317-324, 1999.
Lu et al., J. Mol. Neuro., 10:67-70, 1998.
Malo et al., Cytogenet. Cell Genet., 67:178-186, 1994.
Malo et al., Proc. Natl. Acad. Sci. USA, 91:2975-2979, 1994.
McConnell et al., Science, 257:1906-1912, 1992.
McPhee et al., J. Biol. Chem., 273-1121-1129, 1998.
Miyaji-Yamaguchi et al., Journal of Mol. Biol., 290:547-557, 1999.
Morvan et al., Nucleic Acids Research, 14:5019-5035, 1986.
Moulard et al., J. Hum. Genet., 65:1396-1400, 1999.
Muir et al., Cerebrovascular Diseases, 10:431-436, 2000.
Nakashima et al., J. Bone Joint Surg. Am., 81:603-615, 1999.
NCBI Accession No. NM 001081676 printed Oct. 1, 2007.
NCBI Accession No. NM 001081677 printed Oct. 1, 2007.
NCBI Accession No. X03638, Sep. 24, 2008.
Nielsen et al., Curr. Opin. Biotechnol., 10:71-75, 1999.
Noda et al., Nature, 320:188-192, 1986.
Noda and Numa, J. Receptor Res., 7:467-497, 1987.
Okuwaki et al., J. Biol. Chem., 273:34511-34518, 1998.
Ottaman et al., Nat. Genet., 10:56-60, 1995.
Ottaman et al., Am. J. Hum. Genet., 60:667-675, 1997.
Ottman et al., Epilepsia, 30:157-161, 1989.
Plummer and Meisler, Genomics, 57:323-331, 1999.
Pugsley et al., Eur. J. Pharmacol., 342:93-104,1998.
Reckziegel et al., J. Physiology, 509.1:139-150, 1998.
Rudinger et al., University Park Press, pp. 1-7, 1976.
Schroeder et al., Nature, 396:687-690, 1998.
Scott et al., Science, 249:386-390, 1990.
Sequence alignments for SEQ ID No. 65 with GenBank Accession Nos. AF035685 and AF035686, Aug. 16, 2006.
Sillampää et al., ActaNeurol. Scand. 84:523, 1991.
Singh et al., Nat. Genet. 18:25-29, 1998.
Sjolander et al., Anal. Chem., 63:2338-2345, 1991.
Steinlein et al., Nat. Genet. 11:201-203, 1995.
Szabo et al., Curr. Opinion, Struct. Biol., 5:699-705, 1995.
Tamaskovic et al., Biological Chemistry, 380:569-578, 1999.
Taylor et al., Adv. Pharmacol., 39:47-98, 1997.
Tian et al., Brain Res., 680:164-172, 1995.
Wallace et al., Nature Genet. 19:366-370, 1998.
Wang et al., J. Clin. Invest., 99:1714-1720, 1997.
Zuchermann et al., J. Med. Chem., 37:2678-2685.
Kohling, Epilepsia, 43:1278-1295, 2002.
Ann. N.Y. Acad. Sci., 868:1, 1999 (PubMed Citation downloaded Nov. 14, 2006).

* cited by examiner

Ch 2q23-q31

Centromere

| | | |
|---|---|---|
| 1cM | D2S142 | |
| | D2S284 | |
| 4cM | | |
| | D2S156/ | |
| 4cM | D2S354 | |
| | D2S111 | |
| 5cM | | |
| | D2S294 | |
| 2cM | | |
| | D2S335 | |
| | | IGE locus |
| 6cM | | 29 cM |
| | D2S324 | |
| 2cM | | |
| | D2S384 | |
| 2cM | | |
| | D2S152 | |
| 8cM | | |

Telomere    D2S311

1Ax00.1
NaC-340 TGTGTTCTGCCCCAGTGAGACT,
NaC-341 CTTCCTGCTCTGCCCAAACTGAAT
257 bp 53.4C

1Ax00.2
NaC-342 GGCGATGTAATGTAAGGTGCTGTC,
NaC-343 GTGCCTTCAGTTGCAATTGTTCAG
259 bp 54.5C

1Ax01.1
NaC-268, TTAGGAATTTCATATGCAGAATAA,
NaC-269 TGGGCCATTTTCGTCGTC
201 bp 50.9C

1Ax01.2
NaC-270 GAAAGACGCATTGCAGAAGAAAAGG,
NaC-271 CTATTGGCATGTGTTGGTGCTACA
277 bp 54.4C

1Ax02
NaC-45 GTGCTGGTTTCTCATTTAACTTTAC,
NaC-46 TTCCCAACTTAATTTGATATTTAGC
319 bp 49.9C

1Ax03
NaC-87, GCAGTTTGGGCTTTTCAATGTTAG,
NaC-88, GACACAGTTTCARAATCCCRAATG
234 bp 48.9C

1Ax04
NaC-63, TTAGGGCTACGTTTCATTTGTATG,
NaC-64, AGCACTGATGGAAAACCAAACTAT
338 bp 50.8C

1Ax05
NaC-164 AGCCCATGCAGTAATATAAATCCT,
NaC-165 TCCAGGCTGATAAGCTATGTCTAA
488 bp 52.8C

FIG. 2

1Ax06
NaC-276, CTGTGGCCTGCCTGAGCGTATT,
NaC-277 CCAATTCTACTTTTTAAGGAAATG
248 bp 50.3C

1Ax07
NaC-272, AAATACTTGTGCCTTTGAA,
NaC-273, GTACATACAATATACACAGATGC
240 bp 46.7C

1Ax08
Nac-89, AGGCAGCAGAACGACTTGTAATA,
NaC-90, ATCCGGTTTTAATTTCATAACTCA
267 bp 51.9C

1Ax09.2
NaC-217 GTTGAGCACCCTTAGTGAATAATA,
NaC-218 TCACACGCTCTAGACTACTTCTCT
337 bp 52.7C

1Ax10a NaC-29, TGCAAATACTTCAGCCCTTTCAAA,
NaC-30, TTCCCCACCAGACTGCTCTTTC
239 bp 55.1C

1Ax10a
NaC-31, GCAGCAGGCAGGCTCTCA,
NaC-32, TCTCCCATGTTTTAATTTTCAACC
293 bp 54.5C

1Ax10b
NaC-67, ATAATCTTGCAAAATGAAATCACA,
NaC-68, ATCCGGGATGACCTACTGG
307 bp 53.7C

1Ax10b
NaC-65, GATAACGAGAGCCGTAGAGATTCC,
NaC-66, AGCCAGCCATGCCTGAACTA
282 bp 56.4C

FIG. 2 (cont'd)

1Ax10c
NaC-39, TGTTTGCTTGTCATATTGCTCAA,
NaC-40, TGCACTATTCCCAACTCACAAA
286 bp 50.7C

1Ax11.1
NaC-69 AAGGGTGTCTCTGTAACAAAAATG,
NaC-70, GTGATGGCCAGGTCAACAAA
269 bp 50.8C

1Ax11.2
NaC-71 CTGGGACTGTTCTCCATATTGGTT,
NaC-72, TTTGCAGGGGCCAGGAAG
294 bp 53.3°C

1Ax12
NaC-41 CATTGTGGGAAAATAGCATAAGC,
NaC-42, GCAAGAACCCTGAATGTTAGAAA
334 bp 51.2C

1Ax13.1
NaC-92 TAATGCTTTTAAGAATCATACAAA,
NaC-93, CCAGCGTGGGAGTTGACAATC
256 bp 51.1C

1Ax13.2
NaC-75 CGGCATGCAGCTCTTTGGTA,
NaC-91, ATGTGCCATGCTGGTGTATTTC
277 bp 55.6C

1Ax14.1
NaC-79 CACCCATCTTCTAATCACTATGC,
NaC-80, CAGCAATTTGGAGATTATTCATT
254 bp 50.4C

1Ax14.2
NaC-81 GCAGCCACTGATGATGATAA,
NaC-82, CTGCCAGTTCCTATACCACTT
269 bp 49.4C

FIG. 2 (cont'd)

1Ax14.3
NaC-83 TACAGCAGAAATTGGGAAAGAT,
NaC-84, GTATTCATACCTACCCACACCTAT
269 bp 50.2C

1Ax15
NaC-202 TTCTTGGCAGGCAACTTATTACC,
NaC-203 TAAGCTGCACTCCAAATGAAAGAT
233 bp 53.1C

1Ax16.1
NaC-187, GGCTGAATGTTTCCACAACT,
NaC-168 GTTCAACTATTCGGAAACACG
277 bp 51.4C

1Ax16.2
NaC-188, AGGCAGAGGAAAACAATGG,
NaC-189, ACAAGGTGGGATAATTAAAAATG
234 bp 50.3C

1Ax17
NaC-143, GTTTCTCTGCCCTCCTATTCC,
NaC-144, AAGCTACCTTGAACAGAGACA
330 bp 48.8C

1Ax18
NaC-139, AATGATGATTCTGTTTATTA,
NaC-140, AATTTGCCATTCCTTTTG
272 bp 46.1C

1Ax19.1
NaC-219 TTGACATCGAAGACGTGAATAATC,
NaC-220 CCATCTGGGCTCATAAACTTGTA
285 bp 49.3C

1Ax20
NaC-338 CCCTTTGAAAATTATATCAGTAA,
NaC-339 ATTTGGTCGTTTATGCTTTATTC
230 bp 47.6C

FIG. 2 (cont'd)

1Ax21
NaC-252, TCCAGCACTAAAATGTATGGTAAT,
NaC-253, ATTTGGCAGAGAAAACACTCC
261 bp 49.8C

1Ax22
NaC-254, TTTTAGCCATCCATTTTCTATTTT,
NaC-255, TATTTTCCCCCATATCATTTGA
223 bp 49.1C

1Ax23.1
NaC-256 TTTGCAAGAAACTAGAAAGTC,
NaC-257 TTGATGCGTGACAAAATGG
250 bp 48.3C

1Ax23.2
NaC-258 GACCAGAGTGAATATGTGACTACC,
NaC-259 CTGGGATGATCTTGAATCTAATC
246 bp 49.5C

1Ax24.1
NaC-221 GCAACTCAGTTCATGGAATTTGAA,
NaC-222 CTTGTTTTCGTTTTAAAGTAGTA
289 bp 56.1C

1Ax24.2
NaC-213 CAAAGATCACCCTGGAAGCTCAGTT,
NaC-223 TTCAAGCGCAGCTGCAAACTGAGAT
277 bp 55.8C

1Ax24.3
NaC-260 ACATCGGCCTCCTACTCTTCCTA,
NaC-261 ACAGATGGGTTCCCACAGTCC
268 bp 55.3C

1Ax24.4
NaC-262 TAACGCATGATTTCTTCACTGGTT,
NaC-263 ATCCCAAAGATGGCGTAGATGA
262 bp 54.9C

FIG. 2 (cont'd)

1Ax24.5
NaC-308, TGAGAAATAGGCTAAGGACCTCTA,
NaC-309 CCTAGGGGCTGGATTCC
244 bp 53.2C

1Ax24.6
NaC-310, AAGGGGTGCAAACCTGTGATTTT,
NaC-311 AGGGCCATGTGGTTGCCATAC
252 bp 53.4C

1Ax24.7
NaC-312 CTTCCGGTTTATGTTTTCATTTCT,
NaC-313 TCTTTATTAGTTTTGCACATTTTA
278 bp 48.4C

1Ax24.8
NaC-364 CAATCCTTCCAAGGTCTCCTATC,
NaC-365 TTTCATCTTTGCCTTCTTGCTCAT
326 bp 52.4C

1Ax24.9
NaC-366 CATGTCCACTGCAGCTTGTCCA,
NaC-367 TCCCCTTTACACAGAGTCACAGTT
292 bp 53.1C

FIG. 2 (cont'd)

a. Glu1238Asp:
normal:                    GCA TTT GAA GAT ATA;
patient R10191 with IGE:   GCA TTT GAC GAT ATA.

b. Ser1773Tyr:
normal:                    ATC ATA TcC TTC CTG;
patient R9049 with IGE:    ATC ATA TmC TTC CTG; TCC>TAC

FIG. 3

2Ax00.1 NaC-235 ATGGGTTGAATGACTTTCTGACAT, NaC-236,
AGGCATTTCCTGTACAGGGACTAC
266 bp 52.7C

2Ax00.2 NaC-237 ACAGGAAATGCCTCTTCTTACTTC, NaC-238,
TTTCCCCAAGGATTCTACTACTGT
277 bp 50.6C

2Ax01 NaC-100, AGTGCATGTAACTGACACAATCAC, NaC-101,
CTTGCGTTCCTGTTTGGGTCTCT
241 bp 53.7C

2Ax01 NaC-11 TCCGCTTCTTTACCAGGGAATC, NaC-102,
AGGCAGTGAAGGCAACTTGACTAA
259 bp 55.1C

2Ax02 NaC-96, CAGGGCAATATTTATAAATAATGG, NaC-97,
TTTGGAAAATGTGTAGCTCAATAA
289 bp 48.7C

2Ax03 NaC-43, AAGGCATGGTAGTGCATAAAAG, NaC-44,
ATGAAACATAAAGGGAGGTCAA
201 bp 49.3°C

2Ax04 NaC-47, AATGTGAGCTTGGCTATTGTCTCT, NaC-48,
ATAGGCTCCCACCAGTGATTTAC
213 bp 50.9°C

2Ax05 NaC-49, AGGCCCCTTATATCTCCAACTG, NaC-50,
CAACAAGGCTTCTGCACAAAAG
241 bp 53.9°C

2Ax05.2 NaC-110, CTTGGTGGCTTGCCTTGAC, NaC-111,
TCATGAGTGTCGCCATCAGC
223 bp 51.1C

FIG. 4

2Ax05.3 NaC-112, GGAAAGCTGATGGCGACACT, NaC-113,
CTGAGACATTGCCCAGGTCC
329 bp 53.0C

2Ax05.4 NaC-114, TTTTTACCCGTTGCTTTCTTTA, NaC-115,
TATCCCTTGCTCTTTCATTTATCT
224 bp 50.9C

2Ax06.1 NaC-169, GCCGGTAAAATAGCTGTTGAGTAG, NaC-170,
GCCATTGCAAACATTTATTTCGTA
206 bp 53.3C

2Ax06.2 NaC-171, GCGTGTTTGCGCTAATAG, NaC-172,
CTAAGTCACTTGATTCACATCTAA
295 bp 48.0C

2Ax07 Nac-196, ACAGGGTGGCTGAAGTGTTTTA, NaC-197,
GTGGGAGGTGGCAGGTTATT
199 bp 52.6C

2Ax08 NaC-118, CAATTAGCAGACTTGCCGTTATT, NaC-119,
TCTCTTGAGTTCGGTGTTTTATGA
252 bp 52.9C

2Ax09 NaC-120, ACCGAACTCAAGAGAATTGCTGTA, NaC-121,
AAAGGACCGTATGCTTGTTCACTA
334 bp 52.9C

2Ax10a.1 NaC-161 TATGAATGCGCATTTTACTCTTTG, NaC-156,
TGGAGCTCAACTTAGATGCTACTG
286 bp 52.1C

2Ax10a.2 NaC-13 GGTGCTGGTGGGATAGGAGTTTTT, NaC-162,
TCCATTAAATTCTGGCATATTCTT
316 bp 50.9C

2Ax10b.1 NaC-145 TCAGAGGGGTGCTTTCTTCCACAT, NaC-14,
CTTCGGCTGTCATTGTCCTCAAAG
298 bp 55.6C

FIG. 4 (cont'd)

2Ax10b.2 NaC-146, GCAAAGGACATTGGCTCTGAGAAT, NaC-147,
CTGCCTGCACCAGTCACAACTCT
324 bp 59.4C

2Ax10c NaC-190, TGGGCTTTGCTGCTTTCAA, NaC-191,
AGTAACTGTGACGCAGGACTTTA
218 bp 51.5C

2Ax11.1 NaC-148, CCCTGTTCCTCCAGCAGATTA, NaC-70,
GTGATGGCCAGGTCAACAAA
283 bp 51.5C

2Ax11.2 NaC-149, TTTGATTTGGGACTGTTGTAAAC, NaC-150,
AAGGCAATTATAAACTCTTTCAAG
233 bp 52.0C

2Ax12 NaC-159, TGGGAGTTAAATTAAGTTGCTCAA, NaC-160,
ACATTTTATGAACACTCCCAGTTA
285 bp 50.4C

2Ax13.1 NaC-239 ATTAACACTGTTCTTGCTTTTAT, NaC-240,
GTGCCAGCGTGGGAGTTC
239 bp 51.1C

2Ax13.2 NaC-241 GTGGGGGCTCTAGGAAACCT, NaC-242,
TTTAATGAAAATGAGGAAAATGTT
324 bp 53.7C

2Ax14.1 NaC-134, GACCAAGCATTTTTATTTCATTC, NaC-135,
AGTGGCAGCAAGATTGTCA
234 bp 49.6C

2Ax14.2 NaC-136, GGCCTTGCTTTTGAGTTCC, NaC-137,
GGTCTTTGCCTATTTCTATGGTG
257 bp 51.1C

FIG. 4 (cont'd)

2Ax14.3 NaC-266, TTAAACCGCTTGAAGATCTAAATA, NaC-267,
TATACACCAAAATATCTCCTTAT
319 bp 48.5C

2Ax15 NaC-314 GGGGCACACCTAATTAATTTTTAT, NaC-315,
AAAGAGGATACTCAAGACCACATA
(247 bp) 51.5C

2Ax16 NaC-344 CCCACCAACACAAATATACCTAAT, NaC-345,
TGAAGGGAAAGGGAAAAGATTT
283 bp 52.2C

2Ax17 NaC-346 TCCAGCCTTAGGCACCTGATAA, NaC-347,
ATAAAGCAGCAAAGTGCAGCATAC
310 bp 52.4C

2Ax18 NaC-348 AAGGCTGAACTGTGTAGACATTTT, NaC-349,
TGACATTTCCATGGTACAAAGTGT
262 bp 52.2C

2Ax19.1 NaC-350 TTTGTTGTTGGCTTTTCACTTAT, NaC-351,
CCACCTGGCAGTTTGATTG
268 bp 51.9C

2Ax19.2 NaC-352 TAAGCGTGGTCAACAACTACAGT, NaC-353,
ATTCTTGCCAGCATTTATTGTC
260 bp 50.2C

2Ax20 NaC-354 CAAAACATTGCCCCAAAAG, NaC-355,
TCAAACTAAACAATTTCCCTCTAA
239 bp 48.1C

2Ax21 NaC-306, GATAATTAAAAACTCACTGATGTA, NaC-307,
GGAGGCTAAAGGAAAGAGTATG
288 bp 46.6C

2Ax22 NaC-356 ATTTTATAGCCAGCAAAGAACAC, NaC-357,
CTAGAAATTCGGGCTGTGAA
230 bp 49.6C

FIG. 4 (cont'd)

2Ax23.1 NaC-358 CTGCTTTGTGACCTAAGGCAAGTT, NaC-359,
GTGACCATGTTAAGGCAGATGAGG
290 bp 51.4C

2Ax23.2 NaC-360 GGAATGGTCTTTGATTTTGTAACC, NaC-361,
TCCTTAACTGAATAAAAGCACCTC
290 bp 51.6C

2Ax24.1 NaC-207 TGGAACACCCATCAAAGAAGATACT, NaC-208,
GTGGGAGTCCTGTTGACACAAC
278 bp 52.8C

2Ax24.2 NaC-209 AGCGATTCATGGCATCAAAC, NaC-210,
ACGTGGTGGAAGGCGTCATA
270 bp 52.9C

2Ax24.3 NaC-211 GCGACCCAGTTTATAGAGTTTGCC, NaC-212,
CTTGTTTGCGTTTCAACGTGGTC
289 bp 56.1C

2Ax24.4 NaC-213 CAAAGATCACCCTGGAAGCTCAGTT, NaC-214,
ATCCAGGGCATCTGCAAAATCAGAA
277 bp 55.8C

2Ax24.5 NaC-215 TGCCTATGTTAAGAGGGAAGTTGGG, NaC-216,
ATGACCGCGATGTACATGTTCAG
279 bp 55.3C

2Ax24.6 NaC-278 TCAATTGTTTACAGCCCGTGATG, NaC-279,
TTTATACAAAGGCAGACAACAT
302 bp 52.0C

2Ax24.7 NaC-280 AGGCGTAATGGCTACTCAGACGA, NaC-281,
GTAATCCCTCTCCCCGAACATAAAC
251 bp 53.8C

2Ax24.8 NaC-282 TTTGATTCACGGGTTGTTTACTCTTA, NaC-283,
TTCTATGGAACATTTACAGGCACATT
294 bp 52.1C

FIG. 4 (cont'd)

2Ax24.9 NaC-284 TAATGTGCCTGTAAATGTTCCATAGA, NaC-285,
CAGGCTTCTTAGAAAGGACTGATAGG
264 bp 50.6C

2Ax24.10 NaC-286 GTCCCAGCAGCATGACTATC, NaC-287,
CCCACTGGGTAAAATTACTAAC
249 bp 49.4C

2Ax24.11 NaC-288 TAGCCATCTTCTGCTCTTGGT, NaC-289,
TGGCTTCCCATATTAGACTTCTG
307 bp 51.3C

2Ax24.12 NaC-290 TCTTGCCTATGCTGCTGTATCTTA, NaC-291,
AGTCGGGCTTTTCATCATTGAG
207 bp 51.8C

2Ax24.13 NaC-292 TTCTTCATGTCATTAAGCAATAGG, NaC-293,
TTCAATTTAAAAGTGCTAGGAACA
299 bp 49.4C

2Ax24.14 NaC-294 CTTCAGGTGGATGTCACAGTCACTA, NaC-295,
ATTCAAGCAATGCCAAGAGTATCA
263 bp 51.5C

2Ax24.15 NaC-296 CTTTCAATAGTAATGCCTTATCAT, NaC-297,
TCCTGCATGCATTTCACCAAC
348 bp 49.6C

2Ax24.16 NaC-362 CTGTTCACATTTTGTAAAACTAAT, NaC-263,
ATCCCAAAGATGGCGTAGATGA
309 bp 50.8C

2Ax24.17 NaC-325 CACGCTGCTCTTTGCTTTGA, NaC-363,
GATCTTTGTCAGGGTCACAGTCT
269 bp 54.0C

FIG. 4 (cont'd)

a. Lys908Arg:

normal: TAC AAA GAA;
9782 (Patient with IGE): TAC AGA GAA;

b. leu768val, in individuals 8197, 9062 et 9822 (all IGE patients).

FIG. 5

3Ax00a.1 NaC-390 TGTGTCCGCCAGTAGATGG, NaC-391,
TTTTTGACCACAGAGGTTTACAA
233 bp 51.4C

3Ax00a.2 NaC-392 GAAGCGGAGGCATAAGCAGA, NaC-393,
GGTGCAGATAATGAAATGTTTTGT
253 bp 51.3C

3Ax00b NaC-394 CACCCCTATGCCAAATGTCAAAGA, NaC-395,
CAAAAACAAACTTATACCCAGAAG
293 bp 51.6C

3Ax00c NaC-396 CAAATATTGGGCAAACCCTAAT, NaC-397,
AAGGTGCCATCACAAAATCAT
225 bp 50.7C

3Ax01.1 NaC-51 ATCGCTTGCTTTCCTAACTCTTGT, NaC-52,
AAGTCACTATTTGGCTTTGGTTG
260 bp 53.1C

3Ax01.2 NaC-53 AGAAGCCCAAAAAGGAACAAGATA, NaC-54,
GGCCCAGAAAGTATATTACAGTT
231 bp 50.8C

3Ax02 NaC-85, TCCTTAAATAAGCCCATGTCTAAT, NaC-86,
TCTCAAAGAAATTTTACAGATACT
273 bp 47.3C

3Ax03 NaC-27, AATGGCCATGGTAACCTACTAACA, NaC-28,
CAGGCTATACCCACAAGGAGATT
212 bp 51.8C

3Ax04 NaC-94, TGTTAATTTTGGCTTGGATGTT, NaC-95,
TCACTCCTTTGCGCTTATCAA
198 bp 50.8C

3Ax05.1 NaC-247, AGGGCTCTATGTGCCAAACC, NaC-248,
AGGGGCCTACTACCTTACACCAG
213 bp 52.2C

3Ax05.2 NaC-249 TGTAATCCCAGGTAAGAAGAAAC, NaC-250,
TACCGGGATGAACTGTAATAATAA
304 bp 51.8C

3Ax06.1 NaC-192,TTCTGGCACTCTTCCTCAGGTAAC, NaC-193,
GTCCCATTTGAATCCATTGTGC
261 bp 55.4C

3Ax06.2 NaC-194,GGCCCCCAAGCGATTCTG, NaC-195,
TGTACACCCACAGTCTCAACTATT
209 bp 50.3C

3Ax07 NaC-204, ACAGCCACCTTTGTAAATAA, NaC-205,
TTTTTCGCAAAGAGTTCTAT
220 bp 46.6C

3Ax08 NaC-98, AAACTGACCCTACCTCCATTTCTC, NaC-99,
ACTCAGCCTATGCTTTTCATTTCA
247 bp 53.2C

3Ax09 NaC-37 CAGATATTTATTTGGGGACATTAT, NaC-38,
AAATCTTTGCKTTTATCACTCAGT
295 bp 52.0C

3Ax10a.1 NaC-198 TAGTGCCTGGCTTTGTTTTATGAC, NaC-199,
CGGATTTGGGAAAGCTGTCTCT
225 bp 54.3C

3Ax10a.2 NaC-200 AGAGCACCTTGAAGGAAACAACAA, NaC-274,
TCCCTCAACTGAAGTACAGATAGT
253 bp 51.2C

3Ax10b NaC-33, ATAATTGCGTTCTTCCCCTACCC, NaC-34,
AAGCCCTGGCACCATCCTG
301 bp 56.2°C

3Ax10c NaC-35, _TTTGCAAAGAAATGCTATGT, NaC-36,
CTGGGTAACAGACTTCAGTAAT
303 bp 51.4°C

FIG. 6 (cont'd)

3Ax11.1 NaC-122, ATGGGATTGTCTTCTCAAGTTTCT, NaC-123,
GATGGCAAGATCAACAAATGGA
294 bp 50.3C

3Ax11.2 NaC-124, CTTGATCTGGGACTGCTGTGATG, NaC-125,
AGGATATAATTTTTGGTTCAACA
284 bp 51.5C

3Ax12 NaC-61, TTTTCAGTGCTCTTGATAGTAGTG, NaC-62,
GTGCCAATGAGCGACAGG
254 bp 50.7°C

3Ax13.1 NaC-73, CCACGTGTGGTTCTATGATACC, NaC-74,
ACCGTGGGAGCGTACAGTCA
298 bp 52.3C

3Ax13.2 NaC-75, CGGCATGCAGCTCTTTGGTA, NaC-76,
TGGCCACGTTCCTAGCTACTGTC
291 bp 55.9C

3Ax14.1 NaC-55, GAGTTCCCTTTTTAGGCTGTTATT, NaC-56,
TCTTATTGCCTTCATGGATTTCTA
285 bp 50.5C

3Ax14.2 NaC-57, TGAAAAATAAGATGCGGGAGTG, NaC-58,
GTGAGGCTGGGGTTGTTTATG
247 bp 51.7C

3Ax14.3 NaC-59, GAGATGGGAATGGAACCACCA, NaC-60,
TTCGATAATGCATATAAGCACAA
297 bp 51.7C

3Ax15 NaC-318 AAGGGGGAAAATCACATCTTT, NaC-319,
TTAAATGAGGCATATTCAGTCTCC
235 bp 51.8C

3Ax16 NaC-116, GGAAGTGGAGTGGGGAAGG, NaC-117,
ATTCTTGCCAATATGCATTTCACT
271 bp 51.1C

FIG. 6 (cont'd)

3Ax17 NaC-157,TTCTTTTGTACTCACTATTATACTAA, NaC-158,
AAACTTGCCTCTTTTAAAAACAAT
317 bp 46.6C

3Ax18 NaC-374 TACCACACCCTATACCTTCAGTCA, NaC-375,
GAGTATGGCACCCTTTTCTATCTA
275 bp 51.4C

3Ax19.1 NaC-386 GCTATGTTCCCCTCGCTGTCT, NaC-387,
TGCTTGCCAAGAGCCTGAC
231 bp 53.6C

3Ax19.2 NaC-388 GCTGGCAAGTTCTACCACTGTG, NaC-389,
CAAACGAAGAACATCAGGGAAATA
247 bp 53.0C

3Ax20 NaC-376 TTCACAATATTGTACAAAAGTTA, NaC-377,
ATTACCACCAATATTCACCATAAG
230 bp 46.4C

3Ax21 NaC-378 TCAGGGTAAGGCAAAAGTAGCAC, NaC-379,
GAACCCCAGAATGAAGAAAGGTAA
294 bp 50.2C

3Ax22 NaC-380 TTTGTGAAAGTACTATTGGAACAC, NaC-381,
ACGCATGGCTTTGGAACAT
204 bp 49.6C

3Ax23.1 NaC-382 CCCGTATGTGGAAGGGCTTTAT, NaC-383,
CTAGGTTGATCCGGGACAAAACTA
246 bp 52.9C

3Ax23.2 NaC-384 AACGGATGACCAGGGCAAATAC, NaC-385,
CTAGAAGGTCCTGGGGCAACTG
234 bp 54.8C

3Ax24.1 NaC-317 AAGCCATCATGTAAAGTGAAAAG, NaC-320,
ATCCCAAAGATGGCATAGATA
274 bp 52.5C

FIG. 6 (cont'd)

3Ax24.2 NaC-325 CACGCTGCTCTTTGCTTTGA, NaC-326,
TGAGCTGCCAGGGTGAATTG
282 bp 54.9C

3Ax24.3 NaC-327 TTGCTAGCACCTATTCTTAATAGTGC NaC-328,
CCAGGGCAGCTGCAAAATCAGAG
318 bp 54.2C

3Ax24.4 NaC-329 CCCGATGCGACCCAGTTTA, NaC-330,
TGGAGGGGTTTGATGCCATA
250 bp 55.2C

3Ax24.5 NaC-331 GATGGATGCCCTTCGAATACAGA, NaC-332,
TTCCCATTTAGTTTGTCAATAATC
258 bp 50.6C

3Ax24.6 NaC-321 AAGGGGAGGATTGACTTACCTAT, NaC-333,
TTGGCATGGACCTCCTCTTGA
302 bp 51.5C

FIG. 6 (cont'd)

a. Asn43DEL:
9706 (allele 1; IGE patient): CAA GAT AAT GAT GAT GAG;
9632 (allele 2; patient has IGE): CAA GAT --- GAT GAT GAG;
allele 1 = 131/146 (0.90);
allele 2= 15/146 (0.10);
for IGE patients: homozygotes (22): 3958, 9632; heterozygotes (12): 9049, 9152, 9649, 9710, 9896, 10069, 10191, 10213, 9993, 10009, 10256 (note that 2 patients are homozygous for the rare allele; all patients have IGE); in controls: allele 1 = 45/154 (0.94); allele 2 = 9/154 (0.06) and no 22 homozygotes found.

b. normal:             tggtgtaaggtag,
10670 (IGE patient):   tggtataaggtag c. normal:             ccccttatatctccaac,
10250 (IGE patient):   cccttatayctccaac;

d. Val1035Ile:
normal:                AAA TAC GTA ATC GAT,
9269 (IGE patient):    AAA TAC RTA ATC GAT; GTA>ATA = Val>Ile.

FIG. 7

NUCLEIC ACID ENCODING SODIUM CHANNEL SCN3A ALPHA SUBUNITS

CROSS-REFERENCE TO RELATED APPLICATIONS

This application is a continuation application of U.S. application Ser. No. 10/664,422, filed Sep. 17, 2003, now U.S. Pat. No. 7,485,449 which itself is a divisional of U.S. patent application Ser. No. 09/718,355 filed Nov. 24, 2000 (now abandoned), and which claims priority on U.S. provisional application Ser. No. 60/167,623 filed Nov. 26, 1999. The patent applications identified above are incorporated here by reference in their entirety to provide continuity of disclosure.

SEQUENCE LISTING

This application contains a Sequence Listing in computer readable form entitled "Amended_Seq_Listing_OA100517.txt", created Feb. 2, 2009 and amended on Aug. 13, 2010, having a size of 407 Ko. The computer readable form is incorporated herein by reference.

FIELD OF THE INVENTION

The present invention relates to epilepsy. More particularly, the present invention relates to idiopathic generalized epilepsy (IGE) and to the identification of three loci mapping to chromosome 2, which show a linkage with epilepsy in patients. The invention further relates to nucleic acid sequences, and protein sequences of these loci (SCNA), to variations and mutations in these sequences and to the use thereof to assess, diagnose, prognose or treat epilepsy.

BACKGROUND OF THE INVENTION

Epilepsy is one of the most common neurological conditions, occurring in about 1.0% of the general population. The disease is characterised by paroxysmal abnormal electrical discharges in the brain, which lead to transient cerebral dysfunction in the form of a seizure. A seizure is considered partial when the epileptic discharge is limited to part of one brain hemisphere, or generalised when it involves both cerebral hemispheres at the onset. The current classification of the epileptic syndromes rests on two criteria: 1) seizure type which may be generalised or partial at the onset, according to clinical and EEG features; and 2) etiology, which may be idiopathic, cryptogenic and symptomatic. Symptomatic epilepsies have multiple and heterogeneous causes including brain injury, CNS infection, migrational and metabolic disorders. In the majority (65%) of the patients with either generalised or partial epilepsy, there is no underlying cause (idiopathic) or the cause is though to be hidden or occult (cryptogenic). Also, in the idiopathic epileptic syndromes, there is no evidence of cerebral dysfunction other than the seizure, and the neurological examination is normal. There is now increasing evidence that in this latter group, genetic factors are important, especially for the idiopathic generalised epilepsy (IGE). In a recent study, Berkovic et al (1998) showed a 62% concordance rate in monozygotic twins overall for epilepsy. In this study, a higher concordance rate has been found in the generalised compared to the partial epilepsies, with 76% concordance rate for IGE. Recent studies using molecular genetic approaches have shown that many susceptibility genes for the epilepsies in human involve membrane ion channel and related proteins. These studies include the syndrome of benign familial neonatal convulsions where two loci have been identified [EBN1 on chromosome 20, the KCNQ2 gene (a potassium channel); and EBN2 on chromosome 8, the KCNQ3 gene (also a potassium channel)] (Bievert et al, 1998; Charlier et al, 1998; Singh et al, 1998), as well as autosomal dominant nocturnal frontal lobe epilepsy [ADNFLE—chromosome 20, and the CHRNA4 gene (the neuronal nicotinic acetylcholine receptor alpha 4 subunit)] (Steinlein et al, 1995). More recently, there was a clinical description of a new syndrome (GEFS), which consisted of generalised epilepsy with febrile seizures. According to the current classification of epileptic syndrome, this syndrome would fall in the category of IGE, based on the seizure and electroencaphalographic features. However, febrile seizures were present in all probants with GEFS, and the pattern of inheritance was clearly autosomal dominant, which are not part of the usual IGE phenotype. This unique GEFS syndrome has been shown to be associated with a mutation on the beta-1 subunit of brain voltage-gated sodium channel (SCN1B) gene (Wallace et al, 1998). In addition, three different groups, including the group of the present inventors, have identified another locus on chromosome 2 in large kindred with this specific syndrome (GEFS). This region contains many candidate genes, including a cluster of alpha subunits of sodium channels (SCNA). Voltage-gated sodium channels play an important role in the generation of action potential in nerve cells and muscle. The alpha subunit (SCNA) is the main component of the channel, and would be sufficient to generate an efficient channel when expressed in cells in vitro. In turn, the beta-1 and 2 subunits need an alpha subunit to give an effective channel. The role of these subunits would be to modify the kinetic properties of the channel, mainly by fast inactivation of the sodium currents. The mutation found in the GEFS syndrome on the SCN1B gene was shown to reduce the fast inactivation of the sodium channels as compared to a normal SCNB1, when co-expressed with an alpha subunit. It is probable that this could be the mechanism by which the mutation induce an hyperexcitability state in the brain, leading to seizure in humans. Interestingly, the mechanism of action of most of the anticonvulsant drugs is through a reduction of the repetitive firing of neurons, which is also known to be dependent on fast inactivation. These finding make it likely that additional epilepsy genes will be identified by mutations in ion channels.

There thus remains a need to identify whether IGE is caused by a mutation in a sodium channel (SCNA). There also remains a need to assess whether a mutation(s) in SCNA is associated with GEFs. There also remains a need to determine whether a mutation that affects the fast inactivation of a sodium channel, given the particular phenotype of GEFS or IGE, could be linked to a region which includes SCNA genes.

The present invention seeks to meet these and other needs.

The present description refers to a number of documents, the content of which is herein incorporated by reference in their entirety.

SUMMARY OF THE INVENTION

In one embodiment, the present invention relates to a genetic assay for determining predisposition to epilepsy.

In another embodiment, the present invention relates to a use of at least one of the loci of the present invention or an equivalent thereof (e.g., a loci in linkage disequilibrium therewith) as a marker for epilepsy and to determine the optimal treatment thereof (e.g., to guide the treatment modalities, thereby optimizing treatment to a particular clinical situation).

Yet in another embodiment, the present invention relates to an assay to screen for drugs for the treatment and/or prevention of epilepsy. In a particular embodiment, such assays can be designed using cells from patients having a known genotype at one of the loci of the present invention. These cells harboring recombinant vectors can enable an assessment of the functionality of the SCN1A, and/or SCN2A and/or SCN3A and a combination thereof. Non-limiting examples of assays that could be used in accordance with the present invention include cis-trans assays similar to those described in U.S. Pat. No. 4,981,784.

It shall be understood that the determination of allelic variations in at least one of the loci of the present invention can be combined to the determination of allelic variation in other gene/markers linked to a predisposition to epilepsy. This combination of genotype analyses could lead to better diagnosis programs and/or treatment of epilepsy. Non-limiting examples of such markers include SCN1B, EBN1, KCNQ2, EBN2, KCNQ3, ADNFLE and CHRNA4.

In accordance with the present invention, there is therefore provided a method of determining an individual's predisposition to epilepsy, which comprises determining the genotype of at least one locus selected from the group consisting of SCN1A, SCN2A and SCN3A. In one particular embodiment, the present invention provides a method of determining an individual's predisposition to epilepsy, which comprises determining a polymorphism (directly or indirectly by linkage disequilibrium) in a biological sample of an individual and analyzing the allelic variation in at least one of the loci selected from SCN1A, SCN2A and SCN3A, thereby determining an individual's predisposition to epilepsy.

In accordance with the present invention, there is also provided a method for identifying, from a library of compounds, a compound with therapeutic effect on epilepsy or other neurological disorders comprising providing a screening assay comprising a measurable biological activity of SCN1A, SCN2A or SCN3A protein or gene; contacting the screening assay with a test compound; and detecting if the test compound modulates the biological activity of SCN1A, SCN2A or SCN3A protein or gene; wherein a test compound which modulates the biological activity is a compound with this therapeutic effect.

Also provided within the present invention is a compound having therapeutic effect on epilepsy or other neurological disorders, identified by a method comprising: providing a screening assay comprising a measurable biological activity of SCN1A, SCN2A or SCN3A protein or gene; contacting the screening assay with a test compound; and detecting if the test compound modulates the biological activity of SCN1A, SCN2A or SCN3A protein or gene, wherein a test compound which modulates the biological activity is a compound with this therapeutic effect.

SCN1A, SCN2A and SCN3A refers to genes and proteins for Sodium Channel, Neuronal Type I, Alpha Subunit isoforms, and are described at OMIM # 182389 (Online Mendelian Inheritance in Man). These genes are structurally distinct sodium channel alpha-subunit isoforms in brain, also known as brain types I, II and III, respectively. Gene, cDNA and protein sequences for the various isoforms are shown in SEQ ID NOS:1-98.

Numerous methods for determining a genotype are known and available to the skilled artisan. All these genotype determination methods are within the scope of the present invention. In a particular embodiment of a method of the present invention, the determination of the genotype comprises an amplification of a segment of one of the loci selected from the group consisting of SCN1A, SCN2A and SCN3A and in a particularly preferred embodiment, the amplification is carried out using polymerase chain reaction.

In a particular embodiment, a pair of primers is designed to specifically amplify a segment of one of the markers of the present invention. This pair of primers is preferably derived from a nucleic acid sequence of SCN1A, SCN2A or SCN3A or from sequences flanking these genes, to amplify a segment of SCN1A, SCN2A or SCN3A (or to amplify a segment of a loci in linkage disequilibrium with at least one of the loci of the present invention). While a number of primers are exemplified herein, other primer pairs can be designed, using the sequences of the SCN1A, SCN2A and SCN3A nucleic acids molecules described hereinbelow. The same would apply to primer pairs from loci in linkage disequilibrium with the markers of the present invention.

Restriction fragment length polymorphisms can be used to determine polymorphisms at the SCN1A, SCN2A and SCN3A loci (and equivalent loci).

While human SCN1A, SCN2A and SCN3A are preferred sequences (nucleic acid and proteins) in accordance with the present invention, the invention should not be so limited. Indeed, in view of the significant conservation of these genes throughout evolution, sequences from different species, and preferably mammalian species, could be used in the assays of the present invention. One non-limiting example is the rat SCN1A ortholog gene which shows 95% identity with the human SCN1A gene. The significant conservation of the mouse SCN1A gene can also be observed in OMIM (see above).

In order to provide a clear and consistent understanding of terms used in the present description, a number of definitions are provided hereinbelow.

As used herein the term "RFLP" refers to restriction fragment length polymorphism.

The terms "polymorphism", "DNA polymorphism" and the like, refer to any sequence in the human genome which exists in more than one version or variant in the population.

The term "linkage disequilibrium" refers to any degree of non-random genetic association between one or more allele(s) of two different polymorphic DNA sequences, that is due to the physical proximity of the two loci. Linkage disequilibrium is present when two DNA segments that are very close to each other on a given chromosome will tend to remain unseparated for several generations with the consequence that alleles of a DNA polymorphism (or marker) in one segment will show a non-random association with the alleles of a different DNA polymorphism (or marker) located in the other DNA segment nearby. Hence, testing of a marker in linkage desiquilibrium with the polymorphisms of the present invention at the SCN1A, SCN2A and/or SCN3A genes (indirect testing), will give almost the same information as testing for the SCN1A, SCN2A and SCN3A polymorphisms directly. This situation is encountered throughout the human genome when two DNA polymorphisms that are very close to each other are studied. Linkage disequilibriums are well known in the art and various degrees of linkage disequilibrium can be encountered between two genetic markers so that some are more closely associated than others.

It shall be recognized by the person skilled in the art to which the present invention pertains, that since some of the polymorphisms or mutations herein identified in the SCN1A, SCN2A and/or SCN3A genes can be within the coding region of the genes and therefore expressed, that the present invention should not be limited to the identification of the polymorphisms/mutations at the DNA level (whether on genomic DNA, amplified DNA, cDNA, or the like). Indeed, the herein-identified polymorphisms and/or mutations could be detected at the mRNA or protein level. Such detections of polymorphism identification on mRNA or protein are known in the art. Non-limiting examples include detection based on oligos designed to hybridize to mRNA or ligands such as antibodies which are specific to the encoded polymorphism (i.e., specific to the protein fragment encoded by the distinct polymorphisms).

Nucleotide sequences are presented herein by single strand, in the 5' to 3' direction, from left to right, using the one letter nucleotide symbols as commonly used in the art and in accordance with the recommendations of the IUPAC-IUB Biochemical Nomenclature Commission.

Unless defined otherwise, the scientific and technological terms and nomenclature used herein have the same meaning as commonly understood by a person of ordinary skill to which this invention pertains. Generally, the procedures for cell cultures, infection, molecular biology methods and the like are common methods used in the art. Such standard techniques can be found in reference manuals such as for example Sambrook et al. (1989, Molecular Cloning—A Laboratory Manual, Cold Spring Harbor Laboratories) and Ausubel et al. (1994, Current Protocols in Molecular Biology, Wiley, New York).

The present description refers to a number of routinely used recombinant DNA (rDNA) technology terms. Nevertheless, definitions of selected examples of such rDNA terms are provided for clarity and consistency.

As used herein, "nucleic acid molecule", refers to a polymer of nucleotides. Non-limiting examples thereof include DNA (i.e., genomic DNA, cDNA, RNA molecules (i.e., mRNA) and chimeras of DNA and RNA. The nucleic acid molecule can be obtained by cloning techniques or synthesized. DNA can be double-stranded or single-stranded (coding strand or non-coding strand [antisense]).

The term "recombinant DNA" as known in the art refers to a DNA molecule resulting from the joining of DNA segments. This is often referred to as genetic engineering.

The term "DNA segment", is used herein, to refer to a DNA molecule comprising a linear stretch or sequence of nucleotides. This sequence when read in accordance with the genetic code, can encode a linear stretch or sequence of amino acids which can be referred to as a polypeptide, protein, protein fragment and the like.

The terminology "amplification pair" refers herein to a pair of oligonucleotides (oligos) of the present invention, which are selected to be used together in amplifying a selected nucleic acid sequence by one of a number of types of amplification processes, preferably a polymerase chain reaction. Other types of amplification processes include ligase chain reaction, strand displacement amplification, or nucleic acid sequence-based amplification, as explained in greater detail below. As commonly known in the art, the oligos are designed to bind to a complementary sequence under selected conditions.

The nucleic acid (i.e., DNA, RNA or chimeras thereof) for practicing the present invention may be obtained according to well known methods.

Oligonucleotide probes or primers of the present invention may be of any suitable length, depending on the particular assay format and the particular needs and targeted genomes employed. In general, the oligonucleotide probes or primers are at least 12 nucleotides in length, preferably between 15 and 24 molecules, and they may be adapted to be especially suited to a chosen nucleic acid amplification system. As commonly known in the art, the oligonucleotide probes and primers can be designed by taking into consideration the melting point of hydrizidation thereof with its targeted sequence (see below and in Sambrook et al., 1989, Molecular Cloning—A Laboratory Manual, 2nd Edition, CSH Laboratories; Ausubel et al., 1989, in Current Protocols in Molecular Biology, John Wiley & Sons Inc., N.Y.).

The term "DNA" molecule or sequence (as well as sometimes the term "oligonucleotide") refers to a molecule comprised of the deoxyribonucleotides adenine (A), guanine (G), thymine (T) and/or cytosine (C). Sometimes, in a double-stranded form, it can comprise or include a "regulatory element" according to the present invention, as the term is defined herein. The term "oligonucleotide" or "DNA" can be found in linear DNA molecules or fragments, viruses, plasmids, vectors, chromosomes or synthetically derived DNA. As used herein, particular double-stranded DNA sequences may be described according to the normal convention of giving only the sequence in the 5' to 3' direction. Of course, as very well-known, DNA molecules or sequences are often in single stranded form.

"Nucleic acid hybridization" refers generally to the hybridization of two single-stranded nucleic acid molecules having complementary base sequences, which under appropriate conditions will form a thermodynamically favored double-stranded structure. Examples of hybridization conditions can be found in the two laboratory manuals referred to above (Sambrook et al., 1989, supra and Ausubel et al., 1989, supra) and are commonly known in the art. In the case of a hybridization to a nitrocellulose filter, as for example in the well known Southern blotting procedure, a nitrocellulose filter can be incubated overnight at 65° C. with a labeled probe in a solution containing 50% formamide, high salt (5×SSC or 5×SSPE), 5×Denhardt's solution, 1% SDS, and 100 µg/ml denatured carrier DNA (i.e. salmon sperm DNA). The non-specifically binding probe can then be washed off the filter by several washes in 0.2×SSC/0.1% SDS at a temperature which is selected in view of the desired stringency: room temperature (low stringency), 42° C. (moderate stringency) or 65° C. (high stringency). The selected temperature is based on the melting temperature (Tm) of the DNA hybrid. Of course, RNA-DNA hybrids can also be formed and detected. In such cases, the conditions of hybridization and washing can be adapted according to well known methods by the person of ordinary skill. Stringent conditions will be preferably used (Sambrook et al., 1989, supra).

Probes of the invention can be utilized with naturally occurring sugar-phosphate backbones as well as modified backbones including phosphorothioates, dithionates, alkyl phosphonates and "-nucleotides and the like. Modified sugar-phosphate backbones are generally taught by Miller, 1988, Ann. Reports Med. Chem. 23:295 and Moran et al., 1987, Nucleic Acids Res., 14:5019. Probes of the invention can be constructed of either ribonucleic acid (RNA) or deoxyribonucleic acid (DNA), and preferably of DNA.

The types of detection methods in which probes can be used include Southern blots (DNA detection), dot or slot blots (DNA, RNA), and Northern blots (RNA detection). Although less preferred, labeled proteins could also be used to detect a particular nucleic acid sequence to which it binds. More recently, PNAs have been described (Nielsen et al. 1999, Current Opin. Biotechnol. 10:71-75). PNAs could also be used to detect the polymorphisms of the present invention. Other detection methods include kits containing probes on a dipstick setup and the like.

Although the present invention is not specifically dependent on the use of a label for the detection of a particular nucleic acid sequence, such a label might be beneficial, by increasing the sensitivity of the detection. Furthermore, it enables automation. Probes can be labeled according to numerous well known methods (Sambrook et al., 1989, supra). Non-limiting examples of labels include $^3$H, $^{14}$C, $^{32}$P, and $^{35}$S, Non-limiting examples of detectable markers include ligands, fluorophores, chemiluminescent agents, enzymes, and antibodies. Other detectable markers for use with probes, which can enable an increase in sensitivity of the method of the invention, include biotin and radionucleotides. It will become evident to the person of ordinary skill that the choice of a particular label dictates the manner in which it is bound to the probe.

As commonly known, radioactive nucleotides can be incorporated into probes of the invention by several methods. Non-limiting examples thereof include kinasing the 5' ends of the probes using gamma $^{32}$P ATP and polynucleotide kinase, using the Klenow fragment of Pol I of E. coli in the presence of radioactive dNTP (i.e., uniformly labeled DNA probe using random oligonucleotide primers in low-melt gels), using the SP6/T7 system to transcribe a DNA segment in the presence of one or more radioactive NTP, and the like.

As used herein, "oligonucleotides" or "oligos" define a molecule having two or more nucleotides (ribo or deoxyribonucleotides). The size of the oligo will be dictated by the particular situation and ultimately on the particular use thereof and adapted accordingly by the person of ordinary skill. An oligonucleotide can be synthetised chemically or derived by cloning according to well known methods.

As used herein, a "primer" defines an oligonucleotide which is capable of annealing to a target sequence, thereby creating a double stranded region which can serve as an initiation point for nucleic acid synthesis under suitable conditions.

Amplification of a selected, or target, nucleic acid sequence may be carried out by a number of suitable methods. See generally Kwoh et al., 1990, Am. Biotechnol. Lab. 8:14-25. Numerous amplification techniques have been described and can be readily adapted to suit particular needs of a person of ordinary skill. Non-limiting examples of amplification techniques include polymerase chain reaction (PCR), ligase chain reaction (LCR), strand displacement amplification (SDA), transcription-based amplification, the Q$ replicase system and NASBA (Kwoh et al., 1989, Proc. Natl. Acad. Sci. USA 86, 1173-1177; Lizardi et al., 1988, BioTechnology 6:1197-1202; Malek et al., 1994, Methods Mol. Biol., 28:253-260; and Sambrook et al., 1989, supra). Preferably, amplification will be carried out using PCR.

Polymerase chain reaction (PCR) is carried out in accordance with known techniques. See, e.g., U.S. Pat. Nos. 4,683,195; 4,683,202; 4,800,159; and 4,965,188 (the disclosures of all three U.S. patent are incorporated herein by reference). In general, PCR involves, a treatment of a nucleic acid sample (e.g., in the presence of a heat stable DNA polymerase) under hybridizing conditions, with one oligonucleotide primer for each strand of the specific sequence to be detected. An extension product of each primer which is synthesized is complementary to each of the two nucleic acid strands, with the primers sufficiently complementary to each strand of the specific sequence to hybridize therewith. The extension product synthesized from each primer can also serve as a template for further synthesis of extension products using the same primers. Following a sufficient number of rounds of synthesis of extension products, the sample is analysed to assess whether the sequence or sequences to be detected are present. Detection of the amplified sequence may be carried out by visualization following EtBr staining of the DNA following gel electrophores, or using a detectable label in accordance with known techniques, and the like. For a review on PCR techniques (see PCR Protocols, A Guide to Methods and Amplifications, Michael et al., Eds, Acad. Press, 1990).

Ligase chain reaction (LCR) is carried out in accordance with known techniques (Weiss, 1991, Science 254:1292). Adaptation of the protocol to meet the desired needs can be carried out by a person of ordinary skill. Strand displacement amplification (SDA) is also carried out in accordance with known techniques or adaptations thereof to meet the particular needs (Walker et al., 1992, Proc. Natl. Acad. Sci. USA 89:392-396; and ibid., 1992, Nucleic Acids Res. 20:1691-1696).

As used herein, the term "gene" is well known in the art and relates to a nucleic acid sequence defining a single protein or polypeptide. A "structural gene" defines a DNA sequence which is transcribed into RNA and translated into a protein having a specific amino acid sequence thereby giving rise to a specific polypeptide or protein. It will be readily recognized by the person of ordinary skill, that the nucleic acid sequence of the present invention can be incorporated into anyone of numerous established kit formats which are well known in the art.

A "heterologous" (i.e. a heterologous gene) region of a DNA molecule is a subsegment of DNA within a larger segment that is not found in association therewith in nature. The term "heterologous" can be similarly used to define two polypeptidic segments not joined together in nature. Non-limiting examples of heterologous genes include reporter genes such as luciferase, chloramphenicol acetyl transferase, β-galactosidase, and the like which can be juxtaposed or joined to heterologous control regions or to heterologous polypeptides.

The term "vector" is commonly known in the art and defines a plasmid DNA, phage DNA, viral DNA and the like, which can serve as a DNA vehicle into which DNA of the present invention can be cloned. Numerous types of vectors exist and are well known in the art.

The term "expression" defines the process by which a gene is transcribed into mRNA (transcription), the mRNA is then being translated (translation) into one polypeptide (or protein) or more.

The terminology "expression vector" defines a vector or vehicle as described above but designed to enable the expression of an inserted sequence following transformation into a host. The cloned gene (inserted sequence) is usually placed under the control of control element sequences such as promoter sequences. The placing of a cloned gene under such control sequences is often referred to as being operably linked to control elements or sequences.

Operably linked sequences may also include two segments that are transcribed onto the same RNA transcript. Thus, two sequences, such as a promoter and a "reporter sequence" are operably linked if transcription commencing in the promoter will produce an RNA transcript of the reporter sequence. In order to be "operably linked" it is not necessary that two sequences be immediately adjacent to one another.

Expression control sequences will vary depending on whether the vector is designed to express the operably linked gene in a prokaryotic or eukaryotic host or both (shuttle vectors) and can additionally contain transcriptional elements such as enhancer elements, termination sequences, tissue-specificity elements, and/or translational initiation and termination sites.

Prokaryotic expressions are useful for the preparation of large quantities of the protein encoded by the DNA sequence of interest. This protein can be purified according to standard protocols that take advantage of the intrinsic properties thereof, such as size and charge (i.e., SDS gel electrophoresis, gel filtration, centrifugation, ion exchange chromatography . . . ). In addition, the protein of interest can be purified via affinity chromatography using polyclonal or monoclonal antibodies. The purified protein can be used for therapeutic applications.

The DNA construct can be a vector comprising a promoter that is operably linked to an oligonucleotide sequence of the present invention, which is in turn, operably linked to a heterologous gene, such as the gene for the luciferase reporter molecule. "Promoter" refers to a DNA regulatory region capable of binding directly or indirectly to RNA polymerase in a cell and initiating transcription of a downstream (3' direction) coding sequence. For purposes of the present invention, the promoter is bound at its 3' terminus by the transcription initiation site and extends upstream (5' direction) to include the minimum number of bases or elements necessary to initiate transcription at levels detectable above background. Within the promoter will be found a transcription initiation site (conveniently defined by mapping with S1 nuclease), as well as protein binding domains (consensus sequences) responsible for the binding of RNA polymerase. Eukaryotic promoters will often, but not always, contain "TATA" boses and "CCAT" boxes. Prokaryotic promoters contain Shine-Dalgarno sequences in addition to the −10 and −35 consensus sequences.

In accordance with one embodiment of the present invention, an expression vector can be constructed to assess the functionality of specific alleles of the SCN1A, SCN2A and SCN3A sodium channels. Non-limiting examples of such expression vectors include a vector comprising the nucleic acid sequence encoding one of the sodium channels (or part thereof) according to the present invention. These vectors can be transfected in cells. The sequences of the alpha subunit of the sodium channels in accordance with the present invention and their structure-function relationship could be assessed by a number of methods known to the skilled artisan. One non-limiting example includes the use of cells expressing the β-1 and β-2 subunits and the sequence of an alpha subunit in accordance with the present invention. For example, an alpha subunit having a mutation, which is linked to epilepsy, could be compared to a sequence devoid of that mutation, as a control. In such cells, the functionality of the sodium channel could be tested as known to the skilled artisan and these cells could be used to screen for agents which could modulate the activity of the sodium channel. For example, agents could be tested and selected, which would reduce the hyperexcitability state of the sodium channel (e.g., their reduction in fast inactivation). Agents known to the person of ordinary skill as affecting other sodium channels could be tested, for example, separately or in batches. Of course, it will be understood that the SCN1A, SCN2A and/or SCN3A genes expressed by these cells can be modified at will (e.g., by in vitro mutagenesis or the like).

As used herein, the designation "functional derivative" denotes, in the context of a functional derivative of a sequence whether a nucleic acid or amino acid sequence, a molecule that retains a biological activity (either function or structural; e.g., sodium channel function or structure) that is substantially similar to that of the original sequence. This functional derivative or equivalent may be a natural derivative or may be prepared synthetically. Such derivatives include amino acid sequences having substitutions, deletions, or additions of one or more amino acids, provided that the biological activity of the protein is conserved. The same applies to derivatives of nucleic acid sequences which can have substitutions, deletions, or additions of one or more nucleotides, provided that the biological activity of the sequence is generally maintained. When relating to a protein sequence, the substituting amino acid generally has chemico-physical properties which are similar to that of the substituted amino acid. The similar chemico-physical properties include, similarities in charge, bulkiness, hydrophobicity, hydrophylicity and the like. The term "functional derivatives" is intended to include "fragments", "segments", "variants", "analogs" or "chemical derivatives" of the subject matter of the present invention. The genetic code, the chemico-physical characteristics of amino acids and teachings relating to conservative vs. non-conservative mutations are well-known in the art. Non-limiting examples of textbooks teaching such information are Stryer, Biochemistry, 3rd ed.; and Lehninger, Biochemistry, 3rd ed. The functional derivatives of the present invention can be synthesized chemically or produced through recombinant DNA technology. all these methods are well known in the art.

The term "variant" refers herein to a protein or nucleic acid molecule which is substantially similar in structure and biological activity to the protein or nucleic acid of the present invention.

As used herein, "chemical derivatives" is meant to cover additional chemical moieties not normally part of the subject matter of the invention. Such moieties could affect the physico-chemical characteristic of the derivative (i.e., solubility, absorption, half life, decrease of toxicity and the like). Such moieties are exemplified in Remington's Pharmaceutical Sciences (1980). Methods of coupling these chemical-physical moieties to a polypeptide or nucleic acid sequence are well known in the art.

The term "allele" defines an alternative form of a gene which occupies a given locus on a chromosome.

As commonly known, a "mutation" is a detectable change in the genetic material which can be transmitted to a daughter cell. As well known, a mutation can be, for example, a detectable change in one or more deoxyribonucleotide. For example, nucleotides can be added, deleted, substituted for, inverted, or transposed to a new position. Spontaneous mutations and experimentally induced mutations exist. The result of a mutations of nucleic acid molecule is a mutant nucleic acid molecule. A mutant polypeptide can be encoded from this mutant nucleic acid molecule.

As used herein, the term "purified" refers to a molecule having been separated from a cellular component. Thus, for example, a "purified protein" has been purified to a level not found in nature. A "substantially pure" molecule is a molecule that is lacking in all other cellular components.

As used herein, "SCNA biological activity" refers to any detectable biological activity of SCN1A, SCN2A or SCN3A gene or protein (herein sometimes collectively called SCNA genes or SCNA proteins). This includes any physiological function attributable to an SCNA gene or protein. It can include the specific biological activity of SCNA proteins which is efflux of sodium or related ions. This includes measurement of channel properties such as, but not limited to: 1) the voltage-dependence of activation, a measure of the strength of membrane depolarization necessary to open the channels, 2) the voltage-dependence of steady state inactivation, a measure of the fraction of channels available to open at the resting membrane potential; and 3) the time course of inactivation. At a larger scale, SCNA biological activity includes transmission of impulses through cells, wherein changes in transmission characteristics caused by modulators of SCNA proteins can be identified. Non-limiting examples of such measurements of these biological activities may be made directly or indirectly, such as through the transient accumulation of ions in a cell, dynamics of membrane depolarization, etc. SCNA biological activity is not limited, however, to these most important biological activities herein identified. Biological activities may also include simple binding or pKa analysis of SCNA with compounds, substrates, interacting proteins, and the like. For example, by measuring the effect of a test compound on its ability to increase or inhibit such SCNA binding or interaction is measuring a biological activity of SCNA according to this invention. SCNA biological activity includes any standard biochemical measurement of SCNA such as conformational changes, phosphorylation status or any other feature of the protein that can be measured with techniques known in the art. Finally, SCNA biological activity also includes activities related to SCNA gene transcription or translation, or any biological activities of such transcripts or translation products.

As used herein, the terms "molecule", "compound", "agent" or "ligand" are used interchangeably and broadly to refer to natural, synthetic or semi-synthetic molecules or compounds. The term "molecule" therefore denotes for example chemicals, macromolecules, cell or tissue extracts (from plants or animals) and the like. Non limiting examples of molecules include nucleic acid molecules, peptides, ligands (including, for example, antibodies and carbohydrates) and pharmaceutical agents. The agents can be selected and screened by a variety of means including random screening, rational selection and by rational design using for example protein or ligand modelling methods such as computer modelling. The terms "rationally selected" or "rationally designed" are meant to define compounds which have been chosen based on the configuration of the interacting domains of the present invention. As will be understood by the person of ordinary skill, macromolecules having non-naturally occurring modifications are also within the scope of the term "molecule". For example, peptidomimetics, well known in the pharmaceutical industry and generally referred to as peptide analogs can be generated by modelling as mentioned above. Similarly, in a preferred embodiment, the polypeptides of the present invention are modified to enhance their stability. It should be understood that in most cases this modification should not alter the biological activity of the protein. The molecules identified in accordance with the teachings of the present invention have a therapeutic value in diseases or conditions in which sodium transport through the sodium channels is compromised by a mutation (or combination thereof) in one of the genes identified in accordance with the present invention. Alternatively, the molecules identified in accordance with the teachings of the present invention find utility in the development of compounds which can modulate the activity of the alpha subunit sodium channels and/or the action potential in nerve cells and muscles cells (e.g., restore the fast inactivation of the sodium channel to normal levels).

As used herein, agonists and antagonists also include potentiators of known compounds with such agonist or antagonist properties. In one embodiment, modulators of the fast inactivation of the sodium channel in accordance with the present invention can be identified and selected by contacting the indicator cell with a compound or mixture or library of molecules for a fixed period of time.

As used herein the recitation "indicator cells" refers to cells that express at least one sodium channel α subunit (SCNA) according to the present invention. As alluded to above, such indicator cells can be used in the screening assays of the present invention. In certain embodiments, the indicator cells have been engineered so as to express a chosen derivative, fragment, homolog, or mutant of the combination of genotypes of the present invention. The cells can be yeast cells or higher eukaryotic cells such as mammalian cells. In one particular embodiment, the indicator cell would be a yeast cell harboring vectors enabling the use of the two hybrid system technology, as well known in the art (Ausubel et al., 1994, supra) and can be used to test a compound or a library thereof. In another embodiment, the cis-trans assay as described in U.S. Pat. No. 4,981,784, can be adapted and used in accordance with the present invention. Such an indicator cell could be used to rapidly screen at high-throughput a vast array of test molecules. In a particular embodiment, the reporter gene is luciferase or β-Gal.

It shall be understood that the "in vivo" experimental model can also be used to carry out an "in vitro" assay. For example, cellular extracts from the indicator cells can be prepared and used in an "in vitro" test. A non-limiting example thereof include binding assays.

In some embodiments, it might be beneficial to express a fusion protein. The design of constructs therefor and the expression and production of fusion proteins and are well known in the art (Sambrook et al., 1989, supra; and Ausubel et al., 1994, supra).

Non-limiting examples of such fusion proteins include hemaglutinin fusions and Gluthione-S-transferase (GST) fusions and Maltose binding protein (MBP) fusions. In certain embodiments, it might be beneficial to introduce a protease cleavage site between the two polypeptide sequences which have been fused. Such protease cleavage sites between two heterologously fused polypeptides are well known in the art.

In certain embodiments, it might also be beneficial to fuse the protein of the present invention to signal peptide sequences enabling a secretion of the fusion protein from the host cell. Signal peptides from diverse organisms are well known in the art. Bacterial OmpA and yeast Suc2 are two non-limiting examples of proteins containing signal sequences. In certain embodiments, it might also be beneficial to introduce a linker (commonly known) between the interaction domain and the heterologous polypeptide portion. Such fusion protein find utility in the assays of the present invention as well as for purification purposes, detection purposes and the like.

For certainty, the sequences and polypeptides useful to practice the invention include without being limited thereto mutants, homologs, subtypes, alleles and the like. It shall be understood that generally, the sequences of the present invention should encode a functional (albeit defective) alpha subunit of sodium channels (SCNA). It will be clear to the person of ordinary skill that whether the SCNA sequence of the present invention, variant, derivative, or fragment thereof retains its function, can be determined by using the teachings and assays of the present invention and the general teachings of the art.

It should be understood that the SCNA protein of the present invention can be modified, for example by in vitro mutagenesis, to dissect the structure-function relationship thereof and permit a better design and identification of modulating compounds. However, some derivative or analogs having lost their biological function may still find utility, for example for raising antibodies. These antibodies could be used for detection or purification purposes. In addition, these antibodies could also act as competitive or non-competitive inhibitor and be found to be modulators of the activity of the SCNA proteins of the present invention.

A host cell or indicator cell has been "transfected" by exogenous or heterologous DNA (e.g., a DNA construct) when such DNA has been introduced inside the cell. The transfecting DNA may or may not be integrated (covalently linked) into chromosomal DNA making up the genome of the cell. In prokaryotes, yeast, and mammalian cells for example, the transfecting DNA may be maintained on a episomal element such as a plasmid. With respect to eukaryotic cells, a stably transfected cell is one in which the transfecting DNA has become integrated into a chromosome so that it is inherited by daughter cells through chromosome replication. This stability is demonstrated by the ability of the eukaryotic cell to establish cell lines or clones comprised of a population of daughter cells containing the transfecting DNA. Transfection methods are well known in the art (Sambrook et al., 1989, supra; Ausubel et al., 1994 supra). The use of a mammalian cell as indicator can provide the advantage of furnishing an intermediate factor, which permits for example the interaction of two polypeptides which are tested, that might not be present in lower eukaryotes or prokaryotes. It will be understood that extracts from mammalian cells for example could be used in certain embodiments, to compensate for the lack of certain factors.

In general, techniques for preparing antibodies (including monoclonal antibodies and hybridomas) and for detecting antigens using antibodies are well known in the art (Campbell, 1984, In "Monoclonal Antibody Technology: Laboratory Techniques in Biochemistry and Molecular Biology", Elsevier Science Publisher, Amsterdam, The Netherlands) and in Harlow et al., 1988 (in: Antibody—A Laboratory Manual, CSH Laboratories). The present invention also provides polyclonal, monoclonal antibodies, or humanized versions thereof, chimeric antibodies and the like which inhibit or neutralize their respective interaction domains and/or are specific thereto.

From the specification and appended claims, the term therapeutic agent should be taken in a broad sense so as to also include a combination of at least two such therapeutic agents. Further, the DNA segments or proteins according to the present invention could be introduced into individuals in a number of ways. For example, cells can be isolated from the afflicted individual, transformed with a DNA construct according to the invention and reintroduced to the afflicted individual in a number of ways. Alternatively, the DNA construct can be administered directly to the afflicted individual. The DNA construct can also be delivered through a vehicle such as a liposome, which can be designed to be targeted to a specific cell type, and engineered to be administered through different routes.

For administration to humans, the prescribing medical professional will ultimately determine the appropriate form and dosage for a given patient, and this can be expected to vary according to the chosen therapeutic regimen (i.e., DNA construct, protein, cells), the response and condition of the patient as well as the severity of the disease.

Composition within the scope of the present invention should contain the active agent (i.e., molecule, hormone) in an amount effective to achieve the desired therapeutic effect while avoiding adverse side effects. Typically, the nucleic acids in accordance with the present invention can be administered to mammals (i.e., humans) in doses ranging from 0.005 to 1 mg per kg of body weight per day of the mammal which is treated. Pharmaceutically acceptable preparations and salts of the active agent are within the scope of the present invention and are well known in the art (Remington's Pharmaceutical Science, 16th Ed., Mack Ed.). For the administration of polypeptides, antagonists, agonists and the like, the amount administered should be chosen so as to avoid adverse side effects. The dosage will be adapted by the clinician in accordance with conventional factors such as the extent of the disease and different parameters from the patient. Typically, 0.001 to 50 mg/kg/day will be administered to the mammal.

The present invention also relates to a kit for diagnosing and/or prognosing epilepsy, and/or predicting response to a medication comprising an assessment of a genotype at SCNA loci of the present invention (or loci in linkage disequilibrium therewith) using a nucleic acid fragment, a protein or a ligand, a restriction enzyme or the like, in accordance with the present invention. For example, a compartmentalized kit in accordance with the present invention includes any kit in which reagents are contained in separate containers. Such containers include small glass containers, plastic containers or strips of plastic or paper. Such containers allow the efficient transfer of reagents from one compartment to another compartment such that the samples and reagents are not cross-contaminated and the agents or solutions of each container can be added in a quantitative fashion from one compartment to another. Such containers will include in one particular embodiment a container which will accept the test sample (DNA protein or cells), a container which contains the primers used in the assay, containers which contain enzymes, containers which contain wash reagents, and containers which contain the reagents used to detect the extension products.

BRIEF DESCRIPTION OF THE DRAWINGS

Having thus generally described the invention, reference will now be made to the accompanying drawings, showing by way of illustration a preferred embodiment thereof, and in which:

FIG. 2 shows the PCR primers used for genomic PCR-SSCP of SCN1A;

FIG. 3 shows the sequence of the SCN1A mutations found in epilepsy patients;

FIG. 4 shows the PCR primers used for genomic PCR-SSCP of SCN2A;

FIG. 5 shows the mutation found in epilepsy patients in SCN2A;

FIG. 6 shows the PCR primers used for genomic PCR-SSCP of SCN3A; and

FIG. 7 shows the mutation found in epilepsy patients in SCN3A.

Figure 1:
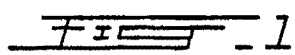
FIG. 1 shows the IGE candidate region on ch 2q23-q31. Order and distance between markers are according to Gyapay et al., 1994.

Sequences are also shown in the Sequence Listing. For example, SEQ ID NO.:1 shows the nucleic acid sequence of the adult form of SCN1A; SEQ ID NO.:2 shows the nucleic acid sequence of the neonatal form of SCN1A; SEQ ID NO.:3 shows the protein sequence of the adult form of SCN1A; SEQ ID NO.:4 shows the protein sequence of the neonatal form of SCN1A; SEQ ID NOs.:5-32 show the genomic sequence of SCN1A; SEQ ID NO.:33 shows the cDNA sequence of the adult form of SCN2A; SEQ ID NO.:34 shows the cDNA sequence of the neonatal form of SCN2A; SEQ ID NO.:35 shows the protein sequence of the adult form of SCN2A; SEQ ID NO.:36 shows the protein sequence of the neonatal form of SCN2A; SEQ ID NOs.:37-64 show the genomic sequence of SCN2A; SEQ ID NO.:65 shows the cDNA sequence of the adult form of SCN3A; SEQ ID NO.:66 shows the cDNA sequence of the neonatal form of SCN3A; SEQ ID NO.:67 shows the protein sequence of the adult form of SCN3A; SEQ ID NO.:68 shows the protein sequence of the neonatal form of SCN3A; and SEQ ID NOs.:69-98 show the genomic sequence of SCN3A. Rat SCNA1 sequences can be found in GenBank under accession numbers M22253 and X03638.

Other objects, advantages and features of the present invention will become more apparent upon reading of the following non-restrictive description of preferred embodiments with reference to the accompanying drawing which is exemplary and should not be interpreted as limiting the scope of the present invention.

DESCRIPTION OF THE PREFERRED EMBODIMENT

Epilepsy is one of the most common neurological conditions, affecting 1-2% of the general population. Familial aggregation studies have shown an increased risk for epilepsy in relatives of probands with different types of epilepsy, and especially for the idiopathic generalized epilepsies (IGEs). The epilepsy genes identified to date account for a very small proportion of all the epilepsies. In addition, they have been identified in rare syndromes where the pattern of inheritance was clearly Mendelian. This is not the case for the vast majority of epileptic patients, however, where the pattern of inheritance is not compatible with a simple Mendelian model. In fact, most authors consider epilepsy to be the result of a combination of many different genetic and environmental factors, features of a complex trait. While the pattern of inheritance is not mendelian, sporadic IGE cases may be caused by specific mutations in the same genes. Based on this assumption, a large cohort of IGE patients was tested for mutation in the SCNA genes.

In order to localize the gene causing epilepsy in a large family segregating an autosomal dominant form of IGE, 41 family members, including 21 affected individuals, were genotyped. A detailed clinical description of this family has been reported elsewhere (Scheffer and Berkovic 1997). The majority of patients in this family present a benign epilepsy syndrome occurring in childhood and characterized by frequent generalized tonic-clonic seizures not always associated with fever: a syndrome called febrile seizures plus (FS+). However, several patients presented other types of generalized seizures (GTCS) as well, such as myoclonic seizures and absences (Scheffer and Berkovic 1997). Mean age at onset was 2.2 years and offset was 11.7 years. Neurological examination and intellect were normal in all individuals except one, who had moderate intellectual disability. EEG recordings were normal in most patients. However, in three individuals generalized epileptiform activity was found and four patients had mild or moderate diffuse background slowing. Table 1 shows the different types of seizures found in the 21 patients included in this study.

TABLE 1

Different types of generalized seizures found in the 21 patients included in the linkage analysis.

| Type of seizures | n |
|---|---|
| Febrile convulsions alone | 9 |
| GTCSs[a] + absence seizures | 4 |
| GTCSs + myoclonic seizures | 1 |
| GTCSs + atonic seizures | 1 |
| Solitary afebril GTCS | 1 |
| Secondary epilepsy + mental retardation | 1 |
| Unwitnessed events | 4 |

[a]GTCS: generalized tonic clonic seizure

A genome wide search examining 190 markers identified linkage of IGE to chromosome (ch) 2 based on an initial positive lod score for marker D2S294 (Z=4.4, ($\theta$=0). A total of 24 markers were tested on ch 2q in order to define the smallest IGE candidate region. Table 2 shows the two-point lod scores for 17 markers spanning the IGE candidate region. The highest lod score (Zmax=5.29; ($\theta$=0) was obtained with marker D2S324. Critical recombination events mapped the IGE gene to a 29cM region flanked by markers D2S156 and D2S311, assigning the IGE locus to ch 2q23-q31 (FIG. 1). Although the relationship of FS+ with other IGE phenotypes remains unclear, the observation that in this family, several affected individuals have different types of generalized seizures, suggests that seizure predisposition determined by the ch 2q-IGE gene could be modified by other genes and/or environmental factors, to produce different seizure types.

TABLE 2

Two-point lod-scores for 17 markers localized on ch 2q23-q31.

| | Recombination fractions | | | | | | | | |
|---|---|---|---|---|---|---|---|---|---|
| Locus | 0 | 0.05 | 0.1 | 0.15 | 0.2 | 0.3 | 0.4 | Zmax | $\theta$max |
| D2S142 | 0.99 | 1.94 | 1.97 | 1.85 | 1.68 | 1.22 | 0.66 | 1.98 | 0.078 |
| D2S284 | 1.3 | 1.18 | 1.06 | 0.94 | 0.82 | 0.57 | 0.3 | 1.3 | 0 |
| D2S306 | 1.9 | 2.82 | 2.74 | 2.52 | 2.25 | 1.6 | 0.85 | 2.82 | 0.057 |
| D2S156 | 2.15 | 3.05 | 2.96 | 2.73 | 2.43 | 1.73 | 0.93 | 3.05 | 0.056 |
| D2S354 | 4.72 | 4.26 | 3.82 | 3.4 | 2.97 | 2.1 | 1.13 | 4.72 | 0 |
| D2S111 | 5.15 | 4.71 | 4.26 | 3.78 | 3.29 | 2.26 | 1.17 | 5.15 | 0 |
| D2S124 | 3.5 | 3.2 | 2.89 | 2.58 | 2.26 | 1.58 | 0.84 | 3.5 | 0 |
| D2S382 | 4.31 | 3.93 | 3.54 | 3.14 | 2.74 | 1.91 | 1.02 | 4.31 | 0 |
| D2S399 | 0.48 | 0.4 | 0.33 | 0.27 | 0.22 | 0.14 | 0.08 | 0.48 | 0 |
| D2S294 | 4.4 | 4.04 | 3.65 | 3.25 | 2.84 | 2 | 1.07 | 4.4 | 0 |
| D2S335 | 4.76 | 4.32 | 3.91 | 3.51 | 3.1 | 2.22 | 1.21 | 4.76 | 0 |
| D2S333 | 1.42 | 1.23 | 1.04 | 0.87 | 0.72 | 0.45 | 0.22 | 1.4 | 0 |
| D2S324 | 5.29 | 4.72 | 4.16 | 3.63 | 3.13 | 2.15 | 1.14 | 5.29 | 0 |
| D2S384 | 3.85 | 3.52 | 3.17 | 2.82 | 2.45 | 1.69 | 0.89 | 3.85 | 0 |
| D2S152 | 1.9 | 1.7 | 1.52 | 1.36 | 1.2 | 0.87 | 0.48 | 1.9 | 0 |
| D2S311 | −0.81 | 1.62 | 1.66 | 1.58 | 1.46 | 1.11 | 0.63 | 1.66 | 0.085 |
| D2S155 | −5.21 | 0.57 | 1.12 | 1.29 | 1.29 | 1.04 | 0.59 | 1.3 | 0.17 |

Haplotypes using 17 markers spanning the IGE candidate region were constructed (data not shown). The centromeric boundary was defined by a recombination event between the markers D2S156 and D2S354; whereas a recombination between the markers D2S152 and D2S311 set the telomeric boundary. These critical recombination events localized the IGE gene to a 29cM region flanked by markers D2S156 and D2S311 (FIG. 1).

Over the last four decades, family studies provided two important pieces of evidence supporting the role of genetic factors in determining susceptibility to seizures: 1) familial aggregation studies have shown evidence for an increased risk for epilepsy in relatives of probands with different types of epilepsy. In two studies standardized morbidity ratios for unprovoked seizures in relatives of individuals with idiopathic childhood-onset epilepsy varied from 2.5 to 3.4 in siblings and 6.7 in offspring (Anneger et al., 1982; Ottman et al. 1989); and 2) the presence of higher concordance rates for epilepsy in monozygotic than in dizygotic twins. Different studies showed concordance rates varying from 54 to 11% in monozygotic twins and 10 to 5% in dizygotic pairs (Inouye 1960; Lennox, 1960; Harvald and Hauge 1965; Corey et al. 1991; Silanpaa et al 1991).

It is now generally accepted that seizure susceptibility probably reflects complex interactions of multiple factors affecting neuronal excitability and that most common genetic epilepsies display familial aggregation patterns that are not explained by segregation of a single autosomal gene (Andermann 1982; Ottman et al. 1995). This of course significantly makes more complex one's ability to isolate genes which predispose or induce epilepsy. However, some specific epileptic syndromes, which aggregate in families, may result from definable monogenic abnormalities. These families present a unique opportunity to rapidly map genes that play a role in determining predisposition to seizures.

To date, there are a total of six loci (Greenberg et al. 1988; Leppert et al 1989; Lewis et al. 1993; Elmslie et al. 1997; Guipponi et al. 1997; Wallace et al. 1998), for which three genes have been identified in specific IGE syndromes (Bievert et al. 1998; Singh et al. 1998; Wallace et al. 1998). Interestingly, all three genes are ion channels, including a mutation found in the Na+-channel (1 in a Tasmania family with febrile seizures and generalized epilepsy (Wallace et al. 1998). While the candidate interval identified in our kindred remains large, a number of interesting genes map to the region. These include a cluster of Na+ channel genes and K+ channel genes (electronic data base search), as well as the GAD1 gene, which encodes for glutamate decarboxylase, an enzyme involved in the syntheses of (-aminobutyric acid (GABA) (Bu and Tobin 1994). GABA is one of the major neurotransmitters involved in synaptic inhibition in the central nervous system (Barnard et al. 1987). However, the large size of the candidate interval will require further refinement of the locus prior to the identification of the gene responsible for IGE in the kindred studied herein.

Fifty-three % (9/17) of affected individuals in the large IGE family described herein, who had their seizures classified, had only febrile convulsions. However, 41% of patients (7/17) presented with different types of generalized seizures. These findings may indicate that, although the predisposition to IGE in this family is determined by a single gene localized on ch2q23-q31, the different types of generalized seizures occurring in the same family may have resulted from interactions among genetic and/or environmental modifiers.

In conclusion, a locus for IGE was mapped on ch 2q23-q31. This locus seems to be associated with a specific IGE syndrome, FS+. However, the relationship of FS+ with other IGE phenotypes, and the role of the ch 2q locus in other FS+ families and in other forms of IGE are still undetermined.

Having identified a locus for IGE on chromosome 2q23-q31, it was next verified whether mutations and/or polymorphisms could be linked to epilepsy. Public data bases were screened to identify potential genes in that chromosome region. The blasts of the data bases were also oriented to identify more specifically, membrane channels since seizures in mice and human are known to be associated with membrane channels. Having identified membrane channel coding sequences or parts thereof by the computer searches, the candidate genes, potentially involved in epilepsy, had to be validated as susceptibility genes for the disease. Two approaches were used. The first one was to test the candidate genes for mutations in a family comprising members having the disease (data not shown). The second approach was as follows. Since it is known that epilepsy results from a lower seizure threshold, and that generalized epilepsy results, in many instances, from a generalized lowering of the seizure threshold, the following hypothesis was formulated. The gene which results in epilepsy in the large family (that enabled the focusing chromosome 2q23-q31) should have other, less severe, mutations that would cause epilepsy in people who have only a weak family history of epilepsy. The sodium channel genes were chosen because they are involved in key electrical functions and could thus be good candidates. To formally test the hypothesis, many (60 to 70) unrelated cases of epilepsy were tested for mutations in these candidate genes. Surprisingly, mutations were found in all three candidate genes.

In order to assess whether mutations/polymorphisms could be identified and correlated to epilepsy, a panel of 70 to 80 epileptic patients (IGE) were tested for mutations in SCN1A, SCN2A and SCN3A, using Single-strand conformation polymorphism (SSCP). SSCP analysis enables the detection of mutations as small as single-base substitutions. Indeed, such substitutions, by altering the conformations of single-strand DNA molecules, affect the electrophoretic mobilities thereof in non-denaturing gels. Thus, one can distinguish among sequences by comparing the mobilities of wild type (wt), mutant DNA, or different alleles of a given locus. The identification of single base substitutions of genes using SSCP is well known in the art, and numerous protocols are available therefor. A non-limiting example thereof includes fluorescence-based SSCP analysis, following PCR carried out using fluorescent-labeled primers specific for the DNA regions one wishes to amplify.

Upon the identification of differences between normal and epileptic mobilities for one of the SCNA loci of the present invention, the amplified fragments were sequenced and the nucleic acid sequences between a normal patient and an epileptic patient (IGE) compared. This comparison enabled the identification of mutations in SCN1A, SCN2A, and SCN3A. To assess, whether this difference in sequence or mutation was significantly associated with the disease, SSCP analysis was performed once again using a large cohort of normal patients. This analysis enabled to show that the mutations identified by SSCP and confirmed by sequence analysis were not present in the large cohort of normal patients tested, thereby showing that the mutations identified correlated with IGE, for the population tested.

Taken together, these results show that SCN1A, SCN2A and SCN3A are validated genes associated with epilepsy and more specifically with IGE.

This invention now establishes, for the first time, that SCN1A, SCN2A, and SCN3A, is directly responsible for idiopathic generalized epilepsy (IGE) in certain human populations. Further, this discovery suggests that compounds which modulate the activity of SCN1A, SCN2A and SCN3A may have application far beyond the small groups of families with IGE, and may have applicability for treating many or all forms of epilepsy and related neurological disorders. It is therefore an object of this invention to provide screening assays using SCN1A, SCN2A and/or SCN3A which can identify compounds which have therapeutic benefit for epilepsy and related neurological disorders. This invention also claims those compounds, the use of these compounds in treating epilepsy and related neurological disorders, and any use of any compounds identified using such a screening assay in treating epilepsy and related neurological disorders.

Generally, high throughput screens for one or more SCN1A, SCN2A or SCN3A (herein collectively called SCNA) sodium channels modulators i.e. candidate or test compounds or agents (e.g., peptides, peptidomimetics, small molecules or other drugs) may be based on assays which measure biological activity of SCNA. The invention therefore provides a method (also referred to herein as a "screening assay") for identifying modulators, which have a stimulatory or inhibitory effect on, for example, SCNA biological activity or expression, or which bind to or interact with SCNA proteins, or which have a stimulatory or inhibitory effect on, for example, the expression or activity of SCNA interacting proteins (targets) or substrates.

Examples of methods available for cell-based assays and instrumentation for screening ion-channel targets are described in the review by Gonzalez et al. (Drug Discov. Today 4:431-439, 1999), and high-throughput screens for ion-channel drugs are described in review by Denyer et al. (Drug Discov. Today 3:323-332, 1998). Such assays include efflux of sodium or related ions that can be measured in a cell line (recombinant or non-recombinant) using fluorescence-based assays using both sodium indicator dyes and voltage sensing dyes. Preferred assays employ $^{14}C$ guanidine flux and/or sodium indicator dyes such as SBFI and voltage sensing dyes such as DiBAC. Oxonal dyes such as $DiBAC_4$ are responsive to membrane depolarization. Hyper-polarization results in removal of the dye from the cell by passive diffusion, while depolarization results in concentration of the dye within the cell.

In one embodiment, the invention provides assays for screening candidate or test compounds which interact with substrates of a SCNA protein or biologically active portion thereof.

In another embodiment, the invention provides assays for screening candidate or test compounds which bind to or modulate the activity of a SCNA protein or polypeptide or biologically active portion thereof.

In one embodiment, an assay is a cell-based assay in which a cell which expresses a SCNA protein or biologically active portion thereof, either natural or recombinant in origin, is contacted with a test compound and the ability of the test compound to modulate SCNA biological activity, e.g., modulation of sodium efflux activity, or binding to a sodium channel or a portion thereof, or any other measurable biological activity of SCNA is determined. Determining the ability of the test compound to modulate SCNA activity can be accomplished by monitoring, for example, the release of a neurotransmitter or other compound, from a cell which expresses SCNA such as a neuronal cell, e.g. a substantia nigra neuronal cell, or a cardiac cell upon exposure of the test compound to the cell. Furthermore, determining the ability of the test compound to modulate SCNA activity can be accomplished by monitoring, for example, the change in current or the change in release of a neurotransmitter from a cell which expresses SCNA upon exposure to a test compound. Currents in cells can be measured using the patch-clamp technique as described in the Examples below using the techniques described in, for example, Hamill et al. 1981 Pfluegers Arch. 391:85-100. Alternatively, changes in current can be measured by dye based fluorescence assays described below.

Determining the ability of the test compound to modulate binding of SCNA to a substrate can be accomplished, for example, by coupling the SCNA agent or substrate with a radioisotope or enzymatic label such that binding of the SCNA substrate to SCNA can be determined by detecting the labeled SCNA substrate in a complex. For example, compounds (e.g., SCNA agents or substrates) can be labeled with $^{125}I$, $^{35}S$, $^{14}C$, or $^{3}H$, either directly or indirectly, and the radioisotope detected by direct counting radio-emission or by scintillation counting. Alternatively, compounds can be enzymatically labeled with, for example, horseradish peroxidase or alkaline phosphatase. In these assays, compounds which inhibit or increase substrate binding to SCNA are useful for the therapeutic objectives of the invention.

It is also within the scope of this invention to determine the ability of a compound (e.g., SCNA substrate) to interact with SCNA without the labeling of any of the interactants. For example. a microphysiometer can be used to detect the interaction of a compound with SCNA without the labeling of either the compound or the SCNA (McConnell H. M. et al. (1992), Science 257:1906-1912). As used herein, a "microphysiometer" (e.g., Cytosensor™) is an analytical instrument that measures the rate at which a cell acidifies its environment using a light-addressable potentiometric sensor (LAPS). Changes in this acidification rate can be used as an indicator of the interaction between a compound and SCNA.

Modulators of SCNA can also be identified through the changes they induce in membrane potential. A suitable instrument for measuring such changes is the VIPR™ (voltage ion probe reader) from Aurora Biosciences. This instrument works together with a series of voltage-sensing ion probe assays. The probes sense changes in transmembrane electrical potential through a voltage-sensitive FRET mechanism for which the ratio donor fluorescence emission to acceptor fluorescence emission reveals the extent of cell depolarization for both sodium and potassium channels. Depolarization results from transport of a quencher across the membrane and far enough away from a membrane-bound fluorescence emitter to relieve the initial quenching and produce light at the emission wavelength of the emitter. The system follows fluorescence at two wavelengths, both the intensities and ratios change during cell depolarization. The reader permits detection of sub-second, real-time optical signals from living cells in a microplate format. The system is amenable to manual operation for assay development or automation via robots for high-throughput screening.

In another embodiment, the assay is a cell-based assay comprising a contacting of a cell containing a target molecule (e.g., another molecule, substrate or protein that interacts with or binds to SCNA) with a test compound and determining the ability of the test compound to indirectly modulate (e.g., stimulate or inhibit) the biological activity of SCNA by binding or interacting with the target molecule. Determining the ability of the test compound to indirectly modulate the activity of SCNA can be accomplished, for example, by determining the ability of the test compound to bind to or interact with the target molecule and thereby to indirectly modulate SCNA, to modulate sodium efflux, or to modulate other biological activities of SCNA. Determining the ability of the SCNA protein or a biologically active fragment thereof, to bind to or interact with the target molecule can be accomplished by one of the methods described above or known in the art for determining direct binding. In a preferred embodiment, determining the ability of the test compound's ability to bind to or interact with the target molecule and thereby to modulate the SCNA protein can be accomplished by determining a secondary activity of the target molecule. For example, the activity of the target molecule can be determined by detecting induction of a cellular second messenger of the target (e.g., intracellular $Ca^{2+}$, diacylglycerol, IP3, and the like), detecting catalytic/enzymatic activity of the target on an appropriate substrate, detecting the induction of a reporter gene (comprising a target-responsive regulatory element operatively linked to a nucleic acid encoding a detectable marker, such as luciferase), or detecting a target-regulated cellular response such as the release of a neurotransmitter. Alternatively, recombinant cell lines may employ recombinant reporter proteins which respond, either directly or indirectly to sodium efflux or secondary messengers all as known in the art.

In yet another embodiment, an assay of the present invention is a cell-free assay in which a SCNA protein or biologically active portion thereof, either naturally occurring or recombinant in origin, is contacted with a test compound and the ability of the test compound to bind to, or otherwise modulate the biological activity of, the SCNA protein or biologically active portion thereof is determined. Preferred biologically active portions of the SCNA proteins to be used in assays of the present invention include fragments which participate in interactions with non-SCNA molecules, (e.g., other channels for sodium, potassium or Ca+ or fragments thereof, or fragments with high surface probability scores for protein-protein or protein-substrate interactions). Binding of the test compound to the SCNA protein can be determined either directly or indirectly as described above. In a preferred embodiment, the assay includes contacting the SCNA protein or biologically active portion thereof with a known compound which binds SCNA to form an assay mixture, contacting the assay mixture with a test compound, and determining the ability of the test compound to interact with a SCNA protein, wherein determining the ability of the test compound to interact with a SCNA protein comprises determining the ability of the test compound to preferentially bind to SCNA or biologically active portion thereof as compared to the known compound.

In another embodiment, the assay is a cell-free assay in which a SCNA protein or biologically active portion thereof is contacted with a test compound and the ability of the test compound to modulate (e.g., stimulate or inhibit) the activity of the SCNA protein or biologically active portion thereof is determined. Determining the ability of the test compound to modulate the activity of a SCNA protein can be accomplished, for example, by determining the ability of the SCNA protein to bind to a SCNA target molecule by one of the methods described above for determining direct binding. Determining the ability of the SCNA protein to bind to a SCNA target molecule can also be accomplished using a technology such as real-time Biomolecular Interaction Analysis (BIA, Sjolander, S, and Urbaniczky, C. (1991) Anal. Chem. 63:2338-2345 and Szabo et al. (1995) Curr. Opin. Struct. Biol. 5:699-705). As used herein, "BIA" refers to a technology for studying biospecific interactions in real time, without labeling any of the interactants (e.g., BIA core). Changes in the optical phenomenon of surface plasmon resonance (SPR) can be used as an indication of real-time reactions between biological molecules.

In an alternative embodiment, determining the ability of the test compound to modulate the activity of a SCNA protein can be accomplished by determining the ability of the test compound to modulate the activity of an upstream or downstream effector of a SCNA target molecule. For example, the activity of the test compound on the effector molecule can be determined or the binding of the effector to SCNA can be determined as previously described.

The cell-free assays of the present invention are amenable to use of both soluble and/or membrane-bound forms of isolated proteins. In the case of cell-free assays in which a membrane-bound form of an isolated protein is used (e.g., a sodium channel) it may be desirable to utilize a solubilizing agent such that the membrane-bound form of the isolated protein is maintained in solution. Examples of such solubilizing agents include non-ionic detergents such as n-octylglucoside, n-dodecylglucoside, n-dodecylmaltoside, octanoyl-N-methylglucamide, decanoyl-N-methylglucamide, Triton® X-100, Triton®X-114, Thesit®, Isotridecypoly(ethylene glycol ether)n.3-[(3-cholamidopropyl)dimethyl-amino]-l-propanesulfonate (CHAPS), 3-[(3-cholamidopropyl)dimethylamino]-2-hydroxy-l-propanesulfonate (CHAPSO), or N-dodecyl-N,N-dimethyl-3-ammnonio-l-propane sulfonate.

In more than one embodiment of the above assay methods of the present invention, it may be desirable to immobilize either SCNA or its target molecule to facilitate separation of complexed from uncomplexed forms of one or both of the proteins, as well as to accommodate automation of the assay. Binding of a. test compound to a SCNA protein or interaction of a SCNA protein with a target molecule in the presence and absence of a candidate compound, can be accomplished in any vessel suitable for containing the reactants. Examples of such vessels include microtitre plates, test tubes and microcentrifuge tubes. In one embodiment a fusion protein can be provided which adds a domain that allows one or both of the proteins to be bound to a matrix. For example. glutathione-S-transferase/SCNA fusion proteins or glutathione-S-transferase/target fusion proteins can be adsorbed onto glutathione sepharose beads (Sigma Chemical, St. Louis, Mo.) or glutathione derivatized microtitre plates, which are then combined with the test compound or the test compound and either the non-adsorbed target protein or SCNA protein and the mixture incubated under conditions conducive to complex formation (e.g., at physiological conditions for salt and pH). Following incubation the beads or microtitre plate wells are washed to remove any unbound components, the matrix immobilized in the case of beads, complex determined either directly or indirectly, for example, as described above. Alternatively, the complexes can be dissociated from the matrix, and the level of SCNA binding or activity determined using standard techniques.

Other techniques for immobilizing proteins on matrices (and well-known in the art) can also be used in the screening assays of the invention. For example, either a SCNA protein or a SCNA target molecule can be immobilized utilizing conjugation of biotin and streptavidin. Biotinylated SCNA protein or target molecules can be prepared from biotin-NHS (N-hydroxy-succinimide) using techniques known in the art (e.g., biotinylation kit, Pierce Chemicals, Rockford, Ill.), and immobilized in the wells of streptavidin-coated 96 well plates (Pierce Chemical). Alternatively, antibodies reactive with SCNA protein or target molecules but which do not interfere with binding of the SCNA protein to its target molecule can be derivatized to the wells of the plate, and unbound target or SCNA protein trapped in the wells by antibody conjugation. Methods for detecting such complexes, in addition to those described above for the GST-immobilized complexes, include immunodetection of complexes using antibodies reactive with the SCNA protein or target molecule, as well as enzyme-linked assays which rely on detecting an enzymatic activity associated with the SCNA protein or target molecule.

In a preferred embodiment, candidate or test compounds or agents are tested for their ability to inhibit or stimulate a SCNA molecule's ability to modulate vesicular traffic and protein transport in a cell, e.g. a neuronal or cardiac cell using the assays described in for example Komada M. et al. (1999) Genes Dev. 13(11):1475-85, and Roth M. G. et al. (1999) Chem. Phys. Lipids. 98(12):141-52.

In another preferred embodiment candidate, or test compounds or agents are tested for their ability to inhibit or stimulate or regulate the phosphorylation state of a SCNA channel protein or portion thereof, or an upstream or downstream target protein, using for example an in vitro kinase assay. Briefly, a SCNA target molecule (e.g., an immunoprecipitated sodium channel from a cell line expressing such a molecule), can be incubated with radioactive ATP, e.g., [gamma-$^{32}$P]-ATP, in a buffer containing $M_gCl_2$ and $M_nCl_2$, e.g., 10 mM $M_gCl_2$ and 5 mM $M_nCl_2$. Following the incubation, the immunoprecipitated SCNA target molecule (e.g., the sodium channel), can be separated by SDS-polyacrylamide gel electrophoresis under reducing conditions, transferred to a membrane, e.g., a PVDF membrane, and autoradiographed. The appearance of detectable bands on the auto radiograph indicates that the SCNA substrate, e.g., the sodium channel, has been phosphorylated. Phosphoaminoacid analysis of the phosphorylated substrate can also be performed in order to determine which residues on the SCNA substrate are phosphorylated. Briefly, the radiophosphorylated protein band can be excised from the SDS gel and subjected to partial acid hydrolysis. The products can then be separated by one-dimensional electrophoresis and analyzed on, for example, a phosphoimager and compared to ninhydrin-stained phosphoaminoacid standards. Assays such as those described in, for example, Tamaskovic R. et al. (1999) Biol. Chem. 380(5): 569-78.

In another preferred embodiment, candidate or test compounds or agents are tested for their ability to inhibit or stimulate a SCNA molecule's ability to associate with (e.g., bind) calcium, using for example, the assays described in Liu L. (1999) Cell Signal. 11(5):317-24 and Kawai T. et al. (1999) Oncogene 18(23):3471-80.

In another preferred embodiment, candidate or test compounds or agents are tested for their ability to inhibit or stimulate a SCNA molecule's ability to modulate chromatin formation in a cell using for example the assays described in Okuwaki M. et al. (1998) J. Biol. Chem. 273(51):34511-8 and Miyaji-Yamaguchi M. (1999) J. Mol. Biol. 290(2): 547-557.

In yet another preferred embodiment candidate or test compounds or agents are tested for their ability to inhibit or stimulate a SCNA molecule's ability to modulate cellular proliferation, using for example, the assays described in Baker F. L. et al. (1995) Cell Prolif. 28(1):1-15, Cheviron N. et al. (1996) Cell Prolif. 29(8):437-46. Hu Z. W. et al. (1999) J: Pharmacol. Exp. Ther. 290(1):28-37 and Elliott K. et al. (1999) Oncogene 18(24):3564-73.

In a preferred embodiment, candidate or test compounds or agents are tested for their ability to inhibit or stimulate a SCNA molecule's ability to regulate it's association with the cellular cytoskeleton. Using for example, the assays similar to those described in Gonzalez C. et al. (1998) Cell Mol. Biol. 44(7):1117-27 and Chia C. P. et al. (1998) Exp. Cell Res. 244(1):340-8.

In another preferred embodiment, candidate or test compounds or agents are tested for their ability to inhibit or stimulate a SCNA molecule's ability to modulate membrane excitability, using for example, the assays described in Bar-Sagi D. et al. (1985) J. Biol. Chem. 260(8):4740-4 and Barker J. L. et al. (1984) Neurosci. Lett. 47(3):313-8.

In another preferred embodiment, candidate or test compounds or agents are tested for their ability to inhibit or stimulate a SCNA molecule's ability to modulate cytokine signaling in a cell, (e.g., a neuronal or cardiac cell), the assays described in Nakashima Y. et al. (1999) J. Bone Joint Surg. Am. 81 (5):603-15.

In another embodiment, modulators of SCNA expression are identified in a method wherein a cell is contacted with a candidate compound and the expression of SCNA mRNA or protein in the cell is determined. The level of expression of SCNA mRNA or protein in the presence of the candidate compound is compared to the level of expression of SCNA mRNA or protein in the absence of the candidate compound. The candidate compound can then be identified as a modulator of SCNA expression based on this comparison. For example, when expression of SCNA mRNA or protein is greater (statistically significantly greater) in the presence of the candidate compound than in its absence, the candidate compound is identified as a stimulator of SCNA mRNA or protein expression. Alternatively, when expression of SCNA mRNA or protein is less (statistically significantly less) in the presence of the candidate compound than in its absence, the candidate compound is identified as an inhibitor of SCNA mRNA or protein expression. The level of SCNA mRNA or protein expression in the cells can be determined by methods described herein or other methods known in the art for detecting SCNA mRNA or protein.

The assays described above may be used as initial or primary screens to detect promising lead compounds for further development. Often, lead compounds will be further assessed in additional, different screens. Therefore, this invention also includes secondary SCNA screens which may involve electrophysiological assays utilizing mammalian cell lines expressing the SCNA channels such as patch clamp technology or two electrode voltage clamp and FRET-based voltage sensor. Standard patch clamp assays express wild type and mutant channels in *Xenopus* oocytes, and examine their properties using voltage-clamp electrophysiological recording. Wild type sodium channels are closed at hyperpolarized membrane potentials. In response to membrane depolarization the channels open within a few hundred microseconds, resulting in an inward sodium flux, which is terminated within a few milliseconds by channel inactivation. In whole cell recordings, rapid activation and inactivation of thousands of sodium channels distributed throughout the cell membrane results in a transient inward sodium current that rises rapidly to peak amplitude and then decays to baseline within a few milliseconds.

Tertiary screens may involve the study of the identified modulators in rat and mouse models for epilepsy. Accordingly, it is within the scope of this invention to further use an agent identified as described herein in an appropriate animal model. For example, an test compound identified as described herein (e.g., a SCNA modulating agent, an antisense SCNA nucleic acid molecule, a SCNA-specific antibody, or a SCNA-binding partner) can be used in an animal model to determine the efficacy, toxicity, or side effects of treatment with such an agent. Alternatively, an agent identified as described herein can be used in an animal model to determine the mechanism of action of such an agent. Furthermore, this invention pertains to uses of novel agents identified by the above-described screening assays for treatment (e.g., treatments of different types of epilepsy or CNS disorders), as described herein.

The test compounds of the present invention can be obtained using any of the numerous approaches in combinatorial library methods known in the art, including: biological libraries; spatially addressable parallel solid phase or solution phase libraries; synthetic library methods requiring deconvolution; the 'one-bead one-compound' library method; and synthetic library methods using affinity chromatography selection. The biological library approach is limited to peptide libraries, while the other four approaches are applicable to peptide, non-peptide oligomer or small molecule libraries of compounds (Lam, Anticancer Drug Des. 12: 145, 1997). Examples of methods for the synthesis of molecular libraries can be found in the art, for example in: DeWitt et al. (1993) Proc. Natl. Acad. Sci. USA. 90:6909; Erb et al. (1994) Proc. Natl. Acad. Sci. USA 91:11422; Zuckermann et al. (1994), J. Med. Chem. 37:2678; Cho et al. (1993) Science 261:1303; Carrell et al. (1994) Angew. Chem., Int. Ed Engl. 33:2059; Carell et al. (1994) Angew. Chem. Jnl. Ed. Engl. 33:2061; and in Gallop et al. (1994). Med. Chem. 37:1233. Libraries of compounds may be presented in solution (e.g., Houghten (1992) Biotechniques 13:412-421), or on beads (Lam (1991) Nature 354:82-84), chips (Fodor (1993) Nature 364:555-556), bacteria (Ladner U.S. Pat. No. 5,223,409), spores (Ladner U.S. Pat. No. '409), plasmids (Cull et al. (1992) Proc Natl Acad Sci USA 89:1865-1869) or on phage (Scott and Smith (1990); Science 249:386-390). Examples of methods for the synthesis of molecular libraries can be found in the art, for example in: DeWitt et al. (1993) Proc. Natl. Acad. Sci. USA. 90:6909; Erb et al. (1994) Proc. Natl. Acad. Sci. USA 91: 11422; Zuckermann et al. (1994), J: Med. Chem. 37:2678; Cho et al. (1993), Science 261:1303; Carrel et al. (1994) Angew. Chem. Int. Ed. Engl. 33:2059, or luciferase, and the enzymatic label detected by determination of conversion of an appropriate substrate to product.

In summary, based on the disclosure herein, those skilled in the art can develop SCNA screening assays which are useful for identifying compounds which are useful for treating epilepsy and other disorders which relate to potentiation of SCNA expressing cells. The assays of this invention may be developed for low-throughput, high-throughput, or ultra-high throughput screening formats.

The assays of this invention employ either natural or recombinant SCNA protein. Cell fraction or cell free screening assays for modulators of SCNA biological activity can use in situ, purified, or purified recombinant SCNA proteins. Cell based assays can employ cells which express SCNA protein naturally, or which contain recombinant SCNA gene constructs, which constructs may optionally include inducible promoter sequences. In all cases, the biological activity of SCNA can be directly or indirectly measured; thus modulators of SCNA biological activity can be identified. The modulators themselves may be further modified by standard combinatorial chemistry techniques to provide improved analogs of the originally identified compounds.

Finally, portions or fragments of the SCNA cDNA sequences identified herein (and the corresponding complete gene sequences) can be used in numerous ways as polynucleotide reagents. For example, these sequences can be used to: (i) map their respective genes on a chromosome and thus, locate gene regions associated with genetic disease (mutations/polymorphisms) related to epilepsy or CNS disorders that involve SCNA directly or indirectly; (ii) identify an individual from a minute biological sample (tissue typing); and (iii) aid in forensic identification of a biological sample.

The present invention is illustrated in further detail by the following non-limiting examples.

Example 1

Molecular Analysis

Genomic DNA was extracted from blood samples (Sambrook et al. 1989) or lymphoblastoid cell lines (Anderson and Gusella 1984) from each individual. A panel of 210 dinucleotide (CA)n repeat polymorphic markers with high heterozygosity (75%) were chosen from the 1993-94 Généthon map (Gyapay et al. 1994). Dinucleotide markers were spaced an average of 20 cM from each other throughout the 22 autosomes.

Genotyping of microsatellite markers was accomplished by polymerase chain reaction (PCR). The reaction mixture was prepared in a total volume of 13:1, using 80 ng genomic DNA; 1.25:1 10× buffer with 1.5 mM MgCl2; 0.65:1 BSA (2.0 mg/ml); 10 ng of each oligonucleotide primer; 200 mM dCTP, dGTP and dTTP; 25 mM dATP; 1.5 mCi [35S] dATP; and 0.5 units Taq DNA polymerase (Perkin-Elmer). Reaction samples were transferred to 96 well plates and were subjected to: 35 cycles of denaturation for 30 seconds at 94° C., annealing for 30 seconds at temperatures varying from 55° C. to 57° C. depending on the specificity of the oligonucleotide primers, and elongation for 30 seconds at 72° C. PCR reaction products were electrophoresed on 6% denaturing polyacrylamide sequencing gels.

Example 2

Genetic Analysis

Two-point linkage analysis was carried out using the MLINK program version 5.1 from the LINKAGE computer package (Lathrop et al. 1984). Precise values for Zmax were calculated with the ILINK program from the same computer package. Lod scores were generated based on an autosomal dominant mode of inheritance, 80% penetrance, disease gene frequency of 1:500 and allele frequencies for all allele markers calculated from the pedigree using the computer program ILINK (Lathrop et al. 1984).

Example 3

Mutations in SCN1A in IGE Patients

Genomic DNA from IGE and normal patients was obtained by conventional methods. Primers used to amplify the genomic DNA are shown in FIG. 2. Following PCR, SSCP analysis was performed and mutations in SCN1A were identified as follows (FIG. 3):

(1) Glu1238Asp; normal: GCA TTT GAA GAT ATA; patient R10191 who has an idiopathic generalized epilepsy (IGE): GCA TTT GAC GAT ATA (found in 1 of 70 IGE patients). The mutation is thus a conservative aa change, in the extracellular domain between III-S1 and III-S2. Furthermore, this residue is located at the junction between the TM domain and the extracellular domain. It may thus influence gating activity. The aa change between adult and neonatal isoforms is at a similar juxta-TM domain position (between I-S3 and I-S4).

(2) Ser1773Tyr; normal: ATC ATA TcC TTC CTG, patient R9049 (affected with IGE): ATC ATA TmC TTC CTG: (TCC>TAC). This mutation is in the middle of IV-S6 TM domain; found in 1/70 IGE patients, and 0/150 control subjects tested. This mutation is interesting from a biological point of view for a number of reasons. First, this region of SCN gene (IV-S6) has been found to play a critical role in fast inactivation of the SCN, by mutagenesis experiments in rat SCN (McPhee et al., 1998). This is highly relevant for pathophysiology of epilepsy, since this may increase neuronal hyperexcitability. Moreover, in patients with GEFs, a mutation has been found in the SCNB1 subunit, causing impairment of the fast inactivation of the SCN (Wallace et al, 1999). Finally, many of the antiepileptic drugs (e.g., phenyloin, carbamazepine) primarily act by reducing the repetitive firing of neuron, which also involves fast inactivation of the SCN.

Example 4

Mutations in SCN2A in IGE Patients

Genomic DNA from IGE and normal patients was obtained by conventional methods. Primers used to amplify the genomic DNA are shown in FIG. 4. Following PCR, SSCP analysis was performed and mutations in SCN2A were identified as follows (FIG. 5):

(1) Lys908Arg: normal: TAC AAA GAA for patient numbers always preceded by R; R9782 (Patient with IGE): TAC A GA GAA. The mutation is thus a conservative aa change, located in an extracellular domain between TM domains IIS5 and IIS6; in 1/70 IGE patients; 0/96 normal controls. The mutation involves an important component of the SCN gene, since the S5 and S6 segments are thought to form the wall of the transmembrane pore which allows the sodium to enter the cell. This may have an influence on the gating control of the pore.

(2) Leu768Val, in individuals R8197, R9062 and R9822 (all IGE patients) (found in 3/70 IGE patients and 0/65 control subjects). The mutations is in the IV-S6 component of the sodium channel, which is important in the inactivation of the channel (see above for more detail).

Example 5

Mutations in SCN3A in IGE Patients

Genomic DNA from IGE and normal patients was obtained by conventional methods. Primers used to amplify the genomic DNA are shown in FIG. 6. Following PCR, SSCP analysis was performed and mutations in SCN3A were identified as follows (FIG. 7):

(1) Asn43DEL: allele 1: CM GAT AAT GAT GAT GAG; allele 2: CAA GAT—GAT GAT GAG; in open reading frame deletes 1 aa: DNDDEN->QDDDEN, in the cytoplasmic N-terminal segment; in IGE patients, the frequency of allele 1=131/146 (0.90); allele 2=15/146 (0.10); for IGE patients: homozygotes (22): R3958, R9632; heterozygotes (12): R9049, R9152, R9649, R9710, R9896, R10069, R10191, R10213, R9993, R10009, R10256. Of note, 2 patients are homozygous for the rare allele and all patients have IGE. In controls: allele 1=145/154 (0.94); allele 2=9/154 (0.06) and no 22 homozygotes were found.

(2) normal: tggtgtaaggtag, R10670 (IGE patient): tggtataaggtag, in conserved intron between 5N & 5A exons, significance uncertain.

(3) normal: cccttatatctccaac, R10250 (IGE patient): cccttatayctccaac; in conserved intron between 5N & 5A exons, significance uncertain.

(4) Val1035Ile: normal: AAA TAC GTA ATC GAT, R9269 (IGE patient): AAA TAC RTA ATC GAT; (GTA>ATA=Val>Ile). The mutation is thus a conservative aa change which destroys a SnaBI site (this could thus be used as a polymorphism identifiable by restriction enzyme digestion). In SCN1A, this Val is a Ile, therefore probably not a causative mutation. In cytoplasmic domain bw II-S6 & III-S1 TMs; found in 1/70 IGE alleles; and 0/70 controls.

Example 6

SCN1A is Involved in Idiopathic Generalized Epilepsy

The assumption that SCN1A gene is involved in idiopathic generalised epilepsy in humans is based on many sets of evidence. First, a mutation has been found in a large Australian family with autosomal dominant epilepsy. The phenotype is idiopathic generalised epilepsy that is associated with febrile seizures (GEFS syndrome). The gene for this family has been previously mapped to the long arm of chromosome 2. The maximum lod score is 6.83 for marker D2S111. The candidate region is very large, spanning 21 cM between markers D2S156 and D2S311. However, within this interval, there is a cluster of sodium channel genes, including SCN1A which was hypothesized to be a candidate gene for the disease.

Screening by SSCP of a small panel of three (3) affected patients form the family, and 3 normal controls was carried-out at first. All the exons of the SCN1A gene have been amplified by PCR, and a SSCP variant in exon 4 was found for all of the affected individuals, and none of the controls. By sequencing an affected patient and a control, an A-T substitution at nucleotide 565 was found. This variation destroys a BamHI restriction site, this enzyme was thus used as a diagnostic test to screen all the affected patients from the family, as well as more control cases. All affected patients from the family have A565T substitution, and none of the unaffected patients in the same kindred. An A565T substitution was not found in more than 400 control chromosomes.

The A565T substitution correspond to a non-conservative amino acid change (D188V). This amino acid is conserved in all sodium channels thus far identified, in all species. The only exception is SCN2A identified in rat by Numa et al, where the aspartic acid is replaced by asparagine. However, it is likely that this represents an error during replication of cDNA, since other investigators have cloned the same gene in rat and found that the aspartic acid is conserved at position 188. Moreover, the same group has shown that D188N has a functional effect on channel activation in oocytes (Escayg et al., *Nature Genetics*. 24(4):343-5, 2000). Of note, this A565T substitution has not been found in 150 epileptic patients and in 200 control patients. Thus, this substitution has yet to be identified after 700 chromosomes assessments.

In view of proving that D188V in SCN1A, identified in the large Australian family studied, is a pathogenic mutation, the oligonucleotide mismatch mutagenesis technique was used to introduce the mutation in rat SCN1A clone. RNA was isolated from mutant and wild-type clones, and injected into oocytes in view of recording sodium currents by the patch-clamp technique. The amplitude of the currents was dramatically reduced for the mutant. Also, a small shift in the inactivation curve was observed for the mutant, as compared to the wild-type. Taken together, these preliminary results confirm a functional effect of D188V mutation on SCN1A gene. (more detail below).

The results presented herein are corroborated by studies from other investigators. For example, several other groups have also found linkage to the same locus on chromosome 2 for families with GEFS or very similar syndromes. Mutations in SCN1A (Thr875Met mutation; Arg1648His) have been found to be the cause of the epileptic syndrome in at least two (2) of these families (Escayg et al., *Nature Genetics*. 24(4): 343-5, 2000). Also, GEFS syndrome has been shown to be caused by mutation in SCN1B gene. It is demonstrated that the beta subunits interact with alpha subunits of voltage-gated sodium channels to alter kinetics of sodium currents in cells. These data suggest a common mechanism for generating abnormal neuronal discharges in the brain of patients with idiopathic generalised epilepsy.

Finally, in the process of screening patients from the large kindred with GEFS described above, a large cohort of patients with idiopathic generalised epilepsy was also screened by SSCP. Two (2) SSCP variants, that were subsequently sequenced were thereby identified. The variation observed are shown in Table 3:

TABLE 3

| exon | DNA variation | IGE alleles | Control alleles |
|---|---|---|---|
| 1Ax17 | Glu1238Asp; conservative AA change in extracellular domain between III-S1 and III-S2 | 3/254 | 0/284 |
| 1Ax24.2 | Ser1773Tyr; middle of IV-S6 TM domain | 1/252 | 0/334 |

Previous functional studies have shown that amino acid substitution in the transmembrane domain of SCN2A significantly affects the rate of inactivation of the channel. It is thus likely that Ser1773Tyr will have an effect on the SCN1A gene function. Such functional studies are currently underway.

Example 7

Further Validation of the Role of SCN1A, SCN2A, SCN3A, and Specific Mutations Thereof in IGE and Epilepsy in General A number of methods could be used to further validate the role of SCN1A, SCN2A, SCN3A, and specific mutations thereof in IGE. For example, additional patients could be screened for mutations in SCN1A, SCN2A, or SCN3A. Furthermore, additional normal patients could be screened in order to validate that the mutations identified significantly correlate with disease, as opposed to reflecting a polymorphism which is not linked to IGE. Polymorphisms which are not directly linked to IGE, if in linkage disequilibrium with a functional mutation linked to IGE, could still be useful in diagnosis and/or prognosis assays. In addition, functional studies can be carried. Numerous methods are amenable to the skilled artisan. One particularly preferred functional assay involves the use of Xenopus oocytes and recombinant constructs harboring normal or mutant sequence of SCN1A, SCN2A, or SCN3A. Xenopus oocytes have been used in functional assays to dissect the structure-function relationship of the cyclic AMP-modulated potassium channel using recombinant KCNQ2 and KCNQ3 (Schroeder et al., 1998). As well, it has been used to dissect the structure-function relationship of the beta subunit of the sodium channel (SCN1B gene; Wallace et al. 1998).

One such example of functional studies was investigated by assessing the effects of mutation D188V in the SCN1A gene on sodium channel function by introducing the mutation into a cDNA encoding the rat ortholog SCN1A gene. This rat gene shares >95% identity with the human SCN1A gene. The expression of wild type and mutant channels in Xenopus oocytes, and the examination of their properties using voltage-clamp electrophysiological recording is amenable to this Xenopus system. Wild type sodium channels are closed at hyperpolarized membrane potentials. In response to membrane depolarization the channels open within a few hundred microseconds, resulting in an inward sodium flux, which is terminated within a few milliseconds by channel inactivation. In whole cell recordings, rapid activation and inactivation of thousands of sodium channels distributed throughout the cell membrane results in a transient inward sodium current that rises rapidly to peak amplitude and then decays to baseline within a few milliseconds. Among the channel properties that are likely to be altered by mutations linked to epilepsy are: 1) the voltage-dependence of activation, a measure of the strength of membrane depolarization necessary to open the channels; 2) the voltage-dependence of steady state inactivation, a measure of the fraction of channels available to open at the resting membrane potential; and 3) the time course of inactivation. Preliminary results indicate that D188V mutant channels are identical to wild type channels with respect to the voltage-dependence of activation and to inactivation time course. However, steady state inactivation for the mutant channels is shifted to membrane potentials that are slightly more positive than observed in wild type channels. This positive shift should increase the fraction of channels available to open at rest. This could increase neuronal excitability and contribute to epileptogenesis. Thus, a functional consequence of a naturally occurring mutation in a sodium channel gene has been tentatively identified. Thus, the functional consequence of the D188M mutant could at least in part explain its role in epilepsy. Such a functional consequence is expected to be observed with other mutations identified above in SCNA1, SCNA2 and SCNA3.

It is recognized by the inventors that certain therapeutic agents have been identified for cardiac, muscular, chronic pain, acute pain and other disorders, and analgesics and anesthetics that are modulators of sodium channels. Use of these sodium channel modulators for treating epilepsy and related neurological disorders also falls within the scope of this invention. In one embodiment of this invention, sodium channel blockers are modified to achieve improved transport across the blood brain barrier in order to have direct effect on neuronal SCNA proteins and genes. Descriptions of such compounds are found at Hunter, J C et al. Current Opinion in CPNS Invest. Drugs. 1999 1(11):72-81; Muir K W et al. 2000. Cerebrovasc. Disc. 10(6):431-436; Winterer, G. 2000. Pharmacopsychiatry 33(5):182-8; Clare et al. 2000. Drug. Discov. Today 5(11):506-520; Taylor C P et al. 2000. Adv. Pharmacol. 39:47-98, and Pugsley M K et al. 1998. Eur. J. Pharmacol. 342 (1)93-104.

It is also recognized by the inventors that compounds which modulate (i.e., either upregulate or downregulate) transcription and translation of SCNA genes are useful for treating epilepsy or related neurological disorders. According to this invention, test compounds which modulate the activity of promoter elements and regulatory elements of sodium channel genes are useful for treating these disorders.

Although the present invention has been described hereinabove by way of preferred embodiments thereof, it can be modified, without departing from the spirit and nature of the subject invention as defined in the appended claims.

REFERENCES

1) Andermann E (1982) Multifactorial inheritance of generalized and focal epilepsy. In: Anderson V E, Hauser W A, Penry J K, Sing C F (eds) GeneticBasis of the Epilepsies. New York, Raven Press, pp: 355-374
2) Anderson M A and Gusella J F (1984) Use of cyclosporin A in establishing Epstein Barr virus-transformed human lymphoblastoid cell lines. In Vitro 20:856-858
3) Anneger J F, Hauser W A, Anderson V E (1982) Risk of seizures among relatives of patients with epilepsy: families in a defined population. In: Anderson V E, Hauser W A, Sing L, Porter R (eds) The Genetic Basis of the Epilepsies, Raven Press, New York, pp
4) Barnard E A, Darlison M G, Seeburg P (1987) Molecular biology of the GABAA receptor: the receptor/channel superfamily. Trends Neurosci 10:502-509
5) Berkovic S F, et al. Epilepsies in twins: genetics of the major epileptic syndromes. Ann Neurol. 43:435-445 (1998)
6) Bievert C, Schoeder B C, Kubisch C, Berkovic S F, Propping P, Jentsch T J, Steinlein O K (1998) A potassium channel mutation in neonatal human epilepsy. Science
7) Bu D F, Tobin A J (1994) The exon-intron organization of the genes (GAD1 and GAD2) encoding two human glutamate decarboxylases (GAD67 and GAD65) suggests that they derive from a common ancestral GAD. Genomics 1:222-228
8) Charlier C, et al. A pore mutation in a novel KGT-like potassium channel gene in an idiopathic epilepsy family. Nat. Genet. 18:53-55 (1998)
9) Commission on Classification and Terminology of the International League against Epilepsy (1989) Proposal for revised clinical and eletroencephalographic classification of epileptic seizures. Epilepsia 22:489-501

10) Corey L A, Berg K, Pellock J M, Solaas M H, Nance W E, DeLorenzo R J (1991) The occurrence of epilepsy and febrile seizures in Virginian and Norwegian twins. Neurology
11) Elmslie F V, Rees M, Williamson M P, Kerr M, Kjeldsen M J, Pang K A, Sundqvist A, et al (1997) Genetic mapping of a major susceptibility locus for juvenile myoclonic epilepsy on chromosome 15q. Hum Mol Genet. 6:1329-1334
12) Engel J J, Pedley T A (1998) What is epilepsy ? In: Engel J J, Pedley T A (eds) Epilepsy a Comprehensive Textbook, Lippincott-Raven Publishers, Philadelphia, pp: 1-10
13) Escayg et al., *Nature Genetics*. 24(4):343-5, 2000
14) Greenberg D A, Delgado-Escueta A V, Widelitz H, Sparkes R S, Treiman L, Maldonado H M, et al (1988) Juvenile myoclonic epilepsy (JME) may be linked to the BF and HLA loci on human chromosome 6. Am J Hum Genet. 31:185-192
15) Guipponi M, Rivier F, Vigevano F, Beck C, Crespel A, Echenne B, Lucchini P, et al (1997) Linkage mapping of benign familial infantile seizures (BFIS) to chromosome 19q. Hum Mol Genet. 6:473-477
16) Gyapay G, Morissette J, Vignal A, et al. (1994) The 1993-94 Genethon human genetic linkage map. Nat Genet. 7:246-339
17) Harvald B and Hauge M (1965) Hereditary factors elucidated by twin studies. In: Neel J V, Shaw M W, Schull W J (eds) Genetics and the Epidemiology of Chronic Diseases, Washington Public Health Service Publications 1163:61-76
18) Inouye E (1960) Observations on forty twin index cases with chronic epilepsy and their co-twins. J Nerv Ment Dis 130: 401-416
19) Lathrop G M, Lalouel J M, (1984) Easy calculations of lod scores and genetic risks on small computers. Am J Hum Genet. 36:460-465
20) Lennox W G, Lennox M A (1960) Epilepsy and related disorders. Boston, Little Brown.
21) Leppert M, Anderson V E, Quattlebaum T, Staufe D, O'Connell P, Nakamura Y, Lalouel J M, et al (1989) Benign familial neonatal convulsions linked to genetic markers on chromosome 20. Nature 337:647-648
22) Lewis T B, Leach R J, Ward K, O'Connell P, Ryan S G (1993) Genetic Heterogeneity in benign familial neonatal convulsions: identification of a new locus on chromosome 8q. Am J Hum Genet. 53:670-675
23) McPhee et al., 1998, J. Biol. Chem. 273:1121-1129
24) Ottman R, Annegers J F, Hauser W A, Kurland L T (1989) Seizure risk in offspring of parents with generalized versus partial epilepsy. Epilepsia 30:157-161
25) Ottman R, Hauser W A, Barker-Cummings C, Lee J H, Risch N (1997) Segregation analysis of cryptogenic epilepsy and an empirical test of the validity of the results. Am J Hum Genet. 60:667-675
26) Sambrook J, Fritsch E F, Maniatis T (eds) (1989) Molecular cloning: a laboratory manual, 2nd ed. Cold Spring Harbor Laboratory, Cold Spring Harbor, N.Y., pp E.3-E.4
27) Scheffer I E and Berkovic S F (1997) Generalised epilepsy with febrile seizures plus: a genetic disorder with heterogeneous clinical phenotypes. Brain 120: 479-490
28) Schroeder et al., 1998, Nature 396:687-690.
29) Silanpaa M, Koskenvuo M, Romanov K, Kaprio J (1991) Genetic factors in epileptic seizures: evidence from a large twin population. Acta Neurol Scand 84:523-526
30) Singh N A, Charlier C, Stauffer D, DuPont B R, Leach R J, Melis R, Ronen G M, et al (1998) A novel potassium channel gene, KCNQ2, is mutated in an inherited epilepsy of newborns. Nat Genet. 18:25-29
31) Steinlein O K, et al. A missense mutation in the neuronal nicotinic acetylcholine receptor alpha 4 subunit is associated with autosomal dominant nocturnal frontal lobe epilepsy. Nat. Genet. 11:201-203 (1995).
32) Wallace R H, Wang D W, Sing R, Scheffer I E, George-Jr A L, Phillips H A, Saar K, et al (1998) Febrile seizures and generalized epilepsy associated with a mutation in the Na+-channel (1 subunit gene SCN1B. Nat Genet. 19:366-370

What is claimed is:

1. A purified nucleic acid molecule variant of the human SCN3A sodium channel, wherein said nucleic acid molecule comprises a nucleic acid sequence selected from the group consisting of:
   (a) the nucleic acid sequence of SEQ ID NO: 410, which encodes a variant of an alpha subunit of SCN3A and comprises a deletion mutation which deletes an asparagine at position 43 of the corresponding wild-type human SCN3A sequence as set forth in SEQ ID NO: 67;
   (b) a nucleic acid encoding an alpha subunit of SCN3A, wherein the encoded protein comprises an amino acid sequence that differs from SEQ ID NO:67 only by deletion of the asparagine at position 43 thereof;
   (c) the nucleic acid sequence of SEQ ID NO: 411, which encodes a variant of an alpha subunit of SCN3A and comprises a guanine to adenine mutation that translates into an isoleucine instead of a valine at position 1035 (Val1035lle) of the corresponding wild-type human SCN3A sequence as set forth in SEQ ID NO: 67;
   (d) a nucleic acid encoding an alpha subunit of SCN3A, wherein the encoded protein comprises an amino acid sequence that differs from SEQ ID NO:67 only in that an isoleucine is substituted for valine at position 1035 thereof;
   (e) a full length complement of any one of (a)-(d);
   (f) a nucleic acid sequence encoding a variant SCN3A alpha subunit, which hybridizes under high stringency conditions to the nucleic acid sequence of (e), wherein said high stringency conditions comprise a hybridization at 65° C. in 5×SSC, 5×Denhardt's solution, 1% SDS, and 100 μg/mL denatured salmon sperm DNA, wherein said nucleic acid sequence comprises a nucleic acid sequence selected from at least one of:
      (i) residues 189 to 242 of SEQ ID NO: 94;
      (ii) residues 221 to 358 of SEQ ID NO: 95;
      (iii) residues 254 to 358 of SEQ ID NO: 96;
      (iv) residues 211 to 481 of SEQ ID NO: 97; and
      (v) residues 156 to 1351 of SEQ ID NO: 98; and
   (g) a full length complement of (f).

2. The purified nucleic acid molecule of claim 1 for selecting a compound for treating or preventing idiopathic generalized epilepsy.

3. The purified nucleic acid molecule of claim 1, wherein the nucleic acid sequence in (f) encodes a variant of an SCN3A alpha subunit as set forth in SEQ ID NO: 67 and comprising:
   (a) a deletion mutation which deletes an asparagine at position 43 of SEQ ID NO: 67; or
   (b) an isoleucine instead of a valine at position 1035 (Val1035lle) of SEQ ID NO: 67.

4. The purified nucleic acid molecule of claim 1, wherein said nucleic acid molecule comprises the nucleic acid sequence selected from the group consisting of:
   (i) the nucleic acid sequence of SEQ ID NO: 410;
   (ii) the nucleic acid sequence of SEQ ID NO: 411; and
   (iii) a full-length complement of (i) or (ii).

5. The purified nucleic acid molecule of claim 4, wherein the presence of said nucleic acid molecule in a sample of a subject indicates that the subject has an increased risk of idiopathic generalized epilepsy.

6. A vector comprising the nucleic acid molecule of claim 4.

7. An isolated cell comprising the vector of claim 4.

8. A purified nucleic acid molecule comprising a nucleic acid sequence selected from the group consisting of:
   (a) the nucleic acid sequence of SEQ ID NO: 409, which encodes an alpha subunit of human SCN3A;
   (b) a nucleic acid sequence encoding an alpha subunit of the human SCN3A as set forth in SEQ ID NO: 67;
   (c) a full-length complement of (a) or (b);
   (d) a nucleic acid sequence encoding an SCN3A alpha subunit of a sodium channel, which hybridizes under high stringency conditions to the nucleic acid sequence (c), wherein said high stringency conditions comprise a hybridization at 65° C. in 5×SSC, 5×Denhardt's solution, 1% SDS, and 100 μg/mL denatured salmon sperm DNA, wherein said nucleic acid sequence comprises a nucleic acid sequence selected from at least one of:
      (i) residues 189 to 242 of SEQ ID NO: 94;
      (ii) residues 221 to 358 of SEQ ID NO: 95;
      (iii) residues 254 to 358 of SEQ ID NO: 96;
      (iv) residues 211 to 481 of SEQ ID NO: 97; and
      (V) residues 156 to 1351 of SEQ ID NO: 98; and
   (e) a full length complement of (d).

9. The purified nucleic acid molecule of claim 8 for selecting a compound for treating or preventing idiopathic generalized epilepsy.

10. The purified nucleic acid molecule of claim 8, wherein the nucleic acid sequence in (d) encodes an alpha subunit of the human SCN3A as set forth in SEQ ID NO: 67.

11. The purified nucleic acid molecule of claim 8, wherein said nucleic acid molecule comprises the nucleic acid sequence of SEQ ID NO:409 or a full-length complement thereof.

12. A vector comprising the nucleic acid molecule of claim 8.

13. An isolated cell comprising the vector of claim 12.

14. A purified nucleic acid molecule comprising a nucleic acid sequence selected from the group consisting of:
   (a) a nucleic acid sequence having at least 95% overall identity to SEQ ID NO: 410 or 411 encoding a variant of an alpha subunit of SCN3A having SCN3A biological activity;
   (b) a nucleic acid sequence having at least 95% overall identity to SEQ ID NO: 409 encoding an alpha subunit of SCN3A having SCN3A biological activity; and
   (c) the full length complement of (a) or (b).

* * * * *

SEQUENCE LISTING

```
<160> NUMBER OF SEQ ID NOS: 411

<210> SEQ ID NO 1
<211> LENGTH: 8378
<212> TYPE: DNA
<213> ORGANISM: Homo sapiens

<400> SEQUENCE: 1
tactgcagag gtctctggtg catgtgtgta tgtgtgcgtt tgtgtgtgtt tgtgtgtctg      60
tgtgttctgc cccagtgaga ctgcagccct tgtaaatact ttgacacctt ttgcaagaag     120
gaatctgaac aattgcaact gaaggcacat tgttatcatc tcgtctttgg gtgatgctgt     180
tcctcactgc agatggataa ttttcctttt aatcaggaat ttcatatgca gaataaatgg     240
taattaaaat gtgcaggatg acaagatgga gcaaacagtg cttgtaccac caggacctga     300
cagcttcaac ttcttcacca gagaatctct tgcggctatt gaaagacgca ttgcagaaga     360
aaaggcaaag aatcccaaac cagacaaaaa agatgacgac gaaaatggcc caaagccaaa     420
tagtgacttg gaagctggaa agaaccttcc atttatttat ggagacattc ctccagagat     480
ggtgtcagag cccctggagg acctggaccc ctactatatc aataagaaaa ctttatagt     540 attgaataaa gggaaggcca tcttccggtt cagtgccacc tctgccctgt acattttaac     600
```

```
tcccttcaat cctcttagga aaatagctat taagattttg gtacattcat tattcagcat   660
gctaattatg tgcactattt tgacaaactg tgtgttatg acaatgagta accctcctga    720
ttggacaaag aatgtagaat acaccttcac aggaatatat acttttgaat cacttataaa   780
aattattgca aggggattct gtttagaaga ttttactttc cttcgggatc catgaactg    840 gctcgatttc actgtcatta catttgcgta cgtcacagag tttgtggacc tgggcaatgt   900
ctcggcattg agaacattca gagttctccg agcattgaag acgatttcag tcattccagg   960
cctgaaaacc attgtgggag ccctgatcca gtctgtgaag aagctctcag atgtaatgat  1020
cctgactgtg ttctgtctga gcgtatttgc tctaattggg ctgcagctgt tcatgggcaa  1080
cctgaggaat aaatgtatac aatggcctcc caccaatgct tccttggagg aacatagtat  1140
agaaaagaat ataactgtga attataatgg tacacttata aatgaaactg tctttgagtt  1200
tgactggaag tcatatattc aagattcaag atatcattat ttcctggagg gttttttaga  1260
tgcactacta tgtggaaata gctctgatgc aggccaatgt ccagagggat atatgtgtgt  1320
gaaagctggt agaaatccca attatggcta cacaagcttt gataccttca gttgggcttt  1380
tttgtccttg tttcgactaa tgactcagga cttctgggaa aatctttatc aactgacatt  1440
acgtgctgct gggaaaacgt acatgatatt ttttgtattg gtcattttct tgggctcatt  1500
ctacctaata aatttgatcc tggctgtggt ggccatggcc tacgaggaac agaatcaggc  1560
caccttggaa gaagcagaac agaaagaggc cgaatttcag cagatgattg aacagcttaa  1620
aaagcaacag gaggcagctc agcaggcagc aacggcaact gcctcagaac attccagaga  1680
gcccagtgca gcaggcaggc tctcagacag ctcatctgaa gcctctaagt tgagttccaa  1740
gagtgctaag gaaagaagaa atcggaggaa gaaaagaaaa cagaaagagc agtctggtgg  1800
ggaagagaaa gatgaggatg aattccaaaa atctgaatct gaggacagca tcaggaggaa  1860
aggttttcgc ttctccattg aagggaaccg attgacatat gaaaagaggt actcctcccc  1920
acaccagtct ttgttgagca tccgtggctc cctattttca ccaaggcgaa atagcagaac  1980
aagccttttc agctttagag ggcgagcaaa ggatgtggga tctgagaacg acttcgcaga  2040
tgatgagcac agcaccttg aggataacga gagccgtaga gattccttgt tgtgccccg    2100 acgacacgga gagagacgca acagcaacct gagtcagacc agtaggtcat cccggatgct  2160
ggcagtgttt ccagcgaatg ggaagatgca cagcactgtg gattgcaatg gtgtggtttc  2220
cttggttggt ggaccttcag ttcctacatc gcctgttgga cagcttctgc cagaggtgat  2280
aatagataag ccagctactg atgacaatgg aacaaccact gaaactgaaa tgagaaagag  2340
aaggtcaagt tctttccacg tttccatgga cttttctagaa gatccttccc aaaggcaacg  2400
agcaatgagt atagccagca ttctaacaaa tacagtagaa gaacttgaag aatccaggca  2460
gaaatgccca ccctgttggt ataaattttc caacatattc ttaatctggg actgttctcc  2520
atattggtta aaagtgaaac atgttgtcaa cctggttgtg atggaccat ttgttgacct   2580 ggccatcacc atctgtattg tcttaaatac tcttttcatg gccatggagc actatccaat  2640 gacgaccat ttcaataatg tgcttacagt aggaaacttg gttttcactg ggatctttac   2700
agcagaaatg tttctgaaaa ttattgccat ggatccttac tattatttcc aagaaggctg  2760
gaatatcttt gacggtttta ttgtgacgct agcctggta gaacttggac tcgccaatgt   2820
ggaaggatta tctgttctcc gttcatttcg attgctgcga gttttcaagt ggcaaaaatc  2880
ttggccaacg ttaaatatgc taataaagat catcggcaat tccgtggggg ctctgggaaa  2940 tttaacccte gtcttggcca tcatcgtctt cattttttgcc gtggtcggca tgcagctctt  3000
```

-continued

| | |
|---|---|
| tggtaaaagc tacaaagatt gtgtctgcaa gatcgccagt gattgtcaac tcccacgctg | 3060 |
| gcacatgaat gacttcttcc actccttcct gattgtgttc cgcgtgctgt gtggggagtg | 3120 |
| gatagagacc atgtgggact gtatggaggt tgctggtcaa gccatgtgcc ttactgtctt | 3180 |
| catgatggtc atggtgattg gaaacctagt ggtcctgaat ctctttctgg ccttgcttct | 3240 |
| gagctcattt agtgcagaca accttgcagc cactgatgat gataatgaaa tgaataatct | 3300 |
| ccaaattgct gtggatagga tgcacaaagg agtagcttat gtgaaaagaa aaatatatga | 3360 |
| atttattcaa cagtccttca ttaggaaaca aaagatttta gatgaaatta accacttga | 3420 |
| tgatctaaac aacaagaaag acagttgtat gtccaatcat acagcagaaa ttgggaaaga | 3480 |
| tcttgactat cttaaagatg taaatggaac tacaagtggt ataggaactg cagcagtgt | 3540 |
| tgaaaaatac attattgatg aaagtgatta catgtcattc ataaacaacc ccagtcttac | 3600 |
| tgtgactgta ccaattgctg taggagaatc tgactttgaa aatttaaaca cggaagactt | 3660 |
| tagtagtgaa tcggatctgg aagaaagcaa agagaaactg aatgaaagca gtagctcatc | 3720 |
| agaaggtagc actgtggaca tcggcgcacc tgtagaagaa cagcccgtag tggaacctga | 3780 |
| agaaactctt gaaccagaag cttgtttcac tgaaggctgt gtacaaagat tcaagtgttg | 3840 |
| tcaaatcaat gtggaagaag gcagaggaaa acaatggtgg aacctgagaa ggacgtgttt | 3900 |
| ccgaatagtt gaacataact ggtttgagac cttcattgtt ttcatgattc tccttagtag | 3960 |
| tggtgctcgg catttgaaga tatatatatt gatcagcgaa agacgattaa gacgatgttg | 4020 |
| gaatatgctg acaaggtttt cacttacatt ttcattctgg aaatgcttct aaaatgggtg | 4080 |
| gcatatggct atcaaacata tttcaccaat gcctggtgtt ggctggactt cttaattgtt | 4140 |
| gatgtttcat tggtcagttt aacagcaaat gccttgggtt actcagaact tggagccatc | 4200 |
| aaatctctca ggacactaag agctctgaga cctctaagag ccttatctcg atttgaaggg | 4260 |
| atgagggtgg ttgtgaatgc cctttagga gcaattccat ccatcatgaa tgtgcttctg | 4320 |
| gtttgtctta tattctggct aattttcagc atcatgggcg taaatttgtt tgctggcaaa | 4380 |
| ttctaccact gtattaacac cacaactggt gacaggtttg acatcgaaga cgtgaataat | 4440 |
| catactgatt gcctaaaact aatagaaaga atgagactc ctcgatggaa aaatgtgaaa | 4500 |
| gtaaactttg ataatgtagg atttgggtat ctctctttgc ttcaagttgc cacattcaaa | 4560 |
| ggatggatgg atataatgta tgcagcagtt gattccagaa atgtggaact ccagcctaag | 4620 |
| tatgaagaaa gtctgtacat gtatctttac tttgttattt tcatcatctt ggtccttc | 4680 |
| ttcacccttga acctgtttat tggtgtcatc atagataatt caaccagca gaaaagaag | 4740 |
| tttggaggtc aagacatctt tatgacagaa gaacagaaga atactataa tgcaatgaaa | 4800 |
| aaattaggat cgaaaaaacc gcaaaagcct atacctcgac caggaaacaa atttcaagga | 4860 |
| atggtctttg acttcgtaac cagacaagtt tttgacataa gcatcatgat tctcatctgt | 4920 |
| cttaacatgg tcacaatgat ggtggaaaca gatgaccaga gtgaatatgt gactaccatt | 4980 |
| tgtcacgca tcaatctggt gttcattgtg ctatttactg gagagtgtgt actgaaactc | 5040 |
| atctctctac gccattatta ttttaccatt ggatggaata tttttgattt tgtggttgtc | 5100 |
| attctctcca ttgtaggtat gtttcttgcc gagctgatag aaaagtattt cgtgtcccct | 5160 |
| accctgttcc gagtgatccg tcttgctagg attggccgaa tcctacgtct gatcaaagga | 5220 |
| gcaaagggga tccgcacgct gctctttgct tgatgatgt cccttcctgc gttgtttaac | 5280 |
| atcggcctcc tactcttcct agtcatgttc atctacgcca tctttgggat gtccaacttt | 5340 |
| gcctatgtta agagggaagt tgggatcgat gacatgttca actttgagac ctttggcaac | 5400 |

```
agcatgatct gcctattcca aattacaacc tctgctggct gggatggatt gctagcaccc    5460
attctcaaca gtaagccacc cgactgtgac cctaataaag ttaaccctgg aagctcagtt    5520
aagggagact gtgggaaccc atctgttgga attttctttt ttgtcagtta catcatcata    5580
tccttcctgg ttgtggtgaa catgtacatc gcggtcatcc tggagaactt cagtgttgct    5640
actgaagaaa gtgcagagcc tctgagtgag gatgactttg agatgttcta tgaggtttgg    5700
gagaagtttg atcccgatgc aactcagttc atggaatttg aaaaattatc tcagtttgca    5760
gctgcgcttg aaccgcctct caatctgcca caaccaaaca aactccagct cattgccatg    5820
gatttgccca tggtgagtgg tgaccggatc cactgtcttg atatcttatt tgcttttaca    5880
aagcgggttc taggagagag tggagagatg gatgctctac gaatacagat ggaagagcga    5940
ttcatggctt ccaatccttc caaggtctcc tatcagccaa tcactactac tttaaaacga    6000
aaacaagagg aagtatctgc tgtcattatt cagcgtgctt acagacgcca ccttttaaag    6060
cgaactgtaa aacaagcttc ctttacgtac aataaaaaca aaatcaaagg tggggctaat    6120
cttcttataa aagaagacat gataattgac agaataaatg aaaactctat tacagaaaaa    6180
actgatctga ccatgtccac tgcagcttgt ccaccttcct atgaccgggt gacaaagcca    6240
attgtggaaa acatgagca agaaggcaaa gatgaaaaag ccaaagggaa ataaatgaaa    6300
ataaataaaa ataattgggt gacaaattgt ttacagcctg tgaaggtgat gtattttat     6360
caacaggact cctttaggag gtcaatgcca aactgactgt ttttacacaa atctccttaa    6420
ggtcagtgcc tacaataaga cagtgacccc ttgtcagcaa actgtgactc tgtgtaaagg    6480
ggagatgacc ttgacaggag gttactgttc tcactaccag ctgacactgc tgaagataag    6540
atgcacaatg gctagtcaga ctgtagggac cagtttcaag gggtgcaaac ctgtgatttt    6600
ggggttgttt aacatgaaac actttagtgt agtaattgta tccactgttt gcatttcaac    6660
tgccacattt gtcacatttt tatggaatct gttagtggat tcatcttttt gttaatccat    6720
gtgtttatta tatgtgacta tttttgtaaa cgaagtttct gttgagaaat aggctaagga    6780
cctctataac aggtatgcca cctgggggt atggcaacca catggccctc ccagctacac     6840
aaagtcgtgg tttgcatgag ggcatgctgc acttagagat catgcatgag aaaaagtcac    6900
aagaaaaaca aattcttaaa tttcaccata tttctgggag gggtaattgg gtgataagtg    6960
gaggtgcttt gttgatcttg ttttgcgaaa tccagcccct agaccaagta gattatttgt    7020
gggtaggcca gtaaatctta gcaggtgcaa acttcattca aatgtttgga gtcataaatg    7080
ttatgtttct ttttgttgta ttaaaaaaaa aacctgaata gtgaatattg cccctcaccc    7140
tccaccgcca gaagactgaa ttgaccaaaa ttactctttta taaatttctg cttttttcctg   7200
cactttgttt agccatcttc ggctctcagc aaggttgaca ctgtatatgt taatgaaatg    7260
ctatttatta tgtaaatagt cattttaccc tgtggtgcac gtttgagcaa acaaataatg    7320
acctaagcac agtatttatt gcatcaaata tgtaccacaa gaaatgtaga gtgcaagctt    7380
tacacaggta ataaaatgta ttctgtacca tttatagata gtttggatgc tatcaatgca    7440
tgtttatatt accatgctgc tgtatctggt ttctctcact gctcagaatc tcatttatga    7500
gaaaccatat gtcagtggta aagtcaagga aattgttcaa cagatctcat ttatttaagt    7560
cattaagcaa tagtttgcag cacttttaaca gcttttttggt tattttttaca ttttaagtgg   7620
ataacatatg gtatatagcc agactgtaca gacatgttta aaaaaacaca ctgcttaacc    7680
tattaaaatat gtgtttagaa ttttataagc aaatataaat actgtaaaaa gtcactttat    7740
tttatttttc agcattatgt acataaatat gaagaggaaa ttatcttcag gttgatatca    7800
```

```
caatcacttt tcttactttc tgtccatagt acttttcat gaaagaaatt tgctaaataa    7860
gacatgaaaa caagactggg tagttgtaga tttctgcttt ttaaattaca tttgctaatt    7920
ttagattatt tcacaatttt aaggagcaaa ataggttcac gattcatatc caaattatgc    7980
tttgcaattg gaaaagggtt taaaatttta tttatatttc tggtagtacc tgcactaact    8040
gaattgaagg tagtgcttat gttattttg ttctttttt ctgacttcgg tttatgtttt    8100
catttctttg gagtaatgct gctctagttg ttctaaatag aatgtgggct tcataatttt    8160
tttttccaca aaaacagagt agtcaactta tatagtcaat tacatcagga cattttgtgt    8220
ttcttacaga agcaaaccat aggctcctct tttccttaaa actacttaga taaactgtat    8280
tcgtgaactg catgctggaa aatgctacta ttatgctaaa taatgctaac caacatttaa    8340
aatgtgcaaa actaataaag attacatttt ttatttta                           8378

<210> SEQ ID NO 2
<211> LENGTH: 8378
<212> TYPE: DNA
<213> ORGANISM: Homo sapiens

<400> SEQUENCE: 2
tactgcagag gtctctggtg catgtgtgta tgtgtgcgtt tgtgtgtgtt tgtgtgtctg      60
tgtgttctgc cccagtgaga ctgcagcccct tgtaaatact ttgacacctt ttgcaagaag     120
gaatctgaac aattgcaact gaaggcacat tgttatcatc tcgtctttgg gtgatgctgt     180
tcctcactgc agatggataa ttttcctttt aatcaggaat tcatatgca gaataaatgg      240
taattaaaat gtgcaggatg acaagatgga gcaaacagtg cttgtaccac caggacctga     300
cagcttcaac ttcttcacca gagaatctct tgcggctatt gaaagacgca ttgcagaaga     360
aaaggcaaag aatcccaaac cagacaaaaa agatgacgac gaaaatggcc caaagccaaa     420
tagtgacttg gaagctggaa agaaccttcc atttatttat ggagacattc ctccagagat     480
ggtgtcagag cccctggagg acctggaccc ctactatatc aataagaaaa cttttatagt     540
attgaataaa gggaaggcca tcttccggtt cagtgccacc tctgccctgt acattttaac     600
tccccttcaat cctcttagga aaatagctat taagatttg gtacattcat tattcagcat     660
gctaattatg tgcactattt tgacaaactg tgtgtttatg acaatgagta accctcctga     720
ttggacaaag aatgtagaat acaccttcac aggaatatat acttttgaat cacttataaa     780
aattattgca aggggattct gtttagaaga ttttactttc cttcgggatc catggaactg     840
gctcgatttc actgtcatta catttgcgtt tgtaacagaa tttgtaaacc taggcaattt     900
ttcagctctt cgcactttca gagtcttgag agctttgaaa actatttcgg taattccagg     960
cctgaaaacc attgtgggag ccctgatcca gtctgtgaag aagctctcag atgtaatgat    1020
cctgactgtg ttctgtctga gcgtatttgc tctaattggg ctgcagctgt tcatgggcaa    1080
cctgaggaat aaatgtatac aatggcctcc caccaatgct tccttggagg aacatagtat    1140
agaaaagaat ataactgtga attataatgg tacacttata aatgaaactg tctttgagtt    1200
tgactggaag tcatatattc aagattcaag atatcattat ttcctggagg gttttttaga    1260
tgcactacta tgtggaaata gctctgatgc aggccaatgt ccagagggat atatgtgtgt    1320
gaaagctgga agaaatccca attatggcta cacaagcttt gataccttca gttgggcttt    1380
tttgtccttg tttcgactaa tgactcagga cttctgggaa aatctttatc aactgacatt    1440
acgtgctgct gggaaaacgt acatgatatt ttttgtattg gtcattttct tgggctcatt    1500
ctacctaata aatttgatcc tggctgtggt ggccatggcc tacgaggaac agaatcaggc    1560
```

```
caccttggaa gaagcagaac agaaagaggc cgaatttcag cagatgattg aacagcttaa   1620
aaagcaacag gaggcagctc agcaggcagc aacggcaact gcctcagaac attccagaga   1680
gcccagtgca gcaggcaggc tctcagacag ctcatctgaa gcctctaagt tgagttccaa   1740
gagtgctaag gaaagaagaa atcggaggaa gaaaagaaaa cagaaagagc agtctggtgg   1800
ggaagagaaa gatgaggatg aattccaaaa atctgaatct gaggacagca tcaggaggaa   1860
aggttttcgc ttctccattg aagggaaccg attgacatat gaaaagaggt actcctcccc   1920
acaccagtct tgttgagca tccgtggctc cctattttca ccaaggcgaa atagcagaac   1980
aagccttttc agctttagag ggcgagcaaa ggatgtggga tctgagaacg acttcgcaga   2040
tgatgagcca gcacctttga ggataacgag agccgtagag attccttgtt tgtgccccga   2100
cgacacggag agagacgcaa cagcaacctg agtcagacca gtaggtcatc ccggatgctg   2160
gcagtgtttc cagcgaatgg gaagatgcac agcactgtgg attgcaatgg tgtggtttcc   2220
ttggttggtg gaccttcagt tcctacatcg cctgttggac agcttctgcc agaggtgata   2280
atagataagc cagctactga tgacaatcg acaaccactg aaactgaaat gagaaagaga   2340
aggtcaagtt ctttccacgt ttccatggac tttctagaag atccttccca aaggcaacga   2400
gcaatgagta tagccagcat tctaacaaat acagtagaag aacttgaaga atccaggcag   2460
aaatgcccac cctgttggta taaattttcc aacatattct taatctggga ctgttctcca   2520
tattggttaa aagtgaaaca tgttgtcaac ctggttgtga tggacccatt tgttgacctg   2580
gccatcacca tctgtattgt cttaaatact cttttcatgg ccatggagca ctatccaatg   2640
acggaccatt tcaataatgt gcttacagta ggaaacttgg ttttcactgg gatctttaca   2700
gcagaaatgt ttctgaaaat tattgccatg gatccttact attatttcca agaaggctgg   2760
aatatctttg acggttttat tgtgacgctt agcctggtag aacttggact cgccaatgtg   2820
gaaggattat ctgttctccg ttcatttcga ttgctgcgag ttttcaagtt ggcaaaatct   2880
tggccaacgt taaatatgct aataaagatc atcggcaatt ccgtgggggc tctgggaaat   2940
ttaaccctcg tcttggccat catcgtcttc attttgccg tggtcggcat gcagctcttt   3000
ggtaaaagct acaaagattg tgtctgcaag atcgccagtg attgtcaact cccacgctgg   3060
cacatgaatg acttcttcca ctccttcctg attgtgttcc gcgtgctgtg tggggagtgg   3120
atagagacca tgtgggactg tatggaggtt gctggtcaag ccatgtgcct tactgtcttc   3180
atgatggtca tggtgattgg aaacctagtg gtcctgaatc tctttctggc cttgcttctg   3240
agctcattta gtgcagacaa ccttgcagcc actgatgatg ataatgaaat gaataatctc   3300
caaattgctg tggataggat gcacaaagga gtagcttatg tgaaaagaaa aatatatgaa   3360
tttattcaac agtccttcat taggaaacaa aagattttag atgaaattaa accacttgat   3420
gatctaaaca caagaaaga cagttgtatg tccaatcata cagcagaaat tgggaaagat   3480
cttgactatc ttaaagatgt aaatggaact acaagtggta taggaactgg cagcagtgtt   3540
gaaaaataca ttattgatga aagtgattac atgtcattca taaacaaccc cagtcttact   3600
gtgactgtac caattgctgt aggagaatct gactttgaaa atttaaacac ggaagacttt   3660
agtagtgaat cggatctgga agaaagcaaa gagaaactga atgaaagcag tagctcatca   3720
gaaggtagca ctgtggacat cggcgcacct gtagaagaac agcccgtagt ggaacctgaa   3780
gaaactcttg aaccagaagc ttgtttcact gaaggctgtg tacaaagatt caagtgttgt   3840
caaatcaatg tggaagaagg cagaggaaaa caatggtgga acctgagaag gacgtgtttc   3900
cgaatagttg aacataactg gtttgagacc ttcattgttt tcatgattct ccttagtagt   3960
```

```
ggtgctctgg catttgaaga tatatatatt gatcagcgaa agacgattaa gacgatgttg    4020
gaatatgctg acaaggtttt cacttacatt ttcattctgg aaatgcttct aaaatgggtg    4080
gcatatggct atcaaaatat ttcaccaatg cctggtgttg gctggacttc ttaattgttg    4140
atgtttcatt ggtcagttta acagcaaatg ccttgggtta ctcagaactt ggagccatca    4200
aatctctcag gacactaaga gctctgagac ctctaagagc cttatctcga tttgaaggga    4260
tgagggtggt tgtgaatgcc cttttaggag caattccatc catcatgaat gtgcttctgg    4320
tttgtcttat attctggcta attttcagca tcatgggcgt aaatttgttt gctggcaaat    4380
tctaccactg tattaacacc acaactggtg acaggtttga catcgaagac gtgaataatc    4440
atactgattg cctaaaacta atagaaagaa atgagactgc tcgatggaaa aatgtgaaag    4500
taaactttga taatgtagga tttgggtatc tctctttgct tcaagttgcc acattcaaag    4560
gatggatgga tataatgtat gcagcagttg attccagaaa tgtggaactc cagcctaagt    4620
atgaagaaag tctgtacatg tatctttact ttgttatttt catcatcttt gggtccttct    4680
tcaccttgaa cctgttattt ggtgtcatca tagataattt caaccagcag aaaaagaagt    4740
ttggaggtca agacatcttt atgacagaag aacagaagaa atactataat gcaatgaaaa    4800
aattaggatc gaaaaaaccg caaaagccta tacctcgacc aggaaacaaa tttcaaggaa    4860
tggtctttga cttcgtaacc agacaagttt ttgacataag catcatgatt ctcatctgtc    4920
ttaacatggt cacaatgatg gtggaaacag atgaccagag tgaatatgtg actaccattt    4980
tgtcacgcat caatctggtg ttcattgtgc tatttactgg agagtgtgta ctgaaactca    5040
tctctctacg ccattattat tttaccattg gatggaatat ttttgatttt gtggttgtca    5100
ttctctccat tgtaggtatg tttcttgccg agctgataga aaagtatttc gtgtccccta    5160
ccctgttccg agtgatccgt cttgctagga ttggccgaat cctacgtctg atcaaaggag    5220
caaaggggat ccgcacgctg ctcttttgctt tgatgatgtc ccttcctgcg ttgtttaaca    5280
tcggcctcct actcttccta gtcatgttca tctacgccat ctttgggatg tccaactttg    5340
cctatgttaa gagggaagtt gggatcgatg acatgttcaa ctttgagacc tttggcaaca    5400
gcatgatctg cctattccaa attacaacct ctgctggctg ggatggattg ctagcaccca    5460
ttctcaacag taagccaccc gactgtgacc ctaataaagt taaccctgga agctcagtta    5520
agggagactg tgggaaccca tctgttggaa ttttctttttt tgtcagttac atcatcatat    5580
ccttcctggt tgtggtgaac atgtacatcg cggtcatcct ggagaacttc agtgttgcta    5640
ctgaagaaag tgcagagcct ctgagtgagg atgactttga tgttctat gaggtttggg    5700 agaagtttga tcccgatgca actcagttca tggaatttga aaaattatct cagtttgcag    5760
ctgcgcttga accgcctctc aatctgccac aaccaaacaa actccagctc attgccatgg    5820
atttgcccat ggtgagtggt gaccggatcc actgtcttga tatcttattt gcttttacaa    5880
agcgggttct aggagagagt ggagagatgg atgctctacg aatacagatg gaagagcgat    5940
tcatggcttc caatccttcc aaggtctcct atcagccaat cactactact ttaaaacgaa    6000
aacaaggaga agtatctgct gtcattattc agcgtgctta cagacgccac cttttaaagc    6060
gaactgtaaa acaagcttcc tttacgtaca ataaaaacaa aatcaaaggt ggggctaatc    6120
ttcttataaa agaagacatg ataattgaca gaataaatga aaactctatt acagaaaaaa    6180
ctgatctgac catgtccact gcagcttgtc caccttccta tgaccgggtg acaaagccaa    6240
ttgtggaaaa acatgagcaa gaaggcaaag atgaaaagc caagggaaa taatgaaaa    6300 taaataaaaa taattgggtg acaaattgtt tacagcctgt gaaggtgatg tatttttatc    6360
```

```
aacaggactc ctttaggagg tcaatgccaa actgactgtt tttacacaaa tctccttaag    6420
gtcagtgcct acaataagac agtgacccct tgtcagcaaa ctgtgactct gtgtaaaggg    6480
gagatgacct tgacaggagg ttactgttct cactaccagc tgacactgct gaagataaga    6540
tgcacaatgg ctagtcagac tgtagggacc agtttcaagg ggtgcaaacc tgtgattttg    6600
gggttgttta acatgaaaca ctttagtgta gtaattgtat ccactgtttg catttcaact    6660
gccacatttg tcacattttt atggaatctg ttagtggatt catcttttg ttaatccatg     6720 tgtttattat atgtgactat ttttgtaaac gaagtttctg ttgagaaata ggctaaggac    6780
ctctataaca ggtatgccac ctgggggta tggcaaccac atggccctcc cagctacaca     6840
aagtcgtggt ttgcatgagg gcatgctgca cttagagatc atgcatgaga aaaagtcaca    6900
agaaaaacaa attcttaaat ttcaccatat ttctgggagg ggtaattggg tgataagtgg    6960
aggtgctttg ttgatcttgt tttgcgaaat ccagccccta gaccaagtag attatttgtg    7020
ggtaggccag taaatcttag caggtgcaaa cttcattcaa atgtttggag tcataaatgt    7080
tatgtttctt tttgttgtat taaaaaaaaa acctgaatag tgaatattgc ccctcaccct    7140
ccaccgccag aagactgaat tgaccaaaat tactctttat aaatttctgc ttttttcctgc   7200 actttgttta gccatcttcg gctctcagca aggttgacac tgtatatgtt aatgaaatgc    7260
tatttattat gtaaatagtc attttacccct gtggtgcacg tttgagcaaa caaataatga   7320
cctaagcaca gtatttattg catcaaatat gtaccacaag aaatgtagag tgcaagcttt    7380
acacaggtaa taaatgtat tctgtaccat ttatagatag tttggatgct atcaatgcat     7440
gtttatatta ccatgctgct gtatctggtt tctctcactg ctcagaatct catttatgag    7500
aaaccatatg tcagtggtaa agtcaaggaa attgttcaac agatctcatt tatttaagtc    7560
attaagcaat agtttgcagc actttaacag ctttttggtt attttttacat tttaagtgga   7620 taacatatgg tatatagcca gactgtacag acatgtttaa aaaaacacac tgcttaacct    7680
attaaatatg tgtttagaat tttataagca aatataaata ctgtaaaaag tcactttatt    7740
ttatttttca gcattatgta cataaatatg aagaggaaat tatcttcagg ttgatatcac    7800
aatcactttt cttactttct gtccatagta ctttttcatg aaagaaattt gctaaataag    7860
acatgaaaac aagactgggt agttgtagat ttctgctttt taaattacat ttgctaattt    7920
tagattattt cacaattta aggagcaaaa taggttcacg attcatatcc aaattatgct     7980
ttgcaattgg aaaagggttt aaaattttat ttatatttct ggtagtacct gcactaactg    8040
aattgaaggt agtgcttatg ttattttgt tctttttttc tgacttcggt ttatgttttc     8100
atttctttgg agtaatgctg ctctagattg ttctaaatag aatgtgggct tcataatttt    8160
tttttccaca aaaacagagt agtcaactta tatagtcaat tacatcagga cattttgtgt    8220
ttcttacaga agcaaaccat aggctcctct tttccttaaa actacttaga taaactgtat    8280
tcgtgaactg catgctggaa aatgctacta ttatgctaaa taatgctaac caacatttaa    8340
aatgtgcaaa actaataaag attacatttt ttatttta                            8378
```

<210> SEQ ID NO 3
<211> LENGTH: 2009
<212> TYPE: PRT
<213> ORGANISM: Homo sapiens

<400> SEQUENCE: 3

Met Glu Gln Thr Val Leu Val Pro Pro Gly Pro Asp Ser Phe Asn Phe
1               5                   10                  15

Phe Thr Arg Glu Ser Leu Ala Ala Ile Glu Arg Arg Ile Ala Glu Glu

```
                20                  25                  30
Lys Ala Lys Asn Pro Lys Pro Asp Lys Asp Asp Glu Asn Gly
            35                  40                  45
Pro Lys Pro Asn Ser Asp Leu Glu Ala Gly Lys Asn Leu Pro Phe Ile
        50                  55                  60
Tyr Gly Asp Ile Pro Pro Glu Met Val Ser Glu Pro Leu Glu Asp Leu
65                  70                  75                  80
Asp Pro Tyr Tyr Ile Asn Lys Lys Thr Phe Ile Val Leu Asn Lys Gly
                85                  90                  95
Lys Ala Ile Phe Arg Phe Ser Ala Thr Ser Ala Leu Tyr Ile Leu Thr
            100                 105                 110
Pro Phe Asn Pro Leu Arg Lys Ile Ala Ile Lys Ile Leu Val His Ser
            115                 120                 125
Leu Phe Ser Met Leu Ile Met Cys Thr Ile Leu Thr Asn Cys Val Phe
        130                 135                 140
Met Thr Met Ser Asn Pro Pro Asp Trp Thr Lys Asn Val Glu Tyr Thr
145                 150                 155                 160
Phe Thr Gly Ile Tyr Thr Phe Glu Ser Leu Ile Lys Ile Ile Ala Arg
                165                 170                 175
Gly Phe Cys Leu Glu Asp Phe Thr Phe Leu Arg Asp Pro Trp Asn Trp
            180                 185                 190
Leu Asp Phe Thr Val Ile Thr Phe Ala Tyr Val Thr Glu Phe Val Asp
            195                 200                 205
Leu Gly Asn Val Ser Ala Leu Arg Thr Phe Arg Val Leu Arg Ala Leu
            210                 215                 220
Lys Thr Ile Ser Val Ile Pro Gly Leu Lys Thr Ile Val Gly Ala Leu
225                 230                 235                 240
Ile Gln Ser Val Lys Lys Leu Ser Asp Val Met Ile Leu Thr Val Phe
                245                 250                 255
Cys Leu Ser Val Phe Ala Leu Ile Gly Leu Gln Leu Phe Met Gly Asn
            260                 265                 270
Leu Arg Asn Lys Cys Ile Gln Trp Pro Pro Thr Asn Ala Ser Leu Glu
            275                 280                 285
Glu His Ser Ile Glu Lys Asn Ile Thr Val Asn Tyr Asn Gly Thr Leu
            290                 295                 300
Ile Asn Glu Thr Val Phe Glu Phe Asp Trp Lys Ser Tyr Ile Gln Asp
305                 310                 315                 320
Ser Arg Tyr His Tyr Phe Leu Glu Gly Phe Leu Asp Ala Leu Leu Cys
                325                 330                 335
Gly Asn Ser Ser Asp Ala Gly Gln Cys Pro Glu Gly Tyr Met Cys Val
            340                 345                 350
Lys Ala Gly Arg Asn Pro Asn Tyr Gly Tyr Thr Ser Phe Asp Thr Phe
            355                 360                 365
Ser Trp Ala Phe Leu Ser Leu Phe Arg Leu Met Thr Gln Asp Phe Trp
            370                 375                 380
Glu Asn Leu Tyr Gln Leu Thr Leu Arg Ala Ala Gly Lys Thr Tyr Met
385                 390                 395                 400
Ile Phe Phe Val Leu Val Ile Phe Leu Gly Ser Phe Tyr Leu Ile Asn
                405                 410                 415
Leu Ile Leu Ala Val Val Ala Met Ala Tyr Glu Glu Gln Asn Gln Ala
            420                 425                 430
Thr Leu Glu Glu Ala Glu Gln Lys Glu Ala Glu Phe Gln Gln Met Ile
            435                 440                 445
```

-continued

```
Glu Gln Leu Lys Lys Gln Gln Glu Ala Ala Gln Gln Ala Ala Thr Ala
            450                 455                 460

Thr Ala Ser Glu His Ser Arg Glu Pro Ser Ala Ala Gly Arg Leu Ser
465                 470                 475                 480

Asp Ser Ser Glu Ala Ser Lys Leu Ser Ser Lys Ser Ala Lys Glu
                485                 490                 495

Arg Arg Asn Arg Arg Lys Lys Arg Lys Gln Lys Glu Gln Ser Gly Gly
                500                 505                 510

Glu Glu Lys Asp Glu Asp Glu Phe Gln Lys Ser Glu Ser Glu Asp Ser
            515                 520                 525

Ile Arg Arg Lys Gly Phe Arg Phe Ser Ile Glu Gly Asn Arg Leu Thr
530                 535                 540

Tyr Glu Lys Arg Tyr Ser Ser Pro His Gln Ser Leu Leu Ser Ile Arg
545                 550                 555                 560

Gly Ser Leu Phe Ser Pro Arg Arg Asn Ser Arg Thr Ser Leu Phe Ser
                565                 570                 575

Phe Arg Gly Arg Ala Lys Asp Val Gly Ser Glu Asn Asp Phe Ala Asp
                580                 585                 590

Asp Glu His Ser Thr Phe Glu Asp Asn Glu Ser Arg Arg Asp Ser Leu
            595                 600                 605

Phe Val Pro Arg Arg His Gly Glu Arg Arg Asn Ser Asn Leu Ser Gln
610                 615                 620

Thr Ser Arg Ser Ser Arg Met Leu Ala Val Phe Pro Ala Asn Gly Lys
625                 630                 635                 640

Met His Ser Thr Val Asp Cys Asn Gly Val Val Ser Leu Val Gly Gly
                645                 650                 655

Pro Ser Val Pro Thr Ser Pro Val Gly Gln Leu Leu Pro Glu Val Ile
                660                 665                 670

Ile Asp Lys Pro Ala Thr Asp Asp Asn Gly Thr Thr Thr Glu Thr Glu
            675                 680                 685

Met Arg Lys Arg Arg Ser Ser Ser Phe His Val Ser Met Asp Phe Leu
690                 695                 700

Glu Asp Pro Ser Gln Arg Gln Arg Ala Met Ser Ile Ala Ser Ile Leu
705                 710                 715                 720

Thr Asn Thr Val Glu Glu Leu Glu Glu Ser Arg Gln Lys Cys Pro Pro
                725                 730                 735

Cys Trp Tyr Lys Phe Ser Asn Ile Phe Leu Ile Trp Asp Cys Ser Pro
                740                 745                 750

Tyr Trp Leu Lys Val Lys His Val Asn Leu Val Val Met Asp Pro
            755                 760                 765

Phe Val Asp Leu Ala Ile Thr Ile Cys Ile Val Leu Asn Thr Leu Phe
770                 775                 780

Met Ala Met Glu His Tyr Pro Met Thr Asp His Phe Asn Asn Val Leu
785                 790                 795                 800

Thr Val Gly Asn Leu Val Phe Thr Gly Ile Phe Thr Ala Glu Met Phe
                805                 810                 815

Leu Lys Ile Ile Ala Met Asp Pro Tyr Tyr Tyr Phe Gln Glu Gly Trp
                820                 825                 830

Asn Ile Phe Asp Gly Phe Ile Val Thr Leu Ser Leu Val Glu Leu Gly
            835                 840                 845

Leu Ala Asn Val Glu Gly Leu Ser Val Leu Arg Ser Phe Arg Leu Leu
            850                 855                 860

Arg Val Phe Lys Leu Ala Lys Ser Trp Pro Thr Leu Asn Met Leu Ile
865                 870                 875                 880
```

-continued

```
Lys Ile Ile Gly Asn Ser Val Gly Ala Leu Gly Asn Leu Thr Leu Val
            885                 890                 895
Leu Ala Ile Ile Val Phe Ile Phe Ala Val Val Gly Met Gln Leu Phe
            900                 905                 910
Gly Lys Ser Tyr Lys Asp Cys Val Cys Lys Ile Ala Ser Asp Cys Gln
            915                 920                 925
Leu Pro Arg Trp His Met Asn Asp Phe Phe His Ser Phe Leu Ile Val
            930                 935                 940
Phe Arg Val Leu Cys Gly Glu Trp Ile Glu Thr Met Trp Asp Cys Met
945                 950                 955                 960
Glu Val Ala Gly Gln Ala Met Cys Leu Thr Val Phe Met Met Val Met
            965                 970                 975
Val Ile Gly Asn Leu Val Val Leu Asn Leu Phe Leu Ala Leu Leu Leu
            980                 985                 990
Ser Ser Phe Ser Ala Asp Asn Leu Ala Ala Thr Asp Asp Asp Asn Glu
            995                1000                1005
Met Asn Asn Leu Gln Ile Ala Val Asp Arg Met His Lys Gly Val
           1010                1015                1020
Ala Tyr Val Lys Arg Lys Ile Tyr Glu Phe Ile Gln Gln Ser Phe
           1025                1030                1035
Ile Arg Lys Gln Lys Ile Leu Asp Glu Ile Lys Pro Leu Asp Asp
           1040                1045                1050
Leu Asn Asn Lys Lys Asp Ser Cys Met Ser Asn His Thr Ala Glu
           1055                1060                1065
Ile Gly Lys Asp Leu Asp Tyr Leu Lys Asp Val Asn Gly Thr Thr
           1070                1075                1080
Ser Gly Ile Gly Thr Gly Ser Ser Val Glu Lys Tyr Ile Ile Asp
           1085                1090                1095
Glu Ser Asp Tyr Met Ser Phe Ile Asn Asn Pro Ser Leu Thr Val
           1100                1105                1110
Thr Val Pro Ile Ala Val Gly Glu Ser Asp Phe Glu Asn Leu Asn
           1115                1120                1125
Thr Glu Asp Phe Ser Ser Glu Ser Asp Leu Glu Glu Ser Lys Glu
           1130                1135                1140
Lys Leu Asn Glu Ser Ser Ser Ser Ser Glu Gly Ser Thr Val Asp
           1145                1150                1155
Ile Gly Ala Pro Val Glu Glu Gln Pro Val Val Glu Pro Glu Glu
           1160                1165                1170
Thr Leu Glu Pro Glu Ala Cys Phe Thr Glu Gly Cys Val Gln Arg
           1175                1180                1185
Phe Lys Cys Cys Gln Ile Asn Val Glu Glu Gly Arg Gly Lys Gln
           1190                1195                1200
Trp Trp Asn Leu Arg Arg Thr Cys Phe Arg Ile Val Glu His Asn
           1205                1210                1215
Trp Phe Glu Thr Phe Ile Val Phe Met Ile Leu Leu Ser Ser Gly
           1220                1225                1230
Ala Leu Ala Phe Glu Asp Ile Tyr Ile Asp Gln Arg Lys Thr Ile
           1235                1240                1245
Lys Thr Met Leu Glu Tyr Ala Asp Lys Val Phe Thr Tyr Ile Phe
           1250                1255                1260
Ile Leu Glu Met Leu Leu Lys Trp Val Ala Tyr Gly Tyr Gln Thr
           1265                1270                1275
Tyr Phe Thr Asn Ala Trp Cys Trp Leu Asp Phe Leu Ile Val Asp
```

-continued

```
            1280                1285                1290

Val Ser Leu Val Ser Leu Thr Ala Asn Ala Leu Gly Tyr Ser Glu
    1295                1300                1305

Leu Gly Ala Ile Lys Ser Leu Arg Thr Leu Arg Ala Leu Arg Pro
    1310                1315                1320

Leu Arg Ala Leu Ser Arg Phe Glu Gly Met Arg Val Val Val Asn
    1325                1330                1335

Ala Leu Leu Gly Ala Ile Pro Ser Ile Met Asn Val Leu Leu Val
    1340                1345                1350

Cys Leu Ile Phe Trp Leu Ile Phe Ser Ile Met Gly Val Asn Leu
    1355                1360                1365

Phe Ala Gly Lys Phe Tyr His Cys Ile Asn Thr Thr Thr Gly Asp
    1370                1375                1380

Arg Phe Asp Ile Glu Asp Val Asn Asn His Thr Asp Cys Leu Lys
    1385                1390                1395

Leu Ile Glu Arg Asn Glu Thr Ala Arg Trp Lys Asn Val Lys Val
    1400                1405                1410

Asn Phe Asp Asn Val Gly Phe Gly Tyr Leu Ser Leu Leu Gln Val
    1415                1420                1425

Ala Thr Phe Lys Gly Trp Met Asp Ile Met Tyr Ala Ala Val Asp
    1430                1435                1440

Ser Arg Asn Val Glu Leu Gln Pro Lys Tyr Glu Glu Ser Leu Tyr
    1445                1450                1455

Met Tyr Leu Tyr Phe Val Ile Phe Ile Ile Phe Gly Ser Phe Phe
    1460                1465                1470

Thr Leu Asn Leu Phe Ile Gly Val Ile Ile Asp Asn Phe Asn Gln
    1475                1480                1485

Gln Lys Lys Lys Phe Gly Gly Gln Asp Ile Phe Met Thr Glu Glu
    1490                1495                1500

Gln Lys Lys Tyr Tyr Asn Ala Met Lys Lys Leu Gly Ser Lys Lys
    1505                1510                1515

Pro Gln Lys Pro Ile Pro Arg Pro Gly Asn Lys Phe Gln Gly Met
    1520                1525                1530

Val Phe Asp Phe Val Thr Arg Gln Val Phe Asp Ile Ser Ile Met
    1535                1540                1545

Ile Leu Ile Cys Leu Asn Met Val Thr Met Met Val Glu Thr Asp
    1550                1555                1560

Asp Gln Ser Glu Tyr Val Thr Thr Ile Leu Ser Arg Ile Asn Leu
    1565                1570                1575

Val Phe Ile Val Leu Phe Thr Gly Glu Cys Val Leu Lys Leu Ile
    1580                1585                1590

Ser Leu Arg His Tyr Tyr Phe Thr Ile Gly Trp Asn Ile Phe Asp
    1595                1600                1605

Phe Val Val Val Ile Leu Ser Ile Val Gly Met Phe Leu Ala Glu
    1610                1615                1620

Leu Ile Glu Lys Tyr Phe Val Ser Pro Thr Leu Phe Arg Val Ile
    1625                1630                1635

Arg Leu Ala Arg Ile Gly Arg Ile Leu Arg Leu Ile Lys Gly Ala
    1640                1645                1650

Lys Gly Ile Arg Thr Leu Leu Phe Ala Leu Met Met Ser Leu Pro
    1655                1660                1665

Ala Leu Phe Asn Ile Gly Leu Leu Leu Phe Leu Val Met Phe Ile
    1670                1675                1680
```

```
Tyr Ala Ile Phe Gly Met Ser Asn Phe Ala Tyr Val Lys Arg Glu
    1685            1690                1695

Val Gly Ile Asp Asp Met Phe Asn Phe Glu Thr Phe Gly Asn Ser
    1700            1705                1710

Met Ile Cys Leu Phe Gln Ile Thr Thr Ser Ala Gly Trp Asp Gly
    1715            1720                1725

Leu Leu Ala Pro Ile Leu Asn Ser Lys Pro Pro Asp Cys Asp Pro
    1730            1735                1740

Asn Lys Val Asn Pro Gly Ser Ser Val Lys Gly Asp Cys Gly Asn
    1745            1750                1755

Pro Ser Val Gly Ile Phe Phe Phe Val Ser Tyr Ile Ile Ile Ser
    1760            1765                1770

Phe Leu Val Val Val Asn Met Tyr Ile Ala Val Ile Leu Glu Asn
    1775            1780                1785

Phe Ser Val Ala Thr Glu Glu Ser Ala Glu Pro Leu Ser Glu Asp
    1790            1795                1800

Asp Phe Glu Met Phe Tyr Glu Val Trp Glu Lys Phe Asp Pro Asp
    1805            1810                1815

Ala Thr Gln Phe Met Glu Phe Glu Lys Leu Ser Gln Phe Ala Ala
    1820            1825                1830

Ala Leu Glu Pro Pro Leu Asn Leu Pro Gln Pro Asn Lys Leu Gln
    1835            1840                1845

Leu Ile Ala Met Asp Leu Pro Met Val Ser Gly Asp Arg Ile His
    1850            1855                1860

Cys Leu Asp Ile Leu Phe Ala Phe Thr Lys Arg Val Leu Gly Glu
    1865            1870                1875

Ser Gly Glu Met Asp Ala Leu Arg Ile Gln Met Glu Glu Arg Phe
    1880            1885                1890

Met Ala Ser Asn Pro Ser Lys Val Ser Tyr Gln Pro Ile Thr Thr
    1895            1900                1905

Thr Leu Lys Arg Lys Gln Glu Glu Val Ser Ala Val Ile Ile Gln
    1910            1915                1920

Arg Ala Tyr Arg Arg His Leu Leu Lys Arg Thr Val Lys Gln Ala
    1925            1930                1935

Ser Phe Thr Tyr Asn Lys Asn Lys Ile Lys Gly Gly Ala Asn Leu
    1940            1945                1950

Leu Ile Lys Glu Asp Met Ile Ile Asp Arg Ile Asn Glu Asn Ser
    1955            1960                1965

Ile Thr Glu Lys Thr Asp Leu Thr Met Ser Thr Ala Ala Cys Pro
    1970            1975                1980

Pro Ser Tyr Asp Arg Val Thr Lys Pro Ile Val Glu Lys His Glu
    1985            1990                1995

Gln Glu Gly Lys Asp Glu Lys Ala Lys Gly Lys
    2000            2005

<210> SEQ ID NO 4
<211> LENGTH: 2009
<212> TYPE: PRT
<213> ORGANISM: Homo sapiens

<400> SEQUENCE: 4

Met Glu Gln Thr Val Leu Val Pro Pro Gly Pro Asp Ser Phe Asn Phe
1               5                   10                  15

Phe Thr Arg Glu Ser Leu Ala Ala Ile Glu Arg Arg Ile Ala Glu Glu
                20                  25                  30
```

-continued

Lys Ala Lys Asn Pro Lys Pro Asp Lys Asp Asp Glu Asn Gly
         35                  40                  45

Pro Lys Pro Asn Ser Asp Leu Glu Ala Gly Lys Asn Leu Pro Phe Ile
 50                  55                  60

Tyr Gly Asp Ile Pro Pro Glu Met Val Ser Glu Pro Leu Glu Asp Leu
 65                  70                  75                  80

Asp Pro Tyr Tyr Ile Asn Lys Lys Thr Phe Ile Val Leu Asn Lys Gly
                 85                  90                  95

Lys Ala Ile Phe Arg Phe Ser Ala Thr Ser Ala Leu Tyr Ile Leu Thr
                100                 105                 110

Pro Phe Asn Pro Leu Arg Lys Ile Ala Ile Lys Ile Leu Val His Ser
                115                 120                 125

Leu Phe Ser Met Leu Ile Met Cys Thr Ile Leu Thr Asn Cys Val Phe
130                 135                 140

Met Thr Met Ser Asn Pro Pro Asp Trp Thr Lys Asn Val Glu Tyr Thr
145                 150                 155                 160

Phe Thr Gly Ile Tyr Thr Phe Glu Ser Leu Ile Lys Ile Ile Ala Arg
                165                 170                 175

Gly Phe Cys Leu Glu Asp Phe Thr Phe Leu Arg Asp Pro Trp Asn Trp
                180                 185                 190

Leu Asp Phe Thr Val Ile Thr Phe Ala Phe Val Thr Glu Phe Val Asn
                195                 200                 205

Leu Gly Asn Phe Ser Ala Leu Arg Thr Phe Arg Val Leu Arg Ala Leu
210                 215                 220

Lys Thr Ile Ser Val Ile Pro Gly Leu Lys Thr Ile Val Gly Ala Leu
225                 230                 235                 240

Ile Gln Ser Val Lys Lys Leu Ser Asp Val Met Ile Leu Thr Val Phe
                245                 250                 255

Cys Leu Ser Val Phe Ala Leu Ile Gly Leu Gln Leu Phe Met Gly Asn
                260                 265                 270

Leu Arg Asn Lys Cys Ile Gln Trp Pro Pro Thr Asn Ala Ser Leu Glu
                275                 280                 285

Glu His Ser Ile Glu Lys Asn Ile Thr Val Asn Tyr Asn Gly Thr Leu
290                 295                 300

Ile Asn Glu Thr Val Phe Glu Phe Asp Trp Lys Ser Tyr Ile Gln Asp
305                 310                 315                 320

Ser Arg Tyr His Tyr Phe Leu Glu Gly Phe Leu Asp Ala Leu Leu Cys
                325                 330                 335

Gly Asn Ser Ser Asp Ala Gly Gln Cys Pro Glu Gly Tyr Met Cys Val
                340                 345                 350

Lys Ala Gly Arg Asn Pro Asn Tyr Gly Tyr Thr Ser Phe Asp Thr Phe
                355                 360                 365

Ser Trp Ala Phe Leu Ser Leu Phe Arg Leu Met Thr Gln Asp Phe Trp
370                 375                 380

Glu Asn Leu Tyr Gln Leu Thr Leu Arg Ala Ala Gly Lys Thr Tyr Met
385                 390                 395                 400

Ile Phe Phe Val Leu Val Ile Phe Leu Gly Ser Phe Tyr Leu Ile Asn
                405                 410                 415

Leu Ile Leu Ala Val Val Ala Met Ala Tyr Glu Glu Gln Asn Gln Ala
                420                 425                 430

Thr Leu Glu Glu Ala Glu Gln Lys Glu Ala Glu Phe Gln Gln Met Ile
                435                 440                 445

Glu Gln Leu Lys Lys Gln Gln Glu Ala Ala Gln Gln Ala Ala Thr Ala
450                 455                 460

```
Thr Ala Ser Glu His Ser Arg Glu Pro Ser Ala Ala Gly Arg Leu Ser
465                 470                 475                 480

Asp Ser Ser Ser Glu Ala Ser Lys Leu Ser Lys Ser Ala Lys Glu
                485                 490                 495

Arg Arg Asn Arg Arg Lys Lys Arg Gln Lys Glu Gln Ser Gly Gly
            500                 505                 510

Glu Glu Lys Asp Glu Asp Glu Phe Gln Lys Ser Glu Ser Glu Asp Ser
            515                 520                 525

Ile Arg Arg Lys Gly Phe Arg Phe Ser Ile Glu Gly Asn Arg Leu Thr
            530                 535                 540

Tyr Glu Lys Arg Tyr Ser Ser Pro His Gln Ser Leu Leu Ser Ile Arg
545                 550                 555                 560

Gly Ser Leu Phe Ser Pro Arg Arg Asn Ser Arg Thr Ser Leu Phe Ser
                565                 570                 575

Phe Arg Gly Arg Ala Lys Asp Val Gly Ser Glu Asn Asp Phe Ala Asp
            580                 585                 590

Asp Glu His Ser Thr Phe Glu Asp Asn Glu Ser Arg Arg Asp Ser Leu
            595                 600                 605

Phe Val Pro Arg Arg His Gly Glu Arg Arg Asn Ser Asn Leu Ser Gln
610                 615                 620

Thr Ser Arg Ser Ser Arg Met Leu Ala Val Phe Pro Ala Asn Gly Lys
625                 630                 635                 640

Met His Ser Thr Val Asp Cys Asn Gly Val Val Ser Leu Val Gly Gly
                645                 650                 655

Pro Ser Val Pro Thr Ser Pro Val Gly Gln Leu Leu Pro Glu Val Ile
            660                 665                 670

Ile Asp Lys Pro Ala Thr Asp Asp Asn Gly Thr Thr Thr Glu Thr Glu
            675                 680                 685

Met Arg Lys Arg Arg Ser Ser Ser Phe His Val Ser Met Asp Phe Leu
690                 695                 700

Glu Asp Pro Ser Gln Arg Gln Arg Ala Met Ser Ile Ala Ser Ile Leu
705                 710                 715                 720

Thr Asn Thr Val Glu Glu Leu Glu Glu Ser Arg Gln Lys Cys Pro Pro
                725                 730                 735

Cys Trp Tyr Lys Phe Ser Asn Ile Phe Leu Ile Trp Asp Cys Ser Pro
            740                 745                 750

Tyr Trp Leu Lys Val Lys His Val Val Asn Leu Val Val Met Asp Pro
            755                 760                 765

Phe Val Asp Leu Ala Ile Thr Ile Cys Ile Val Leu Asn Thr Leu Phe
770                 775                 780

Met Ala Met Glu His Tyr Pro Met Thr Asp His Phe Asn Asn Val Leu
785                 790                 795                 800

Thr Val Gly Asn Leu Val Phe Thr Gly Ile Phe Thr Ala Glu Met Phe
                805                 810                 815

Leu Lys Ile Ile Ala Met Asp Pro Tyr Tyr Tyr Phe Gln Glu Gly Trp
            820                 825                 830

Asn Ile Phe Asp Gly Phe Ile Val Thr Leu Ser Leu Val Glu Leu Gly
            835                 840                 845

Leu Ala Asn Val Glu Gly Leu Ser Val Leu Arg Ser Phe Arg Leu Leu
850                 855                 860

Arg Val Phe Lys Leu Ala Lys Ser Trp Pro Thr Leu Asn Met Leu Ile
865                 870                 875                 880

Lys Ile Ile Gly Asn Ser Val Gly Ala Leu Gly Asn Leu Thr Leu Val
```

```
                       885             890            895
Leu Ala Ile Ile Val Phe Ile Phe Ala Val Val Gly Met Gln Leu Phe
                900                  905                 910

Gly Lys Ser Tyr Lys Asp Cys Val Cys Lys Ile Ala Ser Asp Cys Gln
                915                  920                 925

Leu Pro Arg Trp His Met Asn Asp Phe Phe His Ser Phe Leu Ile Val
                930                  935                 940

Phe Arg Val Leu Cys Gly Glu Trp Ile Glu Thr Met Trp Asp Cys Met
945                  950                  955                 960

Glu Val Ala Gly Gln Ala Met Cys Leu Thr Val Phe Met Met Val Met
                965                  970                 975

Val Ile Gly Asn Leu Val Val Leu Asn Leu Phe Leu Ala Leu Leu Leu
                980                  985                 990

Ser Ser Phe Ser Ala Asp Asn Leu Ala Ala Thr Asp Asp Asp Asn Glu
                995                  1000                1005

Met Asn Asn Leu Gln Ile Ala Val Asp Arg Met His Lys Gly Val
        1010                 1015                1020

Ala Tyr Val Lys Arg Lys Ile Tyr Glu Phe Ile Gln Gln Ser Phe
        1025                 1030                1035

Ile Arg Lys Gln Lys Ile Leu Asp Glu Ile Lys Pro Leu Asp Asp
        1040                 1045                1050

Leu Asn Asn Lys Lys Asp Ser Cys Met Ser Asn His Thr Ala Glu
        1055                 1060                1065

Ile Gly Lys Asp Leu Asp Tyr Leu Lys Asp Val Asn Gly Thr Thr
        1070                 1075                1080

Ser Gly Ile Gly Thr Gly Ser Ser Val Glu Lys Tyr Ile Ile Asp
        1085                 1090                1095

Glu Ser Asp Tyr Met Ser Phe Ile Asn Asn Pro Ser Leu Thr Val
        1100                 1105                1110

Thr Val Pro Ile Ala Val Gly Glu Ser Asp Phe Glu Asn Leu Asn
        1115                 1120                1125

Thr Glu Asp Phe Ser Ser Glu Ser Asp Leu Glu Glu Ser Lys Glu
        1130                 1135                1140

Lys Leu Asn Glu Ser Ser Ser Ser Ser Glu Gly Ser Thr Val Asp
        1145                 1150                1155

Ile Gly Ala Pro Val Glu Glu Gln Pro Val Val Glu Pro Glu Glu
        1160                 1165                1170

Thr Leu Glu Pro Glu Ala Cys Phe Thr Glu Gly Cys Val Gln Arg
        1175                 1180                1185

Phe Lys Cys Cys Gln Ile Asn Val Glu Glu Gly Arg Gly Lys Gln
        1190                 1195                1200

Trp Trp Asn Leu Arg Arg Thr Cys Phe Arg Ile Val Glu His Asn
        1205                 1210                1215

Trp Phe Glu Thr Phe Ile Val Phe Met Ile Leu Leu Ser Ser Gly
        1220                 1225                1230

Ala Leu Ala Phe Glu Asp Ile Tyr Ile Asp Gln Arg Lys Thr Ile
        1235                 1240                1245

Lys Thr Met Leu Glu Tyr Ala Asp Lys Val Phe Thr Tyr Ile Phe
        1250                 1255                1260

Ile Leu Glu Met Leu Leu Lys Trp Val Ala Tyr Gly Tyr Gln Thr
        1265                 1270                1275

Tyr Phe Thr Asn Ala Trp Cys Trp Leu Asp Phe Leu Ile Val Asp
        1280                 1285                1290
```

-continued

```
Val Ser Leu Val Ser Leu Thr Ala Asn Ala Leu Gly Tyr Ser Glu
1295                1300                1305

Leu Gly Ala Ile Lys Ser Leu Arg Thr Leu Arg Ala Leu Arg Pro
1310                1315                1320

Leu Arg Ala Leu Ser Arg Phe Glu Gly Met Arg Val Val Val Asn
1325                1330                1335

Ala Leu Leu Gly Ala Ile Pro Ser Ile Met Asn Val Leu Leu Val
1340                1345                1350

Cys Leu Ile Phe Trp Leu Ile Phe Ser Ile Met Gly Val Asn Leu
1355                1360                1365

Phe Ala Gly Lys Phe Tyr His Cys Ile Asn Thr Thr Thr Gly Asp
1370                1375                1380

Arg Phe Asp Ile Glu Asp Val Asn Asn His Thr Asp Cys Leu Lys
1385                1390                1395

Leu Ile Glu Arg Asn Glu Thr Ala Arg Trp Lys Asn Val Lys Val
1400                1405                1410

Asn Phe Asp Asn Val Gly Phe Gly Tyr Leu Ser Leu Leu Gln Val
1415                1420                1425

Ala Thr Phe Lys Gly Trp Met Asp Ile Met Tyr Ala Ala Val Asp
1430                1435                1440

Ser Arg Asn Val Glu Leu Gln Pro Lys Tyr Glu Glu Ser Leu Tyr
1445                1450                1455

Met Tyr Leu Tyr Phe Val Ile Phe Ile Ile Phe Gly Ser Phe Phe
1460                1465                1470

Thr Leu Asn Leu Phe Ile Gly Val Ile Ile Asp Asn Phe Asn Gln
1475                1480                1485

Gln Lys Lys Lys Phe Gly Gly Gln Asp Ile Phe Met Thr Glu Glu
1490                1495                1500

Gln Lys Lys Tyr Tyr Asn Ala Met Lys Lys Leu Gly Ser Lys Lys
1505                1510                1515

Pro Gln Lys Pro Ile Pro Arg Pro Gly Asn Lys Phe Gln Gly Met
1520                1525                1530

Val Phe Asp Phe Val Thr Arg Gln Val Phe Asp Ile Ser Ile Met
1535                1540                1545

Ile Leu Ile Cys Leu Asn Met Val Thr Met Met Val Glu Thr Asp
1550                1555                1560

Asp Gln Ser Glu Tyr Val Thr Thr Ile Leu Ser Arg Ile Asn Leu
1565                1570                1575

Val Phe Ile Val Leu Phe Thr Gly Glu Cys Val Leu Lys Leu Ile
1580                1585                1590

Ser Leu Arg His Tyr Tyr Phe Thr Ile Gly Trp Asn Ile Phe Asp
1595                1600                1605

Phe Val Val Val Ile Leu Ser Ile Val Gly Met Phe Leu Ala Glu
1610                1615                1620

Leu Ile Glu Lys Tyr Phe Val Ser Pro Thr Leu Phe Arg Val Ile
1625                1630                1635

Arg Leu Ala Arg Ile Gly Arg Ile Leu Arg Leu Ile Lys Gly Ala
1640                1645                1650

Lys Gly Ile Arg Thr Leu Leu Phe Ala Leu Met Met Ser Leu Pro
1655                1660                1665

Ala Leu Phe Asn Ile Gly Leu Leu Leu Phe Leu Val Met Phe Ile
1670                1675                1680

Tyr Ala Ile Phe Gly Met Ser Asn Phe Ala Tyr Val Lys Arg Glu
1685                1690                1695
```

| | | | | | | | | | | |
|---|---|---|---|---|---|---|---|---|---|---|
| Val | Gly | Ile | Asp | Asp | Met | Phe | Asn | Phe | Glu | Thr | Phe | Gly | Asn | Ser |
| | 1700 | | | | 1705 | | | | 1710 | |

Val Gly Ile Asp Asp Met Phe Asn Phe Glu Thr Phe Gly Asn Ser
    1700                1705                1710

Met Ile Cys Leu Phe Gln Ile Thr Thr Ser Ala Gly Trp Asp Gly
    1715                1720                1725

Leu Leu Ala Pro Ile Leu Asn Ser Lys Pro Pro Asp Cys Asp Pro
    1730                1735                1740

Asn Lys Val Asn Pro Gly Ser Ser Val Lys Gly Asp Cys Gly Asn
    1745                1750                1755

Pro Ser Val Gly Ile Phe Phe Val Ser Tyr Ile Ile Ile Ser
    1760                1765                1770

Phe Leu Val Val Val Asn Met Tyr Ile Ala Val Ile Leu Glu Asn
    1775                1780                1785

Phe Ser Val Ala Thr Glu Glu Ser Ala Glu Pro Leu Ser Glu Asp
    1790                1795                1800

Asp Phe Glu Met Phe Tyr Glu Val Trp Glu Lys Phe Asp Pro Asp
    1805                1810                1815

Ala Thr Gln Phe Met Glu Phe Glu Lys Leu Ser Gln Phe Ala Ala
    1820                1825                1830

Ala Leu Glu Pro Pro Leu Asn Leu Pro Gln Pro Asn Lys Leu Gln
    1835                1840                1845

Leu Ile Ala Met Asp Leu Pro Met Val Ser Gly Asp Arg Ile His
    1850                1855                1860

Cys Leu Asp Ile Leu Phe Ala Phe Thr Lys Arg Val Leu Gly Glu
    1865                1870                1875

Ser Gly Glu Met Asp Ala Leu Arg Ile Gln Met Glu Glu Arg Phe
    1880                1885                1890

Met Ala Ser Asn Pro Ser Lys Val Ser Tyr Gln Pro Ile Thr Thr
    1895                1900                1905

Thr Leu Lys Arg Lys Gln Glu Glu Val Ser Ala Val Ile Ile Gln
    1910                1915                1920

Arg Ala Tyr Arg Arg His Leu Leu Lys Arg Thr Val Lys Gln Ala
    1925                1930                1935

Ser Phe Thr Tyr Asn Lys Asn Lys Ile Lys Gly Gly Ala Asn Leu
    1940                1945                1950

Leu Ile Lys Glu Asp Met Ile Ile Asp Arg Ile Asn Glu Asn Ser
    1955                1960                1965

Ile Thr Glu Lys Thr Asp Leu Thr Met Ser Thr Ala Ala Cys Pro
    1970                1975                1980

Pro Ser Tyr Asp Arg Val Thr Lys Pro Ile Val Glu Lys His Glu
    1985                1990                1995

Gln Glu Gly Lys Asp Glu Lys Ala Lys Gly Lys
    2000                2005

```
<210> SEQ ID NO 5
<211> LENGTH: 850
<212> TYPE: DNA
<213> ORGANISM: Homo sapiens

<400> SEQUENCE: 5 ctaaataat  gctaaagttt  ttcaagtact  acttgaaaat  agctatattt  actttcaaac      60
cttttcctct  ttgagtcatt  aggttcatga  tattatatag  caatagggaa  tgaaagagaa     120
gcaaggagaa  gcaatactgg  gagattacag  agaagaaagg  aaaaaaggct  gagagaaaag     180
aggttgagga  agaaatcata  aatctggatt  gtgagaaagt  gtttaatatt  tagccactag     240
```

```
atggcgatgt aatgtaaggt gctgtcttga cttttttttt ttttttttga aacaagctat      300
ttgctgattt gtattaggta ccatagagtg aggcgaggat gaagccgaga agatactgca      360
gaggtctctg gtgcatgtgt gtatgtgtgc gtttgtgtgt gtttgtgtgt ctgtgtgttc      420
tgccccagtg agactgcagc ccttgtaaat actttgacac cttttgcaag aaggaatctg      480
aacaattgca actgaaggca cattgttatc atctcgtctt tgggtgatgc tgttcctcac      540
tgcagatgga taattttcct tttaatcagg taagccatct aattgtttca tcttgatttt      600
aagtttattc attccagtta ttcctttgga aaaagagtcc atggaaattc agtttgggca      660
gagcaggaag tccattttg tatgtgtatt cagaccaact gtccccctcc tccctctcct       720
cctcttcttg tcccctcccc cgcgccctcc tctctcaacc ttccatgaac tgaaatcagg      780
tttgttttgc agttcagcat tttgatagaa gatgggattc tttggcctga aatagcttgg      840
catctggcca                                                             850

<210> SEQ ID NO 6
<211> LENGTH: 483
<212> TYPE: DNA
<213> ORGANISM: Homo sapiens

<400> SEQUENCE: 6
acatctctta gtcctctctt aaatatctgt attccttta ttttaggaat ttcatatgca        60
gaataaatgg taattaaaat gtgcaggatg acaagatgga gcaaacagtg cttgtaccac      120
caggacctga cagcttcaac ttcttcacca gagaatctct tgcggctatt gaaagacgca      180
ttgcagaaga aaaggcaaag aatcccaaac cagacaaaaa aagatgacga cgaaaaatgg      240
cccaaagcaa atagtgactt ggaagctgga aagaaccttc catttattta tggagacatt      300
cctccagaga tggtgtcaga gcccctggag gacctggacc cctactatat caataagaaa      360
gtgagtgttt ttttatcag gcatattttt gctgctaatt gcctactgca ttccttggac      420
tgttgtagca ccaacacatg ccaatagcac aaatctagta tctctgttag aatgaacaca      480
ttt                                                                    483

<210> SEQ ID NO 7
<211> LENGTH: 497
<212> TYPE: DNA
<213> ORGANISM: Homo sapiens

<400> SEQUENCE: 7
taagaagaga tccagtgaca gtttgttttc atggggcact ttaggaaatt gtgattgtgc       60
tggtttctca tttaacttta caataattta ttatgacaag taacagaaag tagataacag     120
agtttaagtg gttatactt tcatacttct atgttgtgtt cctgtcttac agactttat       180 agtattgaat aaagggaagg ccatcttccg gttcagtgcc acctctgccc tgtacatttt     240
aactcccttc aatcctctta ggaaaatagc tattaagatt ttggtacatt catatccttt     300
ttcaagtgat taatattaac tatttgtaca tgatctgtaa gcactttata gctaaatatc     360
aaattaagtt gggaaatgtc catattatat aggtttcatc actctcattt tgcatctttg     420
tcatattagc ctcattctta aagttcatta atcacataga cattactgaa acatgtactc     480
tttaacattt tatatat                                                    497

<210> SEQ ID NO 8
<211> LENGTH: 501
<212> TYPE: DNA
<213> ORGANISM: Homo sapiens
```

<400> SEQUENCE: 8

```
tcatatacat tacctcattt aatctataca aatactcagt gaaggtgata ttattaccca      60
cattttacac atgaagaaat tgaaatgtaa ggagattaga agacttgccc acaatgcatt     120
tatccctgaa ttttggctaa gctgcagttt gggcttttca atgttagctt tttgtaatat     180
aacacttgga ttttgatttt cttttgtgtg ttccttaaca ataacctaca ttattcagca     240
tgctaattat gtgcactatt tgacaaact gtgtgtttat gacaatgagt aaccctcctg     300
attggacaaa gaatgtagag taagttcaac ttatattttt aataacatat atacattygg     360
gattytgaaa ctgtgtctta atgtagtctt aaaataaaac tgaagagcat tttattaaag     420
tcattcctag acaaaattac gcagcaagag gacaatgctc attggccctc aggcctgctg     480
gcgttatact gattatcact c                                               501
```

<210> SEQ ID NO 9
<211> LENGTH: 563
<212> TYPE: DNA
<213> ORGANISM: Homo sapiens

<400> SEQUENCE: 9

```
gctaaataga tttcatatac cttgtatttc tcacactact cttaagacac tttacgaaac      60
aactctttgt gttaggaagc tgaatttaaa tttagggcta cgtttcattt gtatgaaatt     120
aaaatccatc tgcttagttt tcttttttag tatttatcta ttccactgat ggagtgataa     180
gaaattggta tgctatgaaa aaacactgtt actttatcaa attttttgga tgcttgtttt     240
cagatacacc ttcacaggaa tatatacttt tgaatcactt ataaaaatta ttgcaagggg     300
attctgttta gaagatttta ctttccttcg ggatccatgg aactggctcg atttcactgt     360
cattacattt gcgtaagtgc cttttbytgaa actttaagag agaacatagt ttggttttcc     420
atcagtgctt atgcttttaa gaataggttt gctttacctg tagaatattt ttgtgtgatt     480
tatacattca aactctggat ttcaatttag cacaacaaag gtctaagtgg aatttcacta     540
tagcatgaag gctttgcagt agt                                             563
```

<210> SEQ ID NO 10
<211> LENGTH: 253
<212> TYPE: DNA
<213> ORGANISM: Homo sapiens

<400> SEQUENCE: 10

```
cttataagcc catgcagtaa tataaatcct gctaaaatct tgaataattc tgatttaatt      60
ctacaggttt gtaacagaat ttgtaaacct aggcaatttt tcagctcttc gcactttcag     120
agtcttgaga gctttgaaaa ctatttcggt aattccaggt aagaagtgat tagagtaaag     180
gataggctct ttgtacctac agcttttttct ttgtgtcctg tttttgtgtt tgtgtgtgaa     240
ctcccgctta cag                                                        253
```

<210> SEQ ID NO 11
<211> LENGTH: 340
<212> TYPE: DNA
<213> ORGANISM: Homo sapiens

<400> SEQUENCE: 11

```
gtaagaagtg attagagtaa aggataggct ctttgtacct acagcttttt ctttgtgtcc      60
tgttttttgtg tttgtgtgtg aactcccgct tacaggtacg tcacagagtt tgtggacctg     120
ggcaatgtct cggcattgag aacattcaga gttctccgag cattgaagac gatttcagtc     180
```

```
attccaggtg agagcaaggt tagataatga gacggaccca tcatgtgatt cagcatcctt    240
ctctgcttga cattcagttt tacagaaaat caggaatcat aagactaggt gttcaaagaa    300
atgattatta tgttagacat agcttatcag cctggagtta                          340

<210> SEQ ID NO 12
<211> LENGTH: 409
<212> TYPE: DNA
<213> ORGANISM: Homo sapiens

<400> SEQUENCE: 12
cacgcgtgct tagccctcat agtaatagcc tcctaccttc aggcctgaaa accattgtgg     60
gagccctgat ccagtctgtg aagaagctct cagatgtaat gatcctgact gtgttctgtc    120
tgagcgtatt tgctctaatt gggctgcagc tgttcatggg caacctgagg aataaatgta    180
tacaatggcc tcccaccaat gcttccttgg aggaacatag tatagaaaag aatataactg    240
tgaattataa tggtacactt ataaatgaaa ctgtctttga gtttgactgg aagtcatata    300
ttcaagattc aagtaagaat tattgttatg tacatttcct taaaaagtag aattggattg    360
tttgtaacac aaaggataaa tacttgaggg gctggatatc ccattttac                409

<210> SEQ ID NO 13
<211> LENGTH: 266
<212> TYPE: DNA
<213> ORGANISM: Homo sapiens

<400> SEQUENCE: 13
cgcgcaaata cttgtgcctt tgaatgaata atatatttaa aattactcaa taaacttaaa     60
agtagaacct gaccttcctg ttctctttga gtgttttttaa caatgcaaat gttcagcata    120
cgactttctt ttttcaaaca ggatatcatt atttcctgga gggttttttta gatgcactac    180 tatgtggaaa tagctctgat gcagggtaag tcaatattgt gtgcatctgt gtatattgta    240
tgtacacaat acatatgtgt atcttt                                          266

<210> SEQ ID NO 14
<211> LENGTH: 604
<212> TYPE: DNA
<213> ORGANISM: Homo sapiens

<400> SEQUENCE: 14
aggtgttgaa aatgcaaatt atcaacaaaa attattttgt aaaatattat tagaaatgct     60
gcaccatatt ttaatgatga caccaagtag ctaataagac tatatgcagt caaaagttgg    120
gaaatagatt agttacttat ttgtcaaact tttattttga ataccaaat ctttctgact    180 aggcaatatc atagcatagt atcagagtaa aaaggcagca gaacgacttg taatactttc    240
ttttacccca cttgcagcca atgtccagag ggatatatgt gtgtgacagc tggtagaaat    300
cccaattatg ctacacaag ctttgatacc ttcagttggg cttttttgtc cttgtttcga    360
ctaatgactc aggacttctg ggaaaatctt tatcaactgg tgagaactaa agagccacac    420 tctccatta agtaaaagta tacaagaaaa ccaattgagt tatgaaatta aaaccggatg    480
ataatatagt agaaagagca gaacttgaca cgagacttga gttcctctat cctattgatt    540
ataacacata ctgagcagag tgatgccaag gattgcaatt ctctcccatt tcttcttggc    600
tcaa                                                                 604

<210> SEQ ID NO 15
<211> LENGTH: 378
<212> TYPE: DNA
```

<213> ORGANISM: Homo sapiens

<400> SEQUENCE: 15

| ttatatctga gttttgctag ccacatgagt aaattgaaag ttgagcaccc ttagtgaata | 60 |
| atattgggaa ataattctga tattttgtt tgcagacatt acgtgctgct gggaaaacgt | 120 |
| acatgatatt ttttgtattg gtcattttct tgggctcatt ctacctaata aatttgatcc | 180 |
| tggctgtggt ggccatggcc tacgaggaac agaatcaggc caccttggaa gaagcagaac | 240 |
| agaaagaggc cgaatttcag cagatgattg aacagcttaa aaagcaacag gaggcagctc | 300 |
| aggtaagctg ccctgctcat ggcactgacc tttatcgtct gatgtactat atgagagaag | 360 |
| tagtctagag cgtgtgat | 378 |

<210> SEQ ID NO 16
<211> LENGTH: 845
<212> TYPE: DNA
<213> ORGANISM: Homo sapiens

<400> SEQUENCE: 16

| caaccctaat taaataccaa tttttaaagt aaatcaaatc ccaaaaagta atgaatttat | 60 |
| tttcttgttg atacatgttg gatattttg aatacgtggt ctgtggagca ttaacagaga | 120 |
| cataataaat gttaccatgg agcaaactaa attatctcca aaagccttca ttaggtagaa | 180 |
| agaaaaaaaa aatctcctct tatacttgca gagaatcttc tctgtgagat gatcttcagt | 240 |
| cagttcaata tattttttaa aagccatgca aatacttcag ccctttcaaa gaaagataca | 300 |
| gtctcttcag gtgctatgtt aaaatcattt ctcttcaata tagcaggcag caacggcaac | 360 |
| tgcctcagaa cattccagag agcccagtgc agcaggcagg ctctcagaca gctcatctga | 420 |
| agcctctaag ttgagttcca agagtgctaa ggaaagaaga aatcggagga agaaaagaaa | 480 |
| acagaaagag cagtctggtg gggaagagaa agatgaggat gaattccaaa atctgaatc | 540 |
| tgaggacagc atcaggaggw aaggttttcg cttctccatt gaagggaacc ggttgacata | 600 |
| tgaaaagagg tactcctccc cacaccaggt atggcactgc tgagtttact gatgcatggt | 660 |
| tgaaaattaa aacatgggag agaggggag atttagaaaa tggactcagg aattttttatc | 720 |
| aactgaatca accactgttg tgttatattt aaacccatcc cttcttcaca tagttatgca | 780 |
| aaaactttac tccacagata tgtaagtcta cagctcggtg tagttaagat aacaccaagt | 840 |
| tgaca | 845 |

<210> SEQ ID NO 17
<211> LENGTH: 965
<212> TYPE: DNA
<213> ORGANISM: Homo sapiens

<400> SEQUENCE: 17

| cattgccata ttctaaggat gtttcccttt gaacttgaga aatggtcgtt cagggtgtgt | 60 |
| gtgtatgtgt gtgtgtgtgt gtttcaatat gttaaggttg caatctatct cctcattctt | 120 |
| taatcccaag ggctagaaac tttctttat caaggtaatt taatttaatg tgaatgcaca | 180 |
| taaaatgaga atgataatca aaaggaatga accatattct gttatgaatg ctgaaatctc | 240 |
| cttctacata atcttgcaaa atgaaatcac attcaaatgt ccatattaat atgactctat | 300 |
| ttgtbtgctc tttcaaactt ctagtctttg ttgagcatcc gtggctccct attttcacca | 360 |
| aggcgaaata gcagaacaag ccttttcagc tttagggggc gagcaaagga tgtgggatct | 420 |
| gagaacgact tcgcagatga tgagcacagc acctttgagg ataacgagag ccgtagagat | 480 |

| | |
|---|---|
| tccttgtttg tgccccgacg acacggagag agacgcaaca gcaacctgag tcagaccagt | 540 |
| aggtcatccc ggatgctggc agtgtttcca gcgaatggga agatgcacag cactgtggat | 600 |
| tgcaatggtg tgggttcctt ggttggtgga ccttcagttc ctacatcgcc tgttggacag | 660 |
| cttctgccag aggtgataat agataagcca gctactgatg acaatgtaag gaagtyttaa | 720 |
| atagttcagg catggctggc tcactattgc tgcaccagcc agtgtgtcta cagaacggca | 780 |
| accttgagaa tgattcctgg ttggtcacgc tgtgaatgca cctgcatctt gtaatatctt | 840 |
| tgatagacta accaactaaa acttaaaacc ttagcagtcg cctgcacaaa cctgaatgca | 900 |
| tttacttatt aaaagtgcta aggattgatt agacacaata attactgcct ccagttggag | 960 |
| gattt | 965 |

<210> SEQ ID NO 18
<211> LENGTH: 641
<212> TYPE: DNA
<213> ORGANISM: Homo sapiens

<400> SEQUENCE: 18

| | |
|---|---|
| aagagtttta tcaactatat taaaattatt ttgtatttta taaaattatg aaatcaggaa | 60 |
| gttaacatct tggttttttgc tgtatgacta aatggttaac agtttgaaca ttccaggcta | 120 |
| atgatacaat aagtcagaaa tatctgccat caccaattga atatgaaagt gcatgatgca | 180 |
| tgtgtttcat gaaattcact gtgtcaccat ttggttgttt gcttgtcata ttgctcaaat | 240 |
| taattgttta atgcattagc attttttttt acagggaaca accactgaaa ctgaaatgag | 300 |
| aaagagaagg tcaagttctt tccacgtttc catggacttt ctagaagatc cttcccaaag | 360 |
| gcaacgagca atgagtatag ccagcattct aacaaataca gtagaaggtt ggtaacaaat | 420 |
| tctatttcg tttcaattat tttccaccaaa cttatattgt ctcatttcaa acaaatatat | 480 |
| ttgtgagttg ggaatagtgc attctaatga aaagacagtc taattcaaga gctgttattt | 540 |
| cttatatcta ctcagatatt ctagaagcct taacaattta ttttaaaatg agtgatattg | 600 |
| ggactaagac tgttttccta actgtgtagc aactctttga a | 641 |

<210> SEQ ID NO 19
<211> LENGTH: 818
<212> TYPE: DNA
<213> ORGANISM: Homo sapiens

<400> SEQUENCE: 19

| | |
|---|---|
| gtgaggcggc acatgaaaga ccacccattt aacctgaggc caagtgctga gccacaatgg | 60 |
| cagtgcataa gacaaaaaac tacccattgt tacctgggcc ctatgtgtgt gtctgatgaa | 120 |
| ataaccttgg gaggtttaga gtaaactgta atttttttaa caagtacaaa aaagggtgtc | 180 |
| tctgtaacaa aaatgtgttg attactgaaa ataagtttag tggatatgaa ataaatgtgt | 240 |
| gtgtataaag tawaccttt ggtgggtctt tttttttttt ttcttaatct agaacttgaa | 300 |
| gaatccaggc agaaatgccc accctgttgg tataaatttt ccaacatatt cttaatctgg | 360 |
| gactgttctc catattggtt aaaagtgaaa catgttgtca acctggttgt gatggaccca | 420 |
| tttgttgacc tggccatcac catctgtatt gtcttaaata ctcttttcat ggccatggag | 480 |
| cactatccaa tgacggacca tttcaataat gtgcttacag taggaaactt ggtaagcata | 540 |
| ttggaaggta aatgtgttta gtcttcaaat tttctgcttg aaaaactgtt tacatttaat | 600 |
| tgtgtatagc agtctttcaa ccatccttca tgcttcctgg cccctgcaaa atcgcaatta | 660 |
| tatttagctg gctatactct acttttttgc caaaaataat caccccttaat gtgctcacaa | 720 |

```
aaactgagaa aggcataggc ctacagcact acttgaaaag tcaacagcaa tatttataat    780
ttttcaggat ccagaagtag ctcatagatt aagaacat                            818

<210> SEQ ID NO 20
<211> LENGTH: 645
<212> TYPE: DNA
<213> ORGANISM: Homo sapiens

<400> SEQUENCE: 20
caagccattt cacccatctg aagacctcag tttccttatc tgtaaagtaa taattgtata     60
ttatctactt cgcgtttcca caaggataaa attaaataat gtatatgawa gtctttcatc    120
aactacaaat tgccatacaa atttaagtta gtaatagaat cattgtggga aaatagcata    180
agcattatgt tctaagagca aatcttatgt catgtatgtt attatctggt ggaattagat    240
taattttgtt ttgatcttag gttttcactg ggatctttac agcagaaatg tttctgaaaa    300
ttattgccat ggatccttac tattatttcc aagaaggctg aatatctttt gacggtttta    360
ttgtgacgct tagcctggta gaacttggac tcgccaatgt ggaagggtta tctgttctcc    420
gttcatttcg attggtaaaa aaaaaaaaaa aaggaaccaa attcaaaaac ctttctaaca    480
ttcagggttc ttgcatagca ttgtcatagt ttttttgcca cacaaccatt aggcattgta    540 agttttctg taacatttgc attgtcaaaa acttttccta catgggaata attctcaatt     600
attaggttac cttagttcaa gggcwaggtc ggaaaggtaa cggtt                   645

<210> SEQ ID NO 21
<211> LENGTH: 829
<212> TYPE: DNA
<213> ORGANISM: Homo sapiens

<400> SEQUENCE: 21
gaattctaat gaccatttct aggtaaagct caatatatat aatgctttta agaatcatac     60
aaatatatat taatctttca ttttccagct gcgagatttc aagttggcaa atcttggcc     120 aacgttaaat atgctaataa agatcatcgg caattccgtg ggggctctgg gaaatttaac    180
cctcgtcttg gccatcatcg tcttcatttt tgccgtggtc ggcatgcagc tctttggtaa    240
aagctacaaa gattgtgtct gcaagatcgc cagtgattgt caactcccac gctggcacat    300
gaatgacttc ttccactcck hcctgattgt gttccgcgtg ctgtgtgggg agtggataga    360
gaccatgtgg gactgtatgg aggttgctgg tcaagccatg tgccttactg tcttcatgat    420
ggtcatggtg attggaaacc tagcggtatg tacccactta agatatgcat tttgaaaata    480
caccagcatg gcacatgtat acatatgtaa ctaacctgca cattgtgcac atgtacccta    540
aaacttaaag tataataaaa aaaagagta taatttaatg gtgactgttt tgtcaaaaag    600
aaaaacaaac tatgattatt ggtttaaaag tccattacct tggatatatt atcactttaa    660
caacacagca atatabcagt gcccctgcat ttttatacc aaattctatt ttgtcagtca    720
ctttatcaca tttttatgt gaattacaat agagtatcat attgagatga gcctaaaagg    780
atgtgctggg accatttat aaattcagag ccaaggaaga gagaagtct                 829

<210> SEQ ID NO 22
<211> LENGTH: 909
<212> TYPE: DNA
<213> ORGANISM: Homo sapiens

<400> SEQUENCE: 22
gaattctcgt attgtacaca tataaatctg ttttcttcta ctcatacaat tttagagtta     60
```

```
acaaaaccttt agattagctc attcaatttc actttacgaa tgggagaact tgagagcaac    120
agaaatcatg tctttgtcca aggatgtgct attgagccag tcacaaattc agatcaccca    180
tcttctaatc actatgctgt ggtgtttcct tctcatcaag ttttagaact tagagttttt    240
tccacactta aaagaaagaa taagtgattg taatctgctc ttccctacat tggtgtaaaa    300
ttataatcat gttttttgttg tttttaaggt cctgaatctc tttctggcct tgcttctgag    360
ctcatttagt gcagacaacc ttgcagccac tgatgatgat aatgaaatga ataatctcca    420
aattgctgtg gataggatgc acaaaggagt agcttatgtg aaaagaaaaa tatatgartt    480
tattcaacag tccttcatta ggaaacaaaa gattttagat gaaattaaac cacttgatga    540
tctaaacaac aagaaagaca gttgtatgtc aatcataca gcagaaattg ggaaagatct    600
tgactatctt aaagatgtaa atggaactac aagtggtata ggaactggca gcagtgttga    660
aaaatacatt attgatgaaa gtgattacat gtcattcata acaaccccca gtcttactgt    720
gactgtacca attgctgtag gagaatctga ctttgaaaat ttaaacacgg aagactttag    780
tagtgaatcg gatctggaag aaagcaaaga ggtaagattc tataggtgtg ggtaggtatg    840
aatacatata catatataca tatacacaca tacagatgay cctcagctta atgatgtttt    900
tacttaaga                                                            909
```

```
<210> SEQ ID NO 23
<211> LENGTH: 516
<212> TYPE: DNA
<213> ORGANISM: Homo sapiens
<220> FEATURE:
<221> NAME/KEY: misc_feature
<222> LOCATION: (393)..(393)
<223> OTHER INFORMATION: n = a, c, t or g
<220> FEATURE:
<221> NAME/KEY: misc_feature
<222> LOCATION: (415)..(415)
<223> OTHER INFORMATION: n = a, c, t or g
<220> FEATURE:
<221> NAME/KEY: misc_feature
<222> LOCATION: (454)..(454)
<223> OTHER INFORMATION: n = a, c, t or g
<220> FEATURE:
<221> NAME/KEY: misc_feature
<222> LOCATION: (513)..(513)
<223> OTHER INFORMATION: n = a, c, t or g

<400> SEQUENCE: 23
```

```
aagcttacat tgtgaattat ggtaaaaggg ttagcacaga caatgatttt cttatttctt    60 cccottattc aatctctctt tttctctaaa aatatctcta cctcaagaag aataaaaaac    120
aaattcatag taataatcct tcttggcagg caacttatta ccaaaattaa ggactttact    180
ttctatgtcc atctcactta cagaaactga atgaaagcag tagctcatca gaaggtagca    240
ctgtggacat cggcgcacct gtagaagaac agcccgtagt ggaacctgaa gaaactcttg    300
aacccgaagc ttgtttcact gaaggtaaag aaaagaatcc taatgttaat cttcatttg     360 gagtgcagct tatttagctg ttggtcagct aanataaatc acatataata aaatngcact    420
ttgtaataga tataattcaa tcacctctaa tatnttgaca gacaaaaaaa cttaaagtct    480
agtgtcatgc tttgattata tctgcccaat atntgg                              516
```

```
<210> SEQ ID NO 24
<211> LENGTH: 640
<212> TYPE: DNA
<213> ORGANISM: Homo sapiens

<400> SEQUENCE: 24
```

```
ccatttaaat gtggctgaat gtttccacaa cttcacacag ctgatgaatg tgctcttact    60
actctaggct tagagagcta tgctagcaag acagagatga gcatagtaat aaaaagacaa   120
gacaaggaca ttgctaaagg atattatgga agcagagaca ctttatctac ttttatttca   180
acactttctg caggctgtgt acaaagattc aagtgttgtc aaatcaatgt ggaagaaggc   240
agaggaaaac aatggtggaa cctgagaagg acgtgtttcc gaatagttga acataactgg   300
tttgagacct tcattgtttt catgattctc cttagtagtg gtgctctggt gagtgagatt   360
aagaaaaggt gatacagcac taattttag aacactctaa tactgatgac ttattaatcc   420
tttgtttcat tgtcttagta tccaatgcat ttttaattat cccaccttgt atcttctata   480
gatttactct ataactctat atttctggat taacttttac tatgtatgta aatataatttt  540 taagaagcta atcattaatt tttgcttact attaaatagc ccagaaagtg tagcccttca   600
gcttattcat taacaccaaa ggatgtgaat attcaattac                         640

<210> SEQ ID NO 25
<211> LENGTH: 607
<212> TYPE: DNA
<213> ORGANISM: Homo sapiens

<400> SEQUENCE: 25
ccacatcagg atacaacatc aagaactatt tcctgactaa gtcaaattaa ttcattggaa    60
tcatactttt cttttcttc caccaatagt ctttcccctg attaaataag taaaagacct   120
ttgcgaggaa aaaaaaaag taacagtaac tactgtttct ctgccctcct attccaatga   180
aatgtcatat gcatatgatt aattttttaa atagcttatg gagtataatt attttttgaaa  240 gctaataatg tgtaacattt tcttatagg catttgaaga tatatatatt gaycagcgaa   300
agacgattaa gacgatgttg gaatatgctg acaaggtttt cacttacatt ttcattctgg   360
aaatgcttct aaaatgggtg gcatatggct atcaaacata tttcaccaat gcctggagtt   420
ggctggactt cttaattgtt gatgtaggta tcgttcatat ttttgtctct gttcaaggta   480
gcttgtctta tttatattca aattctacaa tagtgagtct cagaccacta tgttatgttg   540
acagactata atarccacta aacgcatata tgcaatgaga gtgtcatttc tggaagacaa   600
gggctaa                                                            607

<210> SEQ ID NO 26
<211> LENGTH: 336
<212> TYPE: DNA
<213> ORGANISM: Homo sapiens

<400> SEQUENCE: 26
aaaaattata cttgtcgtat tatatagcaa ctacacattg aatgatgatt ctgtttatta    60
attgttatta ttcytgtgtg tgcaggtttc attggtcagt ttaacagcaa atgccttggg   120
ttactcagaa cttggagcct atcaatctct caggacacta agagctctga gacctctaag   180
agccttatct cgatttgaag ggatgagggt aagaaaaatg aaagaacctg aagtattgta   240
tatagccaaa attaaactaa attaaattta gaaaaaagga aaatgtatg catgcaaaag    300 gaatggcaaa ttcttgcaaa atgctctttta ttgttt                           336

<210> SEQ ID NO 27
<211> LENGTH: 677
<212> TYPE: DNA
<213> ORGANISM: Homo sapiens

<400> SEQUENCE: 27
```

```
cttggttata ttgcctatag ttgttttcct aagtgtattg cttaagaaaa aaaaatgaat        60 tttaagatttt ttttgaacct tgcttttaca tatcctagaa taaatagcat tgatagaaaa      120
aaagaatgga agaccagag attactaggg gaattttttt tctttattaa cagataagaa         180
ttctgacttt tctttttttc cattttgtgta ttaggtggtt gtgaatgccc ttttaggagc       240
aattccatcc atcatgaatg tgcttctggt tgtcttata ttctggctaa ttttcagcat         300
catgggcgta aatttgtttg ctggcaaatt ctaccactgt attaacacca caactggtga        360
caggtttgac atcgaagacg tgaataatca tactgattgc ctaaaactaa tagaaagaaa        420
tgagactgct cgatggaaaa atgtgaaagt aaactttgat aatgtaggat ttgggtatct        480
ctctttgctt caagttgtaa gtgaacacta ttttctctga atatttttat tgtttggaat        540
aataacaaaa taatgacata catctattat ttagttccta agaaaagta tatatttctt         600 tctatttaaa aaatttcaat ttgttagtac aagtttatga gcccagatgg gtgaaaactt       660
tattacatgt aaggact                                                       677

<210> SEQ ID NO 28
<211> LENGTH: 457
<212> TYPE: DNA
<213> ORGANISM: Homo sapiens

<400> SEQUENCE: 28
aatggccatt ttgttcaata tgtgttctag aaatgaaaag ccatactaaa atactgtctt        60
ggtccaaaat ctgtgtaaaa tttgttttga aatgtctttc aaaaatattc ccttttgaaa      120
attatatcag taagaatatt tattaaacat caggtctaaa ttatttttac tccaaagtaa       180
aacatgcatg tccttcttaa taggccacat tcaaaggatg gatggatata atgtatgcag       240
cagttgattc cagaaatgta agtattcctt gtattctaag tcttttttaca atattgatca      300 ggtggtaaaa ttaatcgaat aaagcataaa cgaccaaatg aaatgattct atcttgatttt      360 aaaatatttg ggaaaaagtg tgacaggtaa atattcaagc atagcaatgt ttatcagaaa       420
gatcttacta agataattca acacatgaat tatttttg                               457

<210> SEQ ID NO 29
<211> LENGTH: 379
<212> TYPE: DNA
<213> ORGANISM: Homo sapiens
<220> FEATURE:
<221> NAME/KEY: misc_feature
<222> LOCATION: (43)..(43)
<223> OTHER INFORMATION: n = a, c, t or g

<400> SEQUENCE: 29
cagaaaaaaa aaaatgctg acatattagt aagaataatt ttntctattg ttatgaaaaa        60
gcaccagtga cgatttccag cactaaaatg tatggtaata ttttacaaaa tattcccctt       120
tggtaggtgg aactccagcc taagtatgaa gaaagtctgt acatgtatct ttactttgtt       180
attttcatca tctttgggtc cttcttcacc ttgaacctgt ttattggtgt catcatagat       240
aatttcaacc agcagaaaaa gaagataagt atttctaata ttttctctcc cactgagata      300
gaaaaattat tccttggagt gttttctctg ccaaatgagt acttgaattt agaacaaatg      360
ggagtatata ttataactg                                                    379

<210> SEQ ID NO 30
<211> LENGTH: 393
<212> TYPE: DNA
<213> ORGANISM: Homo sapiens
```

<400> SEQUENCE: 30

```
gtcattttga attatttagg gaattaaaat attatcatac ctaaagagta caattttttt      60
tacatttaa atcccagata taattatact aatcagttga attttgtatt tctttttta      120
gccatccatt ttctatttta acattgaaaa aaatgtacaa aaggacacag ttttaaccag     180
tttgatttt cttttctata ctttggaggt caagacatct ttatgacaga agaacagaag     240
aaatactata atgcaatgaa aaattagga tcgaaaaaac cgcaaaagcc tatacctcga     300
ccaggagtaa aagtatcaa atgatatggg ggaaaataca aaaacaaaaa ctgcatgctt     360
gtctcacaaa aagaaaagt aagctaaaca ttt                                  393
```

<210> SEQ ID NO 31
<211> LENGTH: 539
<212> TYPE: DNA
<213> ORGANISM: Homo sapiens

<400> SEQUENCE: 31

```
ttttaacaat taattatgct ataaattcat tcttacaaaa atcatttgga atgactactt      60
tgcaagaaac tagaaagtca attaatgcag aaagtactta atgctaatgc acatgagaaa    120
aactcctttg ttgttaaaag catttctatt tctctacaga acaaatttca aggaatggtc    180
tttgacttcg taaccagaca agtttttgac ataagcatca tgattctcat ctgtcttaac    240
atggtcacaa tgatggtgga aacagatgac cagagtgaat atgtgactac cattttgtca    300
cgcatcaatc tggtgttcat tgtgctattt actggagagt gtgtactgaa actcatctct    360
ctacgccatt attattttac cattggatgg aatattttg attttgtggt tgtcattctc    420
tccattgtag gtaagaaata tttaaagttc ttaaattcag ttaaataaaa gtgaaagctg    480
aaacaatcaa gattagattc aagatcatcc cagcaatcag agataatcac tgtaaatat     539
```

<210> SEQ ID NO 32
<211> LENGTH: 3403
<212> TYPE: DNA
<213> ORGANISM: Homo sapiens

<400> SEQUENCE: 32

```
agtatatatt atatatagtt gtcatattta ataaactgg gttcaggact ctgaaccttta      60
ccttggagct ttagaagaaa catatgttta ttttaacgca tgatttcttc actggttggt    120
attctcattg tttattcata ggtatgtttc ttgccgagct gatagaaaag tatttcgtgt    180
cccctacccct gttccgagtg atccgtcttg ctaggattgg ccgaatccta cgtctgatca    240
aaggagcaaa ggggatccgc acgctgctct ttgctttgat gatgtccctt cctgcgttgt    300
ttaacatcgg cctcctactc ttcctagtca tgttcatcta cgccatcttt gggatgtcca    360
actttgccta tgttaagagg gaagttggga tcgatgacat gttcaacttt gagacctttg    420
gcaacagcat gatctgccta ttccaaatta caacctctgc tggctgggat ggattgctag    480
cacccattct caacagtaag ccacccgact gtgaccctaa taaagttaac cctggaagct    540
cagttaaggg agactgtggg aacccatctg ttggaatttt cttttttgtc agttacatca    600
tcatatcctt cctggttgtg gtgaacatgt acatcgcggt catcctggag aacttcagtg    660
ttgctactga agaaagtgca gagcctctga gtgaggatga ctttgagatg ttctatgagg    720
tttgggagaa gtttgatccc gatgcaactc agttcatgga atttgaaaaa ttatctcagt    780
ttgcagtgcg cttgaaccgc ctctcaatct gccacaacca aacaaactcc agctcattgc    840
catggatttg cccatggtga gtggtgaccg gatccactgt cttgatatct tatttgcttt    900
```

```
tacaaagcgg gttctaggag agagtggaga gatggatgct ctacgaatac agatggaaga      960
gcgattcatg gcttccaatc cttccaaggt ctcctatcag ccaatcacta ctactttaaa     1020
acgaaaacaa gaggaagtat ctgctgtcat tattcagcgt gcttacagac gccacctttt     1080
aaagcgaact gtaaaacaag cttcctttac gtacaataaa aacaaaatca aggtggggc      1140 taatcttctt ataaagaag acatgataat tgacagaata aatgaaaact ctattacaga      1200
aaaaactgat ctgaccatgt ccactgcagc ttgtccacct tcctatgacc gggtgacaaa     1260
gccaattgtg aaaaacatg agcaagaagg caaagatgaa aaagccaaag ggaaataaat      1320
gaaaataaat aaaaataatt gggtgacaaa ttgtttacag cctgtgaagg tgatgtattt     1380
ttatcaacag gactccttta ggaggtcaat gccaaactga ctgtttttac acaaatctcc     1440
ttaaggtcag tgcctacaat aagacagtga ccccttgtca gcaaactgtg actctgtgta     1500
aaggggagat gaccttgaca ggaggttact gttctcacta ccagctgaca ctgctgaaga     1560
taagatgcac aatggctagt cagactgtag ggaccagttt caaggggtgc aaacctgtga     1620
ttttggggtt gtttaacatg aaacactta gtgtagtaat tgtatccact gtttgcattt      1680
caactgccac atttgtcaca ttttatgga atctgttagt ggattcatct ttttgttaat      1740
ccatgtgttt attatatgtg actattttg taaacgaagt ttctgttgag aaataggcta      1800
aggacctcta taacaggtat gccacctggg gggtatggca accacatggc cctcccagct     1860
acacaaagtc gtggtttgca tgagggcatg ctgcacttag agatcatgca tgagaaaaag     1920
tcacaagaaa aacaaattct taaattcac catatttctg ggaggggtaa ttgggtgata      1980
agtggaggtg ctttgttgat cttgttttgc gaaatccagc ccctagacca agtagattat     2040
ttgtgggtag gccagtaaat cttagcaggt gcaaacttca ttcaaatgtt tggagtcata     2100
aatgttatgt ttcttttgt tgtattaaaa aaaaaccctg aatagtgaat attgcccctc       2160
accctccacc gccagaagac tgaattgacc aaaattactc tttataaatt tctgcttttt     2220
cctgcacttt gtttagccat cttcggctct cagcaaggtt gacactgtat atgttaatga     2280
aatgctattt attatgtaaa tagtcatttt accctgtggt gcacgtttga gcaaacaaat     2340
aatgacctaa gcacagtatt tattgcatca aatatgtacc acaagaaatg tagagtgcaa     2400
gctttacaca ggtaataaaa tgtattctgt accatttata gatagtttgg atgctatcaa     2460
tgcatgttta tattaccatg ctgctgtatc tggtttctct cactgctcag aatctcattt     2520
atgagaaacc atatgtcagt ggtaaagtca aggaaattgt tcaacagatc tcatttattt     2580
aagtcattaa gcaatagttt gcagcacttt aacagctttt tggttatttt tacatttaa      2640 gtggataaca tatggtatat agccagactg tacagacatg tttaaaaaaa cacactgctt     2700
aacctattaa atatgtgttt agaattttat aagcaaatat aaatactgta aaagtcact      2760 ttatttatt tttcagcatt atgtacataa atatgaagag gaaattatct tcaggttgat      2820
atcacaatca cttttcttac tttctgtcca tagtactttt tcatgaaaga aatttgctaa     2880
ataagacatg aaaacaagac tgggtagttg tagatttctg cttttaaat tacatttgct      2940 aattttagat tatttcacaa ttttaaggag caaaataggt tcacgattca tatccaaatt     3000
atgctttgca attggaaaag ggtttaaaat tttatttata tttctggtag tacctgcact     3060
aactgaattg aaggtagtgc ttatgttatt tttgttcttt ttttctgact tcggtttatg     3120
ttttcatttc tttggagtaa tgctgctcta gattgttcta aatagaatgt gggcttcata     3180 atttttttt ccacaaaaac agagtagtca acttatatag tcaattacat caggacattt      3240
tgtgtttctt acagaagcaa accataggct cctctttttcc ttaaaactac ttagataaac    3300
```

-continued

```
tgtattcgtg aactgcatgc tggaaaatgc tactattatg ctaaataatg ctaaccaaca    3360
tttaaaatgt gcaaaactaa taaagattac attttttatt tta                     3403

<210> SEQ ID NO 33
<211> LENGTH: 8349
<212> TYPE: DNA
<213> ORGANISM: Homo sapiens

<400> SEQUENCE: 33
ttcttggtgc cagcttatca atcccaaact ctgggtgtaa agattctac agggcacttt      60 cttatgcaag gagctaaaca gtgattaaag gagcaggatg aaaagatggc acagtcagtg    120
ctggtaccgc caggacctga cagcttccgc ttctttacca gggaatccct tgctgctatt    180
gaacaacgca ttgcagaaga gaaagctaag agacccaaac aggaacgcaa ggatgaggat    240
gatgaaaatg gcccaaagcc aaacagtgac ttggaagcag gaaaatctct tccatttatt    300
tatggagaca ttcctccaga gatggtgtca gtgcccctgg aggatctgga cccctactat    360
atcaataaga aaacgtttat agtattgaat aaagggaaag caatctctcg attcagtgcc    420 accccctgccc tttacatttt aactcccttc aaccctatta gaaaattagc tattaagatt    480
ttggtacatt ctttattcaa tatgctcatt atgtgcacga ttcttaccaa ctgtgtattt    540
atgaccatga gtaaccctcc agactggaca agaatgtgg agtatacctt tacaggaatt    600
tatacttttg aatcacttat taaaatactt gcaaggggct tttgtttaga agatttcaca    660
tttttacggg atccatggaa ttggttggat ttcacagtca ttacttttgc atatgtgaca    720
gagtttgtgg acctgggcaa tgtctcagcg ttgagaacat tcagagttct ccgagcattg    780
aaaacaattt cagtcattcc aggcctgaag accattgtgg gggccctgat ccagtcagtg    840
aagaagcttt ctgatgtcat gatcttgact gtgttctgtc taagcgtgtt tgcgctaata    900
ggattgcagt tgttcatggg caacctacga aataaatgtt tgcaatggcc tccagataat    960 tcttccttg aaataaatat cacttccttc tttaacaatt cattggatgg gaatggtact   1020
actttcaata ggacagtgag catatttaac tgggatgaat atattgagga taaaagtcac   1080
ttttattttt tagagggggca aaatgatgct ctgctttgtg gcaacagctc agatgcaggc   1140
cagtgtcctg aaggatacat ctgtgtgaag gctggtagaa accccaacta tggctacacg   1200
agctttgaca cctttagttg ggcctttttg tccttatttc gtctcatgac tcaagacttc   1260
tgggaaaacc tttatcaact gacactacgt gctgctggga aaacgtacat gatattttt   1320 gtgctggtca ttttcttggg ctcattctat ctaataaatt tgatcttggc tgtggtggcc   1380
atggcctatg aggaacagaa tcaggccaca ttggaagagg ctgaacagaa ggaagctgaa   1440
tttcagcaga tgctcgaaca gttgaaaaag caacaagaag aagctcaggc ggcagctgca   1500
gccgcatctg ctgaatcaag agacttcagt ggtgctggtg ggataggagt tttttcagag   1560
agttcttcag tagcatctaa gttgagctcc aaaagtgaaa aagagctgaa aaacagaaga   1620
aagaaaaaga acagaaaga acagtctgga gaagaagaga aaatgacag agtcctaaaa   1680 tcggaatctg aagacagcat aagaagaaaa ggtttccgtt tttccttgga aggaagtagg   1740
ctgacatatg aaaagagatt ttcttctcca caccagtcct tactgagcat ccgtggctcc   1800
cttttctctc caagacgcaa cagtagggcg agcttttca gcttcagagg tcgagcaaag   1860
gacattggct ctgagaatga ctttgctgat gatgagcaca gcacctttga ggacaatgac   1920
agccgaagag actctctgtt cgtgccgcac agacatggag aacggcgcca cagcaatgtc   1980
agccaggcca gccgtgcctc cagggtgctc cccatcctgc ccatgaatgg gaagatgcat   2040
```

```
agcgctgtgg actgcaatgg tgtggtctcc ctggtcgggg gcccttctac cctcacatct   2100
gctgggcagc tcctaccaga gggcacaact actgaaacag aaataagaaa gagacggtcc   2160
agttcttatc atgttttccat ggatttattg gaagatccta catcaaggca aagagcaatg   2220
agtatagcca gtattttgac caacaccatg aagaacttg aagaatccag acagaaatgc    2280
ccaccatgct ggtataaatt tgctaatatg tgtttgattt gggactgttg taaaccatgg   2340
ttaaaggtga acaccttgt caacctggtt gtaatggacc catttgttga cctggccatc    2400
accatctgca ttgtcttaaa tacactcttc atggctatgg agcactatcc catgacggag   2460
cagttcagca gtgtactgtc tgttggaaac ctggtcttca cagggatctt cacagcagaa   2520
atgtttctca agataattgc catggatcca tattattact ttcaagaagg ctggaatatt   2580
tttgatggtt ttattgtgag ccttagttta atggaacttg gtttggcaaa tgtggaagga   2640
ttgtcagttc tccgatcatt ccggctgctc cgagttttca agttggcaaa atcttggcca   2700
actctaaata tgctaattaa gatcattggc aattctgtgg gggctctagg aaacctcacc   2760
ttggtattgg ccatcatcgt cttcattttt gctgtggtcg gcatgcagct ctttggtaag   2820
agctacaaag aatgtgtctg caagattccc aatgattgtg aactcccacg ctggcacatg   2880
catgactttt tccactcctt cctgatcgtg ttccgcgtgc tgtgtggaga gtggatagag   2940
accatgtggg actgtatgga ggtcgctggc caaaccatgt gccttactgt cttcatgatg   3000
gtcatggtga ttggaaatct agtggttctg aacctcttct tggccttgct tttgagttcc   3060
ttcagttctg acaatcttgc tgccactgat gatgataacg aaatgaataa tctccagatt   3120
gctgtgggaa ggatgcagaa aggaatcgat tttgttaaaa gaaaaatacg tgaatttatt   3180
cagaaagcct ttgttaggaa gcagaaagct ttagatgaaa ttaaaccgct tgaagatcta   3240
aataataaaa aagacagctg tatttccaac cataccacca tagaaatagg caaagacctc   3300
aattatctca aagacggaaa tggaactact agtggcatag gcagcagtgt agaaaaatat   3360
gtcgtggatg aaagtgatta catgtcattt ataaacaacc ctagcctcac tgtgacagta   3420
ccaattgctg ttgagaaatc tgactttgaa aatttaaata ctgaagaatt cagcagcgag   3480
tcagatatgg aggaaagcaa agagaagcta aatgcaacta gttcatctga aggcagcacg   3540
gttgatattg gagctcccgc cgagggagaa cagcctgagg ttgaacctga ggaatccctt   3600
gaacctgaag cctgttttac agaagactgt gtacggaagt tcaagtgttg tcagataagc   3660
atagaagaag gcaaagggaa actctggtgg aatttgagga aaacatgcta taagatagtg   3720
gagcacaatt ggttcgaaac cttcattgtc ttcatgattc tgctgagcag tggggctctg   3780
gcctttgaag atatatacat tgagcagcga aaaaccatta agaccatgtt agaatatgct   3840
gacaaggttt tcacttacat attcattctg gaaatgctgc taaagtgggt tgcatatggt   3900
tttcaagtgt attttaccaa tgcctggtgc tggctagact tcctgattgt tgatgtctca   3960
ctggttagct taactgcaaa tgccttgggt tactcagaac ttggtgccat caaatccctc   4020
agaacactaa gagctctgag gccactgaga gctttgtccc ggtttgaagg aatgagggct   4080
gttgtaaatg ctcttttagg agccattcca tctatcatga atgtacttct ggtttgtctg   4140
atcttttggc taatattcag tatcatggga gtgaatctct tgctggcaa gttttaccat   4200 tgtattaatt acaccactgg agagatgttt gatgtaagcg tggtcaacaa ctacagtgag   4260
tgcaaagctc tcattgagag caatcaaact gccaggtgga aaaatgtgaa agtaaacttt   4320
gataacgtag gacttggata tctgtctcta cttcaagtag ccacgtttaa gggatggatg   4380
gatattatgt atgcagctgt tgattcacga aatgtagaat tacaacccaa gtatgaagac   4440
```

```
aacctgtaca tgtatcttta ttttgtcatc tttattattt ttggttcatt ctttaccttg    4500
aatcttttca ttggtgtcat catagataac ttcaaccaac agaaaaagaa gtttggaggt    4560
caagacattt ttatgacaga agaacagaag aaatactaca atgcaatgaa aaaactgggt    4620
tcaaagaaac cacaaaaacc catacctcga cctgctaaca aattccaagg aatggtcttt    4680
gattttgtaa ccaaacaagt ctttgatatc agcatcatga tcctcatctg ccttaacatg    4740
gtcaccatga tggtggaaac cgatgaccag agtcaagaaa tgacaaacat tctgtactgg    4800
attaatctgg tgtttattgt tctgttcact ggagaatgtg tgctgaaact gatctctctt    4860
cgttactact atttcactat tggatggaat attttttgatt ttgtggtggt cattctctcc    4920
attgtaggaa tgtttctggc tgaactgata gaaaagtatt ttgtgtcccc taccctgttc    4980
cgagtgatcc gtcttgccag gattggccga atcctacgtc tgatcaaagg agcaaagggg    5040
atccgcacgc tgctctttgc tttgatgatg tcccttcctg cgttgtttaa catcggcctc    5100
cttcttttcc tggtcatgtt catctacgcc atctttggga tgtccaattt tgcctatgtt    5160
aagagggaag ttgggatcga tgacatgttc aactttgaga cctttggcaa cagcatgatc    5220
tgcctgttcc aaattacaac ctctgctggc tgggatggat tgctagcacc tattcttaat    5280
agtggacctc cagactgtga ccctgacaaa gatcaccctg gaagctcagt taaaggagac    5340
tgtgggaacc catctgttgg gattttcttt tttgtcagtt acatcatcat atccttcctg    5400
gttgtggtga acatgtacat cgcggtcatc ctggagaact tcagtgttgc tactgaagaa    5460
agtgcagagc ctctgagtga ggatgacttt gagatgttct atgaggtttg ggagaagttt    5520
gatcccgatg cgacccagtt tatagagttt gccaaacttt ctgattttgc agatgccctg    5580
gatcctcctc ttctcatagc aaaacccaac aaagtccagc tcattgccat ggatctgccc    5640
atggtgagtg gtgaccggat ccactgtctt gacatcttat ttgcttttac aaagcgtgtt    5700
ttgggtgaga gtggagagat ggatgcccctt cgaatacaga tggaagagcg attcatggca    5760
tcaaacccct ccaaagtctc ttatgagccc attacgacca cgttgaaacg caaacaagag    5820
gaggtgtctg ctattattat ccagagggct tacagacgct acctcttgaa gcaaaaagtt    5880
aaaaaggtat caagtatata caagaaagac aaaggcaaag aatgtgatgg aacacccatc    5940
aaagaagata ctctcattga taaactgaat gagaattcaa ctccagagaa aaccgatatg    6000
acgccttcca ccacgtctcc accctcgtat gatagtgtga ccaaaccaga aaagaaaaa    6060 tttgaaaaag acaaatcaga aaaggaagac aaagggaaag atatcaggga aagtaaaaag    6120
taaaaagaaa ccaagaattt tccatttttgt gatcaattgt ttacagcccg tgatggtgat    6180
gtgtttgtgt caacaggact cccacaggag gtctatgcca aactgactgt ttttacaaat    6240
gtatacttaa ggtcagtgcc tataacaaga cagagacctc tggtcagcaa actgaaactc    6300
agtaaactgg agaaatagta tcgatgggag gtttctatttt tcacaaccag ctgacactgc    6360
tgaagagcag aggcgtaatg gctactcaga cgataggaac caatttaaag ggggagggga    6420
agttaaattt ttatgtaaat tcaacatgtg acacttgata atagtaattg tcaccagtgt    6480
ttatgtttta actgccacac ctgccatatt tttacaaaac gtgtgctgtg aatttatcac    6540
ttttcttttt aattcacagg ttgtttacta ttatatgtga ctattttgt aaatgggttt    6600 gtgtttgggg agagggatta aagggaggga attctacatt tctctattgt attgtataac    6660
tggatatatt ttaaatggag gcatgctgca attctcattc acacataaaa aaatcacatc    6720
acaaaaggga agagtttact tcttgtttca ggatgttttt agattttgga ggtgcttaaa    6780
tagctattcg tattttttaag gtgtctcatc cagaaaaaat ttaatgtgcc tgtaaatgtt    6840
```

```
ccatagaatc acaagcatta aagagttgtt ttattttac ataacccatt aaatgtacat    6900
gtatatatgt atatatgtat atgtgcgtgt atatacatat atatgtatac acacatgcac    6960
acacagagat atacacatac cattacattg tcattcacag tcccagcagc atgactatca    7020 cattttgat  aagtgtcctt tggcataaaa taaaaatatc ctatcagtcc tttctaagaa     7080
gcctgaattg accaaaaaac atccccacca ccactttata agttgattc tgctttatcc     7140 tgcagtattg tttagccatc ttctgctctt ggtaaggttg acatagtata tgtcaattta    7200
aaaaataaaa gtctgctttg taaatagtaa ttttacccag tggtgcatgt ttgagcaaac    7260
aaaaatgatg atttaagcac actacttatt gcatcaaata tgtaccacag taagtatagt    7320
ttgcaagctt tcaacaggta atatgatgta attggttcca ttatagtttg aagctgtcac    7380
tgctgcatgt ttatcttgcc tatgctgctg tatcttattc cttccactgt tcagaagtct    7440
aatatgggaa gccatatatc agtggtaaag tgaagcaaat tgttctacca agacctcatt    7500
cttcatgtca ttaagcaata ggttgcagca aacaaggaag agcttcttgc tttttattct    7560 tccaaccta  attgaacact caatgatgaa aagcccgact gtacaaacat gttgcaagct    7620
gcttaaatct gtttaaaata tatggttaga gttttctaag aaaatataaa tactgtaaaa    7680
agttcatttt atttttatttt tcagcctttt gtacgtaaaa tgagaaatta aaagtatctc    7740
caggtggatg tcacagtcac tattgttagt ttctgttcct agcacttta  aattgaagca    7800 cttcacaaaa taagaagcaa ggactaggat gcagtgtagg tttctgcttt tttattagta    7860
ctgtaaactt gcacacattt caatgtgaaa caaatctcaa actgagttca atgtttattt    7920
gctttcaata gtaatgcctt atcattgaaa gaggcttaaa gaaaaaaaaa atcagctgat    7980
actcttggca ttgcttgaat ccaatgtttc cacctagtct tttattcag  taatcatcag    8040 tcttttccaa tgtttgttta cacagataga tcttattgac ccatatggca ctagaactgt    8100
atcagatata atatgggatc ccagcttttt ttcctctccc acaaaaccag gtagtgaagt    8160
tatattacca gttacagcaa atactttgt  gtttcacaag caacaataaa tgtagattct    8220
ttatactgaa gctattgact tgtagtgtgt tggtgaatgc atgcaggaag atgctgttac    8280
cataaagaac ggtaaaccac attacaatca agccaaagaa taaaggttcg cttatgtata    8340
tgtatttaa                                                             8349
```

<210> SEQ ID NO 34
<211> LENGTH: 8349
<212> TYPE: DNA
<213> ORGANISM: Homo sapiens

<400> SEQUENCE: 34

```
ttcttggtgc cagcttatca atcccaaact ctgggtgtaa aagattctac agggcacttt      60
cttatgcaag gagctaaaca gtgattaaag gagcaggatg aaaagatggc acagtcagtg     120
ctggtaccgc caggacctga cagcttccgc ttctttacca gggaatccct tgctgctatt     180
gaacaacgca ttgcagaaga gaaagctaag agacccaaac aggaacgcaa ggatgaggat     240
gatgaaaatg gccaaagcc  aaacagtgac ttggaagcag aaaatctct  tccatttatt     300 tatggagaca ttcctccaga gatggtgtca gtgcccctgg aggatctgga cccctactat     360
atcaataaga aaacgtttat agtattgaat aaagggaaag caatctctcg attcagtgcc     420 accccctgccc tttacatttt aactcccttc aaccctatta gaaaattagc tattaagatt     480
ttggtacatt cttttattcaa tatgctcatt atgtgcacga ttcttaccaa ctgtgtattt     540
atgaccatga gtaaccctcc agactggaca aagaatgtgg agtataacctt tacaggaatt    600
```

```
tatacttttg aatcacttat taaaatactt gcaaggggct tttgtttaga agatttcaca      660
tttttacggg atccatggaa ttggttggat ttcacagtca ttacttttgc atatgtgaca      720
gagtttgtgg acctgggcaa tgtctcagcg ttgagaacat tcagagttct ccgagcattg      780
aaaacaattt cagtcattcc aggcctgaag accattgtgg gggccctgat ccagtcagtg      840
aagaagcttt ctgatgtcat gatcttgact gtgttctgtc taagcgtgtt tgcgctaata      900
ggattgcagt tgttcatggg caacctacga aataaatgtt tgcaatggcc tccagataat      960
tcttcctttg aaataaatat cacttccttc tttaacaatt cattggatgg aatggtact     1020 actttcaata ggacagtgag catatttaac tgggatgaat atattgagga taaaagtcac     1080 ttttatttt tagaggggca aaatgatgct ctgctttgtg gcaacagctc agatgcaggc     1140
cagtgtcctg aaggatacat ctgtgtgaag gctggtagaa accccaacta tggctacacg     1200
agctttgaca ccttta gttg ggcctttttg tccttatttc gtctcatgac tcaagacttc     1260
tgggaaaacc tttatcaact gacactacgt gctgctggga aaacgtacat gatatttttt     1320
gtgctggtca ttttcttggg ctcattctat ctaataaatt tgatcttggc tgtggtggcc     1380
atggcctatg aggaacagaa tcaggccaca ttggaagagg ctgaacagaa ggaagctgaa     1440
tttcagcaga tgctcgaaca gttgaaaaag caacaagaag aagctcaggc ggcagctgca     1500
gccgcatctg ctgaatcaag agacttcagt ggtgctggtg ggataggagt ttttcagag     1560 agttcttcag tagcatctaa gttgagctcc aaaagtgaaa aagagctgaa aaacagaaga     1620
aagaaaaaga acagaaaga acagtctgga gaagaagaga aaatgacag agtcctaaaa     1680 tcggaatctg aagacagcat aagaagaaaa ggtttccgtt tttccttgga aggaagtagg     1740
ctgacatatg aaaagagatt ttcttctcca caccagtcct tactgagcat ccgtggctcc     1800
cttttctctc caagacgcaa cagtagggcg agccttttca gcttcagagg tcgagcaaag     1860
gacattggct ctgagaatga ctttgctgat gatgagcaca gcacctttga ggacaatgac     1920
agccgaagag actctctgtt cgtgccgcac agacatggag aacggcgcca cagcaatgtc     1980
agccaggcca ccgtgcctc cagggtgctc cccatcctgc ccatgaatgg gaagatgcat     2040
agcgctgtgg actgcaatgg tgtggtctcc ctggtcgggg gccttctac cctcacatct     2100 gctgggcagc tcctaccaga gggcacaact actgaaacag aaataagaaa gagacggtcc     2160
agttcttatc atgtttccat ggatttattg gaagatccta catcaaggca agagcaatg     2220 agtatagcca gtattttgac caacaccatg gaagaacttg aagaatccag acagaaatgc     2280
ccaccatgct ggtataaatt tgctaatatg tgtttgattt gggactgttg taaaccatgg     2340
ttaaaggtga acaccttgt caacctggtt gtaatggacc catttgttga cctggccatc     2400
accatctgca ttgtcttaaa tacactcttc atggctatgg agcactatcc catgacggag     2460
cagttcagca gtgtactgtc tgttggaaac ctggtcttca cagggatctt cacagcagaa     2520
atgtttctca agataattgc catggatcca tattattact tcaagaagg ctggaatatt     2580 tttgatggtt ttattgtgag ccttagttta atggaacttg gtttggcaaa tgtggaagga     2640
ttgtcagttc tccgatcatt ccggctgctc cgagttttca gttggcaaa atcttggcca     2700 actctaaata tgctaattaa gatcattggc aattctgtgg gggctctagg aaacctcacc     2760
ttggtattgg ccatcatcgt cttcattttt gctgtggtcg gcatgcagct ctttggtaag     2820
agctacaaag aatgtgtctg caagatttcc aatgattgtg aactcccacg ctggcacatg     2880
catgactttt tccactccct cctgatcgtg ttccgcgtgc tgtgtggaga gtggatagag     2940
accatgtggg actgtatgga ggtcgctggc caaaccatgt gccttactgt cttcatgatg     3000
```

```
gtcatggtga ttggaaatct agtggttctg aacctcttct tggccttgct tttgagttcc    3060
ttcagttctg acaatcttgc tgccactgat gatgataacg aaatgaataa tctccagatt    3120
gctgtgggaa ggatgcagaa aggaatcgat tttgttaaaa gaaaaatacg tgaatttatt    3180
cagaaagcct ttgttaggaa gcagaaagct ttagatgaaa ttaaaccgct tgaagatcta    3240
aataataaaa aagacagctg tatttccaac cataccacca tagaaatagg caaagacctc    3300
aattatctca aagacggaaa tggaactact agtggcatag gcagcagtgt agaaaaatat    3360
gtcgtggatg aaagtgatta catgtcattt ataaacaacc ctagcctcac tgtgacagta    3420
ccaattgctg ttggagaatc tgactttgaa aatttaaata ctgaagaatt cagcagcgag    3480
tcagatatgg aggaaagcaa agagaagcta aatgcaacta gttcatctga aggcagcacg    3540
gttgatattg gagctcccgc cgagggagaa cagcctgagg ttgaacctga ggaatcccctt    3600 gaacctgaag cctgttttac agaagactgt gtacggaagt tcaagtgttg tcagataagc    3660
atagaagaag gcaaagggaa actctggtgg aatttgagga aaacatgcta taagatagtg    3720
gagcacaatt ggttcgaaac cttcattgtc ttcatgattc tgctgagcag tggggctctg    3780
gcctttgaag atatatacat tgagcagcga aaaaccatta agaccatgtt agaatatgct    3840
gacaaggttt tcacttacat attcattctg gaaatgctgc taaagtgggt tgcatatggt    3900
tttcaagtgt attttaccaa tgcctggtgc tggctagact tcctgattgt tgatgtctca    3960
ctggttagct taactgcaaa tgccttgggt tactcagaac ttggtgccat caaatccctc    4020
agaacactaa gagctctgag gccactgaga gctttgtccc ggtttgaagg aatgagggct    4080
gttgtaaatg ctcttttagg agccattcca tctatcatga atgtacttct ggtttgtctg    4140
atcttttggc taatattcag tatcatggga gtgaatctct ttgctggcaa gttttaccat    4200
tgtattaatt acaccactgg agagatgttt gatgtaagcg tggtcaacaa ctacagtgag    4260
tgcaaagctc tcattgagag caatcaaact gccaggtgga aaaatgtgaa agtaaacttt    4320
gataacgtag gacttggata tctgtctcta cttcaagtag ccacgtttaa gggatggatg    4380
gatattatgt atgcagctgt tgattcacga aatgtagaat tacaacccaa gtatgaagac    4440
aacctgtaca tgtatctttta ttttgtcatc tttattattt ttggttcatt ctttacctg    4500 aatcttttca ttggtgtcat catagataac ttcaaccaac agaaaaagaa gtttggaggt    4560
caagacattt ttatgacaga agaacagaag aaatactaca atgcaatgaa aaaactgggt    4620
tcaaagaaac cacaaaaacc catacctcga cctgctaaca aattccaagg aatggtcttt    4680
gattttgtaa ccaaacaagt ctttgatatc agcatcatga tcctcatctg ccttaacatg    4740
gtcaccatga tggtggaaac cgatgaccag agtcaagaaa tgacaaacat tctgtactgg    4800
attaatctgg tgtttattgt tctgttcact ggagaatgtg tgctgaaact gatctctctt    4860
cgttactact atttcactat tggatggaat attttttgatt ttgtggtggt cattctctcc    4920
attgtaggaa tgtttctggc tgaactgata gaaaagtatt ttgtgtcccc tacctgttc    4980 cgagtgatcc gtcttgccag gattggccga atcctacgtc tgatcaaagg agcaaagggg    5040
atccgcacgc tgctctttgc tttgatgatg tcccttcctg cgttgtttaa catcggcctc    5100 cttctttttcc tggtcatgtt catctacgcc atctttggga tgtccaattt tgcctatgtt    5160
aagagggaag ttgggatcga tgacatgttc aactttgaga cctttggcaa cagcatgatc    5220
tgcctgttcc aaattacaac ctctgctggc tgggatggat tgctagcacc tattcttaat    5280
agtggacctc cagactgtga ccctgacaaa gatcaccctg gaagctcagt taaaggagac    5340
tgtgggaacc catctgttgg gattttcttt tttgtcagtt acatcatcat atccttcctg    5400
```

```
gttgtggtga acatgtacat cgcggtcatc ctggagaact tcagtgttgc tactgaagaa    5460
agtgcagagc ctctgagtga ggatgacttt gagatgttct atgaggtttg ggagaagttt    5520
gatcccgatg cgacccagtt tatagagttt gccaaacttt ctgattttgc agatgccctg    5580
gatcctcctc ttctcatagc aaaacccaac aaagtccagc tcattgccat ggatctgccc    5640
atggtgagtg gtgaccggat ccactgtctt gacatcttat ttgcttttac aaagcgtgtt    5700
ttgggtgaga gtggagagat ggatgccctt cgaatacaga tggaagagcg attcatggca    5760
tcaaacccct ccaaagtctc ttatgagccc attacgacca cgttgaaacg caaacaagag    5820
gaggtgtctg ctattattat ccagagggct tacagacgct acctcttgaa gcaaaaagtt    5880
aaaaaggtat caagtatata caagaaagac aaaggcaaag aatgtgatgg aacacccatc    5940
aaagaagata ctctcattga taaactgaat gagaattcaa ctccagagaa aaccgatatg    6000
acgccttcca ccacgtctcc accctcgtat gatagtgtga ccaaaccaga aaaagaaaaa    6060
tttgaaaaag acaaatcaga aaaggaagac aaagggaaag atatcaggga aagtaaaaag    6120 taaaagaaa ccaagaattt tccattttgt gatcaattgt ttacagcccg tgatggtgat    6180
gtgtttgtgt caacaggact cccacaggag gtctatgcca aactgactgt ttttacaaat    6240
gtatacttaa ggtcagtgcc tataacaaga cagagacctc tggtcagcaa actgaactc    6300 agtaaactgg agaaatagta tcgatgggag gtttctattt tcacaaccag ctgcactgc    6360 tgaagagcag aggcgtaatg gctactcaga cgataggaac caatttaaag gggggaggga    6420
agttaaattt ttatgtaaat tcaacatgtg acacttgata atagtaattg tcaccagtgt    6480
ttatgtttta actgccacac ctgccatatt tttacaaaac gtgtgctgtg aatttatcac    6540 ttttctttt aattcacagg ttgtttacta ttatatgtga ctatttttgt aaatgggttt    6600
gtgtttgggg agagggatta aagggaggga attctacatt tctctattgt attgtataac    6660
tggatatatt ttaaatggag gcatgctgca attctcattc acacataaaa aaatcacatc    6720 acaaaggga agagtttact tcttgtttca ggatgttttt agattttga ggtgcttaaa    6780 tagctattcg tattttaag gtgtctcatc cagaaaaaat ttaatgtgcc tgtaaatgtt    6840
ccatagaatc acaagcatta aagagttgtt ttatttttac ataacccatt aaatgtacat    6900
gtatatatgt atatatgtat atgtgcgtgt atacacatat atatgtatac acacatgcac    6960
acacagagat atacacatac cattacattg tcattcacag tcccagcagc atgactatca    7020 cattttgat aagtgtcctt tggcataaaa taaaaatatc ctatcagtcc tttctaagaa    7080
gcctgaattg accaaaaaac atccccacca ccactttata aagttgattc tgctttatcc    7140
tgcagtattg tttagccatc ttctgctctt ggtaaggttg acatagtata tgtcaattta    7200
aaaaataaaa gtctgctttg taaatagtaa ttttacccag tggtgcatgt ttgagcaaac    7260
aaaaatgatg atttaagcac actacttatt gcatcaaata tgtaccacag taagtatagt    7320
ttgcaagctt tcaacaggta atatgatgta attggttcca ttatagtttg aagctgtcac    7380
tgctgcatgt ttatcttgcc tatgctgctg tatcttattc cttccactgt tcagaagtct    7440
aatatgggaa gccatatatc agtggtaaag tgaagcaaat tgttctacca agacctcatt    7500
cttcatgtca ttaagcaata ggttgcagca acaaggaag agcttcttgc ttttattct    7560 tccaacctta attgaacact caatgatgaa aagcccgact gtacaaacat gttgcaagct    7620
gcttaaatct gtttaaaata tatggttaga gttttctaag aaaatataaa tactgtaaaa    7680
agttcatttt attttatttt tcagcctttt gtacgtaaaa tgagaaatta aaagtatctt    7740
caggtggatg tcacagtcac tattgttagt ttctgttcct agcactttta aattgaagca    7800
```

-continued

```
cttcacaaaa taagaagcaa ggactaggat gcagtgtagg tttctgcttt ttttattagta    7860 ctgtaaactt gcacacattt caatgtgaaa caaatctcaa actgagttca atgtttattt    7920
gctttcaata gtaatgcctt atcattgaaa gaggcttaaa gaaaaaaaaa atcagctgat    7980
actcttggca ttgcttgaat ccaatgtttc cacctagtct ttttattcag taatcatcag    8040
tcttttccaa tgtttgttta cacagataga tcttattgac ccatatggca ctagaactgt    8100
atcagatata atatgggatc ccagcttttt ttcctctccc acaaaaccag gtagtgaagt    8160
tatattacca gttacagcaa atactttgt gtttcacaag caacaataaa tgtagattct    8220
ttatactgaa gctattgact tgtagtgtgt tggtgaatgc atgcaggaag atgctgttac    8280
cataaagaac ggtaaaccac attacaatca agccaaagaa taaggttcg cttatgtata    8340 tgtatttaa                                                             8349
```

<210> SEQ ID NO 35
<211> LENGTH: 2005
<212> TYPE: PRT
<213> ORGANISM: Homo sapiens

<400> SEQUENCE: 35

```
Met Ala Gln Ser Val Leu Val Pro Pro Gly Pro Asp Ser Phe Arg Phe
  1               5                  10                  15

Phe Thr Arg Glu Ser Leu Ala Ala Ile Glu Gln Arg Ile Ala Glu Glu
             20                  25                  30

Lys Ala Lys Arg Pro Lys Gln Glu Arg Lys Asp Glu Asp Asp Glu Asn
         35                  40                  45

Gly Pro Lys Pro Asn Ser Asp Leu Glu Ala Gly Lys Ser Leu Pro Phe
     50                  55                  60

Ile Tyr Gly Asp Ile Pro Pro Glu Met Val Ser Val Pro Leu Glu Asp
 65                  70                  75                  80

Leu Asp Pro Tyr Tyr Ile Asn Lys Lys Thr Phe Ile Val Leu Asn Lys
                 85                  90                  95

Gly Lys Ala Ile Ser Arg Phe Ser Ala Thr Pro Ala Leu Tyr Ile Leu
            100                 105                 110

Thr Pro Phe Asn Pro Ile Arg Lys Leu Ala Ile Lys Ile Leu Val His
        115                 120                 125

Ser Leu Phe Asn Met Leu Ile Met Cys Thr Ile Leu Thr Asn Cys Val
    130                 135                 140

Phe Met Thr Met Ser Asn Pro Pro Asp Trp Thr Lys Asn Val Glu Tyr
145                 150                 155                 160

Thr Phe Thr Gly Ile Tyr Thr Phe Glu Ser Leu Ile Lys Ile Leu Ala
                165                 170                 175

Arg Gly Phe Cys Leu Glu Asp Phe Thr Phe Leu Arg Asp Pro Trp Asn
            180                 185                 190

Trp Leu Asp Phe Thr Val Ile Thr Phe Ala Tyr Val Thr Glu Phe Val
        195                 200                 205

Asp Leu Gly Asn Val Ser Ala Leu Arg Thr Phe Arg Val Leu Arg Ala
    210                 215                 220

Leu Lys Thr Ile Ser Val Ile Pro Gly Leu Lys Thr Ile Val Gly Ala
225                 230                 235                 240

Leu Ile Gln Ser Val Lys Lys Leu Ser Asp Val Met Ile Leu Thr Val
                245                 250                 255

Phe Cys Leu Ser Val Phe Ala Leu Ile Gly Leu Gln Leu Phe Met Gly
            260                 265                 270

Asn Leu Arg Asn Lys Cys Leu Gln Trp Pro Pro Asp Asn Ser Ser Phe
```

-continued

```
            275                 280                 285
Glu Ile Asn Ile Thr Ser Phe Phe Asn Asn Ser Leu Asp Gly Asn Gly
290                     295                 300

Thr Thr Phe Asn Arg Thr Val Ser Ile Phe Asn Trp Asp Glu Tyr Ile
305                 310                  315                 320

Glu Asp Lys Ser His Phe Tyr Phe Leu Glu Gly Gln Asn Asp Ala Leu
                325                 330                 335

Leu Cys Gly Asn Ser Ser Asp Ala Gly Gln Cys Pro Glu Gly Tyr Ile
            340                 345                 350

Cys Val Lys Ala Gly Arg Asn Pro Asn Tyr Gly Tyr Thr Ser Phe Asp
            355                 360                 365

Thr Phe Ser Trp Ala Phe Leu Ser Leu Phe Arg Leu Met Thr Gln Asp
370                 375                 380

Phe Trp Glu Asn Leu Tyr Gln Leu Thr Leu Arg Ala Ala Gly Lys Thr
385                 390                 395                 400

Tyr Met Ile Phe Phe Val Leu Val Ile Phe Leu Gly Ser Phe Tyr Leu
                405                 410                 415

Ile Asn Leu Ile Leu Ala Val Val Ala Met Ala Tyr Glu Glu Gln Asn
            420                 425                 430

Gln Ala Thr Leu Glu Glu Ala Glu Gln Lys Glu Ala Glu Phe Gln Gln
            435                 440                 445

Met Leu Glu Gln Leu Lys Lys Gln Gln Glu Glu Ala Gln Ala Ala Ala
450                 455                 460

Ala Ala Ala Ser Ala Glu Ser Arg Asp Phe Ser Gly Ala Gly Gly Ile
465                 470                 475                 480

Gly Val Phe Ser Glu Ser Ser Ser Val Ala Ser Lys Leu Ser Ser Lys
                485                 490                 495

Ser Glu Lys Glu Leu Lys Asn Arg Arg Lys Lys Lys Gln Lys Glu
                500                 505                 510

Gln Ser Gly Glu Glu Lys Asn Asp Arg Val Leu Lys Ser Glu Ser
            515                 520                 525

Glu Asp Ser Ile Arg Arg Lys Gly Phe Arg Phe Ser Leu Glu Gly Ser
530                 535                 540

Arg Leu Thr Tyr Glu Lys Arg Phe Ser Ser Pro His Gln Ser Leu Leu
545                 550                 555                 560

Ser Ile Arg Gly Ser Leu Phe Ser Pro Arg Arg Asn Ser Arg Ala Ser
                565                 570                 575

Leu Phe Ser Phe Arg Gly Arg Ala Lys Asp Ile Gly Ser Glu Asn Asp
            580                 585                 590

Phe Ala Asp Asp Glu His Ser Thr Phe Glu Asp Asn Asp Ser Arg Arg
            595                 600                 605

Asp Ser Leu Phe Val Pro Arg Arg His Gly Glu Arg Arg His Ser Asn
            610                 615                 620

Val Ser Gln Ala Ser Arg Ala Ser Arg Val Leu Pro Ile Leu Pro Met
625                 630                 635                 640

Asn Gly Lys Met His Ser Ala Val Asp Cys Asn Gly Val Val Ser Leu
                645                 650                 655

Val Gly Gly Pro Ser Thr Leu Thr Ser Ala Gly Gln Leu Leu Pro Glu
            660                 665                 670

Gly Thr Thr Thr Glu Thr Glu Ile Arg Lys Arg Arg Ser Ser Ser Tyr
            675                 680                 685

His Val Ser Met Asp Leu Leu Glu Asp Pro Thr Ser Arg Gln Arg Ala
        690                 695                 700
```

```
Met Ser Ile Ala Ser Ile Leu Thr Asn Thr Met Glu Glu Leu Glu Glu
705                 710                 715                 720

Ser Arg Gln Lys Cys Pro Pro Cys Trp Tyr Lys Phe Ala Asn Met Cys
            725                 730                 735

Leu Ile Trp Asp Cys Cys Lys Pro Trp Leu Lys Val Lys His Leu Val
        740                 745                 750

Asn Leu Val Val Met Asp Pro Phe Val Asp Leu Ala Ile Thr Ile Cys
    755                 760                 765

Ile Val Leu Asn Thr Leu Phe Met Ala Met Glu His Tyr Pro Met Thr
770                 775                 780

Glu Gln Phe Ser Ser Val Leu Ser Val Gly Asn Leu Val Phe Thr Gly
785                 790                 795                 800

Ile Phe Thr Ala Glu Met Phe Leu Lys Ile Ile Ala Met Asp Pro Tyr
            805                 810                 815

Tyr Tyr Phe Gln Glu Gly Trp Asn Ile Phe Asp Gly Phe Ile Val Ser
        820                 825                 830

Leu Ser Leu Met Glu Leu Gly Leu Ala Asn Val Glu Gly Leu Ser Val
    835                 840                 845

Leu Arg Ser Phe Arg Leu Leu Arg Val Phe Lys Leu Ala Lys Ser Trp
850                 855                 860

Pro Thr Leu Asn Met Leu Ile Lys Ile Ile Gly Asn Ser Val Gly Ala
865                 870                 875                 880

Leu Gly Asn Leu Thr Leu Val Leu Ala Ile Ile Val Phe Ile Phe Ala
            885                 890                 895

Val Val Gly Met Gln Leu Phe Gly Lys Ser Tyr Lys Glu Cys Val Cys
        900                 905                 910

Lys Ile Ser Asn Asp Cys Glu Leu Pro Arg Trp His Met His Asp Phe
    915                 920                 925

Phe His Ser Phe Leu Ile Val Phe Arg Val Leu Cys Gly Glu Trp Ile
930                 935                 940

Glu Thr Met Trp Asp Cys Met Glu Val Ala Gly Gln Thr Met Cys Leu
945                 950                 955                 960

Thr Val Phe Met Met Val Met Val Ile Gly Asn Leu Val Val Leu Asn
            965                 970                 975

Leu Phe Leu Ala Leu Leu Leu Ser Ser Phe Ser Ser Asp Asn Leu Ala
        980                 985                 990

Ala Thr Asp Asp Asp Asn Glu Met Asn Asn Leu Gln Ile Ala Val Gly
    995                 1000                1005

Arg Met Gln Lys Gly Ile Asp Phe Val Lys Arg Lys Ile Arg Glu
    1010                1015                1020

Phe Ile Gln Lys Ala Phe Val Arg Lys Gln Lys Ala Leu Asp Glu
    1025                1030                1035

Ile Lys Pro Leu Glu Asp Leu Asn Asn Lys Lys Asp Ser Cys Ile
    1040                1045                1050

Ser Asn His Thr Thr Ile Glu Ile Gly Lys Asp Leu Asn Tyr Leu
    1055                1060                1065

Lys Asp Gly Asn Gly Thr Thr Ser Gly Ile Gly Ser Ser Val Glu
    1070                1075                1080

Lys Tyr Val Val Asp Glu Ser Asp Tyr Met Ser Phe Ile Asn Asn
    1085                1090                1095

Pro Ser Leu Thr Val Thr Val Pro Ile Ala Val Gly Glu Ser Asp
    1100                1105                1110

Phe Glu Asn Leu Asn Thr Glu Glu Phe Ser Ser Glu Ser Asp Met
    1115                1120                1125
```

```
Glu Glu Ser Lys Glu Lys Leu Asn Ala Thr Ser Ser Ser Glu Gly
    1130                1135                1140

Ser Thr Val Asp Ile Gly Ala Pro Ala Glu Gly Glu Gln Pro Glu
    1145                1150                1155

Val Glu Pro Glu Glu Ser Leu Glu Pro Glu Ala Cys Phe Thr Glu
    1160                1165                1170

Asp Cys Val Arg Lys Phe Lys Cys Cys Gln Ile Ser Ile Glu Glu
    1175                1180                1185

Gly Lys Gly Lys Leu Trp Trp Asn Leu Arg Lys Thr Cys Tyr Lys
    1190                1195                1200

Ile Val Glu His Asn Trp Phe Glu Thr Phe Ile Val Phe Met Ile
    1205                1210                1215

Leu Leu Ser Ser Gly Ala Leu Ala Phe Glu Asp Ile Tyr Ile Glu
    1220                1225                1230

Gln Arg Lys Thr Ile Lys Thr Met Leu Glu Tyr Ala Asp Lys Val
    1235                1240                1245

Phe Thr Tyr Ile Phe Ile Leu Glu Met Leu Leu Lys Trp Val Ala
    1250                1255                1260

Tyr Gly Phe Gln Val Tyr Phe Thr Asn Ala Trp Cys Trp Leu Asp
    1265                1270                1275

Phe Leu Ile Val Asp Val Ser Leu Val Ser Leu Thr Ala Asn Ala
    1280                1285                1290

Leu Gly Tyr Ser Glu Leu Gly Ala Ile Lys Ser Leu Arg Thr Leu
    1295                1300                1305

Arg Ala Leu Arg Pro Leu Arg Ala Leu Ser Arg Phe Glu Gly Met
    1310                1315                1320

Arg Ala Val Val Asn Ala Leu Leu Gly Ala Ile Pro Ser Ile Met
    1325                1330                1335

Asn Val Leu Leu Val Cys Leu Ile Phe Trp Leu Ile Phe Ser Ile
    1340                1345                1350

Met Gly Val Asn Leu Phe Ala Gly Lys Phe Tyr His Cys Ile Asn
    1355                1360                1365

Tyr Thr Thr Gly Glu Met Phe Asp Val Ser Val Val Asn Asn Tyr
    1370                1375                1380

Ser Glu Cys Lys Ala Leu Ile Glu Ser Asn Gln Thr Ala Arg Trp
    1385                1390                1395

Lys Asn Val Lys Val Asn Phe Asp Asn Val Gly Leu Gly Tyr Leu
    1400                1405                1410

Ser Leu Leu Gln Val Ala Thr Phe Lys Gly Trp Met Asp Ile Met
    1415                1420                1425

Tyr Ala Ala Val Asp Ser Arg Asn Val Glu Leu Gln Pro Lys Tyr
    1430                1435                1440

Glu Asp Asn Leu Tyr Met Tyr Leu Tyr Phe Val Ile Phe Ile Ile
    1445                1450                1455

Phe Gly Ser Phe Phe Thr Leu Asn Leu Phe Ile Gly Val Ile Ile
    1460                1465                1470

Asp Asn Phe Asn Gln Gln Lys Lys Lys Phe Gly Gly Gln Asp Ile
    1475                1480                1485

Phe Met Thr Glu Glu Gln Lys Lys Tyr Tyr Asn Ala Met Lys Lys
    1490                1495                1500

Leu Gly Ser Lys Lys Pro Gln Lys Pro Ile Pro Arg Pro Ala Asn
    1505                1510                1515

Lys Phe Gln Gly Met Val Phe Asp Phe Val Thr Lys Gln Val Phe
```

```
                 1520                1525                1530

Asp Ile Ser Ile Met Ile Leu Ile Cys Leu Asn Met Val Thr Met
    1535                1540                1545

Met Val Glu Thr Asp Asp Gln Ser Gln Glu Met Thr Asn Ile Leu
    1550                1555                1560

Tyr Trp Ile Asn Leu Val Phe Ile Val Leu Phe Thr Gly Glu Cys
    1565                1570                1575

Val Leu Lys Leu Ile Ser Leu Arg Tyr Tyr Phe Thr Ile Gly
    1580                1585                1590

Trp Asn Ile Phe Asp Phe Val Val Ile Leu Ser Ile Val Gly
    1595                1600                1605

Met Phe Leu Ala Glu Leu Ile Glu Lys Tyr Phe Val Ser Pro Thr
    1610                1615                1620

Leu Phe Arg Val Ile Arg Leu Ala Arg Ile Gly Arg Ile Leu Arg
    1625                1630                1635

Leu Ile Lys Gly Ala Lys Gly Ile Arg Thr Leu Leu Phe Ala Leu
    1640                1645                1650

Met Met Ser Leu Pro Ala Leu Phe Asn Ile Gly Leu Leu Leu Phe
    1655                1660                1665

Leu Val Met Phe Ile Tyr Ala Ile Phe Gly Met Ser Asn Phe Ala
    1670                1675                1680

Tyr Val Lys Arg Glu Val Gly Ile Asp Asp Met Phe Asn Phe Glu
    1685                1690                1695

Thr Phe Gly Asn Ser Met Ile Cys Leu Phe Gln Ile Thr Thr Ser
    1700                1705                1710

Ala Gly Trp Asp Gly Leu Leu Ala Pro Ile Leu Asn Ser Gly Pro
    1715                1720                1725

Pro Asp Cys Asp Pro Asp Lys Asp His Pro Gly Ser Ser Val Lys
    1730                1735                1740

Gly Asp Cys Gly Asn Pro Ser Val Gly Ile Phe Phe Phe Val Ser
    1745                1750                1755

Tyr Ile Ile Ile Ser Phe Leu Val Val Val Asn Met Tyr Ile Ala
    1760                1765                1770

Val Ile Leu Glu Asn Phe Ser Val Ala Thr Glu Glu Ser Ala Glu
    1775                1780                1785

Pro Leu Ser Glu Asp Asp Phe Glu Met Phe Tyr Glu Val Trp Glu
    1790                1795                1800

Lys Phe Asp Pro Asp Ala Thr Gln Phe Ile Glu Phe Ala Lys Leu
    1805                1810                1815

Ser Asp Phe Ala Asp Ala Leu Asp Pro Pro Leu Leu Ile Ala Lys
    1820                1825                1830

Pro Asn Lys Val Gln Leu Ile Ala Met Asp Leu Pro Met Val Ser
    1835                1840                1845

Gly Asp Arg Ile His Cys Leu Asp Ile Leu Phe Ala Phe Thr Lys
    1850                1855                1860

Arg Val Leu Gly Glu Ser Gly Glu Met Asp Ala Leu Arg Ile Gln
    1865                1870                1875

Met Glu Glu Arg Phe Met Ala Ser Asn Pro Ser Lys Val Ser Tyr
    1880                1885                1890

Glu Pro Ile Thr Thr Thr Leu Lys Arg Lys Gln Glu Glu Val Ser
    1895                1900                1905

Ala Ile Ile Ile Gln Arg Ala Tyr Arg Arg Tyr Leu Leu Lys Gln
    1910                1915                1920
```

-continued

Lys Val Lys Lys Val Ser Ser Ile Tyr Lys Lys Asp Lys Gly Lys
     1925                1930                1935

Glu Cys Asp Gly Thr Pro Ile Lys Glu Asp Thr Leu Ile Asp Lys
     1940                1945                1950

Leu Asn Glu Asn Ser Thr Pro Glu Lys Thr Asp Met Thr Pro Ser
     1955                1960                1965

Thr Thr Ser Pro Pro Ser Tyr Asp Ser Val Thr Lys Pro Glu Lys
     1970                1975                1980

Glu Lys Phe Glu Lys Asp Lys Ser Glu Lys Glu Asp Lys Gly Lys
     1985                1990                1995

Asp Ile Arg Glu Ser Lys Lys
     2000                2005

<210> SEQ ID NO 36
<211> LENGTH: 2005
<212> TYPE: PRT
<213> ORGANISM: Homo sapiens

<400> SEQUENCE: 36

Met Ala Gln Ser Val Leu Val Pro Pro Gly Pro Asp Ser Phe Arg Phe
1               5                   10                  15

Phe Thr Arg Glu Ser Leu Ala Ala Ile Glu Gln Arg Ile Ala Glu Glu
            20                  25                  30

Lys Ala Lys Arg Pro Lys Gln Glu Arg Lys Asp Glu Asp Asp Glu Asn
        35                  40                  45

Gly Pro Lys Pro Asn Ser Asp Leu Glu Ala Gly Lys Ser Leu Pro Phe
    50                  55                  60

Ile Tyr Gly Asp Ile Pro Pro Glu Met Val Ser Val Pro Leu Glu Asp
65                  70                  75                  80

Leu Asp Pro Tyr Tyr Ile Asn Lys Lys Thr Phe Ile Val Leu Asn Lys
                85                  90                  95

Gly Lys Ala Ile Ser Arg Phe Ser Ala Thr Pro Ala Leu Tyr Ile Leu
            100                 105                 110

Thr Pro Phe Asn Pro Ile Arg Lys Leu Ala Ile Lys Ile Leu Val His
        115                 120                 125

Ser Leu Phe Asn Met Leu Ile Met Cys Thr Ile Leu Thr Asn Cys Val
    130                 135                 140

Phe Met Thr Met Ser Asn Pro Pro Asp Trp Thr Lys Asn Val Glu Tyr
145                 150                 155                 160

Thr Phe Thr Gly Ile Tyr Thr Phe Glu Ser Leu Ile Lys Ile Leu Ala
                165                 170                 175

Arg Gly Phe Cys Leu Glu Asp Phe Thr Phe Leu Arg Asp Pro Trp Asn
            180                 185                 190

Trp Leu Asp Phe Thr Val Ile Thr Phe Ala Tyr Val Thr Glu Phe Val
        195                 200                 205

Asn Leu Gly Asn Val Ser Ala Leu Arg Thr Phe Arg Val Leu Arg Ala
    210                 215                 220

Leu Lys Thr Ile Ser Val Ile Pro Gly Leu Lys Thr Ile Val Gly Ala
225                 230                 235                 240

Leu Ile Gln Ser Val Lys Lys Leu Ser Asp Val Met Ile Leu Thr Val
                245                 250                 255

Phe Cys Leu Ser Val Phe Ala Leu Ile Gly Leu Gln Leu Phe Met Gly
            260                 265                 270

Asn Leu Arg Asn Lys Cys Leu Gln Trp Pro Pro Asp Asn Ser Ser Phe
        275                 280                 285

-continued

```
Glu Ile Asn Ile Thr Ser Phe Phe Asn Asn Ser Leu Asp Gly Asn Gly
290                 295                 300
Thr Thr Phe Asn Arg Thr Val Ser Ile Phe Asn Trp Asp Glu Tyr Ile
305                 310                 315                 320
Glu Asp Lys Ser His Phe Tyr Phe Leu Glu Gly Gln Asn Asp Ala Leu
                325                 330                 335
Leu Cys Gly Asn Ser Ser Asp Ala Gly Gln Cys Pro Glu Gly Tyr Ile
                340                 345                 350
Cys Val Lys Ala Gly Arg Asn Pro Asn Tyr Gly Tyr Thr Ser Phe Asp
                355                 360                 365
Thr Phe Ser Trp Ala Phe Leu Ser Leu Phe Arg Leu Met Thr Gln Asp
370                 375                 380
Phe Trp Glu Asn Leu Tyr Gln Leu Thr Leu Arg Ala Ala Gly Lys Thr
385                 390                 395                 400
Tyr Met Ile Phe Phe Val Leu Val Ile Phe Leu Gly Ser Phe Tyr Leu
                405                 410                 415
Ile Asn Leu Ile Leu Ala Val Val Ala Met Ala Tyr Glu Glu Gln Asn
                420                 425                 430
Gln Ala Thr Leu Glu Glu Ala Glu Gln Lys Glu Ala Glu Phe Gln Gln
                435                 440                 445
Met Leu Glu Gln Leu Lys Lys Gln Gln Glu Glu Ala Gln Ala Ala Ala
450                 455                 460
Ala Ala Ala Ser Ala Glu Ser Arg Asp Phe Ser Gly Ala Gly Gly Ile
465                 470                 475                 480
Gly Val Phe Ser Glu Ser Ser Ser Val Ala Ser Lys Leu Ser Ser Lys
                485                 490                 495
Ser Glu Lys Glu Leu Lys Asn Arg Arg Lys Lys Lys Gln Lys Glu
                500                 505                 510
Gln Ser Gly Glu Glu Lys Asn Asp Arg Val Leu Lys Ser Glu Ser
                515                 520                 525
Glu Asp Ser Ile Arg Arg Lys Gly Phe Arg Phe Ser Leu Glu Gly Ser
530                 535                 540
Arg Leu Thr Tyr Glu Lys Arg Phe Ser Ser Pro His Gln Ser Leu Leu
545                 550                 555                 560
Ser Ile Arg Gly Ser Leu Phe Ser Pro Arg Arg Asn Ser Arg Ala Ser
                565                 570                 575
Leu Phe Ser Phe Arg Gly Arg Ala Lys Asp Ile Gly Ser Glu Asn Asp
                580                 585                 590
Phe Ala Asp Asp Glu His Ser Thr Phe Glu Asp Asn Asp Ser Arg Arg
                595                 600                 605
Asp Ser Leu Phe Val Pro His Arg His Gly Glu Arg Arg His Ser Asn
                610                 615                 620
Val Ser Gln Ala Ser Arg Ala Ser Arg Val Leu Pro Ile Leu Pro Met
625                 630                 635                 640
Asn Gly Lys Met His Ser Ala Val Asp Cys Asn Gly Val Val Ser Leu
                645                 650                 655
Val Gly Gly Pro Ser Thr Leu Thr Ser Ala Gly Gln Leu Leu Pro Glu
                660                 665                 670
Gly Thr Thr Thr Glu Thr Glu Ile Arg Lys Arg Arg Ser Ser Ser Tyr
                675                 680                 685
His Val Ser Met Asp Leu Leu Glu Asp Pro Thr Ser Arg Gln Arg Ala
                690                 695                 700
Met Ser Ile Ala Ser Ile Leu Thr Asn Thr Met Glu Glu Leu Glu Glu
705                 710                 715                 720
```

```
Ser Arg Gln Lys Cys Pro Pro Cys Trp Tyr Lys Phe Ala Asn Met Cys
            725                 730                 735

Leu Ile Trp Asp Cys Cys Lys Pro Trp Leu Lys Val Lys His Leu Val
            740                 745                 750

Asn Leu Val Val Met Asp Pro Phe Val Asp Leu Ala Ile Thr Ile Cys
            755                 760                 765

Ile Val Leu Asn Thr Leu Phe Met Ala Met Glu His Tyr Pro Met Thr
770                 775                 780

Glu Gln Phe Ser Ser Val Leu Ser Val Gly Asn Leu Val Phe Thr Gly
785                 790                 795                 800

Ile Phe Thr Ala Glu Met Phe Leu Lys Ile Ile Ala Met Asp Pro Tyr
                805                 810                 815

Tyr Tyr Phe Gln Glu Gly Trp Asn Ile Phe Asp Gly Phe Ile Val Ser
                820                 825                 830

Leu Ser Leu Met Glu Leu Gly Leu Ala Asn Val Glu Gly Leu Ser Val
                835                 840                 845

Leu Arg Ser Phe Arg Leu Leu Arg Val Phe Lys Leu Ala Lys Ser Trp
            850                 855                 860

Pro Thr Leu Asn Met Leu Ile Lys Ile Ile Gly Asn Ser Val Gly Ala
865                 870                 875                 880

Leu Gly Asn Leu Thr Leu Val Leu Ala Ile Ile Val Phe Ile Phe Ala
                885                 890                 895

Val Val Gly Met Gln Leu Phe Gly Lys Ser Tyr Lys Glu Cys Val Cys
                900                 905                 910

Lys Ile Ser Asn Asp Cys Glu Leu Pro Arg Trp His Met His Asp Phe
            915                 920                 925

Phe His Ser Phe Leu Ile Val Phe Arg Val Leu Cys Gly Glu Trp Ile
            930                 935                 940

Glu Thr Met Trp Asp Cys Met Glu Val Ala Gly Gln Thr Met Cys Leu
945                 950                 955                 960

Thr Val Phe Met Met Val Met Val Ile Gly Asn Leu Val Val Leu Asn
                965                 970                 975

Leu Phe Leu Ala Leu Leu Leu Ser Ser Phe Ser Ser Asp Asn Leu Ala
                980                 985                 990

Ala Thr Asp Asp Asp Asn Glu Met Asn Asn Leu Gln Ile Ala Val Gly
                995                 1000                1005

Arg Met Gln Lys Gly Ile Asp Phe Val Lys Arg Lys Ile Arg Glu
    1010                1015                1020

Phe Ile Gln Lys Ala Phe Val Arg Lys Gln Lys Ala Leu Asp Glu
    1025                1030                1035

Ile Lys Pro Leu Glu Asp Leu Asn Asn Lys Lys Asp Ser Cys Ile
    1040                1045                1050

Ser Asn His Thr Thr Ile Glu Ile Gly Lys Asp Leu Asn Tyr Leu
    1055                1060                1065

Lys Asp Gly Asn Gly Thr Thr Ser Gly Ile Gly Ser Ser Val Glu
    1070                1075                1080

Lys Tyr Val Val Asp Glu Ser Asp Tyr Met Ser Phe Ile Asn Asn
    1085                1090                1095

Pro Ser Leu Thr Val Thr Val Pro Ile Ala Val Gly Glu Ser Asp
    1100                1105                1110

Phe Glu Asn Leu Asn Thr Glu Phe Ser Ser Glu Ser Asp Met
    1115                1120                1125

Glu Glu Ser Lys Glu Lys Leu Asn Ala Thr Ser Ser Ser Glu Gly
```

```
              1130                1135                1140

Ser  Thr  Val  Asp  Ile  Gly  Ala  Pro  Ala  Glu  Gly  Glu  Gln  Pro  Glu
     1145                1150                1155

Val  Glu  Pro  Glu  Glu  Ser  Leu  Glu  Pro  Glu  Ala  Cys  Phe  Thr  Glu
     1160                1165                1170

Asp  Cys  Val  Arg  Lys  Phe  Lys  Cys  Cys  Gln  Ile  Ser  Ile  Glu  Glu
     1175                1180                1185

Gly  Lys  Gly  Lys  Leu  Trp  Trp  Asn  Leu  Arg  Lys  Thr  Cys  Tyr  Lys
     1190                1195                1200

Ile  Val  Glu  His  Asn  Trp  Phe  Glu  Thr  Phe  Ile  Val  Phe  Met  Ile
     1205                1210                1215

Leu  Leu  Ser  Ser  Gly  Ala  Leu  Ala  Phe  Glu  Asp  Ile  Tyr  Ile  Glu
     1220                1225                1230

Gln  Arg  Lys  Thr  Ile  Lys  Thr  Met  Leu  Glu  Tyr  Ala  Asp  Lys  Val
     1235                1240                1245

Phe  Thr  Tyr  Ile  Phe  Ile  Leu  Glu  Met  Leu  Leu  Lys  Trp  Val  Ala
     1250                1255                1260

Tyr  Gly  Phe  Gln  Val  Tyr  Phe  Thr  Asn  Ala  Trp  Cys  Trp  Leu  Asp
     1265                1270                1275

Phe  Leu  Ile  Val  Asp  Val  Ser  Leu  Val  Ser  Leu  Thr  Ala  Asn  Ala
     1280                1285                1290

Leu  Gly  Tyr  Ser  Glu  Leu  Gly  Ala  Ile  Lys  Ser  Leu  Arg  Thr  Leu
     1295                1300                1305

Arg  Ala  Leu  Arg  Pro  Leu  Arg  Ala  Leu  Ser  Arg  Phe  Glu  Gly  Met
     1310                1315                1320

Arg  Ala  Val  Val  Asn  Ala  Leu  Leu  Gly  Ala  Ile  Pro  Ser  Ile  Met
     1325                1330                1335

Asn  Val  Leu  Leu  Val  Cys  Leu  Ile  Phe  Trp  Leu  Ile  Phe  Ser  Ile
     1340                1345                1350

Met  Gly  Val  Asn  Leu  Phe  Ala  Gly  Lys  Phe  Tyr  His  Cys  Ile  Asn
     1355                1360                1365

Tyr  Thr  Thr  Gly  Glu  Met  Phe  Asp  Val  Ser  Val  Val  Asn  Asn  Tyr
     1370                1375                1380

Ser  Glu  Cys  Lys  Ala  Leu  Ile  Glu  Ser  Asn  Gln  Thr  Ala  Arg  Trp
     1385                1390                1395

Lys  Asn  Val  Lys  Val  Asn  Phe  Asp  Asn  Val  Gly  Leu  Gly  Tyr  Leu
     1400                1405                1410

Ser  Leu  Leu  Gln  Val  Ala  Thr  Phe  Lys  Gly  Trp  Met  Asp  Ile  Met
     1415                1420                1425

Tyr  Ala  Ala  Val  Asp  Ser  Arg  Asn  Val  Glu  Leu  Gln  Pro  Lys  Tyr
     1430                1435                1440

Glu  Asp  Asn  Leu  Tyr  Met  Tyr  Leu  Tyr  Phe  Val  Ile  Phe  Ile  Ile
     1445                1450                1455

Phe  Gly  Ser  Phe  Phe  Thr  Leu  Asn  Leu  Phe  Ile  Gly  Val  Ile  Ile
     1460                1465                1470

Asp  Asn  Phe  Asn  Gln  Gln  Lys  Lys  Lys  Phe  Gly  Gly  Gln  Asp  Ile
     1475                1480                1485

Phe  Met  Thr  Glu  Glu  Gln  Lys  Lys  Tyr  Tyr  Asn  Ala  Met  Lys  Lys
     1490                1495                1500

Leu  Gly  Ser  Lys  Lys  Pro  Gln  Lys  Pro  Ile  Pro  Arg  Pro  Ala  Asn
     1505                1510                1515

Lys  Phe  Gln  Gly  Met  Val  Phe  Asp  Phe  Val  Thr  Lys  Gln  Val  Phe
     1520                1525                1530
```

-continued

```
Asp Ile Ser Ile Met Ile Leu Ile Cys Leu Asn Met Val Thr Met
1535                1540                1545

Met Val Glu Thr Asp Asp Gln Ser Gln Glu Met Thr Asn Ile Leu
1550                1555                1560

Tyr Trp Ile Asn Leu Val Phe Ile Val Leu Phe Thr Gly Glu Cys
1565                1570                1575

Val Leu Lys Leu Ile Ser Leu Arg Tyr Tyr Phe Thr Ile Gly
1580                1585                1590

Trp Asn Ile Phe Asp Phe Val Val Val Ile Leu Ser Ile Val Gly
1595                1600                1605

Met Phe Leu Ala Glu Leu Ile Glu Lys Tyr Phe Val Ser Pro Thr
1610                1615                1620

Leu Phe Arg Val Ile Arg Leu Ala Arg Ile Gly Arg Ile Leu Arg
1625                1630                1635

Leu Ile Lys Gly Ala Lys Gly Ile Arg Thr Leu Leu Phe Ala Leu
1640                1645                1650

Met Met Ser Leu Pro Ala Leu Phe Asn Ile Gly Leu Leu Leu Phe
1655                1660                1665

Leu Val Met Phe Ile Tyr Ala Ile Phe Gly Met Ser Asn Phe Ala
1670                1675                1680

Tyr Val Lys Arg Glu Val Gly Ile Asp Asp Met Phe Asn Phe Glu
1685                1690                1695

Thr Phe Gly Asn Ser Met Ile Cys Leu Phe Gln Ile Thr Thr Ser
1700                1705                1710

Ala Gly Trp Asp Gly Leu Leu Ala Pro Ile Leu Asn Ser Gly Pro
1715                1720                1725

Pro Asp Cys Asp Pro Asp Lys Asp His Pro Gly Ser Ser Val Lys
1730                1735                1740

Gly Asp Cys Gly Asn Pro Ser Val Gly Ile Phe Phe Phe Val Ser
1745                1750                1755

Tyr Ile Ile Ile Ser Phe Leu Val Val Val Asn Met Tyr Ile Ala
1760                1765                1770

Val Ile Leu Glu Asn Phe Ser Val Ala Thr Glu Glu Ser Ala Glu
1775                1780                1785

Pro Leu Ser Glu Asp Asp Phe Glu Met Phe Tyr Glu Val Trp Glu
1790                1795                1800

Lys Phe Asp Pro Asp Ala Thr Gln Phe Ile Glu Phe Ala Lys Leu
1805                1810                1815

Ser Asp Phe Ala Asp Ala Leu Asp Pro Pro Leu Leu Ile Ala Lys
1820                1825                1830

Pro Asn Lys Val Gln Leu Ile Ala Met Asp Leu Pro Met Val Ser
1835                1840                1845

Gly Asp Arg Ile His Cys Leu Asp Ile Leu Phe Ala Phe Thr Lys
1850                1855                1860

Arg Val Leu Gly Glu Ser Gly Glu Met Asp Ala Leu Arg Ile Gln
1865                1870                1875

Met Glu Glu Arg Phe Met Ala Ser Asn Pro Ser Lys Val Ser Tyr
1880                1885                1890

Glu Pro Ile Thr Thr Thr Leu Lys Arg Lys Gln Glu Glu Val Ser
1895                1900                1905

Ala Ile Ile Ile Gln Arg Ala Tyr Arg Arg Tyr Leu Leu Lys Gln
1910                1915                1920

Lys Val Lys Lys Val Ser Ser Ile Tyr Lys Lys Asp Lys Gly Lys
1925                1930                1935
```

```
Glu Cys Asp Gly Thr Pro Ile Lys Glu Asp Thr Leu Ile Asp Lys
    1940                1945                1950

Leu Asn Glu Asn Ser Thr Pro Glu Lys Thr Asp Met Thr Pro Ser
    1955                1960                1965

Thr Thr Ser Pro Pro Ser Tyr Asp Ser Val Thr Lys Pro Glu Lys
    1970                1975                1980

Glu Lys Phe Glu Lys Asp Lys Ser Glu Lys Glu Asp Lys Gly Lys
    1985                1990                1995

Asp Ile Arg Glu Ser Lys Lys
    2000                2005

<210> SEQ ID NO 37
<211> LENGTH: 912
<212> TYPE: DNA
<213> ORGANISM: Homo sapiens

<400> SEQUENCE: 37
gaattcttta tatgggttga atgactttct gacatagcaa ataaaaagca tgaggagaag       60
cattatctgt taacaaaatt aacacttaaa atcaacaaag ttttaatgtt tcgttccaag      120
aaaagcctgt ggaagatcag ttccacaact gagagctttg gctgcttca gacatatgtc      180 tgtgtgtacg ctgtgaaggt gtttctcttc acagttcccc gccctctagt ggtagttaca      240
ataatgccat tttgtagtcc ctgtacagga aatgcctctt cttacttcag ttaccagaat      300
ccttttacag gaagttaggt gtggtctttg aaggagaatt aaaaaaaaaa aaaaaaaaa       360 aaaaaagatt ttttttttt taaagcatga tggaatttta gctgcagtct tcttggggcc      420
agcttatcaa tcccaaactc tggggtaaa agattctaca ggggtaatgt tttattattc       480
ttattatgct tattctctgt gatgcttctc tacctttaca gtagtagaat ccttggggaa      540
atctgcagag ggaccacttt cattttgaag ctgctggctg catgttttag catgtctctt      600
ctattagaga atccaggcat ggcagtttcc tcccccagtg tgcaaggacc atcttcatgc      660
ctatgtctgt cgctaggcat gagggtctct aggaatgggt gaaaaaatg agggatgttt       720 tggaggcact ataatactgg ggagggcagt ctgctagctg gtagctgaaa ggtcctggtt      780
tacttcaaca ttttttttaa ataaaactgt gcagtagttt ttgttatttt agggttccct      840
ctgttttatc tggtgtatgc tgcagaagtg aactgcataa cacatttcac tcttagaaat      900
gcattccata ta                                                         912

<210> SEQ ID NO 38
<211> LENGTH: 722
<212> TYPE: DNA
<213> ORGANISM: Homo sapiens

<400> SEQUENCE: 38
ctcagtgcat gtaactgaca caatcacctc tatctaatgg tcatgcttct tacctcctgt       60
tctgtagcac tttcttatgc aaggagctaa acagtgatta aggagcagg atgaaaagat       120 ggcacagtca gtgctggtac cgccaggacc tgacagcttc cgcttcttta ccagggaatc      180
ccttgctgct attgaacaac gcattgcaga agagaaagct aagagaccca acaggaacg       240 caaggatgag gatgatgaaa atggcccaaa gccaaacagt gacttggaag cagsaaaatc      300 tcttccatt atttatggag acattcctcc agagatggtg tcagtgcccc tggaggatct       360
ggacccctac tatatcaata agaaagtgag ttcttagtca agttgccttc actgcctatt      420
tactaattgg ttctgggcta gtcccaggga tgatggtgaa aaggctggc ctccttccct       480
```

```
ctgtctaaag tatcactaag atgctggatg ggcctgaccg tgtaatggac caatgatcct      540
agaagtcttt tggaagcact catttgaacc tgcatttgtg agacaggcag agaactggtg      600
aggcatcctc cagcgcggga attaaggaag acaaaagcc tattcacctt cttgaataca       660
aattatatgc ttaaaccagt gtaaattgac cctgattccc taataatgtt gagaagcaaa      720
aa                                                                     722
```

```
<210> SEQ ID NO 39
<211> LENGTH: 561
<212> TYPE: DNA
<213> ORGANISM: Homo sapiens

<400> SEQUENCE: 39
cctatggcat tgatcacaaa ttttcttaat aatcctcatg tcatttatca aatttaggaa       60
agtttatagt gctcagaaaa aaaaagcatc tatcttcatg tcatatgatg gtaattatta      120
tgttatacac tattttacag ggcaatattt ataataatg gttttacttt tctcttaaaa       180
tattcttaat atatattcta agttttgttt tatgtgttgt gttttctttt tcagacgttt      240
atagtattga ataagggaa agcaatctct cgattcagtg ccaccctgc cctttacatt        300 ttaactccct tcaaccctat tagaaaatta gctattaaga ttttggtaca ttcatatcct      360
ttttcaaatc gtcacttaat atgattttct tctttgacca agttattgag ctacacattt      420
tccaaaatat ctgtggttgg caatgttatg tgttctttct ttttctttcc ttttactcaa      480
tcgttagcat gttgcaaaat gagatcacag gtaagtgaat tactttcccc cgtcttctaa      540
gtgtttcttc tctacccaac t                                                561

<210> SEQ ID NO 40
<211> LENGTH: 510
<212> TYPE: DNA
<213> ORGANISM: Homo sapiens

<400> SEQUENCE: 40
acctaaatag cctcaaaata gttgatggct tggcctgaag acaagatcta aatatgaggt       60
tgctgagtta tagaaatggc aaaaaaaagg gtcaataata gaataataag caacaaaata      120
atagtaagca ctaaagtttt aaacttcatg gtggtgaagg catggtagtg cataaaagta      180
agatttttcc attgaacttt gtcttccttg acgatattct actttattca atatgctcat      240
tatgtgcacg attcttacca actgtgtatt tatgaccatg agtaaccctc cagactggac      300
aaagaatgtg gagtaagtat aaatattttt caatattgac ctcccttat gtttcatatt       360 gtgcttttaa caccttgaga cctcctcaat ttctttaaca aatcatgcta gctactgtta      420
accagaccct gattcaaatt catttctgtc actaaatgtc ttctaggaca aagcttgtag      480
tgggctcact tagttgtgta aattactgca                                       510

<210> SEQ ID NO 41
<211> LENGTH: 370
<212> TYPE: DNA
<213> ORGANISM: Homo sapiens
<220> FEATURE:
<221> NAME/KEY: misc_feature
<222> LOCATION: (293)..(293)
<223> OTHER INFORMATION: n= a, c, t or g

<400> SEQUENCE: 41
taagatatgt acttgtaaat taaccactag attttttaatg tgagcttggc tattgtctct      60
caggtatacc tttacaggaa tttatacttt tgaatcactt attaaaatac ttgcaagggg     120
```

```
cttttgttta gaagatttca cattttttacg ggatccatgg aattggttgg atttcacagt      180
cattactttt gcgtaagtat cttaatacat tttctatcct ggaagagtaa atcactggtg      240
ggagcctata ctatattttc cttggtggct tgccttgaca gaccaagcat ttntcttagt      300
aatcatagtt ttcttccaat caaattatcc agtttggaga aattaggaac tatcatagta      360
aattacatgg                                                             370
```

```
<210> SEQ ID NO 42
<211> LENGTH: 370
<212> TYPE: DNA
<213> ORGANISM: Homo sapiens
<220> FEATURE:
<221> NAME/KEY: misc_feature
<222> LOCATION: (133)..(133)
<223> OTHER INFORMATION: n = a, c, t or g

<400> SEQUENCE: 42
caattagcac tgtaaagtaa taaagttttcc caaataacag agattatgat tgatgacaat      60
gccattttcc tcttaattgg gaaagctgat ggcgacactc atgaaattaa aaaggtcttg      120
atgaaagacc aangaagacg tagatttccc taaattctga ataactctga tttaattcta      180
caggtatgta acagaatttg taaacctagg caatgtttca gctcttcgaa cttttcagagt     240 cttgagagct ttgaaaacta tttctgtaat tccaggtaag aagaaaatgg tataaggtgg      300 taggccccctt atatctccaa ctgtttcttg tgttctgtca ttgtgtttgt gtgtgaaccc     360
cctattacag                                                             370
```

```
<210> SEQ ID NO 43
<211> LENGTH: 410
<212> TYPE: DNA
<213> ORGANISM: Homo sapiens

<400> SEQUENCE: 43
gtaagaagaa aatggtataa ggtggtaggc cccttatatc tccaactgtt tcttgtgttc      60
tgtcattgtg tttgtgtgtg aaccccctat tacagatatg tgacagagtt tgtggacctg     120
ggcaatgtct cagcgttgag aacattcaga gttctccgag cattgaaaac aatttcagtc     180
attccaggtg agagctaggt taaacaccga ggctgacttt agctacagtg gtgctacaat     240 cacagcttt tgtcagaagc cttgttgcta gttgcatatt gcaaataaat atgtaaaaaa     300
gcaagaattg gtacatcatt ttttggatgg atttgattct ttgcttttta cccgttgctt     360
tctttaaaac tattctaaat cagcctttga gtttaacaag tgttgcatga              410
```

```
<210> SEQ ID NO 44
<211> LENGTH: 1066
<212> TYPE: DNA
<213> ORGANISM: Homo sapiens
<220> FEATURE:
<221> NAME/KEY: misc_feature
<222> LOCATION: (229)..(229)
<223> OTHER INFORMATION: n = a, c, t or g

<400> SEQUENCE: 44
aaagagtgtt tggaaataca catttggttc atttccattc acagttttct aatgaacata      60
caagttctgc tttcattcat tttcaccagc tagtaggctt tcatgaaaaa tgttattcaa     120
tcacaaacat taaactaata ttgttggcat tctgcatgac attttttattt tccaggccaa    180 gctcatgata tttttgccgg taaaatagct gttgagtagt atatttaant tccccttct      240 gattttgttt gtaggcctga agaccattgt ggggcccctg atccagtcag tgaagaagct    300
```

```
ttctgatgtc atgatcttga ctgtgttctg tctaagcgtg tttgcgctaa taggattgca    360
gttgttcatg ggcaacctac gaaataaatg tttgcaatgg cctccagata attcttcctt    420
tgaaataaat atcacttcct tctttaacaa ttcattggat gggaatggta ctactttcaa    480
taggacagtg agcatattta actgggatga atatattgag gataaaagta agatatactc    540
tataaaccat taagttgttt agttctctaa atattaaata ttatatataa tggaaattat    600
ctcaatttag atgtgaatca agtgacttag actaatttaa gatgatttaa tacatataaa    660
agagatatca aaggatacct tattctattt ttsttatctg tccattgata tagtaaaagt    720
tctcatttga aaatgtgttg tcttatactc atgttgaaag taatttcata ttatgccata    780
ttaaaaagg tttatttggt agacattaat caggttttc agtcatttta ataaataagt     840
cagtagtttg aactattcmg cgtattccac tgaaatgtcg ttaagaagac tgaggggaaa    900
taatttggcc ctatttggtt gatgcaacat atgtattgag tacatatgct atatctgaaa    960
ctagagaaac catttatcaa gatgaaataa gaatttgtgt gctcctcaga aggttaagta   1020
accctgattt agccattcac ttcatccata ttctaattag tccctt               1066
```

```
<210> SEQ ID NO 45
<211> LENGTH: 385
<212> TYPE: DNA
<213> ORGANISM: Homo sapiens

<400> SEQUENCE: 45
```

```
gttcaattat tgtgaaaaat cttctttagc catatatatt tattagttta tccatctcat     60
tatgattgaa acatttgtg agctttgcca cctaaacagg gtggctgaag tgttttacag    120
gattttaatg attcttttcta ttcctttctc tttaaatagg tcacttttat tttttacagg   180
ggcaaaatga tgctctgctt tgtggcaaca gctcagatgc agggtaagtg tatgcttcct    240
actgagtttc agtccacact gctccatcag tgtcaataac ctgccacctc ccactcatcc    300
agtcccacca ctcctcactc aaaaccctcc ataaattcta cttcacggtg actctcagaa    360
tgaccaggat aagtgtagat tctca                                         385
```

```
<210> SEQ ID NO 46
<211> LENGTH: 430
<212> TYPE: DNA
<213> ORGANISM: Homo sapiens

<400> SEQUENCE: 46
```

```
tataataatg acaattatga atcacagagg aatccacaaa gtagacctta tagattctgt     60
cattatataa atcagtccac ttagtgctga gttaagtact gggtaaggtg agagaaatcg    120
gcttttttct agtgcctgta taaaacagac attggcatat attaaaacag gaaaccaat     180
tagcagactt gccgttattg actycctctc tttcctctaa cctaattaca gccagtgtcc    240
tgaaggatac atctgtgtga aggctggtag aaaccccaac tatggctaca cgagctttga    300
cacctttagt tgggcctttt tgtccttatt tcgtctcatg actcaagact tctgggaaaa    360
cctttatcaa ctggtgagaa cagataaaat catтттттctg agaatcataa aacaccgaac    420
tcaagagaat                                                           430
```

```
<210> SEQ ID NO 47
<211> LENGTH: 646
<212> TYPE: DNA
<213> ORGANISM: Homo sapiens

<400> SEQUENCE: 47
```

```
tgctgtagaa tatttatta cttagagtgt aagtttgtaa catcctatat aaaatttatt    60
aaaatctctc ttccattttg cagacactac gtgctgctgg gaaaacgtac atgatatttt   120
ttgtgctggt catttcttg ggctcattct atctaataaa tttgatcttg gctgtggtgg   180
ccatggccta tgaggaacag aatcaggcca cattggaaga ggctgaacag aaggaagctg   240
aatttcagca gatgctcgaa cagttgaaaa agcaacaaga agaagctcag gtatagtgaa   300
caagcatacg gtcctttgtt tttctgtatc taaattcttt aacctaaatg ttgaggtcag   360
tggcaaggta gttgacatta gaaataggtc atatgtgttt ggtaagtgct aggagcctgt   420
ttggttatta agaagttatt actttattgc aatgatctct gtcaatagtg tcaatagtaa   480
tggcatcaaa aaatggataa ttataattgc tttactgaca ttttttctc ccttgtgact    540 ccttgaggaa attaatgatt aacaaaggcc tcatgtactc aaacttgcag agtagataaa   600
cctacatgtc ctcagttgaa gtattttctt aggggaagag gaattc                  646

<210> SEQ ID NO 48
<211> LENGTH: 711
<212> TYPE: DNA
<213> ORGANISM: Homo sapiens
<220> FEATURE:
<221> NAME/KEY: misc_feature
<222> LOCATION: (164)..(164)
<223> OTHER INFORMATION: n = a, c, t or g

<400> SEQUENCE: 48
tatgtatcat cttccatatg aatgcgcatt ttactctttg attggtctaa taacagtgta    60
ctgtgttcta aaacacagaa taaaatggag aattgttttt caagattatc ttcatgatat   120
tgaagctcaa ttaagcagta acatgataat tattttttaa gatnatatgc aacttcccac   180
atactttgcg cccttctagg cggcagctgc agccgcatct gctgaatcaa gagacttcag   240
tggtgctggt gggataggag ttttttcaga gagttcttca gtagcatcta agttgagctc   300
caaaagtgaa aaagagctga aaacagaag aaagaaaaag aaacagaaag aacagtctgg   360
agaagaagag aaaaatgaca gagtcctaaa atcggaatct gaagcacagca taagaagaaa   420 aggtttccgt ttttccttgg aaggaagtag gctgacatat gaaaagagat tttcttctcc   480
acaccaggta aaaatattaa attacatgaa ttgtgttctc ataaattttt taaaagaata   540
tgccagaatt taatgagag aaaaccgcct tccacctgga tggcacaatg ctttcagagt   600
agtgatgatt atcaagtgtt ttggctatca cttcagagaa tttgtgagtt ttgcaacttt   660
ttggaatccc aggaaggaaa ttttagatcc ctctgggttt ggaaaaattt g             711

<210> SEQ ID NO 49
<211> LENGTH: 1026
<212> TYPE: DNA
<213> ORGANISM: Homo sapiens

<400> SEQUENCE: 49
ttatggggac acttctgact atgttgaggt gtgggtaaag taggagaaaa gagagcagaa    60
gatggaaaat ggaggaagga gaaaagcga gagtgaaata gaaaaggtga accttgtaga   120
aagtgccaaa atgccaccag cagtcatcag agggggtgctt tcttccacat gtccaatgac   180
ttatccttga gtaagtcaat gactatgaca caatgaatca aattctgttt ttcagaatgc   240
cagctcttaa ctctcttcat ctcattttg tttcttttct tgttattcat agtccttact    300
gagcatccgt ggctcccttt tctctccaag acgcaacagt agggcgagcc ttttcagctt   360
cagaggtcga gcaaaggaca ttggctctga gaatgacttt gctgatgatg agcacagcac   420
```

| | |
|---|---|
| ctttgaggac aatgacagcc gaagagactc tctgttcgtg ccgcacagac atggagaacg | 480 |
| gcgccacagc aatgtcagcc aggccagccg tgcctccagg gtgctcccca tcctgcccat | 540 |
| gaatgggaag atgcatagcg ctgtggactg caatggtgtg gtctccctgg tcggggccc | 600 |
| ttctaccctc acatctgctg ggcagctcct accagaggtg aggccaacyy magattgcag | 660 |
| ctgatgtgaa gagagttgtg actggtgcag gcaggagtgy ttttccattt mcacatctaa | 720 |
| gaatttkttg agtttsttgc ccaaaggctg ggagtttgtt caatcaagct gttaactgtc | 780 |
| ttgtgaaact sttctattca gactttycta caaagtaatt aaaaacctag gttggctgtc | 840 |
| agagaatata attagamgtm atctttcatc ayyattacta tggtatgaaa ctcgccaaaa | 900 |
| agcaaagcaa caatttatca agcataatgt tygaytaata tagttaaatt aaatccaagg | 960 |
| aaattaatgc tcacaaatta aataaatact taaggatttt gtgattgttg ttcatttaaa | 1020 |
| aggaga | 1026 |

<210> SEQ ID NO 50
<211> LENGTH: 601
<212> TYPE: DNA
<213> ORGANISM: Homo sapiens

<400> SEQUENCE: 50

| | |
|---|---|
| ataggaaagc ccaccttgac aaacccaggg ctccccaaaa gctgaaaatc tgacagactt | 60 |
| taaacaaccc ccaaataatt atcattccaa caatatctta gtgagctttt tacatctgag | 120 |
| aaagcatggt gtatatttag ttaaataaca cctgttgtag gaatgctttg ggctttgctg | 180 |
| cttttcaaaaa tagtggttat ttcatctgaa attctacttc tagggcacaa ctactgaaac | 240 |
| agaaataaga aagagacggt ccagttctta tcatgtttcc atggattat tggaagatcc | 300 |
| tacatcaagg caaagagcaa tgagtatagc cagtattttg accaacacca tggaaggtat | 360 |
| gttaaaagtc ctgcgtcaca gttacttggt gctttcctaa tgatgaaaaa cacttcataa | 420 |
| atttcaataa aatacttcct gacttgatat tgtatcatta ttacacattt tactaaataa | 480 |
| cagtaaaatc cgtgcataac tcatggattc atatattcca cagatttttt ttttttatat | 540 |
| ttagcctgta gaaagctgct gcaaatgtaa ggtatatttg aacaccactt tcataactta | 600 |
| a | 601 |

<210> SEQ ID NO 51
<211> LENGTH: 645
<212> TYPE: DNA
<213> ORGANISM: Homo sapiens

<400> SEQUENCE: 51

| | |
|---|---|
| gcttactagc ctttctgtac tgatccttc tatgacagca aacccattgt aaaattttcc | 60 |
| ctgttcctcc agcagattaa cccataatat cttttaacaa ctttagattt tttaaattcc | 120 |
| ttttaattta aaccaaatct gcttaataga aagtaagcag ttttcatgag gattctaact | 180 |
| ttttttcttc cagaacttga agaatccaga cagaaatgcc caccatgctg gtataaattt | 240 |
| gctaatatgt gtttgatttg ggactgttgt aaaccatggt taaggtgaa acaccttgtc | 300 |
| aacctggttg taatggaccc atttgttgac ctggccatca ccatctgcat tgtcttaaat | 360 |
| acactcttca tggctatgga gcactatccc atgacggagc agttcagcag tgtactgtct | 420 |
| gttggaaacc tggtaagcct cactgagagt ttctcttcct cttgaaagag tttataattg | 480 |
| ccttagtgaa ttttcatatat tgctctcaaa ttaaatatca actaattggc catgtatatc | 540 |
| ttgacatcaa atgtttagca tcccttttaa ataacaaaaa aatgttgcta ccatagtgca | 600 |

```
aaagagtcaa agaatttatg tacaatttga tttagaattg aattt            645
```

<210> SEQ ID NO 52
<211> LENGTH: 485
<212> TYPE: DNA
<213> ORGANISM: Homo sapiens

<400> SEQUENCE: 52

```
tggcccaaac caattttaa atcaggaatt taatttwtat attgttggga gttaaattaa    60
gttgctcaat aattattcgt gtttcaakas tatttgctca tataatgaac tacacttctc   120
atttaggtct tcacagggat cttcacagca gaaatgtttc tcaagataat tgccatggat   180
ccatattatt actttcaaga aggctggaat attttttgatg gttttattgt gagccttagt  240
ttaatggaac ttggttttggc aaatgtggaa ggattgtcag ttctccgatc attccggctg  300
gtaaattaac tgggagtgtt cataaaatgt acttttrtaat taattagtct tcattctcat  360
ctagtaaaaa tggcaagatt tcccatcatt ataatatatt tgaataccct ctaaaacaga   420
ttggattgcc ataccaccaa atggtagttt cttcttcatc atagctttaa taaagttcac   480
ttaaa                                                               485
```

<210> SEQ ID NO 53
<211> LENGTH: 602
<212> TYPE: DNA
<213> ORGANISM: Homo sapiens

<400> SEQUENCE: 53

```
acagatttcc tcctgtgtcc atgtgactaa cccattgtgc acatgtaccc taaaaattag    60
tatataataa taaataaaaa taaaaataaa aataaaaaaa taaaaataaa ataaaattgc   120
agatttttt agaaatgcag agattaacac tgttcttgct tttatttcca gctccgagtt    180
ttcaagttgg caaaatcttg gccaactcta aatatgctaa ttaagatcat tgcaattct    240
gtggggctc taggaaacct caccttggta ttggccatca tcgtcttcat ttttgctgtg    300
gtcggcatgc agctctttgg taagagctac aaagaatgtg tctgcaagat ttccaatgat   360
tgtgaactcc cacgctggca catgcatgac tttttccact ccttcctgat cgtgttccgc   420
gtgctgtgtg gagagtggat agagaccatg tgggactgta tggaggtcgc tggccaaacc   480
atgtgcctta ctgtcttcat gatggtcatg gtgattggaa atctagtggt atgtagcaaa   540
acatttttcc tcattttcat taaaaataat gtaatcatta aaagtgttc aactgaagaa    600
ta                                                                  602
```

<210> SEQ ID NO 54
<211> LENGTH: 803
<212> TYPE: DNA
<213> ORGANISM: Homo sapiens

<400> SEQUENCE: 54

```
gtttcattta gcaatgattt cagtattttc tgcaatgact aataagcaaa tagtgataat    60
agtattattt tatattgacc aagcattttt atttcattca cttttttca gaatagtgta   120
tcatgaatta gcagaaatgc atgttagaat aaaataaggt gtcaagaaca atcttagaaa   180
actaatgatg gaaagcaatt gaagcaatag aatgttttga tcacctgttt ttcctgctgt   240
gtttcaggtt ctgaacctct tcttggcctt gcttttgagt tccttcagtt ctgacaatct   300
tgctgccact gatgatgata acgaaatgaa taatctccag attgctgtgg gaaggatgca   360
gaaaggaatc gattttgtta aagaaaaat acgtgaattt attcagaaag cctttgttag    420
```

```
gaagcagaaa gctttagatg aaattaaacc gcttgaagat ctaaataata aaaagacag      480 ctgtatttcc aaccatacca ccatagaaat aggcaaagac ctcaattatc tcaaagacgg     540
aaatggaact actagtggca taggcagcag tgtagaaaaa tatgtcgtgg atgaaagtga    600
ttacatgtca tttataaaca accctagcct cactgtgaca gtaccaattg ctgttggaga   660
atctgacttt gaaaatttaa atactgaaga attcagcagc gagtcagata tggaggaaag   720
caaagaggta aatgttaaa taaggagata ttttggtgta taatctgt gttaaatatc      780 aggtgtttaa tgcgtgtctc tgt                                            803
```

```
<210> SEQ ID NO 55
<211> LENGTH: 615
<212> TYPE: DNA
<213> ORGANISM: Homo sapiens
<220> FEATURE:
<221> NAME/KEY: misc_feature
<222> LOCATION: (90)..(90)
<223> OTHER INFORMATION: n = a, c, t or g
<220> FEATURE:
<221> NAME/KEY: misc_feature
<222> LOCATION: (378)..(386)
<223> OTHER INFORMATION: n = a, c, t or g

<400> SEQUENCE: 55
atctctatac taggctcaaa cagaagttat ttccgttgtt agcaccatat ttttaaaaga      60
aaaaaaaata ctatggtgtt gtatctaatn ttgtgacccc tgacctttac caaagcggat    120
tggcattatg tttaagttct taattacaga tcaagaaaaa tgcatacaga agatgggggg    180
gggcacacct aattaatttt tatatttaga ttaaagaaaa taattaaatg tgttttttg     240 tgggattgat tttcagaagc taaatgcaac tagttcatct gaaggcagca cggttgatat   300
tggagctccc gccgagggag aacagcctga ggttgaacct gaggaatccc ttgaacctga   360
agcctgtttt acagaagnnn nnnnnnaagc aaaacaataa catatgtggt cttgagtatc   420
ctcttttcta cccatttttt cctatttatt taaatgtctg tttatttgtc taccatctag   480
ttcatctatc tatctgtatc tatctatcta tctatctatc tagtaatcat ctataccat    540 ccaacaactg tacattatt tgtttttttt ttttgcattt gctgtttgaa aaaaaatgca     600
acgttttaaa ggcaa                                                     615
```

```
<210> SEQ ID NO 56
<211> LENGTH: 400
<212> TYPE: DNA
<213> ORGANISM: Homo sapiens

<400> SEQUENCE: 56
gatagctttt gtaagcggaa gctatcttaa aaattaatgt tatttacaat gtattatcag      60
gtaataatgt aaatgaatct cccaccaaca caaatatacc taatcaaaga gtaattttt    120 gtcttcattt ttttcccaca tattttagac tgtgtacgga agttcaagtg ttgtcagata   180
agcatagaag aaggcaaagg gaaactctgg tggaatttga ggaaaacatg ctataagata   240
gtggagcaca attggttcga aaccttcatt gtcttcatga ttctgctgag cagtggggct   300
ctggtaggtg atgcatgatc cactccttca cctttcatct gaaatctttt ccctttccct    360
tcaatcaact catattaccc acttttaaat taaggtgttt                           400
```

```
<210> SEQ ID NO 57
<211> LENGTH: 560
<212> TYPE: DNA
<213> ORGANISM: Homo sapiens
```

-continued

<400> SEQUENCE: 57

| aaattactga aacccttggt tgactgaaat gcccagtcag cagtcattta tgatcagata | 60 |
| atgataaagt aaaattcagc catgggaaac attaaacctt ccagccttag cacctgata | 120 |
| agagcttgca tcgtttcctt ttttaagaaa tcatcaatta gagactgttt ctgatcataa | 180 |
| aatttaatag aattttttga cttacaggcc tttgaagata tatacattga gcagcgaaaa | 240 |
| accattaaga ccatgttaga atatgctgac aaggttttca cttacatatt cattctggaa | 300 |
| atgctgctaa agtgggttgc atatggtttt caagtgtatt ttaccaatgc ctggtgctgg | 360 |
| ctagacttcc tgattgttga tgtgagtatg ctgcactttg ctgctttatt cattggcata | 420 |
| tatgtaatag ttctagcaat ggtgcctgac acagtgtagg cactcagtaa cactgtatca | 480 |
| gcccaaatat aaattatgtt tctcatttca cagtgagagg atgcctcaaa acattttta | 540 |
| ccaatttaaa tacatataca | 560 |

<210> SEQ ID NO 58
<211> LENGTH: 480
<212> TYPE: DNA
<213> ORGANISM: Homo sapiens

<400> SEQUENCE: 58

| aaattcttag ccttttcccc aaacttacta agtcagactc tgctattggt gttttttaaca | 60 |
| agaccctgg gtgattttga aactcatgaa agttcgagaa ttactgattc attgcataga | 120 |
| gcaaggctga actgtgtaga cattttttata tgtaaataag aaaattgtgt tgcttttct | 180 |
| gtataggtct cactggttag cttaactgca aatgccttgg gttactcaga acttggtgcc | 240 |
| atcaaatccc tcagaacact aagagctctg aggccactga gagctttgtc ccggtttgaa | 300 |
| ggaatgaggg taagactgaa tgccttagag tttgtcagaa ttattattga gagcagactg | 360 |
| acactttgta ccatggaaat gtcaaattta tggagaattt gtgtcttaca cattcatact | 420 |
| gacatagcta atcaatcaaa aataaatattt accagatgcc cataatactt ggcactgctg | 480 |

<210> SEQ ID NO 59
<211> LENGTH: 640
<212> TYPE: DNA
<213> ORGANISM: Homo sapiens

<400> SEQUENCE: 59

| taattttaaa attcttagtt ggagctacca gagtctagtt tctacccaat attcaacttt | 60 |
| gaaacagatt tttttaatca tttgactgtt cttttaataa tgtttaaaaa taagtaaata | 120 |
| tttgttgttg gcttttcact tattttttcct tctcatcctg tgccaggttg ttgtaaatgc | 180 |
| tcttttagga gccattccat ctatcatgaa tgtacttctg gtttgtctga tcttttggct | 240 |
| aatattcagt atcatgggag tgaatctctt tgctggcaag ttttaccatt gtattaatta | 300 |
| caccactgga gagatgtttg atgtaagcgt ggtcaacaac tacagtgagt gcaaagctct | 360 |
| cattgagagc aatcaaactg ccaggtggaa aaatgtgaaa gtaaactttg ataacgtagg | 420 |
| acttggatat ctgtctctac ttcaagtagt aagtaatcac tttattattt tccatgatgt | 480 |
| gtaattaaaa tgagtctaaa gttttttcttc ctcataatga gatatccacc tgttagaatg | 540 |
| gctattatca aacagataaa tgacaataaa tgctggcaag aatgtgaaga aaagggaacc | 600 |
| cttgtacatt gttggcaggg atgtaaatta gtatagcttt | 640 |

<210> SEQ ID NO 60
<211> LENGTH: 480
<212> TYPE: DNA

<213> ORGANISM: Homo sapiens

<400> SEQUENCE: 60

```
atttgaagta ttttcaatgc atatcgcaaa acattgcccc aaaagtgaat acaaatttca      60
agcttattta tatgcctgta ttgaatacat gtcaaataga attttgatca attattcaat     120
ttattttcta aaattataat tttgggaaaa aagaaaatga tatgactttt cttacaggcc     180
acgtttaagg gatggatgga tattatgtat gcagctgttg attcacgaaa tgtaagtcta     240
gttagaggga aattgtttag tttgattaaa tgtatatttc tacaatattg taatttagtg     300
atattgtcaa taaataaaa ttatgtgctt aatttataaa acccatctat attataagga     360
taaaatattt aatcatacta tttctttcaa aattatcata ggatgatttt ctctaatcac     420
tctgtatctt ttaacatatc ttttctagta tttagcaagg cacctgacac aaaactttat     480
```

<210> SEQ ID NO 61
<211> LENGTH: 366
<212> TYPE: DNA
<213> ORGANISM: Homo sapiens

<400> SEQUENCE: 61

```
taaaacatgc ttagataatt aaaaactcac tgatgtactt tttgtgaaac aagtactaga      60
tataatggtt acaattcttc atattcttta ggtagaatta caacccaagt atgaagacaa     120
cctgtacatg tatctttatt ttgtcatctt tattattttt ggttcattct ttaccttgaa     180
tcttttcatt ggtgtcatca tagataactt caaccaacag aaaaagaaga taagtatatt     240
aaaacttcat ccttgctctg aaatatgaac taaaatattc atactctttc ctttagcctc     300
caaaatgcaa tcaccaaaaa aagaatataa aattcagaaa ttattttgag acatttgata     360
atcgat                                                                366
```

<210> SEQ ID NO 62
<211> LENGTH: 560
<212> TYPE: DNA
<213> ORGANISM: Homo sapiens

<400> SEQUENCE: 62

```
tcgataagct tttaagcaat taataattca gatagcatgt ttttgatatt tttagtctag      60
aaatatgact aatatggcat aatttatata ttgaataaag gcatctctat aaatacagat     120
attagtaaca atagaatgaa atgtgggagc caattttcac atgattacta aggtggattt     180
tatagccagc aaagaacaca attttaacaa gtgttgcttt catttcttta ctttggaggt     240
caagacattt ttatgacaga agaacagaag aaatactaca atgcaatgaa aaaactgggt     300
tcaaagaaac cacaaaaacc catacctcga cctgctgtaa aataacata ttttcattgc     360
ctgttaaaac tatattacct aaccgtttca gcccgaat ttctagaaac tagttatttt     420
tgtggatttg taacacaaag ttttttacct taacaatggg actagctagc ctaaatagct     480
tgaaaaatgt actttacata tataatatgt ataaattata taatgcataa catatttat     540
atgtaaacat ataaaataca                                                 560
```

<210> SEQ ID NO 63
<211> LENGTH: 650
<212> TYPE: DNA
<213> ORGANISM: Homo sapiens

<400> SEQUENCE: 63

```
gttttgcaag gaattttttt ttttgtaaaa tgttgtgagg attaaagatg tgttttata       60
```

```
aaagctacat ttttgttgc tttcttaaaa tcagaagaat tgaattcgat ttttttaag    120 gtttctaatg gaacttttac atattatttg ttccagaaca aattccaagg aatggtcttt   180
gattttgtaa ccaaacaagt ctttgatatc agcatcatga tcctcatctg ccttaacatg   240
gtcaccatga tggtggaaac cgatgaccag agtcaagaaa tgacaaacat tctgtactgg   300
attaatctgg tgtttattgt tctgttcact ggagaatgtg tgctgaaact gatctctctt   360
cgttactact atttcactat tggatggaat attttttgatt ttgtggtggt cattctctcc   420
attgtaggta agaagaggtg cttttattca gttaaggaat atagtggtaa aaatatgtgt   480
tttaaaactt tagaggtgtt tttcactaat cttttctcatt catcccaaac tcccaaataa   540
aaatctaata gtccattgtt ttagttttag tttgccatttt ctctaattgc atgctgtgct   600
tgaaatgatg agtggaatac aaggaattta tattttcagc tttcatttat             650

<210> SEQ ID NO 64
<211> LENGTH: 3700
<212> TYPE: DNA
<213> ORGANISM: Homo sapiens

<400> SEQUENCE: 64
aatgttataa caccaaacat accagtttca ttttgctcaa caaacattgc agattatttg    60
catatataca tgtacctaac tgtcctgttc acattttgta aaactaatgt acttatgtaa   120
actttcattt gctactatta agtataacaa tattttttgtt atttgttgat tttctacagg   180
aatgtttctg gctgaactga tagaaaagta ttttgtgtcc cctaccctgt tccgagtgat   240
ccgtcttgcc aggattggcc gaatcctacg tctgatcaaa ggagcaaagg ggatccgcac   300
gctgctcttt gctttgatga tgtcccttcc tgcgttgttt aacatcggcc tccttctttt   360
cctggtcatg ttcatctacg ccatctttgg gatgtccaat tttgcctatg ttaagaggga   420
agttgggatc gatgacatgt tcaactttga gacctttggc aacagcatga tctgcctgtt   480
ccaaattaca acctctgctg gctgggatgg attgctagca cctattctta atagtggacc   540
tccagactgt gaccctgaca agatcacccc tggaagctca gttaaaggag actgtgggaa   600
cccatctgtt gggatttttct ttttttgtcag ttacatcatc atatccttcc tggttgtggt   660
gaacatgtac atcgcggtca tcctggagaa cttcagtgtt gctactgaag aaagtgcaga   720
gcctctgagt gaggatgact ttgagatgtt ctatgaggtt tgggagaagt ttgatcccga   780
tgcgacccag tttatagagt ttgccaaact ttctgatttt gcagatgccc tggatcctcc   840
tcttctcata gcaaaaccca acaaagtcca gctcattgcc atggatctgc ccatggtgag   900
tggtgaccgg atccactgtc ttgacatctt atttgctttt acaaagcgtg ttttgggtga   960
gagtggagag atggatgccc ttcgaataca gatggaagag cgattcatgg catcaaaccc  1020
ctccaaagtc tcttatgagc ccattacgac cacgttgaaa cgcaaacaag aggaggtgtc  1080
tgctattatt atccagaggg cttacagacg ctacctcttg aagcaaaaag ttaaaaaggt  1140
atcaagtata tacaagaaag acaaaggcaa agaatgtgat ggaacaccca tcaaagaaga  1200
tactctcatt gataaactga tgagaattc aactccagag aaaaccgata tgacgccttc  1260
caccacgtct ccaccctcgt atgatagtgt gaccaaacca gaaaaagaaa aatttgaaaa  1320
agacaaatca gaaaaggaag acaaagggaa agatatcagg gaaagtaaaa agtaaaaaga  1380
aaccaagaat tttccatttt gtgatcaatt gtttacagcc cgtgatggtg atgtgtttgt  1440
gtcaacagga ctcccacagg aggtctatgc caaactgact gtttttacaa atgtatactt  1500
aaggtcagtg cctataacaa gacagagacc tctggtcagc aaactggaac tcagtaaact  1560
```

-continued

```
ggagaaatag tatcgatggg aggtttctat tttcacaacc agctgacact gctgaagagc    1620
agaggcgtaa tggctactca gacgatagga accaatttaa agggggggagg gaagttaaat    1680 ttttatgtaa attcaacatg tgacacttga taatagtaat tgtcaccagt gtttatgttt    1740
taactgccac acctgccata ttttacaaa acgtgtgctg tgaatttatc acttttcttt    1800
ttaattcaca ggttgtttac tattatatgt gactattttt gtaaatgggt ttgtgtttgg    1860
ggagagggat taaagggagg gaattctaca tttctctatt gtattgtata actggatata    1920
ttttaaatgg aggcatgctg caattctcat tcacacataa aaaaatcaca tcacaaaagg    1980
gaagagttta cttcttgttt caggatgttt ttagattttt gaggtgctta aatagctatt    2040
cgtattttta aggtgtctca tccagaaaaa atttaatgtg cctgtaaatg ttccatagaa    2100
tcacaagcat taaagagttg ttttattttt acataaccca ttaaatgtac atgtatatat    2160
gtatatatgt atatgtgcgt gtatatacat atatatgtat acacacatgc acacacagag    2220
atatacacat accattacat tgtcattcac agtcccagca gcatgactat cacattttg    2280 ataagtgtcc tttggcataa aataaaaata tcctatcagt cctttctaag aagcctgaat    2340
tgaccaaaaa acatcccac caccacttta taaagttgat tctgctttat cctgcagtat    2400
tgtttagcca tcttctgctc ttggtaaggt tgacatagta tatgtcaatt taaaaaataa    2460
aagtctgctt tgtaaatagt aattttaccc agtggtgcat gtttgagcaa acaaaaatga    2520
tgatttaagc acactactta ttgcatcaaa tatgtaccac agtaagtata gtttgcaagc    2580
tttcaacagg taatatgatg taattggttc cattatagtt tgaagctgtc actgctgcat    2640
gtttatcttg cctatgctgc tgtatcttat tccttccact gttcagaagt ctaatatggg    2700
aagccatata tcagtggtaa agtgaagcaa attgttctac caagacctca ttcttcatgt    2760
cattaagcaa taggttgcag caaacaagga agagcttctt gcttttatt cttccaacct    2820 taattgaaca ctcaatgatg aaaagcccga ctgtacaaac atgttgcaag ctgcttaaat    2880
ctgtttaaaa tatatggtta gagttttcta agaaaatata aatactgtaa aaagttcatt    2940
ttattttatt tttcagcctt ttgtacgtaa aatgagaaat taaaagtatc ttcaggtgga    3000
tgtcacagtc actattgtta gtttctgttc ctagcacttt taaattgaag cacttcacaa    3060
aataagaagc aaggactagg atgcagtgta ggtttctgct tttttattag tactgtaaac    3120
ttgcacacat ttcaatgtga aacaaatctc aaactgagtt caatgtttat ttgctttcaa    3180
tagtaatgcc ttatcattga aagaggctta agaaaaaaa aaatcagctg atactcttgg    3240
cattgcttga atccaatgtt tccacctagt cttttattc agtaatcatc agtcttttcc    3300
aatgtttgtt tacacagata gatcttattg acccatatgg cactagaact gtatcagata    3360
taatatggga tcccagcttt ttttcctctc ccacaaaacc aggtagtgaa gttatattac    3420
cagttacagc aaaatacttt gtgtttcaca agcaacaata aatgtagatt ctttatactg    3480
aagctattga cttgtagtgt gttggtgaat gcatgcagga agatgctgtt accataaaga    3540
acggtaaacc acattacaat caagccaaag aataaaggtt cgcttatgta tatgtattta    3600
attgttgtct ttgtttctat ctttgaaatg ccatttaaag gtagatttct atcatgtaaa    3660
aataatctat ctgaaaaaca aatgtaaaga acacacatta                         3700
```

<210> SEQ ID NO 65
<211> LENGTH: 9112
<212> TYPE: DNA
<213> ORGANISM: Homo sapiens

<400> SEQUENCE: 65

```
accatagagt gaatctcaga acaggaagcg gaggcataag cagagaggat tctggaaagg    60
tctctttgtt ttcttatcca cagagaaaga aagaaaaaaa attgtaacta atttgtaaac   120
ctctgtggtc aaaaaaaaaa aaaaaaaaaa aagctgaaca gctgcagagg aagacacgtt   180
atacccctaac catcttggat gctgggcttt gttatgctgt aattcataag gctctgtttt   240
atcagagatt atggagcaag aaaactgaag ccaagccaca tcaaggtttg acagggatga   300
gataccctgtc aaggattcat agtagagtgg cttactggga aaggagcaaa gaatctcttc   360
tagggatatt gtaagaataa atgagataat tcacagaagg gacctggagc ttttccggaa   420
aaaggtgctg tgactatcta aggggaaaag ctgagagtct ggaactagcc tatcttccga   480
ggacttagag acaacagtat gggaatttca acgagacgtt tttactttct tttgaccaag   540
attcaaattc tttattccag cccttgataa gtaaataaga aggtaattcg tatgcaagaa   600
gctacacgta attaaatgtg caggatgaaa agatggcaca ggcactgttg gtaccccag    660
gacctgaaag cttccgcctt tttactagag aatctcttgc tgctatcgaa aaacgtgctg   720
cagaagagaa agccaagaag cccaaaaagg aacaagataa tgatgatgag aacaaaccaa   780
agccaaaatag tgacttggaa gctggaaaga accttccatt tatttatgga gacattcctc   840
cagagatggt gtcagagccc ctggaggacc tggatcccta ctatatcaat aagaaaactt   900
ttatagtaat gaataaagga aaggcaattt cccgattcag tgccacctct gccttgtata   960
ttttaactcc actaaaccct gttaggaaaa ttgctabsaa gattttggta cattctttat  1020
tcagcatgct tatcatgtgc actattttga ccaactgtgt attttatgacc ttgagcaacc  1080
ctcctgactg gacaaagaat gtagagtaca cattcactgg aatctatacc tttgagtcac  1140
ttataaaaat cttggcaaga gggttttgct tagaagattt tacgtttctt cgtgatccat  1200
ggaactggct ggatttcagt gtcattgtga tggcatatgt gacagagttt gtggacctgg  1260
gcaatgtctc agcgttgaga acattccagag ttctccgagc actgaaaaca atttcagtca  1320
ttccaggttt aaagaccatt gtgggggccc tgatccagtc ggtaaagaag ctttctgatg  1380
tgatgatcct gactgtgttc tgtctgagcg tgtttgctct cattgggctg cagctgttca  1440
tgggcaatct gaggaataaa tgtttgcagt ggccccccaag cgattctgct tttgaaacca  1500
acaccacttc ctactttaat ggcacaatgg attcaaatgg acatttgtt aatgtaacaa   1560
tgagcacatt taactggaag gattacattg gagatgacag tcactttat gttttggatg   1620
ggcaaaaaga cccctttactc tgtggaaatg gctcagatgc aggccagtgt ccagaaggat   1680
acatctgtgt gaaggctggt cgaaaccccc actatggcta cacaagcttt gacacccttta   1740
gctgggcttt cctgtctcta tttcgactca tgactcaaga ctactgggaa aatctttacc   1800
agttgacatt acgtgctgct gggaaaacat acatgatatt ttttgtcctg gtcattttct   1860
tgggctcatt ttatttggtg aatttgatcc tggctgtggt ggccatggcc tatgaggggc   1920
agaatcaggc caccttggaa gaagcagaac aaaagagggc cgaatttcag cagatgctcg   1980
aacagcttaa aaagcaacag gaagaagctc aggcagttgc ggcagcatca gctgcttcaa   2040
gagatttcag tggaataggt gggttaggag agctgttgga aagttcttca gaagcatcaa   2100
agttgagttc caaaagtgct aaagaatgga ggaaccgaag gaagaaaaga agacagagag   2160
agcaccttga aggaaacaac aaaggagaga gacagcttt tcccaaatcc gaatctgaag   2220
acagcgtcaa aagaagcagc ttcctttctt ccatggatgg aaacagactg accagtgaca   2280
aaaaattctg ctccccctcat cagtctctct tgagtatccg tggctccctg ttttccccaa   2340
gacgcaatag caaaacaagc attttcagtt tcagaggtcg ggcaaaggat gttggatctg   2400
```

```
aaaatgactt tgctgatgat gaacacagca catttgaaga cagcgaaagc aggagagact    2460
cactgtttgt gccgcacaga catggagagc gacgcaacag taacggcacc accactgaaa    2520
cggaagtcag aaagagaagg ttaagctctt accagatttc aatggagatg ctggaggatt    2580
cctctggaag gcaaagagcc gtgagcatag ccagcattct gaccaacaca atggaagaac    2640
ttgaagaatc tagacagaaa tgtccgccat gctggtatag atttgccaat gtgttcttga    2700
tctgggactg ctgtgatgca tggttaaaag taaaacatct tgtgaattta attgttatgg    2760
atccatttgt tgatcttgcc atcactattt gcattgtctt aaatacccctc tttatggcca    2820 tggagcacta ccccatgact gagcaattca gtagtgtgtt gactgtagga aacctggtct    2880
ttactgggat ttttacagca gaaatggttc tcaagatcat tgccatggat ccttattact    2940
atttccaaga aggctggaat atctttgatg gaattattgt cagcctcagt ttaatggagc    3000
ttggtctgtc aaatgtggag ggattgtctg tactgcgatc attcagactg cttagagttt    3060
tcaagttggc aaaatcctgg cccacactaa atatgctaat taagatcatt ggcaattctg    3120
tgggggctct aggaaacctc accttggtgt tggccatcat cgtcttcatt tttgctgtgg    3180
tcggcatgca gctcttttggt aagagctaca agaatgtgt ctgcaagatc aatgatgact    3240
gtacgctccc acggtggcac atgaacgact tcttccactc cttcctgatt gtgttccgcg    3300
tgctgtgtgg agagtggata gagaccatgt gggactgtat ggaggtcgct ggccaaacca    3360
tgtgccttat tgttttcatg ttggtcatgg tcattggaaa ccttgtggtt ctgaacctct    3420
ttctggcctt attgttgagt tcatttagct cagacaacct tgctgctact gatgatgaca    3480
atgaaatgaa taatctgcag attgcagtag gaagaatgca aaagggaatt gattatgtga    3540
aaaataagat gcgggagtgt ttccaaaaag ccttttttag aaagccaaaa gttatagaaa    3600
tccatgaagg caataagata gacagctgca tgtccaataa tactggaatt gaaataagca    3660
aagagcttaa ttatcttaga gatgggaatg gaaccaccag tggtgtaggt actgaaagca    3720
gtgttgaaaa atacgtaatc gatgaaaatg attatatgtc attcataaac aaccccagcc    3780
tcaccgtcac agtgccaatt gctgttggag agtctgactt tgaaaactta aatactgaag    3840
agttcagcag tgagtcagaa ctagaagaaa gcaaggagaa attaaatgca accagctcat    3900
ctgaaggaag cacagttgat gttgttctac cccgagaagg tgaacaagct gaaactgaac    3960
ccgaagaaga ccttaaaaccg gaagcttgtt ttactgaagg atgtattaaa aagttttccat    4020 tctgtcaagt aagtacagaa gaaggcaaag ggaagatctg gtggaatctt cgaaaaacct    4080
gctacagtat tgttgagcac aactggtttg agactttcat tgtgttcatg atccttctca    4140
gtagtggtgc attggccttt gaagatatat acattgaaca gcgaaagact atcaaaacca    4200
tgctagaata tgctgacaaa gtcttttacct atatattcat tctggaaatg cttctcaaat    4260
gggttgctta tggatttcaa acatatttca ctaatgcctg gtgctggcta gatttcttga    4320
tcgttgatgt ttcttttggtt agcctggtag ccaatgctct tggctactca gaactcggtg    4380
ccatcaaatc attacggaca ttaagagctt taagacctct aagagcctta tcccggtttg    4440
aaggcatgag ggtggttgtg aatgctcttg ttggagcaat tccctctatc atgaatgtgc    4500
tgttggtctg tctcatcttc tggttgatct ttagcatcat gggtgtgaat tgtttgctg    4560 gcaagttcta ccactgtgtt aacatgacaa cgggtaacat gtttgacatt agtgatgtta    4620
acaatttgag tgactgtcag gctcttggca agcaagctcg gtggaaaaac gtgaaagtaa    4680
actttgataa tgttggcgct ggctatcttg cactgcttca agtggccaca tttaaaggct    4740
ggatggatat tatgtatgca gctgttgatt cacgagatgt taaacttcag cctgtatatg    4800
```

-continued

| | | | | | |
|---|---|---|---|---|---|
| aagaaaatct | gtacatgtat | ttatactttg | tcatctttat | catctttggg | tcattcttca | 4860 |
| ctctgaatct | attcattggt | gtcatcatag | ataacttcaa | ccagcagaaa | aagaagtttg | 4920 |
| gaggtcaaga | catctttatg | acagaggaac | agaaaaaata | ttacaatgca | atgaagaaac | 4980 |
| ttggatccaa | gaaacctcag | aaacccatac | ctcgcccagc | aaacaaattc | caaggaatgg | 5040 |
| tctttgattt | tgtaaccaga | caagtctttg | atatcagcat | catgatcctc | atctgcctca | 5100 |
| acatggtcac | catgatggtg | gaaacggatg | accagggcaa | atacatgacc | ctagttttgt | 5160 |
| cccggatcaa | cctagtgttc | attgttctgt | tcactggaga | atttgtgctg | aagctcgtct | 5220 |
| ccctcagaca | ctactacttc | actataggct | ggaacatctt | tgactttgtg | gtggtgattc | 5280 |
| tctccattgt | aggtatgttt | ctggctgaga | tgatagaaaa | gtattttgtg | tccctacct | 5340 |
| tgttccgagt | gatccgtctt | gccaggattg | gccgaatcct | acgtctgatc | aaaggagcaa | 5400 |
| agggatccg | cacgctgctc | tttgcttga | tgatgtccct | tcctgcgttg | tttaacatcg | 5460 |
| gcctcctgct | cttcctggtc | atgtttatct | atgccatctt | tgggatgtcc | aactttgcct | 5520 |
| atgttaaaaa | ggaagctgga | attgatgaca | tgttcaactt | tgagaccttt | ggcaacagca | 5580 |
| tgatctgctt | gttccaaatt | acaacctctg | ctggatggga | tggattgcta | gcacctattc | 5640 |
| ttaatagtgc | accacccgac | tgtgaccctg | acacaattca | ccctggcagc | tcagttaagg | 5700 |
| gagactgtgg | gaacccatct | gttgggattt | tcttttttgt | cagttacatc | atcatatcct | 5760 |
| tcctggtggt | ggtgaacagt | tacatcgcgg | tcatcctgga | gaacttcagt | gttgctactg | 5820 |
| aagaaagtgc | agagccctg | agtgaggatg | actttgagat | gttctatgag | gtttgggaaa | 5880 |
| agtttgatcc | cgatgcgacc | cagtttatag | agttctctaa | actctctgat | tttgcagctg | 5940 |
| ccctggatcc | tcctcttctc | atagcaaaac | ccaacaaagt | ccagcttatt | gccatggatc | 6000 |
| tgcccatggt | cagtggtgac | cggatccact | gtcttgatat | tttatttgcc | tttacaaagc | 6060 |
| gtgtttggg | tgagagtgga | gagatggatg | cccttcgaat | acagatggaa | acagggttta | 6120 |
| tggcatcaaa | cccctccaaa | gtctcttatg | agcctattac | aaccactttg | aaacgtaaac | 6180 |
| aagaggaggt | gtctgccgct | atcattcagc | gtaatttcag | atgttatctt | ttaaagcaaa | 6240 |
| ggttaaaaaa | tatatcaagt | aactataaca | aagaggcaat | aaaggggagg | attgacttac | 6300 |
| ctataaaaca | agacatgatt | attgacaaac | tgaatgggaa | ctccactcca | gaaaaaacag | 6360 |
| atgggagttc | ctctaccacc | tctcctcctt | cctatgatag | tgtaacaaaa | ccagacaagg | 6420 |
| aaaagtttga | gaaagacaaa | ccagaaaaag | aaagcaaagg | aaaagaggtc | agagaaaatc | 6480 |
| aaaagtaaaa | agaaacaaag | aattatcttt | gtgatcaatt | gtttacagcc | tatgaaggta | 6540 |
| aagtatatgt | gtcaactgga | cttcaagagg | aggtccatgc | caaactgact | gttttaacaa | 6600 |
| atactcatag | tcagtgccta | tacaagacag | tgaagtgacc | tctctgtcac | tgcaactctg | 6660 |
| tgaagcaggg | tatcaacatt | gacaagaggt | tgctgttttt | attaccagct | gacactgctg | 6720 |
| aggagaaacc | caatggctac | ctagactata | gggatagttg | tgcaaagtga | acattgtaac | 6780 |
| tacaccaaac | acctttagta | cagtccttgc | atccattcta | tttttaactt | ccatatctgc | 6840 |
| catattttta | caaatttgt | tctagtgcat | ttccatggtc | cccaattcat | agtttattca | 6900 |
| taatgctatg | tcactatttt | tgtaaatgag | gtttacgttg | aagaaacagt | atacaagaac | 6960 |
| cctgtctctc | aaatgatcag | acaaaggtgt | tttgccagag | agataaaatt | tttgctcaaa | 7020 |
| accagaaaaa | gaattgtaat | ggctacagtt | tcagttactt | ccattttcta | gatggcttta | 7080 |
| attttgaaag | tattttagtc | tgttatgttt | gtttctatct | gaacagttat | gtgcctgtaa | 7140 |
| agtctcctct | aatatttaaa | ggattatttt | tatgcaaagt | attctgtttc | agcaagtgca | 7200 |

```
aattttattc taagtttcag agctctatat ttaatttagg tcaaatgctt tccaaaaagt   7260
aatctaataa atccattcta gaaaatatata tctaaagtat tgctttagaa tagttgttcc   7320
actttctgct gcagtattgc tttgccatct tctgctctca gcaaagctga tagtctatgt   7380
caattaaata ccctatgtta tgtaaatagt tattttatcc tgtggtgcat gtttgggcaa   7440
atatatatat agcctgataa acaacttcta ttaaatcaaa tatgtaccac agtgtatgtg   7500
tcttttgcaa gcttccaaca gggatgtatc ctgtatcatt cattaaacat agtttaaagg   7560
ctatcactaa tgcatgttaa tattgcctat gctgctctat tttactcaat ccattcttca   7620
caagtcttgg ttaaagaatg tcacatattg gtgatagaat gaattcaacc tgctctgtcc   7680
attatgtcaa gcagaataat ttgaagctat ttacaaacac ctttactttt gcactttaa   7740 ttcaacatga gtatcatatg gtatctctct agatttcaag gaaacacact ggatactgcc   7800
tactgacaaa acctattctt catattttgc taaaaatatg tctaaaactt gcgcaaatat   7860
aaataatgta aaatataat caactttatt tgtcagcatt ttgtacataa gaaaattatt   7920
ttcaggttga tgacatcaca atttatttta cttatgctt ttgcttttga tttttaatca   7980
caattccaaa cttttgaatc cataagattt ttcaatggat aatttcctaa aataaaagtt   8040
agataatggg ttttatggat ttctttgtta taatatattt tctaccattc caataggaga   8100
tacattggtc aaacactcaa acctagatca ttttctacca actatggttg cctcaatata   8160
accttttatt catagatgtt ttttttatt caactttgt agtatttacg tatgcagact   8220
agtcttattt ttttaattcc tgctgcacta aagctattac aaatataaca tggactttgt   8280 tcttttagc catgaacaaa gtggcaaagt tgtgcaatta cctaacatga tataaatttt   8340
tgttttttgc acaaaccaaa agtttaatgt taattctttt tacaaaacta tttactgtag   8400
tgtattgaag aactgcatgc agggaattgc tattgctaaa aagaatggtg agctacgtca   8460
ttattgagcc aaaagaataa atttcatttt ttattgcatt tcacttattg gcctctgggg   8520 tttttttgttt ttgtttttttg ctgttggcag tttaaaatat atataattaa taaaacctgt   8580
gcttgatctg acatttgtat acataaaagt ttacatgaat tttacaacag actagtgcat   8640
gattcaccaa gcagtactac agaacaaagg caaatgaaaa gcagctttgt gcactttat   8700 gtgtgcaaag gatcaagttc acatgttcca actttcaggt ttgataataa tagtagtaac   8760
cacctacaat agctttcaat ttcaattaac tcccttggct ataagcatct aaactcatct   8820
tctttcaata taattgatgc tatctcctaa ttacttggtg gctaataaat gttacattct   8880
ttgttactta aatgcattat ataaactcct atgtatacat aaggtattaa tgatatagtt   8940
attgagaatt tatattaact ttttttttcaa gaacccttgg atttatgtga ggtcaaaacc   9000
aaactcttat tctcagtgga aaactccagt tgtaatgcat attttaaag acaatttgga   9060 tctaaatatg tatttcataa ttctcccata ataaattata taaggtggct aa            9112
```

<210> SEQ ID NO 66
<211> LENGTH: 9112
<212> TYPE: DNA
<213> ORGANISM: Homo sapiens

<400> SEQUENCE: 66

```
accatagagt gaatctcaga acaggaagcg gaggcataag cagagaggat tctggaaagg     60 tctcttttgtt ttcttatcca cagagaaaga aagaaaaaaa attgtaacta atttgtaaac   120
ctctgtggtc aaaaaaaaaa aaaaaaaaa aagctgaaca gctgcagagg aagacacgtt   180
ataccctaac catcttggat gctgggcttt gttatgctgt aattcataag gctctgtttt   240
```

```
atcagagatt atggagcaag aaaactgaag ccaagccaca tcaaggtttg acagggatga      300
gatacctgtc aaggattcat agtagagtgg cttactggga aaggagcaaa gaatctcttc      360
tagggatatt gtaagaataa atgagataat tcacagaagg gacctggagc ttttccggaa      420
aaaggtgctg tgactatcta aggggaaaag ctgagagtct ggaactagcc tatcttccga      480
ggacttagag acaacagtat gggaatttca acgagacgtt tttactttct tttgaccaag      540
attcaaattc tttattccag cccttgataa gtaaataaga aggtaattcg tatgcaagaa      600
gctacacgta attaaatgtg caggatgaaa agatggcaca ggcactgttg gtaccccag       660 gacctgaaag cttccgcctt tttactagag aatctcttgc tgctatcgaa aaacgtgctg      720
cagaagagaa agccaagaag cccaaaaagg aacaagataa tgatgatgag aacaaaccaa      780
agccaaatag tgacttggaa gctggaaaga accttccatt tatttatgga gacattcctc      840
cagagatggt gtcagagccc ctggaggacc tggatcccta ctatatcaat aagaaaactt      900
ttatagtaat gaataaagga aaggcaattt cccgattcag tgccacctct gccttgtata      960
ttttaactcc actaaaccct gttaggaaaa ttgctabsaa gattttggta cattctttat     1020
tcagcatgct tatcatgtgc actattttga ccaactgtgt atttatgacc ttgagcaacc     1080
ctcctgactg gacaaagaat gtagagtaca cattcactgg aatctatacc tttgagtcac     1140
ttataaaaat cttggcaaga gggttttgct tagaagattt tacgtttctt cgtgatccat     1200
ggaactggct ggatttcagt gtcattgtga tggcgtatgt aacagaattt gtaagcctag     1260
gcaatgtttc agcccttcga actttcagag tcttgagagc tctgaaaact atttctgtaa     1320
tcccaggttt aaagaccatt gtgggggccc tgatccagtc ggtaaagaag ctttctgatg     1380
tgatgatcct gactgtgttc tgtctgagcg tgtttgctct cattgggctg cagctgttca     1440
tgggcaatct gaggaataaa tgtttgcagt ggcccccaag cgattctgct tttgaaacca     1500
acaccacttc ctactttaat ggcacaatgg attcaaatgg acatttgtt aatgtaacaa      1560 tgagcacatt taactggaag gattacattg gagatgacga tcacttttat gttttggatg     1620
ggcaaaaaga ccctttactc tgtgaaaatg gctcagatgc aggccagtgt ccagaaggat     1680
acatctgtgt gaaggctggt cgaaacccca actatggcta cacaagcttt gacacctta      1740 gctgggcttt cctgtctcta tttcgactca tgactcaaga ctactgggaa aatctttacc     1800
agttgacatt acgtgctgct gggaaaacat acatgatatt ttttgtcctg gtcatttttct    1860 tgggctcatt ttatttggtg aatttgatcc tggctgtggt ggccatggcc tatgaggggc     1920
agaatcaggc caccttggaa gaagcagaac aaaaagaggc cgaatttcag cagatgctcg     1980
aacagcttaa aaagcaacag gaagaagctc aggcagttgc ggcagcatca gctgcttcaa     2040
gagatttcag tggaataggt gggttaggag agctgttgga aagttcttca gaagcatcaa     2100
agttgagttc caaaagtgct aaagaatgga ggaaccgaag gaagaaaaga agacagagag     2160
agcaccttga aggaaacaac aaaggagaga gacagagctt tcccaaatcc gaatctgaag     2220
acagcgtcaa aagaagcagc ttccttttct ccatggatgg aaacagactg accagtgaca     2280
aaaaattctg ctccccctcat cagtctctct tgagtatccg tggctccctg ttttccccaa     2340
gacgcaatag caaaacaagc attttcagtt tcagaggtcg ggcaaaggat gttggatctg     2400
aaaatgactt tgctgatgat gaacacagca catttgaaga cagcgaaagc aggagagact     2460 cactgttttgt gccgcacaga catggagagc gacgcaacag taacggcacc accactgaaa     2520
cggaagtcag aaagagaagg ttaagctctt accagatttc aatggagatg ctggaggatt     2580
cctctggaag gcaaagagcc gtgagcatag ccagcattct gaccaacaca atggaagaac     2640
```

```
ttgaagaatc tagacagaaa tgtccgccat gctggtatag atttgccaat gtgttcttga    2700
tctgggactg ctgtgatgca tggttaaaag taaaacatct tgtgaattta attgttatgg    2760
atccatttgt tgatcttgcc atcactattt gcattgtctt aaatacccctc tttatggcca   2820 tggagcacta ccccatgact gagcaattca gtagtgtgtt gactgtagga aacctggtct    2880
ttactgggat ttttacagca gaaatggttc tcaagatcat tgccatggat ccttattact    2940
atttccaaga aggctggaat atctttgatg gaattattgt cagcctcagt ttaatggagc    3000
ttggtctgtc aaatgtggag ggattgtctg tactgcgatc attcagactg cttagagttt    3060
tcaagttggc aaaatcctgg cccacactaa atatgctaat taagatcatt ggcaattctg    3120
tgggggctct aggaaaccctc accttggtgt tggccatcat cgtcttcatt tttgctgtgg   3180
tcggcatgca gctctttggt aagagctaca agaatgtgt ctgcaagatc aatgatgact     3240
gtacgctccc acggtggcac atgaacgact tcttccactc cttcctgatt gtgttccgcg    3300
tgctgtgtgg agagtggata gagaccatgt gggactgtat ggaggtcgct ggccaaacca    3360
tgtgccttat tgttttcatg ttggtcatgg tcattggaaa ccttgtggtt ctgaacctct    3420
ttctggcctt attgttgagt tcatttagct cagacaacct tgctgctact gatgatgaca    3480
atgaaatgaa taatctgcag attgcagtag gaagaatgca aaagggaatt gattatgtga    3540
aaaataagat gcgggagtgt ttccaaaaag cctttttttag aaagccaaaa gttatagaaa   3600
tccatgaagg caataagata gacagctgca tgtccaataa tactggaatt gaaataagca    3660
aagagcttaa ttatcttaga gatgggaatg gaaccaccag tggtgtaggt actggaagca    3720
gtgttgaaaa atacgtaatc gatgaaaatg attatatgtc attcataaac aaccccagcc    3780
tcaccgtcac agtgccaatt gctgttggag agtctgactt tgaaaactta aatactgaag    3840
agttcagcag tgagtcagaa ctagaagaaa gcaaggagaa attaaatgca accagctcat    3900
ctgaaggaag cacagttgat gttgttctac cccgagaagg tgaacaagct gaaactgaac    3960
ccgaagaaga ccttaaaccg gaagcttgtt ttactgaagg atgtattaaa aagtttccat    4020
tctgtcaagt aagtacagaa gaaggcaaag ggaagatctg gtggaatctt cgaaaaaccct  4080 gctacagtat tgttgagcac aactggtttg agactttcat tgtgttcatg atccttctca    4140
gtagtggtgc attggccttt gaagatatat acattgaaca gcgaaagact atcaaaacca    4200
tgctagaata tgctgacaaa gtcttttacct atatattcat tctggaaatg cttctcaaat    4260
gggttgctta tggatttcaa acatatttca ctaatgcctg gtgctggcta gatttcttga    4320
tcgttgatgt ttctttggtt agcctggtag ccaatgctct tggctactca gaactcggtg    4380
ccatcaaatc attacggaca ttaagagctt taagacctct aagagcctta tcccggtttg    4440
aaggcatgag ggtggttgtg aatgctcttg ttggagcaat tccctctatc atgaatgtgc    4500
tgttggtctg tctcatcttc tggttgatct ttagcatcat gggtgtgaat ttgtttgctg    4560
gcaagttcta ccactgtgtt aacatgacaa cgggtaacat gtttgacatt agtgatgtta    4620
acaatttgag tgactgtcag gctcttggca agcaagctcg gtggaaaaac gtgaaagtaa    4680
actttgataa tgttggcgct ggctatcttg cactgcttca agtggccaca tttaaaggct    4740
ggatggatat tatgtatgca gctgttgatt cacgagatgt taaacttcag cctgtatatg    4800
aagaaaatct gtacatgtat ttatactttg tcatctttat catctttggg tcattcttca    4860
ctctgaatct attcattggt gtcatcatag ataacttcaa ccagcagaaa agaagtttg    4920 gaggtcaaga catctttatg acagaggaac agaaaaaata ttacaatgca atgaagaaac    4980
ttggatccaa gaaacctcag aaacccatac ctcgcccagc aaacaaattc caaggaatgg    5040
```

```
tctttgattt tgtaaccaga caagtctttg atatcagcat catgatcctc atctgcctca    5100
acatggtcac catgatggtg aaacggatg  accagggcaa atacatgacc ctagttttgt    5160
cccggatcaa cctagtgttc attgttctgt tcactggaga atttgtgctg aagctcgtct    5220
ccctcagaca ctactacttc actataggct ggaacatctt tgactttgtg gtggtgattc    5280
tctccattgt aggtatgttt ctggctgaga tgatagaaaa gtattttgtg tcccctacct    5340
tgttccgagt gatccgtctt gccaggattg gccgaatcct acgtctgatc aaaggagcaa    5400
aggggatccg cacgctgctc tttgctttga tgatgtccct tcctgcgttg tttaacatcg    5460
gcctcctgct cttcctggtc atgtttatct atgccatctt tgggatgtcc aactttgcct    5520
atgttaaaaa ggaagctgga attgatgaca tgttcaactt tgagaccttt ggcaacagca    5580
tgatctgctt gttccaaatt acaacctctg ctggatggga tggattgcta gcacctattc    5640
ttaatagtgc accacccgac tgtgaccctg acacaattca ccctggcagc tcagttaagg    5700
gagactgtgg gaacccatct gttgggattt tcttttttgt cagttacatc atcatatcct    5760
tcctggtggt ggtgaacagt tacatcgcgg tcatcctgga gaacttcagt gttgctactg    5820
aagaaagtgc agagccctg  agtgaggatg actttgagat gttctatgag gtttgggaaa    5880
agtttgatcc cgatgcgacc cagtttatag agttctctaa actctctgat tttgcagctg    5940
ccctggatcc tcctcttctc atagcaaaac ccaacaaagt ccagcttatt gccatggatc    6000
tgcccatggt cagtggtgac cggatccact gtcttgatat tttatttgcc tttacaaagc    6060 gtgtttggg  tgagagtgga gagatggatg cccttcgaat acagatggaa acaggttta     6120 tggcatcaaa cccctccaaa gtctcttatg agcctattac aaccactttg aaacgtaaac    6180
aagaggaggt gtctgccgct atcattcagc gtaatttcag atgttatctt ttaaagcaaa    6240
ggttaaaaaa tatatcaagt aactataaca aagaggcaat aaaggggagg attgacttac    6300
ctataaaaca agacatgatt attgacaaac tgaatgggaa ctccactcca gaaaaaacag    6360
atgggagttc ctctaccacc tctcctcctt cctatgatag tgtaacaaaa ccagacaagg    6420
aaaagtttga aaagacaaa  ccagaaaaag aaagcaaagg aaaagaggtc agagaaaatc    6480
aaaagtaaaa agaaacaaag aattatcttt gtgatcaatt gtttacagcc tatgaaggta    6540
aagtatatgt gtcaactgga cttcaagagg aggtccatgc caaactgact gttttaacaa    6600
atactcatag tcagtgccta tacaagacag tgaagtgacc tctctgtcac tgcaactctg    6660
tgaagcaggg tatcaacatt gacaagaggt tgctgttttt attaccagct gacactgctg    6720
aggagaaacc caatggctac ctagactata gggatagttg tgcaaagtga acattgtaac    6780
tacaccaaac accttagta  cagtccttgc atccattcta tttttaactt ccatatctgc    6840
catattttta caaatttgt  tctagtgcat ttccatggtc cccaattcat agtttattca    6900
taatgctatg tcactatttt tgtaaatgag gtttacgttg aagaaacagt atacaagaac    6960
cctgtctctc aaatgatcag acaaaggtgt tttgccagag agataaaatt tttgctcaaa    7020
accagaaaaa gaattgtaat ggctacagtt tcagttactt ccatttttcta gatggcttta    7080 attttgaaag tattttagtc tgttatgttt gtttctatct gaacagttat gtgcctgtaa    7140
agtctcctct aatatttaaa ggattatttt tatgcaaagt attctgtttc agcaagtgca    7200
aattttattc taagtttcag agctctatat ttaatttagg tcaaatgctt tccaaaaagt    7260
aatctaataa atccattcta gaaaaatata tctaaagtat tgctttagaa tagttgttcc    7320
actttctgct gcagtattgc tttgccatct tctgctctca gcaaagctga tagtctatgt    7380
caattaaata ccctatgtta tgtaaatagt tattttatcc tgtggtgcat gtttgggcaa    7440
```

-continued

```
atatatatat agcctgataa acaacttcta ttaaatcaaa tatgtaccac agtgtatgtg      7500
tcttttgcaa gcttccaaca gggatgtatc ctgtatcatt cattaaacat agtttaaagg      7560
ctatcactaa tgcatgttaa tattgcctat gctgctctat tttactcaat ccattcttca      7620
caagtcttgg ttaaagaatg tcacatattg gtgatagaat gaattcaacc tgctctgtcc      7680
attatgtcaa gcagaataat ttgaagctat ttacaaacac ctttactttt gcacttttaa      7740 ttaacatga gtatcatatg gtatctctct agatttcaag gaaacacact ggatactgcc      7800
tactgacaaa acctattctt catattttgc taaaaatatg tctaaaactt gcgcaaatat      7860
aaataatgta aaatataat caacttttatt tgtcagcatt ttgtacataa gaaaattatt      7920
ttcaggttga tgacatcaca atttatttta cttatgctt ttgcttttga tttttaatca      7980
caattccaaa cttttgaatc cataagattt ttcaatggaa aatttcctaa aataaaagtt      8040
agataatggg ttttatggat ttctttgtta taatatattt tctaccattc caataggaga      8100
tacattggtc aaacactcaa acctagatca ttttctacca actatggttg cctcaatata      8160 acctttatt catagatgtt ttttttatt caacttttgt agtatttacg tatgcagact      8220
agtcttattt ttttaattcc tgctgcacta aagctattac aaatataaca tggactttgt      8280 tcttttagc catgaacaaa gtggcaaagt tgtgcaatta cctaacatga tataaatttt      8340
tgttttttgc acaaccaaa agtttaatgt taattctttt tacaaaacta tttactgtag      8400
tgtattgaag aactgcatgc agggaattgc tattgctaaa aagaatggtg agctacgtca      8460
ttattgagcc aaaagaataa atttcatttt ttattgcatt tcacttattg gcctctgggg      8520 tttttgttt ttgtttttg ctgttggcag tttaaaatat atataattaa taaaacctgt      8580
gcttgatctg acatttgtat acataaaagt ttacatgaat tttacaacag actagtgcat      8640
gattcaccaa gcagtactac agaacaaagg caaatgaaaa gcagctttgt gcacttttat      8700
gtgtgcaaag gatcaagttc acatgttcca actttcaggt ttgataataa tagtagtaac      8760
cacctacaat agctttcaat ttcaattaac tcccttggct ataagcatct aaactcatct      8820
tctttcaata taattgatgc tatctcctaa ttacttggtg gctaataaat gttacattct      8880
ttgttactta aatgcattat ataaactcct atgtatacat aaggtattaa tgatatagtt      8940
attgagaatt tatattaact ttttttttcaa gaacccttgg atttatgtga ggtcaaaacc      9000
aaactcttat tctcagtgga aaactccagt tgtaatgcat atttttaaag acaatttgga      9060
tctaaatatg tatttcataa ttctcccata ataaattata taaggtggct aa              9112
```

<210> SEQ ID NO 67
<211> LENGTH: 1951
<212> TYPE: PRT
<213> ORGANISM: Homo sapiens
<220> FEATURE:
<221> NAME/KEY: MISC_FEATURE
<222> LOCATION: (122)..(122)
<223> OTHER INFORMATION: Xaa = any amino acid

<400> SEQUENCE: 67

```
Met Ala Gln Ala Leu Leu Val Pro Pro Gly Pro Glu Ser Phe Arg Leu
1               5                   10                  15

Phe Thr Arg Glu Ser Leu Ala Ala Ile Glu Lys Arg Ala Ala Glu Glu
            20                  25                  30

Lys Ala Lys Lys Pro Lys Lys Glu Gln Asp Asn Asp Glu Asn Lys
        35                  40                  45

Pro Lys Pro Asn Ser Asp Leu Glu Ala Gly Lys Asn Leu Pro Phe Ile
    50                  55                  60
```

```
Tyr Gly Asp Ile Pro Pro Glu Met Val Ser Glu Pro Leu Glu Asp Leu
 65                  70                  75                  80

Asp Pro Tyr Tyr Ile Asn Lys Lys Thr Phe Ile Val Met Asn Lys Gly
                 85                  90                  95

Lys Ala Ile Ser Arg Phe Ser Ala Thr Ser Ala Leu Tyr Ile Leu Thr
            100                 105                 110

Pro Leu Asn Pro Val Arg Lys Ile Ala Xaa Lys Ile Leu Val His Ser
        115                 120                 125

Leu Phe Ser Met Leu Ile Met Cys Thr Ile Leu Thr Asn Cys Val Phe
    130                 135                 140

Met Thr Leu Ser Asn Pro Pro Asp Trp Thr Lys Asn Val Glu Tyr Thr
145                 150                 155                 160

Phe Thr Gly Ile Tyr Thr Phe Glu Ser Leu Ile Lys Ile Leu Ala Arg
                165                 170                 175

Gly Phe Cys Leu Glu Asp Phe Thr Phe Leu Arg Asp Pro Trp Asn Trp
            180                 185                 190

Leu Asp Phe Ser Val Ile Val Met Ala Tyr Val Thr Glu Phe Val Asp
        195                 200                 205

Leu Gly Asn Val Ser Ala Leu Arg Thr Phe Arg Val Leu Arg Ala Leu
    210                 215                 220

Lys Thr Ile Ser Val Ile Pro Gly Leu Lys Thr Ile Val Gly Ala Leu
225                 230                 235                 240

Ile Gln Ser Val Lys Lys Leu Ser Asp Val Met Ile Leu Thr Val Phe
                245                 250                 255

Cys Leu Ser Val Phe Ala Leu Ile Gly Leu Gln Leu Phe Met Gly Asn
            260                 265                 270

Leu Arg Asn Lys Cys Leu Gln Trp Pro Pro Ser Asp Ser Ala Phe Glu
        275                 280                 285

Thr Asn Thr Thr Ser Tyr Phe Asn Gly Thr Met Asp Ser Asn Gly Thr
    290                 295                 300

Phe Val Asn Val Thr Met Ser Thr Phe Asn Trp Lys Asp Tyr Ile Gly
305                 310                 315                 320

Asp Asp Ser His Phe Tyr Val Leu Asp Gly Gln Lys Asp Pro Leu Leu
                325                 330                 335

Cys Gly Asn Gly Ser Asp Ala Gly Gln Cys Pro Glu Gly Tyr Ile Cys
            340                 345                 350

Val Lys Ala Gly Arg Asn Pro Asn Tyr Gly Tyr Thr Ser Phe Asp Thr
        355                 360                 365

Phe Ser Trp Ala Phe Leu Ser Leu Phe Arg Leu Met Thr Gln Asp Tyr
    370                 375                 380

Trp Glu Asn Leu Tyr Gln Leu Thr Leu Arg Ala Ala Gly Lys Thr Tyr
385                 390                 395                 400

Met Ile Phe Phe Val Leu Val Ile Phe Leu Gly Ser Phe Tyr Leu Val
                405                 410                 415

Asn Leu Ile Leu Ala Val Val Ala Met Ala Tyr Glu Gly Gln Asn Gln
            420                 425                 430

Ala Thr Leu Glu Glu Ala Glu Gln Lys Glu Ala Glu Phe Gln Gln Met
        435                 440                 445

Leu Glu Gln Leu Lys Lys Gln Gln Glu Ala Gln Ala Val Ala Ala
    450                 455                 460

Ala Ser Ala Ala Ser Arg Asp Phe Ser Gly Ile Gly Gly Leu Gly Glu
465                 470                 475                 480

Leu Leu Glu Ser Ser Ser Glu Ala Ser Lys Leu Ser Ser Lys Ser Ala
                485                 490                 495
```

```
Lys Glu Trp Arg Asn Arg Arg Lys Arg Gln Arg Glu His Leu
            500                 505                 510
Glu Gly Asn Asn Lys Gly Glu Arg Asp Ser Phe Pro Lys Ser Glu Ser
            515                 520                 525
Glu Asp Ser Val Lys Arg Ser Ser Phe Leu Phe Ser Met Asp Gly Asn
        530                 535                 540
Arg Leu Thr Ser Asp Lys Lys Phe Cys Ser Pro His Gln Ser Leu Leu
545                 550                 555                 560
Ser Ile Arg Gly Ser Leu Phe Ser Pro Arg Arg Asn Ser Lys Thr Ser
                565                 570                 575
Ile Phe Ser Phe Arg Gly Arg Ala Lys Asp Val Gly Ser Glu Asn Asp
            580                 585                 590
Phe Ala Asp Asp Glu His Ser Thr Phe Glu Asp Ser Glu Ser Arg Arg
            595                 600                 605
Asp Ser Leu Phe Val Pro His Arg His Gly Glu Arg Arg Asn Ser Asn
            610                 615                 620
Gly Thr Thr Thr Glu Thr Glu Val Arg Lys Arg Arg Leu Ser Ser Tyr
625                 630                 635                 640
Gln Ile Ser Met Glu Met Leu Glu Asp Ser Ser Gly Arg Gln Arg Ala
                645                 650                 655
Val Ser Ile Ala Ser Ile Leu Thr Asn Thr Met Glu Glu Leu Glu Glu
            660                 665                 670
Ser Arg Gln Lys Cys Pro Pro Cys Trp Tyr Arg Phe Ala Asn Val Phe
            675                 680                 685
Leu Ile Trp Asp Cys Cys Asp Ala Trp Leu Lys Val Lys His Leu Val
            690                 695                 700
Asn Leu Ile Val Met Asp Pro Phe Val Asp Leu Ala Ile Thr Ile Cys
705                 710                 715                 720
Ile Val Leu Asn Thr Leu Phe Met Ala Met Glu His Tyr Pro Met Thr
                725                 730                 735
Glu Gln Phe Ser Ser Val Leu Thr Val Gly Asn Leu Val Phe Thr Gly
            740                 745                 750
Ile Phe Thr Ala Glu Met Val Leu Lys Ile Ile Ala Met Asp Pro Tyr
            755                 760                 765
Tyr Tyr Phe Gln Glu Gly Trp Asn Ile Phe Asp Gly Ile Ile Val Ser
            770                 775                 780
Leu Ser Leu Met Glu Leu Gly Leu Ser Asn Val Glu Gly Leu Ser Val
785                 790                 795                 800
Leu Arg Ser Phe Arg Leu Leu Arg Val Phe Lys Leu Ala Lys Ser Trp
                805                 810                 815
Pro Thr Leu Asn Met Leu Ile Lys Ile Ile Gly Asn Ser Val Gly Ala
            820                 825                 830
Leu Gly Asn Leu Thr Leu Val Leu Ala Ile Ile Val Phe Ile Phe Ala
            835                 840                 845
Val Val Gly Met Gln Leu Phe Gly Lys Ser Tyr Lys Glu Cys Val Cys
            850                 855                 860
Lys Ile Asn Asp Asp Cys Thr Leu Pro Arg Trp His Met Asn Asp Phe
865                 870                 875                 880
Phe His Ser Phe Leu Ile Val Phe Arg Val Leu Cys Gly Glu Trp Ile
                885                 890                 895
Glu Thr Met Trp Asp Cys Met Glu Val Ala Gly Gln Thr Met Cys Leu
            900                 905                 910
Ile Val Phe Met Leu Val Met Val Ile Gly Asn Leu Val Val Leu Asn
```

```
            915                 920                 925
Leu Phe Leu Ala Leu Leu Leu Ser Ser Phe Ser Asp Asn Leu Ala
        930                 935                 940
Ala Thr Asp Asp Asn Glu Met Asn Asn Leu Gln Ile Ala Val Gly
945                 950                 955                 960
Arg Met Gln Lys Gly Ile Asp Tyr Val Lys Asn Lys Met Arg Glu Cys
            965                 970                 975
Phe Gln Lys Ala Phe Phe Arg Lys Pro Lys Val Ile Glu Ile His Glu
                980                 985                 990
Gly Asn Lys Ile Asp Ser Cys Met Ser Asn Asn Thr Gly Ile Glu Ile
            995                 1000                1005
Ser Lys Glu Leu Asn Tyr Leu Arg Asp Gly Asn Gly Thr Thr Ser
    1010                1015                1020
Gly Val Gly Thr Gly Ser Ser Val Glu Lys Tyr Val Ile Asp Glu
    1025                1030                1035
Asn Asp Tyr Met Ser Phe Ile Asn Asn Pro Ser Leu Thr Val Thr
    1040                1045                1050
Val Pro Ile Ala Val Gly Glu Ser Asp Phe Glu Asn Leu Asn Thr
    1055                1060                1065
Glu Glu Phe Ser Ser Glu Ser Glu Leu Glu Ser Lys Glu Lys
    1070                1075                1080
Leu Asn Ala Thr Ser Ser Ser Glu Gly Ser Thr Val Asp Val Val
    1085                1090                1095
Leu Pro Arg Glu Gly Glu Gln Ala Glu Thr Glu Pro Glu Glu Asp
    1100                1105                1110
Leu Lys Pro Glu Ala Cys Phe Thr Glu Gly Cys Ile Lys Lys Phe
    1115                1120                1125
Pro Phe Cys Gln Val Ser Thr Glu Glu Gly Lys Gly Lys Ile Trp
    1130                1135                1140
Trp Asn Leu Arg Lys Thr Cys Tyr Ser Ile Val Glu His Asn Trp
    1145                1150                1155
Phe Glu Thr Phe Ile Val Phe Met Ile Leu Leu Ser Ser Gly Ala
    1160                1165                1170
Leu Ala Phe Glu Asp Ile Tyr Ile Glu Gln Arg Lys Thr Ile Lys
    1175                1180                1185
Thr Met Leu Glu Tyr Ala Asp Lys Val Phe Thr Tyr Ile Phe Ile
    1190                1195                1200
Leu Glu Met Leu Leu Lys Trp Val Ala Tyr Gly Phe Gln Thr Tyr
    1205                1210                1215
Phe Thr Asn Ala Trp Cys Trp Leu Asp Phe Leu Ile Val Asp Val
    1220                1225                1230
Ser Leu Val Ser Leu Val Ala Asn Ala Leu Gly Tyr Ser Glu Leu
    1235                1240                1245
Gly Ala Ile Lys Ser Leu Arg Thr Leu Arg Ala Leu Arg Pro Leu
    1250                1255                1260
Arg Ala Leu Ser Arg Phe Glu Gly Met Arg Val Val Val Asn Ala
    1265                1270                1275
Leu Val Gly Ala Ile Pro Ser Ile Met Asn Val Leu Leu Val Cys
    1280                1285                1290
Leu Ile Phe Trp Leu Ile Phe Ser Ile Met Gly Val Asn Leu Phe
    1295                1300                1305
Ala Gly Lys Phe Tyr His Cys Val Asn Met Thr Thr Gly Asn Met
    1310                1315                1320
```

-continued

Phe Asp Ile Ser Asp Val Asn Asn Leu Ser Asp Cys Gln Ala Leu
1325                1330                1335

Gly Lys Gln Ala Arg Trp Lys Asn Val Lys Val Asn Phe Asp Asn
1340                1345                1350

Val Gly Ala Gly Tyr Leu Ala Leu Leu Gln Val Ala Thr Phe Lys
1355                1360                1365

Gly Trp Met Asp Ile Met Tyr Ala Ala Val Asp Ser Arg Asp Val
1370                1375                1380

Lys Leu Gln Pro Val Tyr Glu Glu Asn Leu Tyr Met Tyr Leu Tyr
1385                1390                1395

Phe Val Ile Phe Ile Ile Phe Gly Ser Phe Phe Thr Leu Asn Leu
1400                1405                1410

Phe Ile Gly Val Ile Ile Asp Asn Phe Asn Gln Gln Lys Lys Lys
1415                1420                1425

Phe Gly Gly Gln Asp Ile Phe Met Thr Glu Glu Gln Lys Lys Tyr
1430                1435                1440

Tyr Asn Ala Met Lys Lys Leu Gly Ser Lys Lys Pro Gln Lys Pro
1445                1450                1455

Ile Pro Arg Pro Ala Asn Lys Phe Gln Gly Met Val Phe Asp Phe
1460                1465                1470

Val Thr Arg Gln Val Phe Asp Ile Ser Ile Met Ile Leu Ile Cys
1475                1480                1485

Leu Asn Met Val Thr Met Met Val Glu Thr Asp Asp Gln Gly Lys
1490                1495                1500

Tyr Met Thr Leu Val Leu Ser Arg Ile Asn Leu Val Phe Ile Val
1505                1510                1515

Leu Phe Thr Gly Glu Phe Val Leu Lys Leu Val Ser Leu Arg His
1520                1525                1530

Tyr Tyr Phe Thr Ile Gly Trp Asn Ile Phe Asp Phe Val Val Val
1535                1540                1545

Ile Leu Ser Ile Val Gly Met Phe Leu Ala Glu Met Ile Glu Lys
1550                1555                1560

Tyr Phe Val Ser Pro Thr Leu Phe Arg Val Ile Arg Leu Ala Arg
1565                1570                1575

Ile Gly Arg Ile Leu Arg Leu Ile Lys Gly Ala Lys Gly Ile Arg
1580                1585                1590

Thr Leu Leu Phe Ala Leu Met Met Ser Leu Pro Ala Leu Phe Asn
1595                1600                1605

Ile Gly Leu Leu Leu Phe Leu Val Met Phe Ile Tyr Ala Ile Phe
1610                1615                1620

Gly Met Ser Asn Phe Ala Tyr Val Lys Lys Glu Ala Gly Ile Asp
1625                1630                1635

Asp Met Phe Asn Phe Glu Thr Phe Gly Asn Ser Met Ile Cys Leu
1640                1645                1650

Phe Gln Ile Thr Thr Ser Ala Gly Trp Asp Gly Leu Leu Ala Pro
1655                1660                1665

Ile Leu Asn Ser Ala Pro Pro Asp Cys Asp Pro Asp Thr Ile His
1670                1675                1680

Pro Gly Ser Ser Val Lys Gly Asp Cys Gly Asn Pro Ser Val Gly
1685                1690                1695

Ile Phe Phe Phe Val Ser Tyr Ile Ile Ile Ser Phe Leu Val Val
1700                1705                1710

Val Asn Ser Tyr Ile Ala Val Ile Leu Glu Asn Phe Ser Val Ala
1715                1720                1725

```
Thr Glu Glu Ser Ala Glu Pro Leu Ser Glu Asp Asp Phe Glu Met
    1730            1735                1740
Phe Tyr Glu Val Trp Glu Lys Phe Asp Pro Ala Thr Gln Phe
1745            1750                1755
Ile Glu Phe Ser Lys Leu Ser Asp Phe Ala Ala Ala Leu Asp Pro
    1760            1765                1770
Pro Leu Leu Ile Ala Lys Pro Asn Lys Val Gln Leu Ile Ala Met
    1775            1780                1785
Asp Leu Pro Met Val Ser Gly Asp Arg Ile His Cys Leu Asp Ile
    1790            1795                1800
Leu Phe Ala Phe Thr Lys Arg Val Leu Gly Glu Ser Gly Glu Met
1805            1810                1815
Asp Ala Leu Arg Ile Gln Met Glu Asp Arg Phe Met Ala Ser Asn
    1820            1825                1830
Pro Ser Lys Val Ser Tyr Glu Pro Ile Thr Thr Thr Leu Lys Arg
    1835            1840                1845
Lys Gln Glu Glu Val Ser Ala Ala Ile Ile Gln Arg Asn Phe Arg
    1850            1855                1860
Cys Tyr Leu Leu Lys Gln Arg Leu Lys Asn Ile Ser Ser Asn Tyr
    1865            1870                1875
Asn Lys Glu Ala Ile Lys Gly Arg Ile Asp Leu Pro Ile Lys Gln
    1880            1885                1890
Asp Met Ile Ile Asp Lys Leu Asn Gly Asn Ser Thr Pro Glu Lys
    1895            1900                1905
Thr Asp Gly Ser Ser Ser Thr Thr Ser Pro Pro Ser Tyr Asp Ser
    1910            1915                1920
Val Thr Lys Pro Asp Lys Glu Lys Phe Glu Lys Asp Lys Pro Glu
    1925            1930                1935
Lys Glu Ser Lys Gly Lys Glu Val Arg Glu Asn Gln Lys
    1940            1945                1950

<210> SEQ ID NO 68
<211> LENGTH: 1951
<212> TYPE: PRT
<213> ORGANISM: Homo sapiens
<220> FEATURE:
<221> NAME/KEY: MISC_FEATURE
<222> LOCATION: (122)..(122)
<223> OTHER INFORMATION: Xaa = any amino acid

<400> SEQUENCE: 68

Met Ala Gln Ala Leu Leu Val Pro Pro Gly Pro Glu Ser Phe Arg Leu
1               5                   10                  15
Phe Thr Arg Glu Ser Leu Ala Ala Ile Glu Lys Arg Ala Ala Glu Glu
            20                  25                  30
Lys Ala Lys Lys Pro Lys Lys Glu Gln Asp Asn Asp Asp Glu Asn Lys
        35                  40                  45
Pro Lys Pro Asn Ser Asp Leu Glu Ala Gly Lys Asn Leu Pro Phe Ile
    50                  55                  60
Tyr Gly Asp Ile Pro Pro Glu Met Val Ser Glu Pro Leu Glu Asp Leu
65              70                  75                  80
Asp Pro Tyr Tyr Ile Asn Lys Lys Thr Phe Ile Val Met Asn Lys Gly
                85                  90                  95
Lys Ala Ile Ser Arg Phe Ser Ala Thr Ser Ala Leu Tyr Ile Leu Thr
            100                 105                 110
Pro Leu Asn Pro Val Arg Lys Ile Ala Xaa Lys Ile Leu Val His Ser
```

-continued

```
                115                 120                 125
Leu Phe Ser Met Leu Ile Met Cys Thr Ile Leu Thr Asn Cys Val Phe
        130                 135                 140
Met Thr Leu Ser Asn Pro Pro Asp Trp Thr Lys Asn Val Glu Tyr Thr
145                 150                 155                 160
Phe Thr Gly Ile Tyr Thr Phe Glu Ser Leu Ile Lys Ile Leu Ala Arg
                165                 170                 175
Gly Phe Cys Leu Glu Asp Phe Thr Phe Leu Arg Asp Pro Trp Asn Trp
            180                 185                 190
Leu Asp Phe Ser Val Ile Val Met Ala Tyr Val Thr Glu Phe Val Ser
                195                 200                 205
Leu Gly Asn Val Ser Ala Leu Arg Thr Phe Arg Val Leu Arg Ala Leu
        210                 215                 220
Lys Thr Ile Ser Val Ile Pro Gly Leu Lys Thr Ile Val Gly Ala Leu
225                 230                 235                 240
Ile Gln Ser Val Lys Lys Leu Ser Asp Val Met Ile Leu Thr Val Phe
                245                 250                 255
Cys Leu Ser Val Phe Ala Leu Ile Gly Leu Gln Leu Phe Met Gly Asn
            260                 265                 270
Leu Arg Asn Lys Cys Leu Gln Trp Pro Pro Ser Asp Ser Ala Phe Glu
        275                 280                 285
Thr Asn Thr Thr Ser Tyr Phe Asn Gly Thr Met Asp Ser Asn Gly Thr
290                 295                 300
Phe Val Asn Val Thr Met Ser Thr Phe Asn Trp Lys Asp Tyr Ile Gly
305                 310                 315                 320
Asp Asp Ser His Phe Tyr Val Leu Asp Gly Gln Lys Asp Pro Leu Leu
                325                 330                 335
Cys Gly Asn Gly Ser Asp Ala Gly Gln Cys Pro Glu Gly Tyr Ile Cys
            340                 345                 350
Val Lys Ala Gly Arg Asn Pro Asn Tyr Gly Tyr Thr Ser Phe Asp Thr
        355                 360                 365
Phe Ser Trp Ala Phe Leu Ser Leu Phe Arg Leu Met Thr Gln Asp Tyr
        370                 375                 380
Trp Glu Asn Leu Tyr Gln Leu Thr Leu Arg Ala Ala Gly Lys Thr Tyr
385                 390                 395                 400
Met Ile Phe Phe Val Leu Val Ile Phe Leu Gly Ser Phe Tyr Leu Val
                405                 410                 415
Asn Leu Ile Leu Ala Val Val Ala Met Ala Tyr Glu Gly Gln Asn Gln
            420                 425                 430
Ala Thr Leu Glu Glu Ala Glu Gln Lys Glu Ala Glu Phe Gln Gln Met
        435                 440                 445
Leu Glu Gln Leu Lys Lys Gln Gln Glu Glu Ala Gln Ala Val Ala Ala
        450                 455                 460
Ala Ser Ala Ala Ser Arg Asp Phe Ser Gly Ile Gly Gly Leu Gly Glu
465                 470                 475                 480
Leu Leu Glu Ser Ser Ser Glu Ala Ser Lys Leu Ser Ser Lys Ser Ala
                485                 490                 495
Lys Glu Trp Arg Asn Arg Arg Lys Lys Arg Arg Gln Arg Glu His Leu
            500                 505                 510
Glu Gly Asn Asn Lys Gly Glu Arg Asp Ser Phe Pro Lys Ser Glu Ser
        515                 520                 525
Glu Asp Ser Val Lys Arg Ser Ser Phe Leu Phe Ser Met Asp Gly Asn
        530                 535                 540
```

```
-continued

Arg Leu Thr Ser Asp Lys Lys Phe Cys Ser Pro His Gln Ser Leu Leu
545                 550                 555                 560

Ser Ile Arg Gly Ser Leu Phe Ser Pro Arg Asn Ser Lys Thr Ser
            565                 570                 575

Ile Phe Ser Phe Arg Gly Arg Ala Lys Asp Val Gly Ser Glu Asn Asp
                580                 585                 590

Phe Ala Asp Asp Glu His Ser Thr Phe Glu Asp Ser Glu Ser Arg Arg
            595                 600                 605

Asp Ser Leu Phe Val Pro His Arg His Gly Glu Arg Arg Asn Ser Asn
610                 615                 620

Gly Thr Thr Thr Glu Thr Glu Val Arg Lys Arg Leu Ser Ser Tyr
625                 630                 635                 640

Gln Ile Ser Met Glu Met Leu Glu Asp Ser Ser Gly Arg Gln Arg Ala
                645                 650                 655

Val Ser Ile Ala Ser Ile Leu Thr Asn Thr Met Glu Glu Leu Glu Glu
            660                 665                 670

Ser Arg Gln Lys Cys Pro Pro Cys Trp Tyr Arg Phe Ala Asn Val Phe
            675                 680                 685

Leu Ile Trp Asp Cys Cys Asp Ala Trp Leu Lys Val Lys His Leu Val
    690                 695                 700

Asn Leu Ile Val Met Asp Pro Phe Val Asp Leu Ala Ile Thr Ile Cys
705                 710                 715                 720

Ile Val Leu Asn Thr Leu Phe Met Ala Met Glu His Tyr Pro Met Thr
                725                 730                 735

Glu Gln Phe Ser Ser Val Leu Thr Val Gly Asn Leu Val Phe Thr Gly
            740                 745                 750

Ile Phe Thr Ala Glu Met Val Leu Lys Ile Ile Ala Met Asp Pro Tyr
            755                 760                 765

Tyr Tyr Phe Gln Glu Gly Trp Asn Ile Phe Asp Gly Ile Ile Val Ser
    770                 775                 780

Leu Ser Leu Met Glu Leu Gly Leu Ser Asn Val Glu Gly Leu Ser Val
785                 790                 795                 800

Leu Arg Ser Phe Arg Leu Leu Arg Val Phe Lys Leu Ala Lys Ser Trp
                805                 810                 815

Pro Thr Leu Asn Met Leu Ile Lys Ile Ile Gly Asn Ser Val Gly Ala
            820                 825                 830

Leu Gly Asn Leu Thr Leu Val Leu Ala Ile Ile Val Phe Ile Phe Ala
    835                 840                 845

Val Val Gly Met Gln Leu Phe Gly Lys Ser Tyr Lys Glu Cys Val Cys
    850                 855                 860

Lys Ile Asn Asp Asp Cys Thr Leu Pro Arg Trp His Met Asn Asp Phe
865                 870                 875                 880

Phe His Ser Phe Leu Ile Val Phe Arg Val Leu Cys Gly Glu Trp Ile
                885                 890                 895

Glu Thr Met Trp Asp Cys Met Glu Val Ala Gly Gln Thr Met Cys Leu
            900                 905                 910

Ile Val Phe Met Leu Val Met Val Ile Gly Asn Leu Val Val Leu Asn
            915                 920                 925

Leu Phe Leu Ala Leu Leu Leu Ser Ser Phe Ser Asp Asn Leu Ala
    930                 935                 940

Ala Thr Asp Asp Asp Asn Glu Met Asn Asn Leu Gln Ile Ala Val Gly
945                 950                 955                 960

Arg Met Gln Lys Gly Ile Asp Tyr Val Lys Asn Lys Met Arg Glu Cys
                965                 970                 975
```

-continued

```
Phe Gln Lys Ala Phe Phe Arg Lys Pro Lys Val Ile Glu Ile His Glu
            980             985                 990
Gly Asn Lys Ile Asp Ser Cys Met Ser Asn Asn Thr Gly Ile Glu Ile
        995                 1000                    1005
Ser Lys Glu Leu Asn Tyr Leu Arg Asp Gly Asn Gly Thr Thr Ser
    1010            1015            1020
Gly Val Gly Thr Gly Ser Ser Val Glu Lys Tyr Val Ile Asp Glu
    1025            1030            1035
Asn Asp Tyr Met Ser Phe Ile Asn Asn Pro Ser Leu Thr Val Thr
    1040            1045            1050
Val Pro Ile Ala Val Gly Glu Ser Asp Phe Glu Asn Leu Asn Thr
    1055            1060            1065
Glu Glu Phe Ser Ser Glu Ser Glu Leu Glu Ser Lys Glu Lys
    1070            1075            1080
Leu Asn Ala Thr Ser Ser Ser Glu Gly Ser Thr Val Asp Val Val
    1085            1090            1095
Leu Pro Arg Glu Gly Glu Gln Ala Glu Thr Glu Pro Glu Glu Asp
    1100            1105            1110
Leu Lys Pro Glu Ala Cys Phe Thr Glu Gly Cys Ile Lys Lys Phe
    1115            1120            1125
Pro Phe Cys Gln Val Ser Thr Glu Glu Gly Lys Gly Lys Ile Trp
    1130            1135            1140
Trp Asn Leu Arg Lys Thr Cys Tyr Ser Ile Val Glu His Asn Trp
    1145            1150            1155
Phe Glu Thr Phe Ile Val Phe Met Ile Leu Leu Ser Ser Gly Ala
    1160            1165            1170
Leu Ala Phe Glu Asp Ile Tyr Ile Glu Gln Arg Lys Thr Ile Lys
    1175            1180            1185
Thr Met Leu Glu Tyr Ala Asp Lys Val Phe Thr Tyr Ile Phe Ile
    1190            1195            1200
Leu Glu Met Leu Leu Lys Trp Val Ala Tyr Gly Phe Gln Thr Tyr
    1205            1210            1215
Phe Thr Asn Ala Trp Cys Trp Leu Asp Phe Leu Ile Val Asp Val
    1220            1225            1230
Ser Leu Val Ser Leu Val Ala Asn Ala Leu Gly Tyr Ser Glu Leu
    1235            1240            1245
Gly Ala Ile Lys Ser Leu Arg Thr Leu Arg Ala Leu Arg Pro Leu
    1250            1255            1260
Arg Ala Leu Ser Arg Phe Glu Gly Met Arg Val Val Val Asn Ala
    1265            1270            1275
Leu Val Gly Ala Ile Pro Ser Ile Met Asn Val Leu Leu Val Cys
    1280            1285            1290
Leu Ile Phe Trp Leu Ile Phe Ser Ile Met Gly Val Asn Leu Phe
    1295            1300            1305
Ala Gly Lys Phe Tyr His Cys Val Asn Met Thr Thr Gly Asn Met
    1310            1315            1320
Phe Asp Ile Ser Asp Val Asn Asn Leu Ser Asp Cys Gln Ala Leu
    1325            1330            1335
Gly Lys Gln Ala Arg Trp Lys Asn Val Lys Val Asn Phe Asp Asn
    1340            1345            1350
Val Gly Ala Gly Tyr Leu Ala Leu Leu Gln Val Ala Thr Phe Lys
    1355            1360            1365
Gly Trp Met Asp Ile Met Tyr Ala Ala Val Asp Ser Arg Asp Val
```

-continued

```
            1370                1375                1380
Lys Leu Gln Pro Val Tyr Glu Glu Asn Leu Tyr Met Tyr Leu Tyr
    1385                1390                1395
Phe Val Ile Phe Ile Ile Phe Gly Ser Phe Phe Thr Leu Asn Leu
    1400                1405                1410
Phe Ile Gly Val Ile Ile Asp Asn Phe Asn Gln Gln Lys Lys Lys
    1415                1420                1425
Phe Gly Gly Gln Asp Ile Phe Met Thr Glu Glu Gln Lys Lys Tyr
    1430                1435                1440
Tyr Asn Ala Met Lys Lys Leu Gly Ser Lys Lys Pro Gln Lys Pro
    1445                1450                1455
Ile Pro Arg Pro Ala Asn Lys Phe Gln Gly Met Val Phe Asp Phe
    1460                1465                1470
Val Thr Arg Gln Val Phe Asp Ile Ser Ile Met Ile Leu Ile Cys
    1475                1480                1485
Leu Asn Met Val Thr Met Met Val Glu Thr Asp Asp Gln Gly Lys
    1490                1495                1500
Tyr Met Thr Leu Val Leu Ser Arg Ile Asn Leu Val Phe Ile Val
    1505                1510                1515
Leu Phe Thr Gly Glu Phe Val Leu Lys Leu Val Ser Leu Arg His
    1520                1525                1530
Tyr Tyr Phe Thr Ile Gly Trp Asn Ile Phe Asp Phe Val Val Val
    1535                1540                1545
Ile Leu Ser Ile Val Gly Met Phe Leu Ala Glu Met Ile Glu Lys
    1550                1555                1560
Tyr Phe Val Ser Pro Thr Leu Phe Arg Val Ile Arg Leu Ala Arg
    1565                1570                1575
Ile Gly Arg Ile Leu Arg Leu Ile Lys Gly Ala Lys Gly Ile Arg
    1580                1585                1590
Thr Leu Leu Phe Ala Leu Met Met Ser Leu Pro Ala Leu Phe Asn
    1595                1600                1605
Ile Gly Leu Leu Leu Phe Leu Val Met Phe Ile Tyr Ala Ile Phe
    1610                1615                1620
Gly Met Ser Asn Phe Ala Tyr Val Lys Lys Glu Ala Gly Ile Asp
    1625                1630                1635
Asp Met Phe Asn Phe Glu Thr Phe Gly Asn Ser Met Ile Cys Leu
    1640                1645                1650
Phe Gln Ile Thr Thr Ser Ala Gly Trp Asp Gly Leu Leu Ala Pro
    1655                1660                1665
Ile Leu Asn Ser Ala Pro Pro Asp Cys Asp Pro Asp Thr Ile His
    1670                1675                1680
Pro Gly Ser Ser Val Lys Gly Asp Cys Gly Asn Pro Ser Val Gly
    1685                1690                1695
Ile Phe Phe Phe Val Ser Tyr Ile Ile Ile Ser Phe Leu Val Val
    1700                1705                1710
Val Asn Ser Tyr Ile Ala Val Ile Leu Glu Asn Phe Ser Val Ala
    1715                1720                1725
Thr Glu Glu Ser Ala Glu Pro Leu Ser Glu Asp Asp Phe Glu Met
    1730                1735                1740
Phe Tyr Glu Val Trp Glu Lys Phe Asp Pro Asp Ala Thr Gln Phe
    1745                1750                1755
Ile Glu Phe Ser Lys Leu Ser Asp Phe Ala Ala Ala Leu Asp Pro
    1760                1765                1770
```

| | | | | | | | | | | |
|---|---|---|---|---|---|---|---|---|---|---|
| Pro | Leu | Leu | Ile | Ala | Lys | Pro | Asn | Lys | Val | Gln | Leu | Ile | Ala | Met |
| | 1775 | | | | 1780 | | | | 1785 | |

| Asp | Leu | Pro | Met | Val | Ser | Gly | Asp | Arg | Ile | His | Cys | Leu | Asp | Ile |
| | 1790 | | | | 1795 | | | | 1800 | |

| Leu | Phe | Ala | Phe | Thr | Lys | Arg | Val | Leu | Gly | Glu | Ser | Gly | Glu | Met |
| | 1805 | | | | 1810 | | | | 1815 | |

| Asp | Ala | Leu | Arg | Ile | Gln | Met | Glu | Asp | Arg | Phe | Met | Ala | Ser | Asn |
| | 1820 | | | | 1825 | | | | 1830 | |

| Pro | Ser | Lys | Val | Ser | Tyr | Glu | Pro | Ile | Thr | Thr | Thr | Leu | Lys | Arg |
| | 1835 | | | | 1840 | | | | 1845 | |

| Lys | Gln | Glu | Glu | Val | Ser | Ala | Ala | Ile | Ile | Gln | Arg | Asn | Phe | Arg |
| | 1850 | | | | 1855 | | | | 1860 | |

| Cys | Tyr | Leu | Leu | Lys | Gln | Arg | Leu | Lys | Asn | Ile | Ser | Ser | Asn | Tyr |
| | 1865 | | | | 1870 | | | | 1875 | |

| Asn | Lys | Glu | Ala | Ile | Lys | Gly | Arg | Ile | Asp | Leu | Pro | Ile | Lys | Gln |
| | 1880 | | | | 1885 | | | | 1890 | |

| Asp | Met | Ile | Ile | Asp | Lys | Leu | Asn | Gly | Asn | Ser | Thr | Pro | Glu | Lys |
| | 1895 | | | | 1900 | | | | 1905 | |

| Thr | Asp | Gly | Ser | Ser | Ser | Thr | Thr | Ser | Pro | Pro | Ser | Tyr | Asp | Ser |
| | 1910 | | | | 1915 | | | | 1920 | |

| Val | Thr | Lys | Pro | Asp | Lys | Glu | Lys | Phe | Glu | Lys | Asp | Lys | Pro | Glu |
| | 1925 | | | | 1930 | | | | 1935 | |

| Lys | Glu | Ser | Lys | Gly | Lys | Glu | Val | Arg | Glu | Asn | Gln | Lys |
| | 1940 | | | | 1945 | | | | 1950 | |

```
<210> SEQ ID NO 69
<211> LENGTH: 1380
<212> TYPE: DNA
<213> ORGANISM: Homo sapiens
<220> FEATURE:
<221> NAME/KEY: misc_feature
<222> LOCATION: (839)..(1083)
<223> OTHER INFORMATION: exon 01

<400> SEQUENCE: 69
aatgtattta tttaattgat gataaactgt aataaaatca tagttgtttg ctctaaagta      60
gatatgaaag gtcagatgaa acaataacat acatctggat tgagaaatat cttaataact     120
gatggattat ttttattttc tttatgtatt gtgtgcttca atatcctaat aaataatatt     180
agctaggttc actgatgtat agaatctttt tctacattta gatatttctt gcaaatgttt     240
taccagaaag caacacaaaa atactatcag tgagtatgtg tttacactgt tctctaagga     300
gtcaaattcc tcaccttgaa ataaattcat cccaggaaga gaaaaggttt tcaaaagact     360
agagcaggcc acaagggagc tttcgcaaaa ctctacacgt aaagggtaat gtaaacttaa     420
aacctatttt tcaaacagta atttatatat cttttaattt tagtagttta tgtgtgaaac     480
aatcatgcaa aacaacaaag tgataaaatt ttttaaaaaa attagtgaga tgcaaataac     540
tgaatatgta aaaggtctca tacatattta tatgtagtag ataagttaca ttttttttagt    600
gtgttgggaa attttagctc acatcacctc tctactgtca tcttgggca ctttcatgac      660
tacccatgct tcatgcaggt ttactttcct ccctgtgaca gaggataatg ggaatgtttt     720
ttctttggct caattttgtg tgtgtccgcc agtagatggc gtaccacttt gagtgcgatc     780
ggccttttt  tctttctttt tttttttcct caaagctgtt ttctgatata tgttgggtac     840
catagagtga atctcagaac aggaagcgga ggcataagca gagaggattc tggaaaggtc     900
tctttgtttt cttatccaca gagaaagaaa gaaaaaaaat tgtaactaat ttgtaaacct     960
```

```
ctgtggtcaa aaaaaaaaaa aaaaaaaaaa gctgaacagc tgcagaggaa gacacgttat    1020
accctaacca tcttggatgc tgggctttgt tatgctgtaa ttcataaggc tctgttttat    1080
caggtaagct gacaaaacat ttcattatct gcaccataga acctagctac caggtcattt    1140
tccttacttt aaaatcatct tcatgctgct attttaacc cagtgttgtt taaatgtaaa     1200
ttacaggaac caaaggcatc gtttgatgtg taaactgctt actatttctt tatctttcaa    1260
agaaaataga gcctgtctgg aaatggtgat ttatggtaca tactaggcat caatggtctt    1320 gtgttttgt agatgcttat gattaattgt attcagaaaa atatttttt attatactta     1380
```

```
<210> SEQ ID NO 70
<211> LENGTH: 840
<212> TYPE: DNA
<213> ORGANISM: Homo sapiens
<220> FEATURE:
<221> NAME/KEY: misc_feature
<222> LOCATION: (314)..(510)
<223> OTHER INFORMATION: exon 01b

<400> SEQUENCE: 70
agggaagaac agaaggatgc tcaggagtgc cagcatgcct tcagaaagac taaatggatc      60
aaggctgcca agaaggggg agcacccctg tcccaaccct aggatcctgg cagtggttcc     120
tggtcccatt cttcctaaat catgctaggg catgctttta acaagggtca atatcttgc     180 tttgcatcat ccttgctttc tcgatccagg gccataaaaa aaaaggaat aaaacccaga     240 cacagagcca gagcacccct atgccaaatg tcaaagatta taggctaatt tcacctgtat   300
tctctttcta cagagattat ggagcaagaa aactgaagcc aagccacatc aaggtttgac   360
agggatgaga tacctgtcaa ggattcatag tagagtggct tactgggaaa ggagcaaaga   420
atctcttcta gggatattgt aagaataaat gagataattc acagaaggga cctggagctt   480
ttccggaaaa aggtgctgtg actatctaag gtaactaaac aacttctggg tataagtttg   540
tttttgtgga aaataaacta aaatctctac tatttaacaa ggacagctgt atcaggacca   600
aaagaaggca gaggggtgtt ttcttccttc ctctaccagt ttgttcttcc aaagaggcaa   660
atacatacag ggagacatag cacagatgac cttagggaat ggaatgatgc caaaggctgt   720
tgatgtaaga aagagagatt aactcagttt ttttttgtt tttgtttttt tgttgttgtt     780
gttgttgttt tgagacagag tctctctctg tcgcccaggc tggagtgcag tggcatgaac   840
```

```
<210> SEQ ID NO 71
<211> LENGTH: 780
<212> TYPE: DNA
<213> ORGANISM: Homo sapiens
<220> FEATURE:
<221> NAME/KEY: misc_feature
<222> LOCATION: (321)..(460)
<223> OTHER INFORMATION: exon 01c

<400> SEQUENCE: 71
gatatattaa atttatgta ttttaataaa ttataatgtg catataatca ttaataatat       60
atatattcca caccaaggca tcagtaagaa ttaattttta aagtctgctc taatgtgaat    120
ataaaattat gtaagaactc tgtataataa gctcacagag tacaagaaag gagaggaaaa   180
aagtaaaaga gaactgcgaa agaactatga gggatttcca acagcaaaa ttgtcattga    240 agccatgaga aactctactc actaaattct ttaatttctc agcctaccca aatattgggc   300
aaaccctaat tctcttgcag gggaaaagct gagagtctgg aactagccta tcttccgagg   360
acttagagac aacagtatgg gaatttcaac gagacgtttt tactttcttt tgaccaagat   420
```

-continued

| | |
|---|---|
| tcaaattctt tattccagcc cttgataagt aaataagaag gtaaaggact atttatttgt | 480 |
| aaaaagtttt tcatgatttt gtgatggcac cttgttccat atcatctcag ataaatcaga | 540 |
| ataatttgtg aaaattactc ggtgatttcc acattagata tttttaaacct aatgttatttt | 600 |
| ctaaaacaaa aaccaaccag gagaatccaa ttaagtaaaa tgtatgtatt aatataaatt | 660 |
| agctattccc atctggaaaa gggcagccat ttctgtgttg aggtgcctca atgatactga | 720 |
| ggctgagaca ggttagatga tacaggcata ccattagcag cagactcaat actaacccag | 780 |

<210> SEQ ID NO 72
<211> LENGTH: 1025
<212> TYPE: DNA
<213> ORGANISM: Homo sapiens
<220> FEATURE:
<221> NAME/KEY: misc_feature
<222> LOCATION: (455)..(768)
<223> OTHER INFORMATION: exon 02

<400> SEQUENCE: 72

| | |
|---|---|
| acaaagttat gaaaaggcgg ggggcaggat gcagaataat taagcaattt tattgacaaa | 60 |
| ctthactggc attactcttt tgctgaaagt atactatatt ttggcttaca gtgtcaaaac | 120 |
| agaatttttt aaatgctttt aaaaaatgga caaaattata gatattcttg agtttaaata | 180 |
| taatgtttat atattatata tactgtacat tgtagaatgg ctaaatcaaa ctaattaaca | 240 |
| ttaagtacag acttttgata gatttatgaa cttggcttat tgagaatgag gttgaatgat | 300 |
| gatgttttca agttcaaatg tgtagtgcag tactaaaagc atgacttaat gtttatagct | 360 |
| ttaaaaagtt actaaagaat gacattttgg ttgatgttct tatgcccaat cgcttgcttt | 420 |
| cctaactctt gtgcaatttt tcttttttatt gcaggtaatt cgtatgcaag aagctacacg | 480 |
| taattaaatg tgcaggatga aaagatggca caggcactgt tggtaccccc aggacctgaa | 540 |
| agcttccgcc tttttactag agaatctctt gctgctatcg aaaaacgtgc tgcagaagag | 600 |
| aaagccaaga agcccaaaaa ggaacaagat aatgatgatg agaacaaacc aaagccaaat | 660 |
| agtgacttgg aagctggaaa gaaccttcca tttatttatg gagacattcc tccagagatg | 720 |
| gtgtcagagc ccctggagga cctggatccc tactatatca ataagaaagt gagtattgat | 780 |
| tttagacttc taataaatct ttaatgaaac tcttaactgt aatatacttt tctgggcctt | 840 |
| atatacagca tcacaatttt tcttctgtta aagatttttat aatactcttc actgtcacttt | 900 |
| atttttatca caatataata aaacaaacat ttataagaaa tgaagtcaag agttggttac | 960 |
| agtcaggaaa tatgaataga tgaatgattt ctacaatttc acagtgataa ttcagatagt | 1020 |
| caaaa | 1025 |

<210> SEQ ID NO 73
<211> LENGTH: 433
<212> TYPE: DNA
<213> ORGANISM: Homo sapiens
<220> FEATURE:
<221> NAME/KEY: misc_feature
<222> LOCATION: (177)..(295)
<223> OTHER INFORMATION: exon 03

<400> SEQUENCE: 73

| | |
|---|---|
| tgtaacyata tgttaattta aacatctaac atgtttgtag ttatgatata tcaactggtt | 60 |
| taaacaaacc agtttgaaca aacaaattcy atttttttaaa aaggtcctca tgtatgtaag | 120 |
| ctccttaaat aagcccatgt ctaatttagt aattttactc gtattttctg tttcagactt | 180 |
| ttatagtaat gaataaagga aaggcaattt cccgattcag tgccacctct gccttgtata | 240 |

```
ttttaactcc actaaaccct gttaggaaaa ttgctabsaa gattttggta cattcatatc      300
cttttaatgt gaattgccta aatgctattt ctaacagttg attttaaaga aaatgtcagt      360
tatattttca agtatctgta aaatttcttt gagattaatg gtaacattgt tagtttaatt      420
catttatttg cat                                                        433

<210> SEQ ID NO 74
<211> LENGTH: 450
<212> TYPE: DNA
<213> ORGANISM: Homo sapiens
<220> FEATURE:
<221> NAME/KEY: misc_feature
<222> LOCATION: (175)..(264)
<223> OTHER INFORMATION: exon 04

<400> SEQUENCE: 74
gagtgcacca aggccatatc acaggctttg aagtttctta ttattttatc attgttttaa       60
aacaaataat attaatttca cagttttttgc atcgataaac ttttttgtgt gttttggatc     120
atttataaat ggccatggta acctactaac atttattcct taactataat ctactttatt     180
cagcatgctt atcatgtgca ctattttgac caactgtgta tttatgacct tgagcaaccc     240
tcctgactgg acaaagaatg tagagtaagt aggaataact tctgggaatg agaaatgcac     300
actcaaattc tctagcaatc tccttgtggg tatagcctga cttatggttt ccacttctgt     360
ctaagaaaag ttattttcat aatatgcagc cggtaaggga ggtctttcgg gggagctatt     420
cttctacgag gtaagtattt tcccacaaaa                                      450

<210> SEQ ID NO 75
<211> LENGTH: 701
<212> TYPE: DNA
<213> ORGANISM: Homo sapiens
<220> FEATURE:
<221> NAME/KEY: misc_feature
<222> LOCATION: (341)..(469)
<223> OTHER INFORMATION: exon 05

<400> SEQUENCE: 75
aaaatttacc atttgyggct ttccattaca tttctatcag ataactctgc gctagtaggt       60
caaactagat gattatccat aagatacatg aaactattat tctaaaaccc aaatagttaa     120
accagattag attcctaaag aatatatttt ctcttcagtt taactctttg ctcaggcttg     180
taaaactaac taaatgaata gattatttgg taaatagaag taaggaacaa tattttaatg     240
aattgaaaaa ccacaaaagg ataggatttg ctatgattga aaacatttat tttaacagtt     300
caagcaaaat tgttaatttt ggcttggatg ttttttcctag gtacacattc actggaatct     360
atacctttga gtcacttata aaaatcttgg caagagggtt ttgcttagaa gattttacgt     420
ttcttcgtga tccatggaac tggctggatt tcagtgtcat tgtgatggcg tgagtaactt     480
tgaaaatttg ataagcgcaa aggagtgaaa atagtcatag tacaaacaag gtctttgtgt     540
catatattaa atgtagagct ttcttgttag tcaagttaac tatatgggtt gtgtattttc     600
agaatacata ttagaataca tattgcaatg taaatatatc cagtaaatga tcaataaatg     660
gggttatctt catgtcatat agtctttctc ttcatcaaaa t                         701

<210> SEQ ID NO 76
<211> LENGTH: 286
<212> TYPE: DNA
<213> ORGANISM: Homo sapiens
<220> FEATURE:
<221> NAME/KEY: misc_feature
<222> LOCATION: (103)..(194)
```

<223> OTHER INFORMATION: exon 06N

<400> SEQUENCE: 76

```
atttgttaaa ctcacagggc tctatgtgcc aaacccagca ttaagtcctt atttagtata    60
aactttgcca aaactatcag taactctgat ttaattctgc aggtatgtaa cagaatttgt   120
aagcctaggc aatgtttcag cccttcgaac tttcagagtc ttgagagctc tgaaaactat   180
ttctgtaatc ccaggtaaga agaaactggt gtaaggtagt aggcccctta tatctccaac   240
ttttcttgtg tgttattgtg tttgtgtgtg aactccccta ttacag                  286
```

<210> SEQ ID NO 77
<211> LENGTH: 515
<212> TYPE: DNA
<213> ORGANISM: Homo sapiens
<220> FEATURE:
<221> NAME/KEY: misc_feature
<222> LOCATION: (93)..(184)
<223> OTHER INFORMATION: exon 06A

<400> SEQUENCE: 77

```
gtaagaagaa actggtgtaa ggtagtaggc cccttatatc tccaactttt cttgtgtgtt    60
attgtgtttg tgtgtgaact ccctattac agatatgtga cagagtttgt ggacctgggc   120
aatgtctcag cgttgagaac attcagagtt ctccgagcac tgaaaacaat ttcagtcatt   180
ccaggtgaga gctaggttaa acaccgaggt tgactttaat tattgagttt gaaatcaatt   240
tatatgactt acagcattag ccttgttgct tattattaca gttcatcccg gtaaataatg   300
ccaaatgatg tttcaatgtc agtttagctc ctaaaatttt ataaattaca tgcgtattta   360
taaagtcagc ctttgagttt aacagaaaat tgcatgagac atcttcaaaa aatgctaatt   420
tgggcctctt gcgctctctc tctctctttt tcactaccat ggctttacta acagatttgg   480
attttaccat tcgctgcaga tgtagttcaa aaatg                              515
```

<210> SEQ ID NO 78
<211> LENGTH: 564
<212> TYPE: DNA
<213> ORGANISM: Homo sapiens
<220> FEATURE:
<221> NAME/KEY: misc_feature
<222> LOCATION: (230)..(502)
<223> OTHER INFORMATION: exon 07

<400> SEQUENCE: 78

```
aaacttcctg actagatatt taaaccttca tattgaattt ccagcaagca cactgttcat    60
gtgtaaaatc tgctgttcat ctatttccca aatcatcagg ctatccatac agctttggtg   120
tctaaatagt caagcaatca tttatggggg aaagagaatg tgtgtgacta ttaagaaatc   180
atgatttctg gcactcttcc tcaggtaacc tatagttctc tctctgcagg tttaaagacc   240
attgtggggg ccctgatcca gtcggtaaag aagcttctg atgtgatgat cctgactgtg   300
ttctgtctga gcgtgtttgc tctcattggg ctgcagctgt tcatgggcaa tctgaggaat   360
aaatgtttgc agtggccccc aagcgattct gcttttgaaa ccaacaccac ttcctacttt   420
aatggcacaa tggattcaaa tgggacattt gttaatgtaa caatgagcac atttaactgg   480
aaggataaca ttggagatga cagtaagaag tattacatta tgttaacctt agtgttgctg   540
aatgaatttt caactataaa tagt                                          564
```

<210> SEQ ID NO 79
<211> LENGTH: 497
<212> TYPE: DNA

```
<213> ORGANISM: Homo sapiens
<220> FEATURE:
<221> NAME/KEY: misc_feature
<222> LOCATION: (123)..(186)
<223> OTHER INFORMATION: exon 08

<400> SEQUENCE: 79
tgagactgtg ggtgtacagc cacctttgta ataactgaa  atagtccaac tctgatttat    60
tactaatact aatgtgaata ggattaatat gaaataaaat gggttttttt ttgtattaac   120 aggtcactt  tatgttttgg atgggcaaaa agaccctta  ctctgtggaa atggttcaga   180
tgcagggtaa gaaacataat atatatttt  aagatataga actctttgcg aaaaaaaaaa   240
gtaggtagga aaacaactac atggttatat gtgtagcctt accatgtatg caataaagag   300
cagtgctgct cccctaggaa gtgccttgtc tgccttaccg gattgccact ggtcctaaac   360
tcacagcaat taaaaattat ccctttgtga agaccttcc  ccaaaatttc acagttaaga   420
tgttcttaaa ttgatgctcc aatgtgtgaa ggcccagagt ctgtctttgc tgtacatcta   480
tcagagctgt taggaaa                                                 497

<210> SEQ ID NO 80
<211> LENGTH: 501
<212> TYPE: DNA
<213> ORGANISM: Homo sapiens
<220> FEATURE:
<221> NAME/KEY: misc_feature
<222> LOCATION: (289)..(430)
<223> OTHER INFORMATION: exon 09

<400> SEQUENCE: 80
aaagagtaaa aatatggtaa ggtcagagcc aaaagtgtgt ggttgctagc tttctgccat    60
tctaaatgtc trwaaawatt tatttgcatc taaattttct atcggtcttc ctagtgaatt   120
tcatctgata agtttcacgg tgggcaatca cctaaagtgt tctggaaatt aaagcaagat   180
aattcgtcac agatagcagc tttgggtttt gaaaattcct ataagtcaaa taaattgaaa   240
ttgctgtaat ttctaaactg accctacctc catttctctc tcttatagcc agtgtccaga   300
aggatacatc tgtgtgaagg ctggtcgaaa ccccaactat ggctacacaa gctttgacac   360
ctttagctgg gctttcctgt ctctatttcg actcatgact caagactact gggaaaatct   420
ttaccagttg gtaaggtcca aatgagcatg cataacattt attttatag  acatgtatga   480 aatgaaaagc ataggctgag t                                            501

<210> SEQ ID NO 81
<211> LENGTH: 432
<212> TYPE: DNA
<213> ORGANISM: Homo sapiens
<220> FEATURE:
<221> NAME/KEY: misc_feature
<222> LOCATION: (99)..(305)
<223> OTHER INFORMATION: exon 10

<400> SEQUENCE: 81
agctaattag tctactgact atctaactgt ggtaatcaga tatttatttg gggacattat    60
actaaaatac tgatggaatt atcccccatt tccctagac  attacgtgct gctgggaaaa   120
catacatgat attttttgtc ctggtcattt tcttgggctc attttatttg gtgaatttga   180
tcctggctgt ggtggccatg gcctatgagg ggcagaatca ggccaccttg gaagaagcag   240
aacaaaaaga ggccgaattt cagcagatgc tcgaacagct taaaaagcaa caggaagaag   300
ctcaggtact gagtgataaa mgcaaagatt tatcattatt attmttagtt tctaagtaga   360
```

```
aatagtgtta tactatagag ggtagattgg aactgctttt tcattttata tatmggcatt    420
gtcattagac ac                                                        432

<210> SEQ ID NO 82
<211> LENGTH: 489
<212> TYPE: DNA
<213> ORGANISM: Homo sapiens
<220> FEATURE:
<221> NAME/KEY: misc_feature
<222> LOCATION: (59)..(349)
<223> OTHER INFORMATION: exon 11

<400> SEQUENCE: 82
tgcaaactgt tttcaaagct ctgtgttcta aatagtgcct ggctttgttt tatgacaggc     60
agttgcggca gcatcagctg cttcaagaga tttcagtgga ataggtgggt taggagagct    120
gttggaaagt tcttcagaag catcaaagtt gagttccaaa agtgctaaag aatggaggaa    180
ccgaaggaag aaaagaagac agagagagca ccttgaagga aacaacaaag gagagagaga    240
cagctttccc aaatccgaat ctgaagacag cgtcaaaaga agcagcttcc tttctccat    300 ggatggaaac agactgacca gtgacaaaaa attctgctcc cctcatcagg tatgattttc    360
tactaagtgc tctggtttct ttgtcattgc tattgctttt tagtttttgt attttgtttt    420
ggtacacttt tgtactatct gtacttcagt tgagggacag ggaactaaca tttaatatag    480
ttgtttaaa                                                            489

<210> SEQ ID NO 83
<211> LENGTH: 653
<212> TYPE: DNA
<213> ORGANISM: Homo sapiens
<220> FEATURE:
<221> NAME/KEY: misc_feature
<222> LOCATION: (260)..(460)
<223> OTHER INFORMATION: exon 12

<400> SEQUENCE: 83
gtgaagacta aatgaagtgg ttgtatactt agtaaattgc aaatcagtat tgttagtcag     60
aaaaacactc tttgtactta aatttgcttt aataaaaata tcaaaatata tgtgtcctct    120
ataaatttga ttatccatgt ttaagggcaa gagtatacta actccaaaga aaacagatcc    180
tttaatatta atatttatta aataaattgcg ttcttcccct accccatcc cattcctttc    240 cttttttgctt tctctgcagt ctctcttgag tatccgtggc tccctgtttt ccccaagacg    300
caatagcaaa acaagcattt tcagtttcag aggtcgggca aaggatgttg gatctgaaaa    360
tgactttgct gatgatgaac acagcacatt tgaagacagc gaaagcagga gagactcact    420
gtttgtgccg cacagacatg gagagcgacg caacagtaac gttagtcagg ccagtatgtc    480
atccaggatg gtgccagggc ttccagcaaa tggggaagat gcacagcact gtggattgca    540
atggtgtggt ttccttggtg ggtggaccct cagctctaac gtcacctact gggcaacttc    600
cccagaggtg ataatagatg acctagctgc tactgacatt attcaccaat ttg           653

<210> SEQ ID NO 84
<211> LENGTH: 566
<212> TYPE: DNA
<213> ORGANISM: Homo sapiens
<220> FEATURE:
<221> NAME/KEY: misc_feature
<222> LOCATION: (477)..(477)
<223> OTHER INFORMATION: n = a, c, t or g
<220> FEATURE:
<221> NAME/KEY: misc_feature
<222> LOCATION: (195)..(327)
```

<223> OTHER INFORMATION: exon 13

<400> SEQUENCE: 84

```
gaattctctt aaaggtacta cctgtgatac ttttttaaa aaaaaactgt ttataactta      60
gcaataattc aatattttat tcttgaaatt cttacctgga aaattgcatg tagcatgatt     120
tgcaaagaaa tgctatgtgg tgttgtatta cttattggga agagtggttt gagccatcag    180
tatttggttt gcagggcacc accactgaaa cggaagtcag aaagagaagg ttaagctctt    240
accagatttc aatggagatg ctggaggatt cctctggaag gcaaagagcc gtgagcatag    300
ccagcattct gaccaacaca atggaaggta agagcaggtc atggaacagc caactttctg    360
tgattatgtg ctttgtgaac tattccttct tttcatagaa ttactgaagt ctgttaccca    420
gatcgaacta tatattagac ctaagaatgt gatatatggt gtacattatc acattgntta    480
caaaactaat attggcctta ttcttttga cttgggtcct taccttactt gcagagtgat     540
atttcaacac ttgatattat atcaat                                         566
```

<210> SEQ ID NO 85
<211> LENGTH: 748
<212> TYPE: DNA
<213> ORGANISM: Homo sapiens
<220> FEATURE:
<221> NAME/KEY: misc_feature
<222> LOCATION: (259)..(497)
<223> OTHER INFORMATION: exon 14

<400> SEQUENCE: 85

```
tagtcatttt aaaagcaaaa tattaaattc aaagtgctta ttttctgtat tcaaaagaga      60
aaaaagtcga tctatatgac attttaatta acatttctg aaaatattta atgggattgt     120
cttctcaagt ttcttaagta atatgaactt ctattttcaa atataagcat caattttgtt    180
aaataatgta aaatctacta gcaataataa ctcatttttg ttgttattta ctactcttcc    240
ttgttattgt ccctccagaa cttgaagaat ctagacagaa atgtccgcca tgctggtata    300
gatttgccaa tgtgttcttg atctgggact gctgtgatgc atggttaaaa gtaaaacatc    360
ttgtgaattt aattgttatg gatccatttg ttgatcttgc catcactatt tgcattgtct    420
taaatacct ctttatggcc atggagcact accccatgac tgagcaattc agtagtgtgt     480
tgactgtagg aaacctggta agtacatttg aagtttactt atttactttg gtagatgtgg    540
gagagataga ccaaagggaa agatgtattt gtgctgtgtt gaacccaaaa attatatcct    600
cttcctcat agaagaaat atctaaggaa tattacaggg aatctcagag atacagccta      660
aaactcaact ggtatgaatg ctgattgttt aggccaatgt ctgtgctgat tgatcatggt    720
gtcttaccag ttgtaaacgt ctcaaaat                                       748
```

<210> SEQ ID NO 86
<211> LENGTH: 664
<212> TYPE: DNA
<213> ORGANISM: Homo sapiens
<220> FEATURE:
<221> NAME/KEY: misc_feature
<222> LOCATION: (144)..(317)
<223> OTHER INFORMATION: exon 15

<400> SEQUENCE: 86

```
ctaagacttg aattgatttg tcactattct ctcactttaa attttagata ttttattcc      60
tgtctaatgt tcttctttat aaattcgtgt agcatcagtg ttttcagtgc tcttgatagt    120
agtgctgatc tctaattttt taggtcttta ctgggatttt tacagcagaa atggttctca    180
```

```
agatcattgc catggatcct tattactatt tccaagaagg ctggaatatc tttgatggaa      240
ttattgtcag cctcagttta atggagcttg gtctgtcaaa tgtggaggga ttgtctgtac      300
tgcgatcatt cagactggta tctatttata tatatccctg tcgctcattg cacaacatt       360 tattttgaaa ttgaatcaat gtatatttat ataattatta attttaattt taaatttaca      420
tcaatatgtg acattctaag aaaacatgta acatccyct ttaaagctaa accattttct       480
aagaatgatg aaagcattca aaatactcta taatgattag gtatgtaggg cacattagaa      540
aacctacaag tactttctaa aactgtgttt taagtttatg aagctttttt ggccttacag      600
tctgtaaaga tacgcaaata aaatttaga ccccagttaa ttttagcttt ttattaaccc       660
tact                                                                   664

<210> SEQ ID NO 87
<211> LENGTH: 750
<212> TYPE: DNA
<213> ORGANISM: Homo sapiens
<220> FEATURE:
<221> NAME/KEY: misc_feature
<222> LOCATION: (214)..(570)
<223> OTHER INFORMATION: exon 16

<400> SEQUENCE: 87
tatttttatt tttgcactta aatgatatta tgaccagatt tacaattcta atattgttaa       60 cactatttt tctggatttg aaattgaatc agttcagtat attttgagtt tttacatcta      120
ccacgtgtgg ttctatgata ccacatacta ataaaataat gtctaaaatt atattatgat     180
tactactaac agcatctttt cacttgatta cagcttagag ttttcaagtt ggcaaaatcc     240
tggcccacac taaatatgct aattaagatc attggcaatt ctgtgggggc tctaggaaac     300
ctcaccttgg tgttggccat catcgtcttc attttgctg tggtcggcat gcagctcttt      360
ggtaagagct acaaagaatg tgtctgcaag atcaatgatg actgtacgct cccacgtggg    420
cacatgaacg acttcttcca ctccttcctg attgtgttcc gcgtgctgtg tggagagtgg    480
atagagacca tgtgggactg tatggaggtc gctggccaaa ccatgtgcct tattgttttc    540
atgttggtca tggtcattgg aaaccttgtg gtatgtatgt agtacaaatg ctcataaatt    600
agaacaagag cagacagtag ctaggaacgt ggccagatgt agtaaacata tctctggttt    660
atagtaagtg gcctagactg aaatccccct attagcactc agagaataag caagttattt   720
aacttctcct gggctctggt ttcccatttt                                      750

<210> SEQ ID NO 88
<211> LENGTH: 768
<212> TYPE: DNA
<213> ORGANISM: Homo sapiens
<220> FEATURE:
<221> NAME/KEY: misc_feature
<222> LOCATION: (186)..(656)
<223> OTHER INFORMATION: exon 17

<400> SEQUENCE: 88
ccttagagca ggatattagg tcctttaaag agtgtgtgac ttagacatgg catctgaaat       60
atagtaagca ttcaataaac atttgttgaa ataatttag caaagatcta tgagttccct      120
ttttaggctg ttatttaaat gcatatttca atattaarat aggcattttt ctttttttct     180
tttaggttct gaacctcttt ctggccttat tgttgagttc atttagctca gacaaccttg     240
ctgctactga tgatgacaat gaatgaata atctgcagat tgcagtagga agaatgcaaa     300
agggaattga ttatgtgaaa aataagatgc gggagtgttt ccaaaaagcc ttttttagaa    360
```

```
agccaaaagt tatagaaatc catgaaggca ataagataga cagctgcatg tccaataata    420
ctggaattga aataagcaaa gagcttaatt atcttagaga tgggaatgga accaccagtg    480
gtgtaggtac tggaagcagt gttgaaaaat acgtaatcga tgaaaatgat tatatgtcat    540
tcataaacaa ccccagcctc accgtcacag tgccaattgc tgttggagag tctgactttg    600
aaaacttaaa tactgaagag ttcagcagtg agtcagaact agaagaaagc aaggaggtaa    660
ggaatgcttt taaattttt gttccatttc ctatgataac catgtactac agttatttac    720
tattttcatt gtgcttatat gcattatcga aaagcaatga ttgtaagt                 768

<210> SEQ ID NO 89
<211> LENGTH: 471
<212> TYPE: DNA
<213> ORGANISM: Homo sapiens
<220> FEATURE:
<221> NAME/KEY: misc_feature
<222> LOCATION: (144)..(264)
<223> OTHER INFORMATION: exon 18

<400> SEQUENCE: 89
taattattag tacataatga tcagtaatgc taatagagtt aaatgctatc actacatttt     60
ttttcacaca atgacacagt atttcccagt tagttaaata aaggggaa aatcacatct     120 ttgaaatggg attttgtttc cagaaattaa atgcaaccag ctcatctgaa ggaagcacag    180
ttgatgttgt tctaccccga gaaggtgaac aagctgaaac tgaacccgaa gaagacctta    240
aaccggaagc ttgttttact gaaggtaaac aagctctgat gtgattaaat acaatctccc    300
cttgttcttt acggagactg aatatgcctc atttaaaaaa aaaatttag caaacgaggt    360 gtggtggctt atgcctgtaa ccccaaaatt tgggaggct acggtaggag gattgcttga    420
ccccaggagt ttgagaccac cctgggaaat gtagtaaggc tttgcctcta c             471

<210> SEQ ID NO 90
<211> LENGTH: 623
<212> TYPE: DNA
<213> ORGANISM: Homo sapiens
<220> FEATURE:
<221> NAME/KEY: misc_feature
<222> LOCATION: (203)..(357)
<223> OTHER INFORMATION: exon 19

<400> SEQUENCE: 90
gaattctaag tagctggctg agtatataag tctgagaata attcattata caggagggat     60
gctgacgata actaggaaat gaaggagatg gttaccctat gaaatgatta cctggaagtg    120
gagtggggaa ggggcaagaa agtttatttt ttcctattta agattaaaat atatttttta    180
attaactata tttsattttt aggatgtatt aaaaagtttc cattctgtca agtaagtaca    240
gaagaaggca aagggaagat ctggtggaat cttcgaaaaa cctgctacag tattgttgag    300
cacaactggt ttgagacttt cattgtgttc atgatccttc tcagtagtgg tgcattggta    360
agtgaaatgc atattggcaa gaatcagatt ctggtgaaat agtttattct ccaaaattac    420
cagatgcaaa cactgagctt cagaatcaaa agaaaaggca tatctgtgtc ttgcagagct    480
tggcacccaa ggtttaacga tgcaaaattc agttctgaac aaatcagcac catgaaacag    540
ccagatggaa tttctcatct ggtgtttatc taacagatgt tttcctcact gagacaacca    600
tttgcagaga cattctgtaa cca                                            623

<210> SEQ ID NO 91
<211> LENGTH: 520
<212> TYPE: DNA
```

<213> ORGANISM: Homo sapiens
<220> FEATURE:
<221> NAME/KEY: misc_feature
<222> LOCATION: (156)..(329)
<223> OTHER INFORMATION: exon 20

<400> SEQUENCE: 91

| | | | | | |
|---|---|---|---|---|---|
| ctagttagtc | tttagatttg | tctcatgttc | aatgtttatg | taaaatatca | ataatcaaaa | 60 |
| ttattctttt | gtactcacta | ttatactaag | caatttttc | aaatatttag | aagaagcaag | 120 |
| ccatttaagt | aaaataaaat | attttgatt | cataggcctt | tgaagatata | tacattgaac | 180 |
| agcgaaagac | tatcaaaacc | atgctagaat | atgctacaa | agtctttacc | tatatattca | 240 |
| ttctggaaat | gcttctcaaa | tgggttgctt | atggatttca | aacatatttc | actaatgcct | 300 |
| ggtgctggct | agatttcttg | atcgttgatg | taagtatttt | aagtgatttt | tataaaattg | 360 |
| tttttaaaag | aggcaagttt | gacatttcat | atgtttctgt | tattaaaact | ttcactaata | 420 |
| atgacataat | tatgcagtta | tttaaacaaa | actgtaacat | atgcaacaat | gaggaatatc | 480 |
| tcatgggaaa | gagtagagga | ggtcctaaac | atgggcagtg | | | 520 |

<210> SEQ ID NO 92
<211> LENGTH: 595
<212> TYPE: DNA
<213> ORGANISM: Homo sapiens
<220> FEATURE:
<221> NAME/KEY: misc_feature
<222> LOCATION: (352)..(474)
<223> OTHER INFORMATION: exon 21

<400> SEQUENCE: 92

| | | | | | |
|---|---|---|---|---|---|
| ctaactaata | atttaagcac | acatccatga | aggatctggc | attgaactca | atcctgaatt | 60 |
| atcagtggta | tatgcacaag | ttgaaaaggg | gtccatggta | taaaatatct | aactggagat | 120 |
| attgacacgt | gttgataaat | atgggcaagt | attctggttt | cattggttaa | aaaaagcaa | 180 |
| tagtatgaga | tgagactggc | aatataagat | gaccccacta | tgtggaagat | gaaagttgcc | 240 |
| aaggtatgtc | caaattagta | tttagtctgc | attaaataga | taccacaccc | tatacttca | 300 |
| gtcaacagtt | tatttcttgg | tgaactaatt | aattttttt | tccttttgta | ggtttctttg | 360 |
| gttagcctgg | tagccaatgc | tcttggctac | tcagaactcg | gtgccatcaa | atcattacgg | 420 |
| acattaagag | ctttaagacc | tctaagagcc | ttatcccggt | ttgaaggcat | gagggtaaga | 480 |
| agaatagaca | ctctaattat | tcatgtcaaa | aattacatgt | aggtaatgat | ttagatagaa | 540 |
| aagggtgcca | tactcttctg | atatttattt | caatagaaat | tacagaatta | gaagc | 595 |

<210> SEQ ID NO 93
<211> LENGTH: 787
<212> TYPE: DNA
<213> ORGANISM: Homo sapiens
<220> FEATURE:
<221> NAME/KEY: misc_feature
<222> LOCATION: (284)..(556)
<223> OTHER INFORMATION: exon 22

<400> SEQUENCE: 93

| | | | | | |
|---|---|---|---|---|---|
| ccagcataca | aacattttct | gactccatct | tactatacca | ggtttttaat | gatttctttt | 60 |
| catactgtag | catattttgc | tttccttaaa | accttagctc | tttagttgtg | tcattgtttg | 120 |
| ttttccttca | aatatgtgct | agaaaaatta | gaagaaacaa | cttgtccacc | tagatttta | 180 |
| tttaactctt | ttcaagcaca | tattaatact | aaacaaatac | attgaaggaa | tggtttccat | 240 |
| tcaaaaggtt | tgtaagctat | gttcccctcg | ctgtctcttc | taggtggttg | tgaatgctct | 300 |

```
tgttggagca attccctcta tcatgaatgt gctgttggtc tgtctcatct tctggttgat        360
cttcagcatc atgggtgtga atttgtttgc tggcaagttc taccactgtg ttaacatgac        420
aacgggtaac atgtttgaca ttagtgatgt taacaatttg agtgactgtc aggctcttgg        480
caagcaagct cggtggaaaa acgtgaaagt aaactttgat aatgttggcg ctggctatct        540
tgcactgctt caagtggtaa gtggctactg tacgagtttt gaaaaagttt tcaagatgtt        600
tcaaggaaga ttatttccct gatgttcttc gtttgaatga ctaacatttg acagcatgaa        660
aaaaagttaa tgataacacc tataatatca gcttgaattg atcataaaaa agatgttaca        720
attattttat aatgtatttt ccttagtgtt aagcttttag tatgttttaa tgtgatttta        780
tatttct                                                                  787
```

<210> SEQ ID NO 94
<211> LENGTH: 438
<212> TYPE: DNA
<213> ORGANISM: Homo sapiens
<220> FEATURE:
<221> NAME/KEY: misc_feature
<222> LOCATION: (189)..(242)
<223> OTHER INFORMATION: exon 23

<400> SEQUENCE: 94

```
aaaggaaaca agttccagac tttaaataca aatgttttc  tatttcaatt ttatttcaat        60
ctcttgatat gaaatttcac aatattgtac aaaaagttat ttgttataat actgtcagat       120
tttcatctgg ttaaatgtca ttgttaggtg aaattttttat gaacaattca atatatgtt        180 atttacaggc cacatttaaa ggctggatgg atattatgta tgcagctgtt gattcacgag       240
atgtaagtat cactcaaata ttatttatag gttctagatt tcttatggtg aatattggtg       300
gtaatttaaa cactgataca tccaaaattc tatattagaa catttaatat tgcatataaa       360
aaatgaacag tctgcttcaa tatagatgat gcttgattaa tgtgtgccta atatacaata       420
tgtagctaat atgaaacg                                                      438
```

<210> SEQ ID NO 95
<211> LENGTH: 637
<212> TYPE: DNA
<213> ORGANISM: Homo sapiens
<220> FEATURE:
<221> NAME/KEY: misc_feature
<222> LOCATION: (221)..(358)
<223> OTHER INFORMATION: exon 24

<400> SEQUENCE: 95

```
gtaaggcaca atgggaaaag agaatcaaga acaatcataa aacttgcaaa ccttcatttt        60
actagatcat actagtttta aaaaattgtt tttgtagaac aatatctcag ggtaaggcaa       120
aagtagcact gtattaagta acagcactca ataaattact gatttagtgt aagtatttat       180 agtattttc  atattattta atattttcaa tatcatttag gttaaacttc agcctgtata       240
tgaagaaaat ctgtacatgt atttatactt tgtcatcttt atcatctttg ggtcattctt       300
cactctgaat ctattcattg gtgtcatcat agataacttc aaccagcaga aaagaagat        360 aagtattctt tagctttac  ctttcttcat tctggggttc tgtctgttaa tacagccaaa       420
taaccagaat acctgtggtc atgacagact taaatcatgt ttatattatt ttcagttgcc       480
catgtggtta tttaagctgc agggattcca gcctctagtc agtggctcct ctcaaagttt       540
atctattgga tagcttttctg acccaaaaat gtgtccactc cttcggaccc atccaacggg       600
tctccagtgc tttagcttgg cttacagagc ctttcag                                 637
```

<210> SEQ ID NO 96
<211> LENGTH: 637
<212> TYPE: DNA
<213> ORGANISM: Homo sapiens
<220> FEATURE:
<221> NAME/KEY: misc_feature
<222> LOCATION: (254)..(358)
<223> OTHER INFORMATION: exon 25

<400> SEQUENCE: 96

```
acccttgtgc ctacttttaa acatagtata atcaaattag gatcctgtag cgatcagagt      60
tttatgtacg taaggatttt gcataatatt aagatattca gaatttcaca taaatgggaa     120
aagcaggata aatgtatatg taggaggata atatccactt aaaaattaga aaagattaaa     180
ggaaagacaa atattttttg tgaaagtact attggaacac agaattgtaa ccagttttat     240
actatgtctt tactttggag gtcaagacat ctttatgaca gaggaacaga aaaaatatta     300
caatgcaatg aagaaacttg gatccaagaa acctcagaaa cccatacctc gcccagcagt     360
aagaattact tgtctccttt aatgttccaa agccatgcgt ccatatggtc aaattgagca     420
atgctctgga gcagaacata ttaggtgata tcaccaatat tgagccctaa ttataaagtt     480
catattttgc atcataattc acaacttctg cactcattag gagttaccac attccaaaaa     540
aaggaggtaa tgttctttat aatttgtgag ttgaaaactt ctagctcagg gttcctaata     600
aatacttcca aagcaaggtt cactttcctg ctaccaa                              637
```

<210> SEQ ID NO 97
<211> LENGTH: 759
<212> TYPE: DNA
<213> ORGANISM: Homo sapiens
<220> FEATURE:
<221> NAME/KEY: misc_feature
<222> LOCATION: (211)..(481)
<223> OTHER INFORMATION: exon 26

<400> SEQUENCE: 97

```
tatataaacc aaatatgctt tgtttagcta tataaatttt ttttccattt tttttaacat      60
gaagagaaaa aaagcacaca aaattgtttg gggtaatatg aggagggtgc acatccatcc     120
cgtatgtgga agggctttat ctacaatttt actgcattat tctttatgaa atatatatag     180
taaccttatt tctcttctct cactttctag aacaaattcc aaggaatggt ctttgatttt     240
gtaaccagac aagtctttga tatcagcatc atgatcctca tctgcctcaa catggtcacc     300
atgatggtgg aaacggatga ccagggcaaa tacatgaccc tagttttgtc ccggatcaac     360
ctagtgttca ttgttctgtt cactggagaa tttgtgctga agctcgtctc cctcagacac     420
tactacttca ctataggctg gaacatcttt gactttgtgg tggtgattct ctccattgta     480
ggtaagaaca gcttaattac caagaggtat agttacagag aaacagttgc cccaggacct     540
tctagctgat taacatggaa attggtctg agaataataa tgcatataga tgtaaagttc      600
aacactagca tatttgaata aaaactctga aacctgggtt tattcacaaa gctaactagt     660
tagaaaccat gttaggaata ccagatttgg gaaagaggtg aagaagacag gaaataaaca     720
ttatcaggta ctctcctaat cttaaaccaa ggtcacagg                            759
```

<210> SEQ ID NO 98
<211> LENGTH: 3975
<212> TYPE: DNA
<213> ORGANISM: Homo sapiens
<220> FEATURE:
<221> NAME/KEY: misc_feature
<222> LOCATION: (156)..(1351)

<223> OTHER INFORMATION: exon 27

<400> SEQUENCE: 98

```
aatctgtaat gctaatgcag ggagtggatc caaatattta ataaaggctc atattcataa     60
caagtttgtt gtgttcatag accttaaaaa agataaagcc atcatgtaaa gtgaaaagat    120
attatctgtt tagctgtgtt ctatgttttc cataggtatg tttctggctg agatgataga    180
aaagtatttt gtgtccccta ccttgttccg agtgatccgt cttgccagga ttggccgaat    240
cctacgtctg atcaaaggag caaaggggat ccgcacgctg ctctttgctt tgatgatgtc    300
ccttcctgcg ttgtttaaca tcggcctcct gctcttcctg gtcatgttta tctatgccat    360
ctttgggatg tccaactttg cctatgttaa aaggaagct  ggaattgatg acatgttcaa    420
ctttgagacc tttggcaaca gcatgatctg cttgttccaa attacaacct ctgctggatg    480
ggatggattg ctagcaccta ttcttaatag tgcaccaccc gactgtgacc ctgacacaat    540
tcaccctggc agctcagtta agggagactg tgggaaccca tctgttggga ttttcttttt    600
tgtcagttac atcatcatat ccttcctggt ggtggtgaac agttacatcg cggtcatcct    660
ggagaacttc agtgttgcta ctgaagaaag tgcagagccc ctgagtgagg atgactttga    720
gatgttctat gaggtttggg aaaagtttga tcccgatgcg acccagttta tagagttctc    780
taaactctct gatttgcag  ctgccctgga tcctcctctt ctcatagcaa acccaacaa     840
agtccagctt attgccatgg atctgcccat ggtcagtggt gaccggatcc actgtcttga    900
tattttattt gccttt acaa agcgtgtttt gggtgagagt ggagagatgg atgcccttcg    960
aatacagatg gaagacaggt ttatggcatc aaacccctcc aaagtctctt atgagcctat   1020
tacaaccact ttgaaacgta acaagagga  ggtgtctgcc gctatcattc agcgtaattt   1080
cagatgttat cttttaaagc aaaggttaaa aaatatatca agtaactata acaaagaggc   1140
aataaggggg aggattgact tacctataaa acaagacatg attattgaca aactgaatgg   1200
gaactccact ccagaaaaaa cagatgggag ttcctctacc acctctcctc cttcctatga   1260
tagtgtaaca aaaccagaca aggaaaagtt tgagaaagac aaaccagaaa agaaagcaa   1320
aggaaaagag gtcagagaaa atcaaaagta aaaagaaaca aagaattatc tttgtgatca   1380
attgtttaca gcctatgaag gtaaagtata tgtgtcaact ggacttcaag aggaggtcca   1440
tgccaaactg actgttttaa caaatactca tagtcagtgc ctatacaaga cagtgaagtg   1500
acctctctgt cactgcaact ctgtgaagca gggtatcaac attgacaaga ggttgctgtt   1560
tttattacca gctgacactg ctgaggagaa acccaatggc tacctagact atagggatag   1620
ttgtgcaaag tgaacattgt aactacacca acaccttta  gtacagtcct tgcatccatt   1680
ctatttttaa cttccatatc tgccatattt ttacaaaatt tgttctagtg catttccatg   1740
gtccccaatt catagtttat tcataatgct atgtcactat ttttgtaaat gaggtttacg   1800
ttgaagaaac agtatacaag aaccctgtct ctcaaatgat cagacaaagg tgttttgcca   1860
gagagataaa attttgctc  aaaaccagaa aaagaattgt aatggctaca gtttcagtta   1920
cttccatttt ctagatggct ttaattttga agtattttta gtctgttatg tttgtttcta   1980
tctgaacagt tatgtgcctg taaagtctcc tctaatattt aaaggattat ttttatgcaa   2040
agtattctgt ttcagcaagt gcaaattttta ttctaagttt cagagctcta tatttaattt   2100
aggtcaaatg ctttccaaaa agtaatctaa taaatccatt ctagaaaaat atatctaaag   2160
tattgcttta gaatagttgt tccactttct gctgcagtat tgctttgcca tcttctgctc   2220
tcagcaaagc tgatagtcta tgtcaattaa atacccatg  ttatgtaaat agttatttta   2280
```

-continued

```
tcctgtggtg catgtttggg caaatatata tatagcctga taaacaactt ctattaaatc    2340
aaatatgtac cacagtgtat gtgtcttttg caagcttcca acagggatgt atcctgtatc    2400
attcattaaa catagtttaa aggctatcac taatgcatgt taatattgcc tatgctgctc    2460
tattttactc aatccattct tcacaagtct tggttaaaga atgtcacata ttggtgatag    2520
aatgaattca acctgctctg tccattatgt caagcagaat aatttgaagc tatttacaaa    2580
cacctttact tttgcacttt taattcaaca tgagtatcat atggtatctc tctagatttc    2640
aaggaaacac actggatact gcctactgac aaaacctatt cttcatattt tgctaaaaat    2700
atgtctaaaa cttgcgcaaa tataaataat gtaaaaatat aatcaacttt atttgtcagc    2760
attttgtaca taagaaaatt attttcaggt tgatgacatc acaatttatt ttactttatg    2820
cttttgcttt tgattttttaa tcacaattcc aaacttttga atccataaga tttttcaatg    2880
gataatttcc taaaataaaa gttagataat gggttttatg gatttctttg ttataatata    2940
ttttctacca ttccaatagg agatacattg gtcaaacact caaacctaga tcattttcta    3000
ccaactatgg ttgcctcaat ataacctttt attcatagat gtttttttt attcaacttt    3060 tgtagtattt acgtatgcag actagtctta ttttttttaat tcctgctgca ctaaagctat    3120
tacaaatata acatggactt tgttcttttt agccatgaac aaagtggcaa agttgtgcaa    3180
ttacctaaca tgatataaat ttttgttttt tgcacaaacc aaaagtttaa tgttaattct    3240
ttttacaaaa ctatttactg tagtgtattg aagaactgca tgcagggaat tgctattgct    3300
aaaaagaatg gtgagctacg tcattattga gccaaaagaa taaatttcat tttttattgc    3360
atttcactta ttggcctctg gggttttttg ttttttgtttt ttgctgttgg cagttttaaaa    3420 tatatataat taataaaacc tgtgcttgat ctgacatttg tatacataaa agtttacatg    3480
aattttacaa cagactagtg catgattcac caagcagtac tacagaacaa aggcaaatga    3540
aaagcagctt tgtgcacttt tatgtgtgca aaggatcaag ttcacatgtt ccaactttca    3600
ggtttgataa taatagtagt aaccacctac aatagctttc aatttcaatt aactcccttg    3660
gctataagca tctaaactca tcttctttca atataattga tgctatctcc taattacttg    3720
gtggctaata aatgttacat tctttgttac ttaaatgcat tatataaact cctatgtata    3780
cataaggtat taatgatata gttattgaga atttatatta acttttttt caagaaccct    3840 tggatttatg tgaggtcaaa accaaactct tattctcagt ggaaaactcc agttgtaatg    3900 catatttta aagacaattt ggatctaaat atgtatttca taattctccc ataataaatt    3960
atataaggtg gctaa                                                     3975
```

<210> SEQ ID NO 99
<211> LENGTH: 22
<212> TYPE: DNA
<213> ORGANISM: Artificial Sequence
<220> FEATURE:
<223> OTHER INFORMATION: Description of Artificial Sequence: synthetic oligonucleotide

<400> SEQUENCE: 99

```
tgtgttctgc cccagtgaga ct                                                22
```

<210> SEQ ID NO 100
<211> LENGTH: 24
<212> TYPE: DNA
<213> ORGANISM: Artificial Sequence
<220> FEATURE:
<223> OTHER INFORMATION: Description of Artificial Sequence: synthetic oligonucleotide

```
<400> SEQUENCE: 100
cttcctgctc tgcccaaact gaat                                        24

<210> SEQ ID NO 101
<211> LENGTH: 24
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 101
ggcgatgtaa tgtaaggtgc tgtc                                        24

<210> SEQ ID NO 102
<211> LENGTH: 24
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 102
gtgccttcag ttgcaattgt tcag                                        24

<210> SEQ ID NO 103
<211> LENGTH: 24
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 103
ttaggaattt catatgcaga ataa                                        24

<210> SEQ ID NO 104
<211> LENGTH: 19
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 104
tgggccattt ttcgtcgtc                                              19

<210> SEQ ID NO 105
<211> LENGTH: 25
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 105
gaaagacgca ttgcagaaga aaagg                                       25

<210> SEQ ID NO 106
<211> LENGTH: 24
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 106
```

```
ctattggcat gtgttggtgc taca                                         24
```

<210> SEQ ID NO 107
<211> LENGTH: 25
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 107

```
gtgctggttt ctcatttaac tttac                                        25
```

<210> SEQ ID NO 108
<211> LENGTH: 25
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 108

```
ttcccaactt aatttgatat ttagc                                        25
```

<210> SEQ ID NO 109
<211> LENGTH: 24
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 109

```
gcagtttggg cttttcaatg ttag                                         24
```

<210> SEQ ID NO 110
<211> LENGTH: 24
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 110

```
gacacagttt caraatcccr aatg                                         24
```

<210> SEQ ID NO 111
<211> LENGTH: 24
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 111

```
ttagggctac gtttcatttg tatg                                         24
```

<210> SEQ ID NO 112
<211> LENGTH: 24
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 112

```
agcactgatg gaaaccaaa ctat                                          24
```

```
<210> SEQ ID NO 113
<211> LENGTH: 24
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 113
agcccatgca gtaatataaa tcct                                              24

<210> SEQ ID NO 114
<211> LENGTH: 24
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 114
tccaggctga taagctatgt ctaa                                              24

<210> SEQ ID NO 115
<211> LENGTH: 22
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 115
ctgtggcctg cctgagcgta tt                                                22

<210> SEQ ID NO 116
<211> LENGTH: 24
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 116
ccaattctac tttttaagga aatg                                              24

<210> SEQ ID NO 117
<211> LENGTH: 19
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 117
aaatacttgt gcctttgaa                                                    19

<210> SEQ ID NO 118
<211> LENGTH: 23
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 118
gtacatacaa tatacacaga tgc                                               23

<210> SEQ ID NO 119
```

```
<211> LENGTH: 23
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 119
aggcagcaga acgacttgta ata                                            23

<210> SEQ ID NO 120
<211> LENGTH: 24
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 120
atccggtttt aatttcataa ctca                                           24

<210> SEQ ID NO 121
<211> LENGTH: 24
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 121
gttgagcacc cttagtgaat aata                                           24

<210> SEQ ID NO 122
<211> LENGTH: 24
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 122
tcacacgctc tagactactt ctct                                           24

<210> SEQ ID NO 123
<211> LENGTH: 24
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 123
tgcaaatact tcagcccttt caaa                                           24

<210> SEQ ID NO 124
<211> LENGTH: 22
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 124
ttccccacca gactgctctt tc                                             22

<210> SEQ ID NO 125
<211> LENGTH: 18
<212> TYPE: DNA
```

```
<213> ORGANISM: Artificial Sequence
<220> FEATURE:
<223> OTHER INFORMATION: Description of Artificial Sequence: synthetic
      oligonucleotide

<400> SEQUENCE: 125
gcagcaggca ggctctca                                                  18

<210> SEQ ID NO 126
<211> LENGTH: 24
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 126
tctcccatgt tttaattttc aacc                                           24

<210> SEQ ID NO 127
<211> LENGTH: 24
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 127
ataatcttgc aaaatgaaat caca                                           24

<210> SEQ ID NO 128
<211> LENGTH: 19
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 128
atccgggatg acctactgg                                                 19

<210> SEQ ID NO 129
<211> LENGTH: 24
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 129
gataacgaga gccgtagaga ttcc                                           24

<210> SEQ ID NO 130
<211> LENGTH: 20
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 130
agccagccat gcctgaacta                                                20

<210> SEQ ID NO 131
<211> LENGTH: 23
<212> TYPE: DNA
<213> ORGANISM: Artificial Sequence
<220> FEATURE:
```

<223> OTHER INFORMATION: Description of Artificial Sequence: synthetic
      oligonucleotide

<400> SEQUENCE: 131
tgtttgcttg tcatattgct caa                                            23

<210> SEQ ID NO 132
<211> LENGTH: 22
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 132
tgcactattc ccaactcaca aa                                             22

<210> SEQ ID NO 133
<211> LENGTH: 24
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 133
aagggtgtct ctgtaacaaa aatg                                           24

<210> SEQ ID NO 134
<211> LENGTH: 20
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 134
gtgatggcca ggtcaacaaa                                                20

<210> SEQ ID NO 135
<211> LENGTH: 24
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 135
ctgggactgt tctccatatt ggtt                                           24

<210> SEQ ID NO 136
<211> LENGTH: 18
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 136
tttgcagggg ccaggaag                                                  18

<210> SEQ ID NO 137
<211> LENGTH: 23
<212> TYPE: DNA
<213> ORGANISM: Artificial Sequence
<220> FEATURE:
<223> OTHER INFORMATION: Description of Artificial Sequence: synthetic
      oligonucleotide

```
<400> SEQUENCE: 137
cattgtggga aaatagcata agc                                            23

<210> SEQ ID NO 138
<211> LENGTH: 23
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 138
gcaagaaccc tgaatgttag aaa                                            23

<210> SEQ ID NO 139
<211> LENGTH: 24
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 139
taatgctttt aagaatcata caaa                                           24

<210> SEQ ID NO 140
<211> LENGTH: 21
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 140
ccagcgtggg agttgacaat c                                              21

<210> SEQ ID NO 141
<211> LENGTH: 20
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 141
cggcatgcag ctctttggta                                                20

<210> SEQ ID NO 142
<211> LENGTH: 22
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 142
atgtgccatg ctggtgtatt tc                                             22

<210> SEQ ID NO 143
<211> LENGTH: 23
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 143
```

```
cacccatctt ctaatcacta tgc                                          23

<210> SEQ ID NO 144
<211> LENGTH: 23
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 144
cagcaatttg gagattattc att                                          23

<210> SEQ ID NO 145
<211> LENGTH: 20
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 145
gcagccactg atgatgataa                                              20

<210> SEQ ID NO 146
<211> LENGTH: 21
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 146
ctgccagttc ctataccact t                                            21

<210> SEQ ID NO 147
<211> LENGTH: 22
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 147
tacagcagaa attgggaaag at                                           22

<210> SEQ ID NO 148
<211> LENGTH: 24
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 148
gtattcatac ctacccacac ctat                                         24

<210> SEQ ID NO 149
<211> LENGTH: 23
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 149
ttcttggcag gcaacttatt acc                                          23
```

<210> SEQ ID NO 150
<211> LENGTH: 24
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 150
taagctgcac tccaaatgaa agat                                          24

<210> SEQ ID NO 151
<211> LENGTH: 20
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 151
ggctgaatgt ttccacaact                                               20

<210> SEQ ID NO 152
<211> LENGTH: 21
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 152
gttcaactat tcggaaacac g                                             21

<210> SEQ ID NO 153
<211> LENGTH: 19
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 153
aggcagagga aaacaatgg                                                19

<210> SEQ ID NO 154
<211> LENGTH: 23
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 154
acaaggtggg ataattaaaa atg                                           23

<210> SEQ ID NO 155
<211> LENGTH: 21
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 155
gtttctctgc cctcctattc c                                             21

<210> SEQ ID NO 156
<211> LENGTH: 21
<212> TYPE: DNA
<213> ORGANISM: Artificial Sequence
<220> FEATURE:
<223> OTHER INFORMATION: Description of Artificial Sequence: synthetic oligonucleotide

<400> SEQUENCE: 156
aagctacctt gaacagagac a                                              21

<210> SEQ ID NO 157
<211> LENGTH: 20
<212> TYPE: DNA
<213> ORGANISM: Artificial Sequence
<220> FEATURE:
<223> OTHER INFORMATION: Description of Artificial Sequence: synthetic oligonucleotide

<400> SEQUENCE: 157
aatgatgatt ctgtttatta                                                20

<210> SEQ ID NO 158
<211> LENGTH: 18
<212> TYPE: DNA
<213> ORGANISM: Artificial Sequence
<220> FEATURE:
<223> OTHER INFORMATION: Description of Artificial Sequence: synthetic oligonucleotide

<400> SEQUENCE: 158
aatttgccat tccttttg                                                  18

<210> SEQ ID NO 159
<211> LENGTH: 24
<212> TYPE: DNA
<213> ORGANISM: Artificial Sequence
<220> FEATURE:
<223> OTHER INFORMATION: Description of Artificial Sequence: synthetic oligonucleotide

<400> SEQUENCE: 159
ttgacatcga agacgtgaat aatc                                           24

<210> SEQ ID NO 160
<211> LENGTH: 23
<212> TYPE: DNA
<213> ORGANISM: Artificial Sequence
<220> FEATURE:
<223> OTHER INFORMATION: Description of Artificial Sequence: synthetic oligonucleotide

<400> SEQUENCE: 160
ccatctgggc tcataaactt gta                                            23

<210> SEQ ID NO 161
<211> LENGTH: 23
<212> TYPE: DNA
<213> ORGANISM: Artificial Sequence
<220> FEATURE:
<223> OTHER INFORMATION: Description of Artificial Sequence: synthetic oligonucleotide

<400> SEQUENCE: 161
ccctttgaaa attatatcag taa                                            23

<210> SEQ ID NO 162
<211> LENGTH: 23

-continued

```
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 162
atttggtcgt ttatgcttta ttc                                          23

<210> SEQ ID NO 163
<211> LENGTH: 24
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 163
tccagcacta aaatgtatgg taat                                         24

<210> SEQ ID NO 164
<211> LENGTH: 21
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 164
atttggcaga gaaaacactc c                                            21

<210> SEQ ID NO 165
<211> LENGTH: 24
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 165
ttttagccat ccattttcta tttt                                         24

<210> SEQ ID NO 166
<211> LENGTH: 22
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 166
tattttcccc catatcattt ga                                           22

<210> SEQ ID NO 167
<211> LENGTH: 21
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 167
tttgcaagaa actagaaagt c                                            21

<210> SEQ ID NO 168
<211> LENGTH: 19
<212> TYPE: DNA
<213> ORGANISM: Artificial Sequence
```

<220> FEATURE:
<223> OTHER INFORMATION: Description of Artificial Sequence: synthetic
      oligonucleotide

<400> SEQUENCE: 168
ttgatgcgtg acaaaatgg                                                    19

<210> SEQ ID NO 169
<211> LENGTH: 24
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 169
gaccagagtg aatatgtgac tacc                                              24

<210> SEQ ID NO 170
<211> LENGTH: 23
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 170
ctgggatgat cttgaatcta atc                                               23

<210> SEQ ID NO 171
<211> LENGTH: 24
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 171
gcaactcagt tcatggaatt tgaa                                              24

<210> SEQ ID NO 172
<211> LENGTH: 23
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 172
cttgttttcg ttttaaagta gta                                               23

<210> SEQ ID NO 173
<211> LENGTH: 25
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 173
caaagatcac cctggaagct cagtt                                             25

<210> SEQ ID NO 174
<211> LENGTH: 25
<212> TYPE: DNA
<213> ORGANISM: Artificial Sequence
<220> FEATURE:
<223> OTHER INFORMATION: Description of Artificial Sequence: synthetic oligonucleotide

<400> SEQUENCE: 174
ttcaagcgca gctgcaaact gagat                                    25

<210> SEQ ID NO 175
<211> LENGTH: 23
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 175
acatcggcct cctactcttc cta                                      23

<210> SEQ ID NO 176
<211> LENGTH: 21
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 176
acagatgggt tcccacagtc c                                        21

<210> SEQ ID NO 177
<211> LENGTH: 24
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 177
taacgcatga tttcttcact ggtt                                     24

<210> SEQ ID NO 178
<211> LENGTH: 22
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 178
atcccaaaga tggcgtagat ga                                       22

<210> SEQ ID NO 179
<211> LENGTH: 24
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 179
tgagaaatag gctaaggacc tcta                                     24

<210> SEQ ID NO 180
<211> LENGTH: 17
<212> TYPE: DNA
<213> ORGANISM: Artificial Sequence
<220> FEATURE:
<223> OTHER INFORMATION: Description of Artificial Sequence: synthetic
      oligonucleotide

```
<400> SEQUENCE: 180 cctagggct ggattcc                                                    17

<210> SEQ ID NO 181
<211> LENGTH: 23
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 181
aaggggtgca aacctgtgat ttt                                            23

<210> SEQ ID NO 182
<211> LENGTH: 21
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 182
agggccatgt ggttgccata c                                              21

<210> SEQ ID NO 183
<211> LENGTH: 24
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 183
cttccggttt atgttttcat ttct                                           24

<210> SEQ ID NO 184
<211> LENGTH: 24
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 184
tctttattag ttttgcacat ttta                                           24

<210> SEQ ID NO 185
<211> LENGTH: 23
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 185
caatccttcc aaggtctcct atc                                            23

<210> SEQ ID NO 186
<211> LENGTH: 24
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 186
``` tttcatctttt gccttcttgc tcat                                    24

<210> SEQ ID NO 187
<211> LENGTH: 22
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 187
catgtccact gcagcttgtc ca                                       22

<210> SEQ ID NO 188
<211> LENGTH: 24
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 188
tcccctttac acagagtcac agtt                                     24

<210> SEQ ID NO 189
<211> LENGTH: 15
<212> TYPE: DNA
<213> ORGANISM: Homo sapiens

<400> SEQUENCE: 189
gcatttgaag atata                                               15

<210> SEQ ID NO 190
<211> LENGTH: 15
<212> TYPE: DNA
<213> ORGANISM: Homo sapiens

<400> SEQUENCE: 190
gcatttgacg atata                                               15

<210> SEQ ID NO 191
<211> LENGTH: 15
<212> TYPE: DNA
<213> ORGANISM: Homo sapiens

<400> SEQUENCE: 191
atcatatcct tcctg                                               15

<210> SEQ ID NO 192
<211> LENGTH: 15
<212> TYPE: DNA
<213> ORGANISM: Homo sapiens

<400> SEQUENCE: 192
atcatatmct tcctg                                               15

<210> SEQ ID NO 193
<211> LENGTH: 24
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 193
atgggttgaa tgactttctg acat                                     24

-continued

```
<210> SEQ ID NO 194
<211> LENGTH: 24
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 194
aggcatttcc tgtacaggga ctac                                            24

<210> SEQ ID NO 195
<211> LENGTH: 24
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 195
acaggaaatg cctcttctta cttc                                            24

<210> SEQ ID NO 196
<211> LENGTH: 24
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 196
tttccccaag gattctacta ctgt                                            24

<210> SEQ ID NO 197
<211> LENGTH: 24
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 197
agtgcatgta actgacacaa tcac                                            24

<210> SEQ ID NO 198
<211> LENGTH: 23
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 198
cttgcgttcc tgtttgggtc tct                                             23

<210> SEQ ID NO 199
<211> LENGTH: 22
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 199
tccgcttctt taccagggaa tc                                              22
```

```
<210> SEQ ID NO 200
<211> LENGTH: 24
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 200
aggcagtgaa ggcaacttga ctaa                                              24

<210> SEQ ID NO 201
<211> LENGTH: 24
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 201
cagggcaata tttataaata atgg                                              24

<210> SEQ ID NO 202
<211> LENGTH: 24
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 202
tttggaaaat gtgtagctca ataa                                              24

<210> SEQ ID NO 203
<211> LENGTH: 22
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 203
aaggcatggt agtgcataaa ag                                                22

<210> SEQ ID NO 204
<211> LENGTH: 22
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 204
atgaaacata aagggaggtc aa                                                22

<210> SEQ ID NO 205
<211> LENGTH: 24
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 205
aatgtgagct tggctattgt ctct                                              24

<210> SEQ ID NO 206
<211> LENGTH: 23
```

```
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 206
ataggctccc accagtgatt tac                                           23

<210> SEQ ID NO 207
<211> LENGTH: 22
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 207
aggcccctta tatctccaac tg                                            22

<210> SEQ ID NO 208
<211> LENGTH: 22
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 208
caacaaggct tctgcacaaa ag                                            22

<210> SEQ ID NO 209
<211> LENGTH: 19
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 209
cttggtggct tgccttgac                                                19

<210> SEQ ID NO 210
<211> LENGTH: 20
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 210
tcatgagtgt cgccatcagc                                               20

<210> SEQ ID NO 211
<211> LENGTH: 20
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 211
ggaaagctga tggcgacact                                               20

<210> SEQ ID NO 212
<211> LENGTH: 20
<212> TYPE: DNA
<213> ORGANISM: Artificial Sequence
```

```
<220> FEATURE:
<223> OTHER INFORMATION: Description of Artificial Sequence: synthetic
      oligonucleotide

<400> SEQUENCE: 212
ctgagacatt gcccaggtcc                                                    20

<210> SEQ ID NO 213
<211> LENGTH: 22
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 213
tttttacccg ttgctttctt ta                                                 22

<210> SEQ ID NO 214
<211> LENGTH: 24
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 214
tatcccttgc tctttcattt atct                                               24

<210> SEQ ID NO 215
<211> LENGTH: 24
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 215
gccggtaaaa tagctgttga gtag                                               24

<210> SEQ ID NO 216
<211> LENGTH: 24
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 216
gccattgcaa acatttattt cgta                                               24

<210> SEQ ID NO 217
<211> LENGTH: 18
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 217
gcgtgtttgc gctaatag                                                      18

<210> SEQ ID NO 218
<211> LENGTH: 24
<212> TYPE: DNA
<213> ORGANISM: Artificial Sequence
<220> FEATURE:
<223> OTHER INFORMATION: Description of Artificial Sequence: synthetic
``` oligonucleotide

<400> SEQUENCE: 218
ctaagtcact tgattcacat ctaa                                          24

<210> SEQ ID NO 219
<211> LENGTH: 22
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 219
acagggtggc tgaagtgttt ta                                            22

<210> SEQ ID NO 220
<211> LENGTH: 20
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 220
gtgggaggtg gcaggttatt                                               20

<210> SEQ ID NO 221
<211> LENGTH: 23
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 221
caattagcag acttgccgtt att                                           23

<210> SEQ ID NO 222
<211> LENGTH: 24
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 222
tctcttgagt tcggtgtttt atga                                          24

<210> SEQ ID NO 223
<211> LENGTH: 24
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 223
accgaactca agagaattgc tgta                                          24

<210> SEQ ID NO 224
<211> LENGTH: 24
<212> TYPE: DNA
<213> ORGANISM: Artificial Sequence
<220> FEATURE:
<223> OTHER INFORMATION: Description of Artificial Sequence: synthetic
      oligonucleotide

```
<400> SEQUENCE: 224
aaaggaccgt atgcttgttc acta                                          24

<210> SEQ ID NO 225
<211> LENGTH: 24
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 225
tatgaatgcg cattttactc tttg                                          24

<210> SEQ ID NO 226
<211> LENGTH: 24
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 226
tggagctcaa cttagatgct actg                                          24

<210> SEQ ID NO 227
<211> LENGTH: 24
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 227
ggtgctggtg ggataggagt tttt                                          24

<210> SEQ ID NO 228
<211> LENGTH: 24
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 228
tccattaaat tctggcatat tctt                                          24

<210> SEQ ID NO 229
<211> LENGTH: 24
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 229
tcagaggggt gctttcttcc acat                                          24

<210> SEQ ID NO 230
<211> LENGTH: 24
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 230
```

```
cttcggctgt cattgtcctc aaag                                              24
```

<210> SEQ ID NO 231
<211> LENGTH: 24
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 231

```
gcaaaggaca ttggctctga gaat                                              24
```

<210> SEQ ID NO 232
<211> LENGTH: 23
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 232

```
ctgcctgcac cagtcacaac tct                                               23
```

<210> SEQ ID NO 233
<211> LENGTH: 19
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 233

```
tgggctttgc tgctttcaa                                                    19
```

<210> SEQ ID NO 234
<211> LENGTH: 24
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 234

```
agtaactgtg acgcaggact ttta                                              24
```

<210> SEQ ID NO 235
<211> LENGTH: 21
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 235

```
ccctgttcct ccagcagatt a                                                 21
```

<210> SEQ ID NO 236
<211> LENGTH: 20
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 236

```
gtgatggcca ggtcaacaaa                                                   20
```

```
<210> SEQ ID NO 237
<211> LENGTH: 23
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 237
tttgatttgg gactgttgta aac                                              23

<210> SEQ ID NO 238
<211> LENGTH: 24
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 238
aaggcaatta taaactcttt caag                                             24

<210> SEQ ID NO 239
<211> LENGTH: 24
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 239
tgggagttaa attaagttgc tcaa                                             24

<210> SEQ ID NO 240
<211> LENGTH: 24
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 240
acattttatg aacactccca gtta                                             24

<210> SEQ ID NO 241
<211> LENGTH: 23
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 241
attaacactg ttcttgcttt tat                                              23

<210> SEQ ID NO 242
<211> LENGTH: 18
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 242
gtgccagcgt gggagttc                                                    18

<210> SEQ ID NO 243
```

```
<211> LENGTH: 20
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 243
gtgggggctc taggaaacct                                                    20

<210> SEQ ID NO 244
<211> LENGTH: 24
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 244
tttaatgaaa atgaggaaaa tgtt                                               24

<210> SEQ ID NO 245
<211> LENGTH: 23
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 245
gaccaagcat ttttatttca ttc                                                23

<210> SEQ ID NO 246
<211> LENGTH: 19
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 246
agtggcagca agattgtca                                                     19

<210> SEQ ID NO 247
<211> LENGTH: 19
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 247
ggccttgctt ttgagttcc                                                     19

<210> SEQ ID NO 248
<211> LENGTH: 23
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 248
ggtctttgcc tatttctatg gtg                                                23

<210> SEQ ID NO 249
<211> LENGTH: 24
<212> TYPE: DNA
```

```
<213> ORGANISM: Artificial Sequence
<220> FEATURE:
<223> OTHER INFORMATION: Description of Artificial Sequence: synthetic
      oligonucleotide

<400> SEQUENCE: 249
ttaaaccgct tgaagatcta aata                                              24

<210> SEQ ID NO 250
<211> LENGTH: 23
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 250
tatacaccaa aatatctcct tat                                               23

<210> SEQ ID NO 251
<211> LENGTH: 24
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 251
ggggcacacc taattaattt ttat                                              24

<210> SEQ ID NO 252
<211> LENGTH: 24
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 252
aaagaggata ctcaagacca cata                                              24

<210> SEQ ID NO 253
<211> LENGTH: 24
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 253
cccaccaaca caaatatacc taat                                              24

<210> SEQ ID NO 254
<211> LENGTH: 22
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 254
tgaagggaaa gggaaaagat tt                                                22

<210> SEQ ID NO 255
<211> LENGTH: 22
<212> TYPE: DNA
<213> ORGANISM: Artificial Sequence
<220> FEATURE:
```

```
<223> OTHER INFORMATION: Description of Artificial Sequence: synthetic
      oligonucleotide

<400> SEQUENCE: 255
tccagcctta ggcacctgat aa                                              22

<210> SEQ ID NO 256
<211> LENGTH: 24
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 256
ataaagcagc aaagtgcagc atac                                            24

<210> SEQ ID NO 257
<211> LENGTH: 24
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 257
aaggctgaac tgtgtagaca tttt                                            24

<210> SEQ ID NO 258
<211> LENGTH: 24
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 258
tgacatttcc atggtacaaa gtgt                                            24

<210> SEQ ID NO 259
<211> LENGTH: 23
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 259
tttgttgttg gcttttcact tat                                             23

<210> SEQ ID NO 260
<211> LENGTH: 19
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 260
ccacctggca gtttgattg                                                  19

<210> SEQ ID NO 261
<211> LENGTH: 23
<212> TYPE: DNA
<213> ORGANISM: Artificial Sequence
<220> FEATURE:
<223> OTHER INFORMATION: Description of Artificial Sequence: synthetic
      oligonucleotide
```

```
<400> SEQUENCE: 261
taagcgtggt caacaactac agt                                        23

<210> SEQ ID NO 262
<211> LENGTH: 22
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 262
attcttgcca gcatttattg tc                                         22

<210> SEQ ID NO 263
<211> LENGTH: 19
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 263
caaaacattg ccccaaaag                                             19

<210> SEQ ID NO 264
<211> LENGTH: 24
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 264
tcaaactaaa caatttccct ctaa                                       24

<210> SEQ ID NO 265
<211> LENGTH: 24
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 265
gataattaaa aactcactga tgta                                       24

<210> SEQ ID NO 266
<211> LENGTH: 22
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 266
ggaggctaaa ggaaagagta tg                                         22

<210> SEQ ID NO 267
<211> LENGTH: 23
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 267
```
attttatagc cagcaaagaa cac                     23

<210> SEQ ID NO 268
<211> LENGTH: 20
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 268
ctagaaattc gggctgtgaa                         20

<210> SEQ ID NO 269
<211> LENGTH: 24
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 269
ctgctttgtg acctaaggca agtt                    24

<210> SEQ ID NO 270
<211> LENGTH: 24
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 270
gtgaccatgt taaggcagat gagg                    24

<210> SEQ ID NO 271
<211> LENGTH: 24
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 271
ggaatggtct ttgattttgt aacc                    24

<210> SEQ ID NO 272
<211> LENGTH: 24
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 272
tccttaactg aataaaagca cctc                    24

<210> SEQ ID NO 273
<211> LENGTH: 25
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 273
tggaacaccc atcaaagaag atact                   25

```
<210> SEQ ID NO 274
<211> LENGTH: 23
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 274
gtgggagtcc tgttgacaca aac                                              23

<210> SEQ ID NO 275
<211> LENGTH: 20
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 275
agcgattcat ggcatcaaac                                                  20

<210> SEQ ID NO 276
<211> LENGTH: 20
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 276
acgtggtgga aggcgtcata                                                  20

<210> SEQ ID NO 277
<211> LENGTH: 24
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 277
gcgacccagt ttatagagtt tgcc                                             24

<210> SEQ ID NO 278
<211> LENGTH: 23
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 278
cttgtttgcg tttcaacgtg gtc                                              23

<210> SEQ ID NO 279
<211> LENGTH: 25
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 279
caaagatcac cctggaagct cagtt                                            25
```

<210> SEQ ID NO 280
<211> LENGTH: 25
<212> TYPE: DNA
<213> ORGANISM: Artificial Sequence
<220> FEATURE:
<223> OTHER INFORMATION: Description of Artificial Sequence: synthetic oligonucleotide

<400> SEQUENCE: 280
atccagggca tctgcaaaat cagaa                                          25

<210> SEQ ID NO 281
<211> LENGTH: 25
<212> TYPE: DNA
<213> ORGANISM: Artificial Sequence
<220> FEATURE:
<223> OTHER INFORMATION: Description of Artificial Sequence: synthetic oligonucleotide

<400> SEQUENCE: 281
tgcctatgtt aagagggaag ttggg                                          25

<210> SEQ ID NO 282
<211> LENGTH: 23
<212> TYPE: DNA
<213> ORGANISM: Artificial Sequence
<220> FEATURE:
<223> OTHER INFORMATION: Description of Artificial Sequence: synthetic oligonucleotide

<400> SEQUENCE: 282
atgaccgcga tgtacatgtt cag                                            23

<210> SEQ ID NO 283
<211> LENGTH: 23
<212> TYPE: DNA
<213> ORGANISM: Artificial Sequence
<220> FEATURE:
<223> OTHER INFORMATION: Description of Artificial Sequence: synthetic oligonucleotide

<400> SEQUENCE: 283
tcaattgttt acagcccgtg atg                                            23

<210> SEQ ID NO 284
<211> LENGTH: 22
<212> TYPE: DNA
<213> ORGANISM: Artificial Sequence
<220> FEATURE:
<223> OTHER INFORMATION: Description of Artificial Sequence: synthetic oligonucleotide

<400> SEQUENCE: 284
tttatacaaa ggcagacaac at                                             22

<210> SEQ ID NO 285
<211> LENGTH: 23
<212> TYPE: DNA
<213> ORGANISM: Artificial Sequence
<220> FEATURE:
<223> OTHER INFORMATION: Description of Artificial Sequence: synthetic oligonucleotide

<400> SEQUENCE: 285
aggcgtaatg gctactcaga cga                                            23

<210> SEQ ID NO 286
<211> LENGTH: 25

```
-continued

<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 286
gtaatccctc tccccgaaca taaac                                            25

<210> SEQ ID NO 287
<211> LENGTH: 26
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 287
tttgattcac gggttgttta ctctta                                           26

<210> SEQ ID NO 288
<211> LENGTH: 26
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 288
ttctatggaa catttacagg cacatt                                           26

<210> SEQ ID NO 289
<211> LENGTH: 26
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 289
taatgtgcct gtaaatgttc cataga                                           26

<210> SEQ ID NO 290
<211> LENGTH: 26
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 290
caggcttctt agaaaggact gatagg                                           26

<210> SEQ ID NO 291
<211> LENGTH: 20
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 291
gtcccagcag catgactatc                                                  20

<210> SEQ ID NO 292
<211> LENGTH: 22
<212> TYPE: DNA
<213> ORGANISM: Artificial Sequence
```

```
<220> FEATURE:
<223> OTHER INFORMATION: Description of Artificial Sequence: synthetic
      oligonucleotide

<400> SEQUENCE: 292
cccactgggt aaaattacta ac                                              22

<210> SEQ ID NO 293
<211> LENGTH: 21
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 293
tagccatctt ctgctcttgg t                                               21

<210> SEQ ID NO 294
<211> LENGTH: 23
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 294
tggcttccca tattagactt ctg                                             23

<210> SEQ ID NO 295
<211> LENGTH: 24
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 295
tcttgcctat gctgctgtat ctta                                            24

<210> SEQ ID NO 296
<211> LENGTH: 22
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 296
agtcgggctt ttcatcattg ag                                              22

<210> SEQ ID NO 297
<211> LENGTH: 24
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 297
ttcttcatgt cattaagcaa tagg                                            24

<210> SEQ ID NO 298
<211> LENGTH: 24
<212> TYPE: DNA
<213> ORGANISM: Artificial Sequence
<220> FEATURE:
<223> OTHER INFORMATION: Description of Artificial Sequence: synthetic
``` oligonucleotide

<400> SEQUENCE: 298
ttcaatttaa aagtgctagg aaca                                              24

<210> SEQ ID NO 299
<211> LENGTH: 25
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 299
cttcaggtgg atgtcacagt cacta                                             25

<210> SEQ ID NO 300
<211> LENGTH: 24
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 300
attcaagcaa tgccaagagt atca                                              24

<210> SEQ ID NO 301
<211> LENGTH: 24
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 301
ctttcaatag taatgcctta tcat                                              24

<210> SEQ ID NO 302
<211> LENGTH: 21
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 302
tcctgcatgc atttcaccaa c                                                 21

<210> SEQ ID NO 303
<211> LENGTH: 24
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 303
ctgttcacat tttgtaaaac taat                                              24

<210> SEQ ID NO 304
<211> LENGTH: 22
<212> TYPE: DNA
<213> ORGANISM: Artificial Sequence
<220> FEATURE:
<223> OTHER INFORMATION: Description of Artificial Sequence: synthetic
      oligonucleotide -continued

<400> SEQUENCE: 304
atcccaaaga tggcgtagat ga                                           22

<210> SEQ ID NO 305
<211> LENGTH: 20
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 305
cacgctgctc tttgctttga                                              20

<210> SEQ ID NO 306
<211> LENGTH: 23
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 306
gatctttgtc agggtcacag tct                                          23

<210> SEQ ID NO 307
<211> LENGTH: 9
<212> TYPE: DNA
<213> ORGANISM: Homo sapiens

<400> SEQUENCE: 307 tacaaagaa                                                           9

<210> SEQ ID NO 308
<211> LENGTH: 9
<212> TYPE: DNA
<213> ORGANISM: Homo sapiens

<400> SEQUENCE: 308 tacagagaa                                                           9

<210> SEQ ID NO 309
<211> LENGTH: 9
<212> TYPE: DNA
<213> ORGANISM: Homo sapiens

<400> SEQUENCE: 309 tacagagaa                                                           9

<210> SEQ ID NO 310
<211> LENGTH: 19
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 310
tgtgtccgcc agtagatgg                                               19

<210> SEQ ID NO 311
<211> LENGTH: 23
<212> TYPE: DNA
<213> ORGANISM: Artificial Sequence
<220> FEATURE:
<223> OTHER INFORMATION: Description of Artificial Sequence: synthetic -continued oligonucleotide

<400> SEQUENCE: 311
tttttgacca cagaggttta caa                                    23

<210> SEQ ID NO 312
<211> LENGTH: 20
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 312
gaagcggagg cataagcaga                                        20

<210> SEQ ID NO 313
<211> LENGTH: 24
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 313
ggtgcagata atgaaatgtt ttgt                                   24

<210> SEQ ID NO 314
<211> LENGTH: 24
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 314
cacccctatg ccaaatgtca aaga                                   24

<210> SEQ ID NO 315
<211> LENGTH: 24
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 315
caaaaacaaa cttataccca gaag                                   24

<210> SEQ ID NO 316
<211> LENGTH: 22
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 316
caaatattgg gcaaaccota at                                     22

<210> SEQ ID NO 317
<211> LENGTH: 21
<212> TYPE: DNA
<213> ORGANISM: Artificial Sequence
<220> FEATURE:
<223> OTHER INFORMATION: Description of Artificial Sequence: synthetic
      oligonucleotide

```
<400> SEQUENCE: 317
aaggtgccat cacaaaatca t                                              21

<210> SEQ ID NO 318
<211> LENGTH: 24
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 318
atcgcttgct ttcctaactc ttgt                                           24

<210> SEQ ID NO 319
<211> LENGTH: 23
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 319
aagtcactat ttggctttgg ttg                                            23

<210> SEQ ID NO 320
<211> LENGTH: 24
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 320
agaagcccaa aaaggaacaa gata                                           24

<210> SEQ ID NO 321
<211> LENGTH: 24
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 321
ggcccagaaa agtatattac agtt                                           24

<210> SEQ ID NO 322
<211> LENGTH: 24
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 322
tccttaaata agcccatgtc taat                                           24

<210> SEQ ID NO 323
<211> LENGTH: 24
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 323
```

```
tctcaaagaa attttacaga tact                                              24

<210> SEQ ID NO 324
<211> LENGTH: 24
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 324
aatggccatg gtaacctact aaca                                              24

<210> SEQ ID NO 325
<211> LENGTH: 23
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 325
caggctatac ccacaaggag att                                               23

<210> SEQ ID NO 326
<211> LENGTH: 22
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 326
tgttaatttt ggcttggatg tt                                                22

<210> SEQ ID NO 327
<211> LENGTH: 21
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 327
tcactccttt gcgcttatca a                                                 21

<210> SEQ ID NO 328
<211> LENGTH: 20
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 328
agggctctat gtgccaaacc                                                   20

<210> SEQ ID NO 329
<211> LENGTH: 23
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 329
aggggcctac taccttacac cag                                               23
```

```
<210> SEQ ID NO 330
<211> LENGTH: 23
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 330
tgtaatccca ggtaagaaga aac                                            23

<210> SEQ ID NO 331
<211> LENGTH: 24
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 331
taccgggatg aactgtaata ataa                                           24

<210> SEQ ID NO 332
<211> LENGTH: 24
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 332
ttctggcact cttcctcagg taac                                           24

<210> SEQ ID NO 333
<211> LENGTH: 22
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 333
gtcccatttg aatccattgt gc                                             22

<210> SEQ ID NO 334
<211> LENGTH: 18
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 334
ggcccccaag cgattctg                                                  18

<210> SEQ ID NO 335
<211> LENGTH: 24
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 335
tgtacaccca cagtctcaac tatt                                           24

<210> SEQ ID NO 336
```

```
<211> LENGTH: 20
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 336
acagccacct ttgtaaataa                                              20

<210> SEQ ID NO 337
<211> LENGTH: 20
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 337
tttttcgcaa agagttctat                                              20

<210> SEQ ID NO 338
<211> LENGTH: 24
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 338
aaactgaccc tacctccatt tctc                                         24

<210> SEQ ID NO 339
<211> LENGTH: 24
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 339
actcagccta tgcttttcat ttca                                         24

<210> SEQ ID NO 340
<211> LENGTH: 24
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 340
cagatattta tttggggaca ttat                                         24

<210> SEQ ID NO 341
<211> LENGTH: 24
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 341
aaatctttgc ktttatcact cagt                                         24

<210> SEQ ID NO 342
<211> LENGTH: 24
<212> TYPE: DNA
```

```
<213> ORGANISM: Artificial Sequence
<220> FEATURE:
<223> OTHER INFORMATION: Description of Artificial Sequence: synthetic
      oligonucleotide

<400> SEQUENCE: 342
tagtgcctgg ctttgtttta tgac                                         24

<210> SEQ ID NO 343
<211> LENGTH: 22
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 343
cggatttggg aaagctgtct ct                                           22

<210> SEQ ID NO 344
<211> LENGTH: 24
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 344
agagcacctt gaaggaaaca acaa                                         24

<210> SEQ ID NO 345
<211> LENGTH: 24
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 345
tccctcaact gaagtacaga tagt                                         24

<210> SEQ ID NO 346
<211> LENGTH: 23
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 346
ataattgcgt tcttcccta ccc                                           23

<210> SEQ ID NO 347
<211> LENGTH: 19
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 347
aagccctggc accatcctg                                               19

<210> SEQ ID NO 348
<211> LENGTH: 20
<212> TYPE: DNA
<213> ORGANISM: Artificial Sequence
<220> FEATURE:
```

-continued

<223> OTHER INFORMATION: Description of Artificial Sequence: synthetic
      oligonucleotide

<400> SEQUENCE: 348
tttgcaaaga aatgctatgt                                              20

<210> SEQ ID NO 349
<211> LENGTH: 22
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 349
ctgggtaaca gacttcagta at                                           22

<210> SEQ ID NO 350
<211> LENGTH: 24
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 350
atgggattgt cttctcaagt ttct                                         24

<210> SEQ ID NO 351
<211> LENGTH: 22
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 351
gatggcaaga tcaacaaatg ga                                           22

<210> SEQ ID NO 352
<211> LENGTH: 23
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 352
cttgatctgg gactgctgtg atg                                          23

<210> SEQ ID NO 353
<211> LENGTH: 23
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 353
aggatataat ttttggttca aca                                          23

<210> SEQ ID NO 354
<211> LENGTH: 24
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 354
ttttcagtgc tcttgatagt agtg                                              24

<210> SEQ ID NO 355
<211> LENGTH: 18
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 355
gtgccaatga gcgacagg                                                     18

<210> SEQ ID NO 356
<211> LENGTH: 22
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 356
ccacgtgtgg ttctatgata cc                                                22

<210> SEQ ID NO 357
<211> LENGTH: 20
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 357
accgtgggag cgtacagtca                                                   20

<210> SEQ ID NO 358
<211> LENGTH: 20
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 358
cggcatgcag ctctttggta                                                   20

<210> SEQ ID NO 359
<211> LENGTH: 23
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 359
tggccacgtt cctagctact gtc                                               23

<210> SEQ ID NO 360
<211> LENGTH: 24
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 360
gagttccctt tttaggctgt tatt                                        24

<210> SEQ ID NO 361
<211> LENGTH: 24
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 361
tcttattgcc ttcatggatt tcta                                        24

<210> SEQ ID NO 362
<211> LENGTH: 22
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 362
tgaaaaataa gatgcgggag tg                                          22

<210> SEQ ID NO 363
<211> LENGTH: 21
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 363
gtgaggctgg ggttgtttat g                                           21

<210> SEQ ID NO 364
<211> LENGTH: 21
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 364
gagatgggaa tggaaccacc a                                           21

<210> SEQ ID NO 365
<211> LENGTH: 23
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 365
ttcgataatg catataagca caa                                         23

<210> SEQ ID NO 366
<211> LENGTH: 21
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 366 aaggggggaaa atcacatctt t                                          21

<210> SEQ ID NO 367
<211> LENGTH: 24
<212> TYPE: DNA
<213> ORGANISM: Artificial Sequence
<220> FEATURE:
<223> OTHER INFORMATION: Description of Artificial Sequence: synthetic oligonucleotide

<400> SEQUENCE: 367
ttaaatgagg catattcagt ctcc                                          24

<210> SEQ ID NO 368
<211> LENGTH: 19
<212> TYPE: DNA
<213> ORGANISM: Artificial Sequence
<220> FEATURE:
<223> OTHER INFORMATION: Description of Artificial Sequence: synthetic oligonucleotide

<400> SEQUENCE: 368
ggaagtggag tggggaagg                                                19

<210> SEQ ID NO 369
<211> LENGTH: 24
<212> TYPE: DNA
<213> ORGANISM: Artificial Sequence
<220> FEATURE:
<223> OTHER INFORMATION: Description of Artificial Sequence: synthetic oligonucleotide

<400> SEQUENCE: 369
attcttgcca atatgcattt cact                                          24

<210> SEQ ID NO 370
<211> LENGTH: 26
<212> TYPE: DNA
<213> ORGANISM: Artificial Sequence
<220> FEATURE:
<223> OTHER INFORMATION: Description of Artificial Sequence: synthetic oligonucleotide

<400> SEQUENCE: 370
ttcttttgta ctcactatta tactaa                                        26

<210> SEQ ID NO 371
<211> LENGTH: 24
<212> TYPE: DNA
<213> ORGANISM: Artificial Sequence
<220> FEATURE:
<223> OTHER INFORMATION: Description of Artificial Sequence: synthetic oligonucleotide

<400> SEQUENCE: 371
aaacttgcct cttttaaaaa caat                                          24

<210> SEQ ID NO 372
<211> LENGTH: 24
<212> TYPE: DNA
<213> ORGANISM: Artificial Sequence
<220> FEATURE:
<223> OTHER INFORMATION: Description of Artificial Sequence: synthetic oligonucleotide

<400> SEQUENCE: 372
taccacaccc tataccttca gtca                                          24

```
<210> SEQ ID NO 373
<211> LENGTH: 24
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 373
gagtatggca ccctttctca tcta                                           24

<210> SEQ ID NO 374
<211> LENGTH: 21
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 374
gctatgttcc cctcgctgtc t                                              21

<210> SEQ ID NO 375
<211> LENGTH: 19
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 375
tgcttgccaa gagcctgac                                                 19

<210> SEQ ID NO 376
<211> LENGTH: 22
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 376
gctggcaagt tctaccactg tg                                             22

<210> SEQ ID NO 377
<211> LENGTH: 24
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 377
caaacgaaga acatcaggga aata                                           24

<210> SEQ ID NO 378
<211> LENGTH: 24
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 378
ttcacaatat tgtacaaaaa gtta                                           24

<210> SEQ ID NO 379
<211> LENGTH: 24
```

```
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 379
attaccacca atattcacca taag                                              24

<210> SEQ ID NO 380
<211> LENGTH: 23
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 380
tcagggtaag gcaaaagtag cac                                               23

<210> SEQ ID NO 381
<211> LENGTH: 24
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 381 gaacccaga atgaagaaag gtaa                                               24

<210> SEQ ID NO 382
<211> LENGTH: 24
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 382
tttgtgaaag tactattgga acac                                              24

<210> SEQ ID NO 383
<211> LENGTH: 19
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 383
acgcatggct ttggaacat                                                    19

<210> SEQ ID NO 384
<211> LENGTH: 22
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 384
cccgtatgtg gaagggcttt at                                                22

<210> SEQ ID NO 385
<211> LENGTH: 24
<212> TYPE: DNA
<213> ORGANISM: Artificial Sequence
```

```
<220> FEATURE:
<223> OTHER INFORMATION: Description of Artificial Sequence: synthetic
      oligonucleotide

<400> SEQUENCE: 385
ctaggttgat ccgggacaaa acta                                              24

<210> SEQ ID NO 386
<211> LENGTH: 22
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 386
aacggatgac cagggcaaat ac                                                22

<210> SEQ ID NO 387
<211> LENGTH: 22
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 387
ctagaaggtc ctggggcaac tg                                                22

<210> SEQ ID NO 388
<211> LENGTH: 23
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 388
aagccatcat gtaaagtgaa aag                                               23

<210> SEQ ID NO 389
<211> LENGTH: 21
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 389
atcccaaaga tggcatagat a                                                 21

<210> SEQ ID NO 390
<211> LENGTH: 20
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 390
cacgctgctc tttgctttga                                                   20

<210> SEQ ID NO 391
<211> LENGTH: 20
<212> TYPE: DNA
<213> ORGANISM: Artificial Sequence
<220> FEATURE:
<223> OTHER INFORMATION: Description of Artificial Sequence: synthetic
```

-continued

```
        oligonucleotide

<400> SEQUENCE: 391
tgagctgcca gggtgaattg                                              20

<210> SEQ ID NO 392
<211> LENGTH: 26
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 392
ttgctagcac ctattcttaa tagtgc                                       26

<210> SEQ ID NO 393
<211> LENGTH: 23
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 393
ccagggcagc tgcaaaatca gag                                          23

<210> SEQ ID NO 394
<211> LENGTH: 19
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 394
cccgatgcga cccagttta                                               19

<210> SEQ ID NO 395
<211> LENGTH: 20
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 395
tggaggggtt tgatgccata                                              20

<210> SEQ ID NO 396
<211> LENGTH: 23
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 396
gatggatgcc cttcgaatac aga                                          23

<210> SEQ ID NO 397
<211> LENGTH: 24
<212> TYPE: DNA
<213> ORGANISM: Artificial Sequence
<220> FEATURE:
<223> OTHER INFORMATION: Description of Artificial Sequence: synthetic
      oligonucleotide
```

-continued

<400> SEQUENCE: 397
ttcccattta gtttgtcaat aatc                                                24

<210> SEQ ID NO 398
<211> LENGTH: 23
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 398
aaggggagga ttgacttacc tat                                                 23

<210> SEQ ID NO 399
<211> LENGTH: 21
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 399
ttggcatgga cctcctcttg a                                                   21

<210> SEQ ID NO 400
<211> LENGTH: 13
<212> TYPE: DNA
<213> ORGANISM: Homo sapiens

<400> SEQUENCE: 400
tggtataagg tag                                                            13

<210> SEQ ID NO 401
<211> LENGTH: 18
<212> TYPE: DNA
<213> ORGANISM: Homo sapiens

<400> SEQUENCE: 401
caagataatg atgatgag                                                       18

<210> SEQ ID NO 402
<211> LENGTH: 15
<212> TYPE: DNA
<213> ORGANISM: Homo sapiens

<400> SEQUENCE: 402
caagatgatg atgag                                                          15

<210> SEQ ID NO 403
<211> LENGTH: 13
<212> TYPE: DNA
<213> ORGANISM: Homo sapiens

<400> SEQUENCE: 403
tggtgtaagg tag                                                            13

<210> SEQ ID NO 404
<211> LENGTH: 17
<212> TYPE: DNA
<213> ORGANISM: Homo sapiens

<400> SEQUENCE: 404 cccttatat ctccaac                                                         17

<210> SEQ ID NO 405
<211> LENGTH: 17
<212> TYPE: DNA
<213> ORGANISM: Homo sapiens

<400> SEQUENCE: 405 cccttatay ctccaac                                                      17

<210> SEQ ID NO 406
<211> LENGTH: 15
<212> TYPE: DNA
<213> ORGANISM: Homo sapiens

<400> SEQUENCE: 406
aaatacgtaa tcgat                                                       15

<210> SEQ ID NO 407
<211> LENGTH: 15
<212> TYPE: DNA
<213> ORGANISM: Homo sapiens

<400> SEQUENCE: 407
aaatacataa tcgat                                                       15

<210> SEQ ID NO 408
<211> LENGTH: 15
<212> TYPE: DNA
<213> ORGANISM: Homo sapiens

<400> SEQUENCE: 408
aaatacrtaa tcgat                                                       15

<210> SEQ ID NO 409
<211> LENGTH: 5856
<212> TYPE: DNA
<213> ORGANISM: Homo sapiens
<220> FEATURE:
<221> NAME/KEY: CDS
<222> LOCATION: (1)..(5856)
<220> FEATURE:
<221> NAME/KEY: MISC_FEATURE
<222> LOCATION: (122)..(122)
<223> OTHER INFORMATION: Xaa = any amino acid

<400> SEQUENCE: 409

| atg | gca | cag | gca | ctg | ttg | gta | ccc | cca | gga | cct | gaa | agc | ttc | cgc | ctt | 48 |
|---|---|---|---|---|---|---|---|---|---|---|---|---|---|---|---|---|
| Met | Ala | Gln | Ala | Leu | Leu | Val | Pro | Pro | Gly | Pro | Glu | Ser | Phe | Arg | Leu | |
| 1 | | | | 5 | | | | | 10 | | | | | 15 | | |

| ttt | act | aga | gaa | tct | ctt | gct | gct | atc | gaa | aaa | cgt | gct | gca | gaa | gag | 96 |
|---|---|---|---|---|---|---|---|---|---|---|---|---|---|---|---|---|
| Phe | Thr | Arg | Glu | Ser | Leu | Ala | Ala | Ile | Glu | Lys | Arg | Ala | Ala | Glu | Glu | |
| | | | 20 | | | | | 25 | | | | | 30 | | | |

| aaa | gcc | aag | aag | ccc | aaa | aag | gaa | caa | gat | aat | gat | gat | gag | aac | aaa | 144 |
|---|---|---|---|---|---|---|---|---|---|---|---|---|---|---|---|---|
| Lys | Ala | Lys | Lys | Pro | Lys | Lys | Glu | Gln | Asp | Asn | Asp | Asp | Glu | Asn | Lys | |
| | | 35 | | | | | 40 | | | | | 45 | | | | |

| cca | aag | cca | aat | agt | gac | ttg | gaa | gct | gga | aag | aac | ctt | cca | ttt | att | 192 |
|---|---|---|---|---|---|---|---|---|---|---|---|---|---|---|---|---|
| Pro | Lys | Pro | Asn | Ser | Asp | Leu | Glu | Ala | Gly | Lys | Asn | Leu | Pro | Phe | Ile | |
| 50 | | | | | 55 | | | | | 60 | | | | | | |

| tat | gga | gac | att | cct | cca | gag | atg | gtg | tca | gag | ccc | ctg | gag | gac | ctg | 240 |
|---|---|---|---|---|---|---|---|---|---|---|---|---|---|---|---|---|
| Tyr | Gly | Asp | Ile | Pro | Pro | Glu | Met | Val | Ser | Glu | Pro | Leu | Glu | Asp | Leu | |
| 65 | | | | | 70 | | | | | 75 | | | | | 80 | |

| gat | ccc | tac | tat | atc | aat | aag | aaa | act | ttt | ata | gta | atg | aat | aaa | gga | 288 |
|---|---|---|---|---|---|---|---|---|---|---|---|---|---|---|---|---|
| Asp | Pro | Tyr | Tyr | Ile | Asn | Lys | Lys | Thr | Phe | Ile | Val | Met | Asn | Lys | Gly | |
| | | | | 85 | | | | | 90 | | | | | 95 | | |

| aag | gca | att | tcc | cga | ttc | agt | gcc | acc | tct | gcc | ttg | tat | att | tta | act | 336 |

-continued

```
                Lys Ala Ile Ser Arg Phe Ser Ala Thr Ser Ala Leu Tyr Ile Leu Thr
                                100                 105                 110 cca cta aac cct gtt agg aaa att gct abs aag att ttg gta cat tct       384
Pro Leu Asn Pro Val Arg Lys Ile Ala Xaa Lys Ile Leu Val His Ser
            115                 120                 125 tta ttc agc atg ctt atc atg tgc act att ttg acc aac tgt gta ttt       432
Leu Phe Ser Met Leu Ile Met Cys Thr Ile Leu Thr Asn Cys Val Phe
    130                 135                 140 atg acc ttg agc aac cct cct gac tgg aca aag aat gta gag tac aca       480
Met Thr Leu Ser Asn Pro Pro Asp Trp Thr Lys Asn Val Glu Tyr Thr
145                 150                 155                 160 ttc act gga atc tat acc ttt gag tca ctt ata aaa atc ttg gca aga       528
Phe Thr Gly Ile Tyr Thr Phe Glu Ser Leu Ile Lys Ile Leu Ala Arg
                165                 170                 175 ggg ttt tgc tta gaa gat ttt acg ttt ctt cgt gat cca tgg aac tgg       576
Gly Phe Cys Leu Glu Asp Phe Thr Phe Leu Arg Asp Pro Trp Asn Trp
            180                 185                 190 ctg gat ttc agt gtc att gtg atg gca tat gtg aca gag ttt gtg gac       624
Leu Asp Phe Ser Val Ile Val Met Ala Tyr Val Thr Glu Phe Val Asp
    195                 200                 205 ctg ggc aat gtc tca gcg ttg aga aca ttc aga gtt ctc cga gca ctg       672
Leu Gly Asn Val Ser Ala Leu Arg Thr Phe Arg Val Leu Arg Ala Leu
210                 215                 220 aaa aca att tca gtc att cca ggt tta aag acc att gtg ggg gcc ctg       720
Lys Thr Ile Ser Val Ile Pro Gly Leu Lys Thr Ile Val Gly Ala Leu
225                 230                 235                 240 atc cag tcg gta aag aag ctt tct gat gtg atg atc ctg act gtg ttc       768
Ile Gln Ser Val Lys Lys Leu Ser Asp Val Met Ile Leu Thr Val Phe
                245                 250                 255 tgt ctg agc gtg ttt gct ctc att ggg ctg cag ctg ttc atg ggc aat       816
Cys Leu Ser Val Phe Ala Leu Ile Gly Leu Gln Leu Phe Met Gly Asn
            260                 265                 270 ctg agg aat aaa tgt ttg cag tgg ccc cca agc gat tct gct ttt gaa       864
Leu Arg Asn Lys Cys Leu Gln Trp Pro Pro Ser Asp Ser Ala Phe Glu
    275                 280                 285 acc aac acc act tcc tac ttt aat ggc aca atg gat tca aat ggg aca       912
Thr Asn Thr Thr Ser Tyr Phe Asn Gly Thr Met Asp Ser Asn Gly Thr
290                 295                 300 ttt gtt aat gta aca atg agc aca ttt aac tgg aag gat tac att gga       960
Phe Val Asn Val Thr Met Ser Thr Phe Asn Trp Lys Asp Tyr Ile Gly
305                 310                 315                 320 gat gac agt cac ttt tat gtt ttg gat ggg caa aaa gac cct tta ctc      1008
Asp Asp Ser His Phe Tyr Val Leu Asp Gly Gln Lys Asp Pro Leu Leu
                325                 330                 335 tgt gga aat ggc tca gat gca ggc cag tgt cca gaa gga tac atc tgt      1056
Cys Gly Asn Gly Ser Asp Ala Gly Gln Cys Pro Glu Gly Tyr Ile Cys
            340                 345                 350 gtg aag gct ggt cga aac ccc aac tat ggc tac aca agc ttt gac acc      1104
Val Lys Ala Gly Arg Asn Pro Asn Tyr Gly Tyr Thr Ser Phe Asp Thr
    355                 360                 365 ttt agc tgg gct ttc ctg tct cta ttt cga ctc atg act caa gac tac      1152
Phe Ser Trp Ala Phe Leu Ser Leu Phe Arg Leu Met Thr Gln Asp Tyr
370                 375                 380 tgg gaa aat ctt tac cag ttg aca tta cgt gct gct ggg aaa aca tac      1200
Trp Glu Asn Leu Tyr Gln Leu Thr Leu Arg Ala Ala Gly Lys Thr Tyr
385                 390                 395                 400 atg ata ttt ttt gtc ctg gtc att ttc ttg ggc tca ttt tat ttg gtg      1248
Met Ile Phe Phe Val Leu Val Ile Phe Leu Gly Ser Phe Tyr Leu Val
                405                 410                 415 aat ttg atc ctg gct gtg gtg gcc atg gcc tat gag ggg cag aat cag      1296
```

-continued

```
                Asn Leu Ile Leu Ala Val Val Ala Met Ala Tyr Glu Gly Gln Asn Gln
                                420                 425                 430 gcc acc ttg gaa gaa gca gaa caa aaa gag gcc gaa ttt cag cag atg      1344
Ala Thr Leu Glu Glu Ala Glu Gln Lys Glu Ala Glu Phe Gln Gln Met
            435                 440                 445 ctc gaa cag ctt aaa aag caa cag gaa gaa gct cag gca gtt gcg gca      1392
Leu Glu Gln Leu Lys Lys Gln Gln Glu Glu Ala Gln Ala Val Ala Ala
        450                 455                 460 gca tca gct gct tca aga gat ttc agt gga ata ggt ggg tta gga gag      1440
Ala Ser Ala Ala Ser Arg Asp Phe Ser Gly Ile Gly Gly Leu Gly Glu
465                 470                 475                 480 ctg ttg gaa agt tct tca gaa gca tca aag ttg agt tcc aaa agt gct      1488
Leu Leu Glu Ser Ser Ser Glu Ala Ser Lys Leu Ser Ser Lys Ser Ala
                485                 490                 495 aaa gaa tgg agg aac cga agg aag aaa aga aga cag aga gag cac ctt      1536
Lys Glu Trp Arg Asn Arg Arg Lys Lys Arg Arg Gln Arg Glu His Leu
            500                 505                 510 gaa gga aac aac aaa gga gag aga gac agc ttt ccc aaa tcc gaa tct      1584
Glu Gly Asn Asn Lys Gly Glu Arg Asp Ser Phe Pro Lys Ser Glu Ser
        515                 520                 525 gaa gac agc gtc aaa aga agc agc ttc ctt ttc tcc atg gat gga aac      1632
Glu Asp Ser Val Lys Arg Ser Ser Phe Leu Phe Ser Met Asp Gly Asn
530                 535                 540 aga ctg acc agt gac aaa aaa ttc tgc tcc cct cat cag tct ctc ttg      1680
Arg Leu Thr Ser Asp Lys Lys Phe Cys Ser Pro His Gln Ser Leu Leu
545                 550                 555                 560 agt atc cgt ggc tcc ctg ttt tcc cca aga cgc aat agc aaa aca agc      1728
Ser Ile Arg Gly Ser Leu Phe Ser Pro Arg Arg Asn Ser Lys Thr Ser
                565                 570                 575 att ttc agt ttc aga ggt cgg gca aag gat gtt gga tct gaa aat gac      1776
Ile Phe Ser Phe Arg Gly Arg Ala Lys Asp Val Gly Ser Glu Asn Asp
            580                 585                 590 ttt gct gat gat gaa cac agc aca ttt gaa gac agc gaa agc agg aga      1824
Phe Ala Asp Asp Glu His Ser Thr Phe Glu Asp Ser Glu Ser Arg Arg
        595                 600                 605 gac tca ctg ttt gtg ccg cac aga cat gga gag cga cgc aac agt aac      1872
Asp Ser Leu Phe Val Pro His Arg His Gly Glu Arg Arg Asn Ser Asn
610                 615                 620 ggc acc acc act gaa acg gaa gtc aga aag aga agg tta agc tct tac      1920
Gly Thr Thr Thr Glu Thr Glu Val Arg Lys Arg Arg Leu Ser Ser Tyr
625                 630                 635                 640 cag att tca atg gag atg ctg gag gat tcc tct gga agg caa aga gcc      1968
Gln Ile Ser Met Glu Met Leu Glu Asp Ser Ser Gly Arg Gln Arg Ala
                645                 650                 655 gtg agc ata gcc agc att ctg acc aac aca atg gaa gaa ctt gaa gaa      2016
Val Ser Ile Ala Ser Ile Leu Thr Asn Thr Met Glu Glu Leu Glu Glu
            660                 665                 670 tct aga cag aaa tgt ccg cca tgc tgg tat aga ttt gcc aat gtg ttc      2064
Ser Arg Gln Lys Cys Pro Pro Cys Trp Tyr Arg Phe Ala Asn Val Phe
        675                 680                 685 ttg atc tgg gac tgc tgt gat gca tgg tta aaa gta aaa cat ctt gtg      2112
Leu Ile Trp Asp Cys Cys Asp Ala Trp Leu Lys Val Lys His Leu Val
690                 695                 700 aat tta att gtt atg gat cca ttt gtt gat ctt gcc atc act att tgc      2160
Asn Leu Ile Val Met Asp Pro Phe Val Asp Leu Ala Ile Thr Ile Cys
705                 710                 715                 720 att gtc tta aat acc ctc ttt atg gcc atg gag cac tac ccc atg act      2208
Ile Val Leu Asn Thr Leu Phe Met Ala Met Glu His Tyr Pro Met Thr
                725                 730                 735 gag caa ttc agt agt gtg ttg act gta gga aac ctg gtc ttt act ggg      2256
```

|  |  |
|---|---|
| Glu Gln Phe Ser Ser Val Leu Thr Val Gly Asn Leu Val Phe Thr Gly<br>                  740                            745                      750 |  |
| att ttt aca gca gaa atg gtt ctc aag atc att gcc atg gat cct tat<br>Ile Phe Thr Ala Glu Met Val Leu Lys Ile Ile Ala Met Asp Pro Tyr<br>            755                          760                    765 | 2304 |
| tac tat ttc caa gaa ggc tgg aat atc ttt gat gga att att gtc agc<br>Tyr Tyr Phe Gln Glu Gly Trp Asn Ile Phe Asp Gly Ile Ile Val Ser<br>            770                          775                    780 | 2352 |
| ctc agt tta atg gag ctt ggt ctg tca aat gtg gag gga ttg tct gta<br>Leu Ser Leu Met Glu Leu Gly Leu Ser Asn Val Glu Gly Leu Ser Val<br>785                   790                          795                    800 | 2400 |
| ctg cga tca ttc aga ctg ctt aga gtt ttc aag ttg gca aaa tcc tgg<br>Leu Arg Ser Phe Arg Leu Leu Arg Val Phe Lys Leu Ala Lys Ser Trp<br>            805                          810                    815 | 2448 |
| ccc aca cta aat atg cta att aag atc att ggc aat tct gtg ggg gct<br>Pro Thr Leu Asn Met Leu Ile Lys Ile Ile Gly Asn Ser Val Gly Ala<br>                820                          825                    830 | 2496 |
| cta gga aac ctc acc ttg gtg ttg gcc atc atc gtc ttc att ttt gct<br>Leu Gly Asn Leu Thr Leu Val Leu Ala Ile Ile Val Phe Ile Phe Ala<br>            835                          840                    845 | 2544 |
| gtg gtc ggc atg cag ctc ttt ggt aag agc tac aaa gaa tgt gtc tgc<br>Val Val Gly Met Gln Leu Phe Gly Lys Ser Tyr Lys Glu Cys Val Cys<br>850                   855                          860 | 2592 |
| aag atc aat gat gac tgt acg ctc cca cgg tgg cac atg aac gac ttc<br>Lys Ile Asn Asp Asp Cys Thr Leu Pro Arg Trp His Met Asn Asp Phe<br>865                   870                          875                    880 | 2640 |
| ttc cac tcc ttc ctg att gtg ttc cgc gtg ctg tgt gga gag tgg ata<br>Phe His Ser Phe Leu Ile Val Phe Arg Val Leu Cys Gly Glu Trp Ile<br>            885                          890                    895 | 2688 |
| gag acc atg tgg gac tgt atg gag gtc gct ggc caa acc atg tgc ctt<br>Glu Thr Met Trp Asp Cys Met Glu Val Ala Gly Gln Thr Met Cys Leu<br>            900                          905                    910 | 2736 |
| att gtt ttc atg ttg gtc atg gtc att gga aac ctt gtg gtt ctg aac<br>Ile Val Phe Met Leu Val Met Val Ile Gly Asn Leu Val Val Leu Asn<br>            915                          920                    925 | 2784 |
| ctc ttt ctg gcc tta ttg ttg agt tca ttt agc tca gac aac ctt gct<br>Leu Phe Leu Ala Leu Leu Leu Ser Ser Phe Ser Ser Asp Asn Leu Ala<br>            930   &nbsb;                    935                    940 | 2832 |
| gct act gat gat gac aat gaa atg aat aat ctg cag att gca gta gga<br>Ala Thr Asp Asp Asp Asn Glu Met Asn Asn Leu Gln Ile Ala Val Gly<br>945                   950                          955                    960 | 2880 |
| aga atg caa aag gga att gat tat gtg aaa aat aag atg cgg gag tgt<br>Arg Met Gln Lys Gly Ile Asp Tyr Val Lys Asn Lys Met Arg Glu Cys<br>                965                          970                    975 | 2928 |
| ttc caa aaa gcc ttt ttt aga aag cca aaa gtt ata gaa atc cat gaa<br>Phe Gln Lys Ala Phe Phe Arg Lys Pro Lys Val Ile Glu Ile His Glu<br>            980                          985                    990 | 2976 |
| ggc aat aag ata gac agc tgc atg  tcc aat aat act gga  att gaa ata<br>Gly Asn Lys Ile Asp Ser Cys Met  Ser Asn Asn Thr Gly  Ile Glu Ile<br>            995                        1000                  1005 | 3024 |
| agc aaa gag ctt aat tat ctt aga gat ggg aat gga acc acc agt<br>Ser Lys Glu Leu Asn Tyr Leu Arg Asp Gly Asn Gly Thr Thr Ser<br>         1010                   1015                   1020 | 3069 |
| ggt gta ggt act gga agc agt gtt gaa aaa tac gta atc gat gaa<br>Gly Val Gly Thr Gly Ser Ser Val Glu Lys Tyr Val Ile Asp Glu<br>         1025                   1030                   1035 | 3114 |
| aat gat tat atg tca ttc ata aac aac ccc agc ctc acc gtc aca<br>Asn Asp Tyr Met Ser Phe Ile Asn Asn Pro Ser Leu Thr Val Thr<br>         1040                   1045                   1050 | 3159 |
| gtg cca att gct gtt gga gag tct gac ttt gaa aac tta aat act | 3204 |

-continued

```
Val Pro Ile Ala Val Gly Glu Ser Asp Phe Glu Asn Leu Asn Thr
    1055                1060                1065 gaa gag ttc agc agt gag tca gaa cta gaa gaa agc aag gag aaa        3249
Glu Glu Phe Ser Ser Glu Ser Glu Leu Glu Glu Ser Lys Glu Lys
    1070                1075                1080 tta aat gca acc agc tca tct gaa gga agc aca gtt gat gtt gtt        3294
Leu Asn Ala Thr Ser Ser Ser Glu Gly Ser Thr Val Asp Val Val
    1085                1090                1095 cta ccc cga gaa ggt gaa caa gct gaa act gaa ccc gaa gaa gac        3339
Leu Pro Arg Glu Gly Glu Gln Ala Glu Thr Glu Pro Glu Glu Asp
    1100                1105                1110 ctt aaa ccg gaa gct tgt ttt act gaa gga tgt att aaa aag ttt        3384
Leu Lys Pro Glu Ala Cys Phe Thr Glu Gly Cys Ile Lys Lys Phe
    1115                1120                1125 cca ttc tgt caa gta agt aca gaa gaa ggc aaa ggg aag atc tgg        3429
Pro Phe Cys Gln Val Ser Thr Glu Glu Gly Lys Gly Lys Ile Trp
    1130                1135                1140 tgg aat ctt cga aaa acc tgc tac agt att gtt gag cac aac tgg        3474
Trp Asn Leu Arg Lys Thr Cys Tyr Ser Ile Val Glu His Asn Trp
    1145                1150                1155 ttt gag act ttc att gtg ttc atg atc ctt ctc agt agt ggt gca        3519
Phe Glu Thr Phe Ile Val Phe Met Ile Leu Leu Ser Ser Gly Ala
    1160                1165                1170 ttg gcc ttt gaa gat ata tac att gaa cag cga aag act atc aaa        3564
Leu Ala Phe Glu Asp Ile Tyr Ile Glu Gln Arg Lys Thr Ile Lys
    1175                1180                1185 acc atg cta gaa tat gct gac aaa gtc ttt acc tat ata ttc att        3609
Thr Met Leu Glu Tyr Ala Asp Lys Val Phe Thr Tyr Ile Phe Ile
    1190                1195                1200 ctg gaa atg ctt ctc aaa tgg gtt gct tat gga ttt caa aca tat        3654
Leu Glu Met Leu Leu Lys Trp Val Ala Tyr Gly Phe Gln Thr Tyr
    1205                1210                1215 ttc act aat gcc tgg tgc tgg cta gat ttc ttg atc gtt gat gtt        3699
Phe Thr Asn Ala Trp Cys Trp Leu Asp Phe Leu Ile Val Asp Val
    1220                1225                1230 tct ttg gtt agc ctg gta gcc aat gct ctt ggc tac tca gaa ctc        3744
Ser Leu Val Ser Leu Val Ala Asn Ala Leu Gly Tyr Ser Glu Leu
    1235                1240                1245 ggt gcc atc aaa tca tta cgg aca tta aga gct tta aga cct cta        3789
Gly Ala Ile Lys Ser Leu Arg Thr Leu Arg Ala Leu Arg Pro Leu
    1250                1255                1260 aga gcc tta tcc cgg ttt gaa ggc atg agg gtg gtt gtg aat gct        3834
Arg Ala Leu Ser Arg Phe Glu Gly Met Arg Val Val Val Asn Ala
    1265                1270                1275 ctt gtt gga gca att ccc tct atc atg aat gtg ctg ttg gtc tgt        3879
Leu Val Gly Ala Ile Pro Ser Ile Met Asn Val Leu Leu Val Cys
    1280                1285                1290 ctc atc ttc tgg ttg atc ttt agc atc atg ggt gtg aat ttg ttt        3924
Leu Ile Phe Trp Leu Ile Phe Ser Ile Met Gly Val Asn Leu Phe
    1295                1300                1305 gct ggc aag ttc tac cac tgt gtt aac atg aca acg ggt aac atg        3969
Ala Gly Lys Phe Tyr His Cys Val Asn Met Thr Thr Gly Asn Met
    1310                1315                1320 ttt gac att agt gat gtt aac aat ttg agt gac tgt cag gct ctt        4014
Phe Asp Ile Ser Asp Val Asn Asn Leu Ser Asp Cys Gln Ala Leu
    1325                1330                1335 ggc aag caa gct cgg tgg aaa aac gtg aaa gta aac ttt gat aat        4059
Gly Lys Gln Ala Arg Trp Lys Asn Val Lys Val Asn Phe Asp Asn
    1340                1345                1350 gtt ggc gct ggc tat ctt gca ctg ctt caa gtg gcc aca ttt aaa        4104
```

-continued

| | | | | | | | | | | |
|---|---|---|---|---|---|---|---|---|---|---|
| Val | Gly | Ala | Gly | Tyr | Leu | Ala | Leu | Leu | Gln | Val | Ala | Thr | Phe | Lys | |
| | 1355 | | | | 1360 | | | | | 1365 | | | | | |
| ggc | tgg | atg | gat | att | atg | tat | gca | gct | gtt | gat | tca | cga | gat | gtt | 4149 |
| Gly | Trp | Met | Asp | Ile | Met | Tyr | Ala | Ala | Val | Asp | Ser | Arg | Asp | Val | |
| | 1370 | | | | 1375 | | | | | 1380 | | | | | |
| aaa | ctt | cag | cct | gta | tat | gaa | gaa | aat | ctg | tac | atg | tat | tta | tac | 4194 |
| Lys | Leu | Gln | Pro | Val | Tyr | Glu | Glu | Asn | Leu | Tyr | Met | Tyr | Leu | Tyr | |
| | 1385 | | | | 1390 | | | | | 1395 | | | | | |
| ttt | gtc | atc | ttt | atc | atc | ttt | ggg | tca | ttc | ttc | act | ctg | aat | cta | 4239 |
| Phe | Val | Ile | Phe | Ile | Ile | Phe | Gly | Ser | Phe | Phe | Thr | Leu | Asn | Leu | |
| | 1400 | | | | 1405 | | | | | 1410 | | | | | |
| ttc | att | ggt | gtc | atc | ata | gat | aac | ttc | aac | cag | cag | aaa | aag | aag | 4284 |
| Phe | Ile | Gly | Val | Ile | Ile | Asp | Asn | Phe | Asn | Gln | Gln | Lys | Lys | Lys | |
| | 1415 | | | | 1420 | | | | | 1425 | | | | | |
| ttt | gga | ggt | caa | gac | atc | ttt | atg | aca | gag | gaa | cag | aaa | aaa | tat | 4329 |
| Phe | Gly | Gly | Gln | Asp | Ile | Phe | Met | Thr | Glu | Glu | Gln | Lys | Lys | Tyr | |
| | 1430 | | | | 1435 | | | | | 1440 | | | | | |
| tac | aat | gca | atg | aag | aaa | ctt | gga | tcc | aag | aaa | cct | cag | aaa | ccc | 4374 |
| Tyr | Asn | Ala | Met | Lys | Lys | Leu | Gly | Ser | Lys | Lys | Pro | Gln | Lys | Pro | |
| | 1445 | | | | 1450 | | | | | 1455 | | | | | |
| ata | cct | cgc | cca | gca | aac | aaa | ttc | caa | gga | atg | gtc | ttt | gat | ttt | 4419 |
| Ile | Pro | Arg | Pro | Ala | Asn | Lys | Phe | Gln | Gly | Met | Val | Phe | Asp | Phe | |
| | 1460 | | | | 1465 | | | | | 1470 | | | | | |
| gta | acc | aga | caa | gtc | ttt | gat | atc | agc | atc | atg | atc | ctc | atc | tgc | 4464 |
| Val | Thr | Arg | Gln | Val | Phe | Asp | Ile | Ser | Ile | Met | Ile | Leu | Ile | Cys | |
| | 1475 | | | | 1480 | | | | | 1485 | | | | | |
| ctc | aac | atg | gtc | acc | atg | atg | gtg | gaa | acg | gat | gac | cag | ggc | aaa | 4509 |
| Leu | Asn | Met | Val | Thr | Met | Met | Val | Glu | Thr | Asp | Asp | Gln | Gly | Lys | |
| | 1490 | | | | 1495 | | | | | 1500 | | | | | |
| tac | atg | acc | cta | gtt | ttg | tcc | cgg | atc | aac | cta | gtg | ttc | att | gtt | 4554 |
| Tyr | Met | Thr | Leu | Val | Leu | Ser | Arg | Ile | Asn | Leu | Val | Phe | Ile | Val | |
| | 1505 | | | | 1510 | | | | | 1515 | | | | | |
| ctg | ttc | act | gga | gaa | ttt | gtg | ctg | aag | ctc | gtc | tcc | ctc | aga | cac | 4599 |
| Leu | Phe | Thr | Gly | Glu | Phe | Val | Leu | Lys | Leu | Val | Ser | Leu | Arg | His | |
| | 1520 | | | | 1525 | | | | | 1530 | | | | | |
| tac | tac | ttc | act | ata | ggc | tgg | aac | atc | ttt | gac | ttt | gtg | gtg | gtg | 4644 |
| Tyr | Tyr | Phe | Thr | Ile | Gly | Trp | Asn | Ile | Phe | Asp | Phe | Val | Val | Val | |
| | 1535 | | | | 1540 | | | | | 1545 | | | | | |
| att | ctc | tcc | att | gta | ggt | atg | ttt | ctg | gct | gag | atg | ata | gaa | aag | 4689 |
| Ile | Leu | Ser | Ile | Val | Gly | Met | Phe | Leu | Ala | Glu | Met | Ile | Glu | Lys | |
| | 1550 | | | | 1555 | | | | | 1560 | | | | | |
| tat | ttt | gtg | tcc | cct | acc | ttg | ttc | cga | gtg | atc | cgt | ctt | gcc | agg | 4734 |
| Tyr | Phe | Val | Ser | Pro | Thr | Leu | Phe | Arg | Val | Ile | Arg | Leu | Ala | Arg | |
| | 1565 | | | | 1570 | | | | | 1575 | | | | | |
| att | ggc | cga | atc | cta | cgt | ctg | atc | aaa | gga | gca | aag | ggg | atc | cgc | 4779 |
| Ile | Gly | Arg | Ile | Leu | Arg | Leu | Ile | Lys | Gly | Ala | Lys | Gly | Ile | Arg | |
| | 1580 | | | | 1585 | | | | | 1590 | | | | | |
| acg | ctg | ctc | ttt | gct | ttg | atg | atg | tcc | ctt | cct | gcg | ttg | ttt | aac | 4824 |
| Thr | Leu | Leu | Phe | Ala | Leu | Met | Met | Ser | Leu | Pro | Ala | Leu | Phe | Asn | |
| | 1595 | | | | 1600 | | | | | 1605 | | | | | |
| atc | ggc | ctc | ctg | ctc | ttc | ctg | gtc | atg | ttt | atc | tat | gcc | atc | ttt | 4869 |
| Ile | Gly | Leu | Leu | Leu | Phe | Leu | Val | Met | Phe | Ile | Tyr | Ala | Ile | Phe | |
| | 1610 | | | | 1615 | | | | | 1620 | | | | | |
| ggg | atg | tcc | aac | ttt | gcc | tat | gtt | aaa | aag | gaa | gct | gga | att | gat | 4914 |
| Gly | Met | Ser | Asn | Phe | Ala | Tyr | Val | Lys | Lys | Glu | Ala | Gly | Ile | Asp | |
| | 1625 | | | | 1630 | | | | | 1635 | | | | | |
| gac | atg | ttc | aac | ttt | gag | acc | ttt | ggc | aac | agc | atg | atc | tgc | ttg | 4959 |
| Asp | Met | Phe | Asn | Phe | Glu | Thr | Phe | Gly | Asn | Ser | Met | Ile | Cys | Leu | |
| | 1640 | | | | 1645 | | | | | 1650 | | | | | |
| ttc | caa | att | aca | acc | tct | gct | gga | tgg | gat | gga | ttg | cta | gca | cct | 5004 |

```
                    Phe Gln Ile Thr Thr Ser Ala Gly Trp Asp Gly Leu Leu Ala Pro
                        1655                1660                1665 att ctt aat agt gca cca ccc gac tgt gac cct gac aca att cac          5049
Ile Leu Asn Ser Ala Pro Pro Asp Cys Asp Pro Asp Thr Ile His
        1670                1675                1680 cct ggc agc tca gtt aag gga gac tgt ggg aac cca tct gtt ggg          5094
Pro Gly Ser Ser Val Lys Gly Asp Cys Gly Asn Pro Ser Val Gly
        1685                1690                1695 att ttc ttt ttt gtc agt tac atc atc ata tcc ttc ctg gtg gtg          5139
Ile Phe Phe Phe Val Ser Tyr Ile Ile Ile Ser Phe Leu Val Val
        1700                1705                1710 gtg aac agt tac atc gcg gtc atc ctg gag aac ttc agt gtt gct          5184
Val Asn Ser Tyr Ile Ala Val Ile Leu Glu Asn Phe Ser Val Ala
        1715                1720                1725 act gaa gaa agt gca gag ccc ctg agt gag gat gac ttt gag atg          5229
Thr Glu Glu Ser Ala Glu Pro Leu Ser Glu Asp Asp Phe Glu Met
        1730                1735                1740 ttc tat gag gtt tgg gaa aag ttt gat ccc gat gcg acc cag ttt          5274
Phe Tyr Glu Val Trp Glu Lys Phe Asp Pro Asp Ala Thr Gln Phe
        1745                1750                1755 ata gag ttc tct aaa ctc tct gat ttt gca gct gcc ctg gat cct          5319
Ile Glu Phe Ser Lys Leu Ser Asp Phe Ala Ala Ala Leu Asp Pro
        1760                1765                1770 cct ctt ctc ata gca aaa ccc aac aaa gtc cag ctt att gcc atg          5364
Pro Leu Leu Ile Ala Lys Pro Asn Lys Val Gln Leu Ile Ala Met
        1775                1780                1785 gat ctg ccc atg gtc agt ggt gac cgg atc cac tgt ctt gat att          5409
Asp Leu Pro Met Val Ser Gly Asp Arg Ile His Cys Leu Asp Ile
        1790                1795                1800 tta ttt gcc ttt aca aag cgt gtt ttg ggt gag agt gga gag atg          5454
Leu Phe Ala Phe Thr Lys Arg Val Leu Gly Glu Ser Gly Glu Met
        1805                1810                1815 gat gcc ctt cga ata cag atg gaa gac agg ttt atg gca tca aac          5499
Asp Ala Leu Arg Ile Gln Met Glu Asp Arg Phe Met Ala Ser Asn
        1820                1825                1830 ccc tcc aaa gtc tct tat gag cct att aca acc act ttg aaa cgt          5544
Pro Ser Lys Val Ser Tyr Glu Pro Ile Thr Thr Thr Leu Lys Arg
        1835                1840                1845 aaa caa gag gag gtg tct gcc gct atc att cag cgt aat ttc aga          5589
Lys Gln Glu Glu Val Ser Ala Ala Ile Ile Gln Arg Asn Phe Arg
        1850                1855                1860 tgt tat ctt tta aag caa agg tta aaa aat ata tca agt aac tat          5634
Cys Tyr Leu Leu Lys Gln Arg Leu Lys Asn Ile Ser Ser Asn Tyr
        1865                1870                1875 aac aaa gag gca ata aag ggg agg att gac tta cct ata aaa caa          5679
Asn Lys Glu Ala Ile Lys Gly Arg Ile Asp Leu Pro Ile Lys Gln
        1880                1885                1890 gac atg att att gac aaa ctg aat ggg aac tcc act cca gaa aaa          5724
Asp Met Ile Ile Asp Lys Leu Asn Gly Asn Ser Thr Pro Glu Lys
        1895                1900                1905 aca gat ggg agt tcc tct acc acc tct cct cct tcc tat gat agt          5769
Thr Asp Gly Ser Ser Ser Thr Thr Ser Pro Pro Ser Tyr Asp Ser
        1910                1915                1920 gta aca aaa cca gac aag gaa aag ttt gag aaa gac aaa cca gaa          5814
Val Thr Lys Pro Asp Lys Glu Lys Phe Glu Lys Asp Lys Pro Glu
        1925                1930                1935 aaa gaa agc aaa gga aaa gag gtc aga gaa aat caa aag taa              5856
Lys Glu Ser Lys Gly Lys Glu Val Arg Glu Asn Gln Lys
        1940                1945                1950
```

```
<210> SEQ ID NO 410
<211> LENGTH: 5853
<212> TYPE: DNA
<213> ORGANISM: Homo sapiens
<220> FEATURE:
<221> NAME/KEY: CDS
<222> LOCATION: (1)..(5853)
<220> FEATURE:
<221> NAME/KEY: MISC_FEATURE
<222> LOCATION: (121)..(121)
<223> OTHER INFORMATION: Xaa = any amino acid

<400> SEQUENCE: 410 atg gca cag gca ctg ttg gta ccc cca gga cct gaa agc ttc cgc ctt        48
Met Ala Gln Ala Leu Leu Val Pro Pro Gly Pro Glu Ser Phe Arg Leu
1               5                   10                  15 ttt act aga gaa tct ctt gct gct atc gaa aaa cgt gct gca gaa gag        96
Phe Thr Arg Glu Ser Leu Ala Ala Ile Glu Lys Arg Ala Ala Glu Glu
            20                  25                  30 aaa gcc aag aag ccc aaa aag gaa caa gat gat gat gag aac aaa cca       144
Lys Ala Lys Lys Pro Lys Lys Glu Gln Asp Asp Asp Glu Asn Lys Pro
        35                  40                  45 aag cca aat agt gac ttg gaa gct gga aag aac ctt cca ttt att tat       192
Lys Pro Asn Ser Asp Leu Glu Ala Gly Lys Asn Leu Pro Phe Ile Tyr
    50                  55                  60 gga gac att cct cca gag atg gtg tca gag ccc ctg gag gac ctg gat       240
Gly Asp Ile Pro Pro Glu Met Val Ser Glu Pro Leu Glu Asp Leu Asp
65                  70                  75                  80 ccc tac tat atc aat aag aaa act ttt ata gta atg aat aaa gga aag       288
Pro Tyr Tyr Ile Asn Lys Lys Thr Phe Ile Val Met Asn Lys Gly Lys
                85                  90                  95 gca att tcc cga ttc agt gcc acc tct gcc ttg tat att tta act cca       336
Ala Ile Ser Arg Phe Ser Ala Thr Ser Ala Leu Tyr Ile Leu Thr Pro
            100                 105                 110 cta aac cct gtt agg aaa att gct abs aag att ttg gta cat tct tta       384
Leu Asn Pro Val Arg Lys Ile Ala Xaa Lys Ile Leu Val His Ser Leu
        115                 120                 125 ttc agc atg ctt atc atg tgc act att ttg acc aac tgt gta ttt atg       432
Phe Ser Met Leu Ile Met Cys Thr Ile Leu Thr Asn Cys Val Phe Met
    130                 135                 140 acc ttg agc aac cct cct gac tgg aca aag aat gta gag tac aca ttc       480
Thr Leu Ser Asn Pro Pro Asp Trp Thr Lys Asn Val Glu Tyr Thr Phe
145                 150                 155                 160 act gga atc tat acc ttt gag tca ctt ata aaa atc ttg gca aga ggg       528
Thr Gly Ile Tyr Thr Phe Glu Ser Leu Ile Lys Ile Leu Ala Arg Gly
                165                 170                 175 ttt tgc tta gaa gat ttt acg ttt ctt cgt gat cca tgg aac tgg ctg       576
Phe Cys Leu Glu Asp Phe Thr Phe Leu Arg Asp Pro Trp Asn Trp Leu
            180                 185                 190 gat ttc agt gtc att gtg atg gca tat gtg aca gag ttt gtg gac ctg       624
Asp Phe Ser Val Ile Val Met Ala Tyr Val Thr Glu Phe Val Asp Leu
        195                 200                 205 ggc aat gtc tca gcg ttg aga aca ttc aga gtt ctc cga gca ctg aaa       672
Gly Asn Val Ser Ala Leu Arg Thr Phe Arg Val Leu Arg Ala Leu Lys
    210                 215                 220 aca att tca gtc att cca ggt tta aag acc att gtg ggg gcc ctg atc       720
Thr Ile Ser Val Ile Pro Gly Leu Lys Thr Ile Val Gly Ala Leu Ile
225                 230                 235                 240 cag tcg gta aag aag ctt tct gat gtg atg atc ctg act gtg ttc tgt       768
Gln Ser Val Lys Lys Leu Ser Asp Val Met Ile Leu Thr Val Phe Cys
                245                 250                 255 ctg agc gtg ttt gct ctc att ggg ctg cag ctg ttc atg ggc aat ctg       816
Leu Ser Val Phe Ala Leu Ile Gly Leu Gln Leu Phe Met Gly Asn Leu
```

```
                    260                 265                 270
agg aat aaa tgt ttg cag tgg ccc cca agc gat tct gct ttt gaa acc        864
Arg Asn Lys Cys Leu Gln Trp Pro Pro Ser Asp Ser Ala Phe Glu Thr
        275                 280                 285 aac acc act tcc tac ttt aat ggc aca atg gat tca aat ggg aca ttt        912
Asn Thr Thr Ser Tyr Phe Asn Gly Thr Met Asp Ser Asn Gly Thr Phe
    290                 295                 300 gtt aat gta aca atg agc aca ttt aac tgg aag gat tac att gga gat        960
Val Asn Val Thr Met Ser Thr Phe Asn Trp Lys Asp Tyr Ile Gly Asp
305                 310                 315                 320 gac agt cac ttt tat gtt ttg gat ggg caa aaa gac cct tta ctc tgt       1008
Asp Ser His Phe Tyr Val Leu Asp Gly Gln Lys Asp Pro Leu Leu Cys
                325                 330                 335 gga aat ggc tca gat gca ggc cag tgt cca gaa gga tac atc tgt gtg       1056
Gly Asn Gly Ser Asp Ala Gly Gln Cys Pro Glu Gly Tyr Ile Cys Val
            340                 345                 350 aag gct ggt cga aac ccc aac tat ggc tac aca agc ttt gac acc ttt       1104
Lys Ala Gly Arg Asn Pro Asn Tyr Gly Tyr Thr Ser Phe Asp Thr Phe
        355                 360                 365 agc tgg gct ttc ctg tct cta ttt cga ctc atg act caa gac tac tgg       1152
Ser Trp Ala Phe Leu Ser Leu Phe Arg Leu Met Thr Gln Asp Tyr Trp
    370                 375                 380 gaa aat ctt tac cag ttg aca tta cgt gct gct ggg aaa aca tac atg       1200
Glu Asn Leu Tyr Gln Leu Thr Leu Arg Ala Ala Gly Lys Thr Tyr Met
385                 390                 395                 400 ata ttt ttt gtc ctg gtc att ttc ttg ggc tca ttt tat ttg gtg aat       1248
Ile Phe Phe Val Leu Val Ile Phe Leu Gly Ser Phe Tyr Leu Val Asn
                405                 410                 415 ttg atc ctg gct gtg gtg gcc atg gcc tat gag ggg cag aat cag gcc       1296
Leu Ile Leu Ala Val Val Ala Met Ala Tyr Glu Gly Gln Asn Gln Ala
            420                 425                 430 acc ttg gaa gaa gca gaa caa aaa gag gcc gaa ttt cag cag atg ctc       1344
Thr Leu Glu Glu Ala Glu Gln Lys Glu Ala Glu Phe Gln Gln Met Leu
        435                 440                 445 gaa cag ctt aaa aag caa cag gaa gaa gct cag gca gtt gcg gca gca       1392
Glu Gln Leu Lys Lys Gln Gln Glu Glu Ala Gln Ala Val Ala Ala Ala
    450                 455                 460 tca gct gct tca aga gat ttc agt gga ata ggt ggg tta gga gag ctg       1440
Ser Ala Ala Ser Arg Asp Phe Ser Gly Ile Gly Gly Leu Gly Glu Leu
465                 470                 475                 480 ttg gaa agt tct tca gaa gca tca aag ttg agt tcc aaa agt gct aaa       1488
Leu Glu Ser Ser Ser Glu Ala Ser Lys Leu Ser Ser Lys Ser Ala Lys
                485                 490                 495 gaa tgg agg aac cga agg aag aaa aga aga cag aga gag cac ctt gaa       1536
Glu Trp Arg Asn Arg Arg Lys Lys Arg Arg Gln Arg Glu His Leu Glu
            500                 505                 510 gga aac aac aaa gga gag aga gac agc ttt ccc aaa tcc gaa tct gaa       1584
Gly Asn Asn Lys Gly Glu Arg Asp Ser Phe Pro Lys Ser Glu Ser Glu
        515                 520                 525 gac agc gtc aaa aga agc agc ttc ctt ttc tcc atg gat gga aac aga       1632
Asp Ser Val Lys Arg Ser Ser Phe Leu Phe Ser Met Asp Gly Asn Arg
    530                 535                 540 ctg acc agt gac aaa aaa ttc tgc tcc cct cat cag tct ctc ttg agt       1680
Leu Thr Ser Asp Lys Lys Phe Cys Ser Pro His Gln Ser Leu Leu Ser
545                 550                 555                 560 atc cgt ggc tcc ctg ttt tcc cca aga cgc aat agc aaa aca agc att       1728
Ile Arg Gly Ser Leu Phe Ser Pro Arg Arg Asn Ser Lys Thr Ser Ile
                565                 570                 575 ttc agt ttc aga ggt cgg gca aag gat gtt gga tct gaa aat gac ttt       1776
Phe Ser Phe Arg Gly Arg Ala Lys Asp Val Gly Ser Glu Asn Asp Phe
```

-continued

```
                        580                      585                      590
gct gat gat gaa cac agc aca ttt gaa gac agc gaa agc agg aga gac    1824
Ala Asp Asp Glu His Ser Thr Phe Glu Asp Ser Glu Ser Arg Arg Asp
            595                      600                      605 tca ctg ttt gtg ccg cac aga cat gga gag cga cgc aac agt aac ggc    1872
Ser Leu Phe Val Pro His Arg His Gly Glu Arg Arg Asn Ser Asn Gly
610                      615                      620 acc acc act gaa acg gaa gtc aga aag aga agg tta agc tct tac cag    1920
Thr Thr Thr Glu Thr Glu Val Arg Lys Arg Arg Leu Ser Ser Tyr Gln
625                      630                      635                      640 att tca atg gag atg ctg gag gat tcc tct gga agg caa aga gcc gtg    1968
Ile Ser Met Glu Met Leu Glu Asp Ser Ser Gly Arg Gln Arg Ala Val
                645                      650                      655 agc ata gcc agc att ctg acc aac aca atg gaa gaa ctt gaa gaa tct    2016
Ser Ile Ala Ser Ile Leu Thr Asn Thr Met Glu Glu Leu Glu Glu Ser
            660                      665                      670 aga cag aaa tgt ccg cca tgc tgg tat aga ttt gcc aat gtg ttc ttg    2064
Arg Gln Lys Cys Pro Pro Cys Trp Tyr Arg Phe Ala Asn Val Phe Leu
        675                      680                      685 atc tgg gac tgc tgt gat gca tgg tta aaa gta aaa cat ctt gtg aat    2112
Ile Trp Asp Cys Cys Asp Ala Trp Leu Lys Val Lys His Leu Val Asn
690                      695                      700 tta att gtt atg gat cca ttt gtt gat ctt gcc atc act att tgc att    2160
Leu Ile Val Met Asp Pro Phe Val Asp Leu Ala Ile Thr Ile Cys Ile
705                      710                      715                      720 gtc tta aat acc ctc ttt atg gcc atg gag cac tac ccc atg act gag    2208
Val Leu Asn Thr Leu Phe Met Ala Met Glu His Tyr Pro Met Thr Glu
                725                      730                      735 caa ttc agt agt gtg ttg act gta gga aac ctg gtc ttt act ggg att    2256
Gln Phe Ser Ser Val Leu Thr Val Gly Asn Leu Val Phe Thr Gly Ile
            740                      745                      750 ttt aca gca gaa atg gtt ctc aag atc att gcc atg gat cct tat tac    2304
Phe Thr Ala Glu Met Val Leu Lys Ile Ile Ala Met Asp Pro Tyr Tyr
        755                      760                      765 tat ttc caa gaa ggc tgg aat atc ttt gat gga att att gtc agc ctc    2352
Tyr Phe Gln Glu Gly Trp Asn Ile Phe Asp Gly Ile Ile Val Ser Leu
770                      775                      780 agt tta atg gag ctt ggt ctg tca aat gtg gag gga ttg tct gta ctg    2400
Ser Leu Met Glu Leu Gly Leu Ser Asn Val Glu Gly Leu Ser Val Leu
785                      790                      795                      800 cga tca ttc aga ctg ctt aga gtt ttc aag ttg gca aaa tcc tgg ccc    2448
Arg Ser Phe Arg Leu Leu Arg Val Phe Lys Leu Ala Lys Ser Trp Pro
                805                      810                      815 aca cta aat atg cta att aag atc att ggc aat tct gtg ggg gct cta    2496
Thr Leu Asn Met Leu Ile Lys Ile Ile Gly Asn Ser Val Gly Ala Leu
            820                      825                      830 gga aac ctc acc ttg gtg ttg gcc atc atc gtc ttc att ttt gct gtg    2544
Gly Asn Leu Thr Leu Val Leu Ala Ile Ile Val Phe Ile Phe Ala Val
        835                      840                      845 gtc ggc atg cag ctc ttt ggt aag agc tac aaa gaa tgt gtc tgc aag    2592
Val Gly Met Gln Leu Phe Gly Lys Ser Tyr Lys Glu Cys Val Cys Lys
850                      855                      860 atc aat gat gac tgt acg ctc cca cgg tgg cac atg aac gac ttc ttc    2640
Ile Asn Asp Asp Cys Thr Leu Pro Arg Trp His Met Asn Asp Phe Phe
865                      870                      875                      880 cac tcc ttc ctg att gtg ttc cgc gtg ctg tgt gga gag tgg ata gag    2688
His Ser Phe Leu Ile Val Phe Arg Val Leu Cys Gly Glu Trp Ile Glu
                885                      890                      895 acc atg tgg gac tgt atg gag gtc gct ggc caa acc atg tgc ctt att    2736
Thr Met Trp Asp Cys Met Glu Val Ala Gly Gln Thr Met Cys Leu Ile
```

```
                900           905           910
gtt ttc atg ttg gtc atg gtc att gga aac ctt gtg gtt ctg aac ctc      2784
Val Phe Met Leu Val Met Val Ile Gly Asn Leu Val Val Leu Asn Leu
    915                 920                 925 ttt ctg gcc tta ttg ttg agt tca ttt agc tca gac aac ctt gct gct      2832
Phe Leu Ala Leu Leu Leu Ser Ser Phe Ser Ser Asp Asn Leu Ala Ala
930                 935                 940 act gat gat gac aat gaa atg aat aat ctg cag att gca gta gga aga      2880
Thr Asp Asp Asp Asn Glu Met Asn Asn Leu Gln Ile Ala Val Gly Arg
945                 950                 955                 960 atg caa aag gga att gat tat gtg aaa aat aag atg cgg gag tgt ttc      2928
Met Gln Lys Gly Ile Asp Tyr Val Lys Asn Lys Met Arg Glu Cys Phe
                965                 970                 975 caa aaa gcc ttt ttt aga aag cca aaa gtt ata gaa atc cat gaa ggc      2976
Gln Lys Ala Phe Phe Arg Lys Pro Lys Val Ile Glu Ile His Glu Gly
            980                 985                 990 aat aag ata gac agc tgc atg tcc aat aat act gga att gaa ata agc      3024
Asn Lys Ile Asp Ser Cys Met Ser Asn Asn Thr Gly Ile Glu Ile Ser
        995                 1000                1005 aaa gag ctt aat tat ctt aga gat ggg aat gga acc acc agt ggt          3069
Lys Glu Leu Asn Tyr Leu Arg Asp Gly Asn Gly Thr Thr Ser Gly
1010                1015                1020 gta ggt act gga agc agt gtt gaa aaa tac gta atc gat gaa aat          3114
Val Gly Thr Gly Ser Ser Val Glu Lys Tyr Val Ile Asp Glu Asn
1025                1030                1035 gat tat atg tca ttc ata aac aac ccc agc ctc acc gtc aca gtg          3159
Asp Tyr Met Ser Phe Ile Asn Asn Pro Ser Leu Thr Val Thr Val
1040                1045                1050 cca att gct gtt gga gag tct gac ttt gaa aac tta aat act gaa          3204
Pro Ile Ala Val Gly Glu Ser Asp Phe Glu Asn Leu Asn Thr Glu
1055                1060                1065 gag ttc agc agt gag tca gaa cta gaa gaa agc aag gag aaa tta          3249
Glu Phe Ser Ser Glu Ser Glu Leu Glu Glu Ser Lys Glu Lys Leu
1070                1075                1080 aat gca acc agc tca tct gaa gga agc aca gtt gat gtt gtt cta          3294
Asn Ala Thr Ser Ser Ser Glu Gly Ser Thr Val Asp Val Val Leu
1085                1090                1095 ccc cga gaa ggt gaa caa gct gaa act gaa ccc gaa gaa gac ctt          3339
Pro Arg Glu Gly Glu Gln Ala Glu Thr Glu Pro Glu Glu Asp Leu
1100                1105                1110 aaa ccg gaa gct tgt ttt act gaa gga tgt att aaa aag ttt cca          3384
Lys Pro Glu Ala Cys Phe Thr Glu Gly Cys Ile Lys Lys Phe Pro
1115                1120                1125 ttc tgt caa gta agt aca gaa gaa ggc aaa ggg aag atc tgg tgg          3429
Phe Cys Gln Val Ser Thr Glu Glu Gly Lys Gly Lys Ile Trp Trp
1130                1135                1140 aat ctt cga aaa acc tgc tac agt att gtt gag cac aac tgg ttt          3474
Asn Leu Arg Lys Thr Cys Tyr Ser Ile Val Glu His Asn Trp Phe
1145                1150                1155 gag act ttc att gtg ttc atg atc ctt ctc agt agt ggt gca ttg          3519
Glu Thr Phe Ile Val Phe Met Ile Leu Leu Ser Ser Gly Ala Leu
1160                1165                1170 gcc ttt gaa gat ata tac att gaa cag cga aag act atc aaa acc          3564
Ala Phe Glu Asp Ile Tyr Ile Glu Gln Arg Lys Thr Ile Lys Thr
1175                1180                1185 atg cta gaa tat gct gac aaa gtc ttt acc tat ata ttc att ctg          3609
Met Leu Glu Tyr Ala Asp Lys Val Phe Thr Tyr Ile Phe Ile Leu
1190                1195                1200 gaa atg ctt ctc aaa tgg gtt gct tat gga ttt caa aca tat ttc          3654
Glu Met Leu Leu Lys Trp Val Ala Tyr Gly Phe Gln Thr Tyr Phe
```

|  |  |
|---|---|
| act aat gcc tgg tgc tgg cta gat ttc ttg atc gtt gat gtt tct<br>Thr Asn Ala Trp Cys Trp Leu Asp Phe Leu Ile Val Asp Val Ser<br>1220                  1225                  1230 | 3699 |
| ttg gtt agc ctg gta gcc aat gct ctt ggc tac tca gaa ctc ggt<br>Leu Val Ser Leu Val Ala Asn Ala Leu Gly Tyr Ser Glu Leu Gly<br>1235                  1240                  1245 | 3744 |
| gcc atc aaa tca tta cgg aca tta aga gct tta aga cct cta aga<br>Ala Ile Lys Ser Leu Arg Thr Leu Arg Ala Leu Arg Pro Leu Arg<br>1250                  1255                  1260 | 3789 |
| gcc tta tcc cgg ttt gaa ggc atg agg gtg gtt gtg aat gct ctt<br>Ala Leu Ser Arg Phe Glu Gly Met Arg Val Val Val Asn Ala Leu<br>1265                  1270                  1275 | 3834 |
| gtt gga gca att ccc tct atc atg aat gtg ctg ttg gtc tgt ctc<br>Val Gly Ala Ile Pro Ser Ile Met Asn Val Leu Leu Val Cys Leu<br>1280                  1285                  1290 | 3879 |
| atc ttc tgg ttg atc ttt agc atc atg ggt gtg aat ttg ttt gct<br>Ile Phe Trp Leu Ile Phe Ser Ile Met Gly Val Asn Leu Phe Ala<br>1295                  1300                  1305 | 3924 |
| ggc aag ttc tac cac tgt gtt aac atg aca acg ggt aac atg ttt<br>Gly Lys Phe Tyr His Cys Val Asn Met Thr Thr Gly Asn Met Phe<br>1310                  1315                  1320 | 3969 |
| gac att agt gat gtt aac aat ttg agt gac tgt cag gct ctt ggc<br>Asp Ile Ser Asp Val Asn Asn Leu Ser Asp Cys Gln Ala Leu Gly<br>1325                  1330                  1335 | 4014 |
| aag caa gct cgg tgg aaa aac gtg aaa gta aac ttt gat aat gtt<br>Lys Gln Ala Arg Trp Lys Asn Val Lys Val Asn Phe Asp Asn Val<br>1340                  1345                  1350 | 4059 |
| ggc gct ggc tat ctt gca ctg ctt caa gtg gcc aca ttt aaa ggc<br>Gly Ala Gly Tyr Leu Ala Leu Leu Gln Val Ala Thr Phe Lys Gly<br>1355                  1360                  1365 | 4104 |
| tgg atg gat att atg tat gca gct gtt gat tca cga gat gtt aaa<br>Trp Met Asp Ile Met Tyr Ala Ala Val Asp Ser Arg Asp Val Lys<br>1370                  1375                  1380 | 4149 |
| ctt cag cct gta tat gaa gaa aat ctg tac atg tat tta tac ttt<br>Leu Gln Pro Val Tyr Glu Glu Asn Leu Tyr Met Tyr Leu Tyr Phe<br>1385                  1390                  1395 | 4194 |
| gtc atc ttt atc atc ttt ggg tca ttc ttc act ctg aat cta ttc<br>Val Ile Phe Ile Ile Phe Gly Ser Phe Phe Thr Leu Asn Leu Phe<br>1400                  1405                  1410 | 4239 |
| att ggt gtc atc ata gat aac ttc aac cag cag aaa aag aag ttt<br>Ile Gly Val Ile Ile Asp Asn Phe Asn Gln Gln Lys Lys Lys Phe<br>1415                  1420                  1425 | 4284 |
| gga ggt caa gac atc ttt atg aca gag gaa cag aaa aaa tat tac<br>Gly Gly Gln Asp Ile Phe Met Thr Glu Glu Gln Lys Lys Tyr Tyr<br>1430                  1435                  1440 | 4329 |
| aat gca atg aag aaa ctt gga tcc aag aaa cct cag aaa ccc ata<br>Asn Ala Met Lys Lys Leu Gly Ser Lys Lys Pro Gln Lys Pro Ile<br>1445                  1450                  1455 | 4374 |
| cct cgc cca gca aac aaa ttc caa gga atg gtc ttt gat ttt gta<br>Pro Arg Pro Ala Asn Lys Phe Gln Gly Met Val Phe Asp Phe Val<br>1460                  1465                  1470 | 4419 |
| acc aga caa gtc ttt gat atc agc atc atg atc ctc atc tgc ctc<br>Thr Arg Gln Val Phe Asp Ile Ser Ile Met Ile Leu Ile Cys Leu<br>1475                  1480                  1485 | 4464 |
| aac atg gtc acc atg atg gtg gaa acg gat gac cag ggc aaa tac<br>Asn Met Val Thr Met Met Val Glu Thr Asp Asp Gln Gly Lys Tyr<br>1490                  1495                  1500 | 4509 |
| atg acc cta gtt ttg tcc cgg atc aac cta gtg ttc att gtt ctg<br>Met Thr Leu Val Leu Ser Arg Ile Asn Leu Val Phe Ile Val Leu | 4554 |

-continued

|     | 1505 | | | 1510 | | | 1515 | | | | | |
|-----|------|---|---|------|---|---|------|---|---|---|---|---|
| ttc | act | gga | gaa | ttt | gtg | ctg | aag | ctc | gtc | tcc | ctc | aga cac tac | 4599 |
| Phe | Thr | Gly | Glu | Phe | Val | Leu | Lys | Leu | Val | Ser | Leu | Arg His Tyr | |
| 1520 | | | | 1525 | | | 1530 | | | | | |

| tac | ttc | act | ata | ggc | tgg | aac | atc | ttt | gac | ttt | gtg | gtg gtg att | 4644 |
| Tyr | Phe | Thr | Ile | Gly | Trp | Asn | Ile | Phe | Asp | Phe | Val | Val Val Ile | |
| 1535 | | | | 1540 | | | | 1545 | | | | |

| ctc | tcc | att | gta | ggt | atg | ttt | ctg | gct | gag | atg | ata | gaa aag tat | 4689 |
| Leu | Ser | Ile | Val | Gly | Met | Phe | Leu | Ala | Glu | Met | Ile | Glu Lys Tyr | |
| 1550 | | | | 1555 | | | | 1560 | | | | |

| ttt | gtg | tcc | cct | acc | ttg | ttc | cga | gtg | atc | cgt | ctt | gcc agg att | 4734 |
| Phe | Val | Ser | Pro | Thr | Leu | Phe | Arg | Val | Ile | Arg | Leu | Ala Arg Ile | |
| 1565 | | | | 1570 | | | | 1575 | | | | |

| ggc | cga | atc | cta | cgt | ctg | atc | aaa | gga | gca | aag | ggg | atc cgc acg | 4779 |
| Gly | Arg | Ile | Leu | Arg | Leu | Ile | Lys | Gly | Ala | Lys | Gly | Ile Arg Thr | |
| 1580 | | | | 1585 | | | | 1590 | | | | |

| ctg | ctc | ttt | gct | ttg | atg | atg | tcc | ctt | cct | gcg | ttg | ttt aac atc | 4824 |
| Leu | Leu | Phe | Ala | Leu | Met | Met | Ser | Leu | Pro | Ala | Leu | Phe Asn Ile | |
| 1595 | | | | 1600 | | | | 1605 | | | | |

| ggc | ctc | ctg | ctc | ttc | ctg | gtc | atg | ttt | atc | tat | gcc | atc ttt ggg | 4869 |
| Gly | Leu | Leu | Leu | Phe | Leu | Val | Met | Phe | Ile | Tyr | Ala | Ile Phe Gly | |
| 1610 | | | | 1615 | | | | 1620 | | | | |

| atg | tcc | aac | ttt | gcc | tat | gtt | aaa | aag | gaa | gct | gga | att gat gac | 4914 |
| Met | Ser | Asn | Phe | Ala | Tyr | Val | Lys | Lys | Glu | Ala | Gly | Ile Asp Asp | |
| 1625 | | | | 1630 | | | | 1635 | | | | |

| atg | ttc | aac | ttt | gag | acc | ttt | ggc | aac | agc | atg | atc | tgc ttg ttc | 4959 |
| Met | Phe | Asn | Phe | Glu | Thr | Phe | Gly | Asn | Ser | Met | Ile | Cys Leu Phe | |
| 1640 | | | | 1645 | | | | 1650 | | | | |

| caa | att | aca | acc | tct | gct | gga | tgg | gat | gga | ttg | cta | gca cct att | 5004 |
| Gln | Ile | Thr | Thr | Ser | Ala | Gly | Trp | Asp | Gly | Leu | Leu | Ala Pro Ile | |
| 1655 | | | | 1660 | | | | 1665 | | | | |

| ctt | aat | agt | gca | cca | ccc | gac | tgt | gac | cct | gac | aca | att cac cct | 5049 |
| Leu | Asn | Ser | Ala | Pro | Pro | Asp | Cys | Asp | Pro | Asp | Thr | Ile His Pro | |
| 1670 | | | | 1675 | | | | 1680 | | | | |

| ggc | agc | tca | gtt | aag | gga | gac | tgt | ggg | aac | cca | tct | gtt ggg att | 5094 |
| Gly | Ser | Ser | Val | Lys | Gly | Asp | Cys | Gly | Asn | Pro | Ser | Val Gly Ile | |
| 1685 | | | | 1690 | | | | 1695 | | | | |

| ttc | ttt | ttt | gtc | agt | tac | atc | atc | ata | tcc | ttc | ctg | gtg gtg gtg | 5139 |
| Phe | Phe | Phe | Val | Ser | Tyr | Ile | Ile | Ile | Ser | Phe | Leu | Val Val Val | |
| 1700 | | | | 1705 | | | | 1710 | | | | |

| aac | agt | tac | atc | gcg | gtc | atc | ctg | gag | aac | ttc | agt | gtt gct act | 5184 |
| Asn | Ser | Tyr | Ile | Ala | Val | Ile | Leu | Glu | Asn | Phe | Ser | Val Ala Thr | |
| 1715 | | | | 1720 | | | | 1725 | | | | |

| gaa | gaa | agt | gca | gag | ccc | ctg | agt | gag | gat | gac | ttt | gag atg ttc | 5229 |
| Glu | Glu | Ser | Ala | Glu | Pro | Leu | Ser | Glu | Asp | Asp | Phe | Glu Met Phe | |
| 1730 | | | | 1735 | | | | 1740 | | | | |

| tat | gag | gtt | tgg | gaa | aag | ttt | gat | ccc | gat | gcg | acc | cag ttt ata | 5274 |
| Tyr | Glu | Val | Trp | Glu | Lys | Phe | Asp | Pro | Asp | Ala | Thr | Gln Phe Ile | |
| 1745 | | | | 1750 | | | | 1755 | | | | |

| gag | ttc | tct | aaa | ctc | tct | gat | ttt | gca | gct | gcc | ctg | gat cct cct | 5319 |
| Glu | Phe | Ser | Lys | Leu | Ser | Asp | Phe | Ala | Ala | Ala | Leu | Asp Pro Pro | |
| 1760 | | | | 1765 | | | | 1770 | | | | |

| ctt | ctc | ata | gca | aaa | ccc | aac | aaa | gtc | cag | ctt | att | gcc atg gat | 5364 |
| Leu | Leu | Ile | Ala | Lys | Pro | Asn | Lys | Val | Gln | Leu | Ile | Ala Met Asp | |
| 1775 | | | | 1780 | | | | 1785 | | | | |

| ctg | ccc | atg | gtc | agt | ggt | gac | cgg | atc | cac | tgt | ctt | gat att tta | 5409 |
| Leu | Pro | Met | Val | Ser | Gly | Asp | Arg | Ile | His | Cys | Leu | Asp Ile Leu | |
| 1790 | | | | 1795 | | | | 1800 | | | | |

| ttt | gcc | ttt | aca | aag | cgt | gtt | ttg | ggt | gag | agt | gga | gag atg gat | 5454 |
| Phe | Ala | Phe | Thr | Lys | Arg | Val | Leu | Gly | Glu | Ser | Gly | Glu Met Asp | |

```
                              1805                1810                1815
gcc ctt cga ata cag atg gaa gac agg ttt atg gca tca aac ccc          5499
Ala Leu Arg Ile Gln Met Glu Asp Arg Phe Met Ala Ser Asn Pro
    1820                1825                1830 tcc aaa gtc tct tat gag cct att aca acc act ttg aaa cgt aaa          5544
Ser Lys Val Ser Tyr Glu Pro Ile Thr Thr Thr Leu Lys Arg Lys
1835                1840                1845 caa gag gag gtg tct gcc gct atc att cag cgt aat ttc aga tgt          5589
Gln Glu Glu Val Ser Ala Ala Ile Ile Gln Arg Asn Phe Arg Cys
        1850                1855                1860 tat ctt tta aag caa agg tta aaa aat ata tca agt aac tat aac          5634
Tyr Leu Leu Lys Gln Arg Leu Lys Asn Ile Ser Ser Asn Tyr Asn
    1865                1870                1875 aaa gag gca ata aag ggg agg att gac tta cct ata aaa caa gac          5679
Lys Glu Ala Ile Lys Gly Arg Ile Asp Leu Pro Ile Lys Gln Asp
1880                1885                1890 atg att att gac aaa ctg aat ggg aac tcc act cca gaa aaa aca          5724
Met Ile Ile Asp Lys Leu Asn Gly Asn Ser Thr Pro Glu Lys Thr
        1895                1900                1905 gat ggg agt tcc tct acc acc tct cct cct tcc tat gat agt gta          5769
Asp Gly Ser Ser Ser Thr Thr Ser Pro Pro Ser Tyr Asp Ser Val
    1910                1915                1920 aca aaa cca gac aag gaa aag ttt gag aaa gac aaa cca gaa aaa          5814
Thr Lys Pro Asp Lys Glu Lys Phe Glu Lys Asp Lys Pro Glu Lys
1925                1930                1935 gaa agc aaa gga aaa gag gtc aga gaa aat caa aag taa                  5853
Glu Ser Lys Gly Lys Glu Val Arg Glu Asn Gln Lys
        1940                1945                1950

<210> SEQ ID NO 411
<211> LENGTH: 5856
<212> TYPE: DNA
<213> ORGANISM: Homo sapiens
<220> FEATURE:
<221> NAME/KEY: CDS
<222> LOCATION: (1)..(5856)
<220> FEATURE:
<221> NAME/KEY: MISC_FEATURE
<222> LOCATION: (122)..(122)
<223> OTHER INFORMATION: Xaa = any amino acid

<400> SEQUENCE: 411 atg gca cag gca ctg ttg gta ccc cca gga cct gaa agc ttc cgc ctt       48
Met Ala Gln Ala Leu Leu Val Pro Pro Gly Pro Glu Ser Phe Arg Leu
1               5                   10                  15 ttt act aga gaa tct ctt gct gct atc gaa aaa cgt gct gca gaa gag       96
Phe Thr Arg Glu Ser Leu Ala Ala Ile Glu Lys Arg Ala Ala Glu Glu
                20                  25                  30 aaa gcc aag aag ccc aaa aag gaa caa gat aat gat gat gag aac aaa      144
Lys Ala Lys Lys Pro Lys Lys Glu Gln Asp Asn Asp Asp Glu Asn Lys
            35                  40                  45 cca aag cca aat agt gac ttg gaa gct gga aag aac ctt cca ttt att      192
Pro Lys Pro Asn Ser Asp Leu Glu Ala Gly Lys Asn Leu Pro Phe Ile
        50                  55                  60 tat gga gac att cct cca gag atg gtg tca gag ccc ctg gag gac ctg      240
Tyr Gly Asp Ile Pro Pro Glu Met Val Ser Glu Pro Leu Glu Asp Leu
65                  70                  75                  80 gat ccc tac tat atc aat aag aaa act ttt ata gta atg aat aaa gga      288
Asp Pro Tyr Tyr Ile Asn Lys Lys Thr Phe Ile Val Met Asn Lys Gly
                85                  90                  95 aag gca att tcc cga ttc agt gcc acc tct gcc ttg tat att tta act      336
Lys Ala Ile Ser Arg Phe Ser Ala Thr Ser Ala Leu Tyr Ile Leu Thr
            100                 105                 110
```

| | | | | | | | | | | | | | | | |
|---|---|---|---|---|---|---|---|---|---|---|---|---|---|---|---|
| cca | cta | aac | cct | gtt | agg | aaa | att | gct | abs | aag | att | ttg | gta | cat | tct | 384 |
| Pro | Leu | Asn | Pro | Val | Arg | Lys | Ile | Ala | Xaa | Lys | Ile | Leu | Val | His | Ser | |
| | | 115 | | | | 120 | | | | | 125 | | | | | |
| tta | ttc | agc | atg | ctt | atc | atg | tgc | act | att | ttg | acc | aac | tgt | gta | ttt | 432 |
| Leu | Phe | Ser | Met | Leu | Ile | Met | Cys | Thr | Ile | Leu | Thr | Asn | Cys | Val | Phe | |
| | 130 | | | | | 135 | | | | | 140 | | | | | |
| atg | acc | ttg | agc | aac | cct | cct | gac | tgg | aca | aag | aat | gta | gag | tac | aca | 480 |
| Met | Thr | Leu | Ser | Asn | Pro | Pro | Asp | Trp | Thr | Lys | Asn | Val | Glu | Tyr | Thr | |
| 145 | | | | | 150 | | | | | 155 | | | | | 160 | |
| ttc | act | gga | atc | tat | acc | ttt | gag | tca | ctt | ata | aaa | atc | ttg | gca | aga | 528 |
| Phe | Thr | Gly | Ile | Tyr | Thr | Phe | Glu | Ser | Leu | Ile | Lys | Ile | Leu | Ala | Arg | |
| | | | | 165 | | | | | 170 | | | | | 175 | | |
| ggg | ttt | tgc | tta | gaa | gat | ttt | acg | ttt | ctt | cgt | gat | cca | tgg | aac | tgg | 576 |
| Gly | Phe | Cys | Leu | Glu | Asp | Phe | Thr | Phe | Leu | Arg | Asp | Pro | Trp | Asn | Trp | |
| | | | 180 | | | | | 185 | | | | | 190 | | | |
| ctg | gat | ttc | agt | gtc | att | gtg | atg | gca | tat | gtg | aca | gag | ttt | gtg | gac | 624 |
| Leu | Asp | Phe | Ser | Val | Ile | Val | Met | Ala | Tyr | Val | Thr | Glu | Phe | Val | Asp | |
| | | | 195 | | | | | 200 | | | | | 205 | | | |
| ctg | ggc | aat | gtc | tca | gcg | ttg | aga | aca | ttc | aga | gtt | ctc | cga | gca | ctg | 672 |
| Leu | Gly | Asn | Val | Ser | Ala | Leu | Arg | Thr | Phe | Arg | Val | Leu | Arg | Ala | Leu | |
| | 210 | | | | | 215 | | | | | 220 | | | | | |
| aaa | aca | att | tca | gtc | att | cca | ggt | tta | aag | acc | att | gtg | ggg | gcc | ctg | 720 |
| Lys | Thr | Ile | Ser | Val | Ile | Pro | Gly | Leu | Lys | Thr | Ile | Val | Gly | Ala | Leu | |
| 225 | | | | | 230 | | | | | 235 | | | | | 240 | |
| atc | cag | tcg | gta | aag | aag | ctt | tct | gat | gtg | atg | atc | ctg | act | gtg | ttc | 768 |
| Ile | Gln | Ser | Val | Lys | Lys | Leu | Ser | Asp | Val | Met | Ile | Leu | Thr | Val | Phe | |
| | | | | 245 | | | | | 250 | | | | | 255 | | |
| tgt | ctg | agc | gtg | ttt | gct | ctc | att | ggg | ctg | cag | ctg | ttc | atg | ggc | aat | 816 |
| Cys | Leu | Ser | Val | Phe | Ala | Leu | Ile | Gly | Leu | Gln | Leu | Phe | Met | Gly | Asn | |
| | | | 260 | | | | | 265 | | | | | 270 | | | |
| ctg | agg | aat | aaa | tgt | ttg | cag | tgg | ccc | cca | agc | gat | tct | gct | ttt | gaa | 864 |
| Leu | Arg | Asn | Lys | Cys | Leu | Gln | Trp | Pro | Pro | Ser | Asp | Ser | Ala | Phe | Glu | |
| | | 275 | | | | | 280 | | | | | 285 | | | | |
| acc | aac | acc | act | tcc | tac | ttt | aat | ggc | aca | atg | gat | tca | aat | ggg | aca | 912 |
| Thr | Asn | Thr | Thr | Ser | Tyr | Phe | Asn | Gly | Thr | Met | Asp | Ser | Asn | Gly | Thr | |
| | 290 | | | | | 295 | | | | | 300 | | | | | |
| ttt | gtt | aat | gta | aca | atg | agc | aca | ttt | aac | tgg | aag | gat | tac | att | gga | 960 |
| Phe | Val | Asn | Val | Thr | Met | Ser | Thr | Phe | Asn | Trp | Lys | Asp | Tyr | Ile | Gly | |
| 305 | | | | | 310 | | | | | 315 | | | | | 320 | |
| gat | gac | agt | cac | ttt | tat | gtt | ttg | gat | ggg | caa | aaa | gac | cct | tta | ctc | 1008 |
| Asp | Asp | Ser | His | Phe | Tyr | Val | Leu | Asp | Gly | Gln | Lys | Asp | Pro | Leu | Leu | |
| | | | | 325 | | | | | 330 | | | | | 335 | | |
| tgt | gga | aat | ggc | tca | gat | gca | ggc | cag | tgt | cca | gaa | gga | tac | atc | tgt | 1056 |
| Cys | Gly | Asn | Gly | Ser | Asp | Ala | Gly | Gln | Cys | Pro | Glu | Gly | Tyr | Ile | Cys | |
| | | | 340 | | | | | 345 | | | | | 350 | | | |
| gtg | aag | gct | ggt | cga | aac | ccc | aac | tat | ggc | tac | aca | agc | ttt | gac | acc | 1104 |
| Val | Lys | Ala | Gly | Arg | Asn | Pro | Asn | Tyr | Gly | Tyr | Thr | Ser | Phe | Asp | Thr | |
| | | 355 | | | | | 360 | | | | | 365 | | | | |
| ttt | agc | tgg | gct | ttc | ctg | tct | cta | ttt | cga | ctc | atg | act | caa | gac | tac | 1152 |
| Phe | Ser | Trp | Ala | Phe | Leu | Ser | Leu | Phe | Arg | Leu | Met | Thr | Gln | Asp | Tyr | |
| | 370 | | | | | 375 | | | | | 380 | | | | | |
| tgg | gaa | aat | ctt | tac | cag | ttg | aca | tta | cgt | gct | gct | ggg | aaa | aca | tac | 1200 |
| Trp | Glu | Asn | Leu | Tyr | Gln | Leu | Thr | Leu | Arg | Ala | Ala | Gly | Lys | Thr | Tyr | |
| 385 | | | | | 390 | | | | | 395 | | | | | 400 | |
| atg | ata | ttt | ttt | gtc | ctg | gtc | att | ttc | ttg | ggc | tca | ttt | tat | ttg | gtg | 1248 |
| Met | Ile | Phe | Phe | Val | Leu | Val | Ile | Phe | Leu | Gly | Ser | Phe | Tyr | Leu | Val | |
| | | | | 405 | | | | | 410 | | | | | 415 | | |
| aat | ttg | atc | ctg | gct | gtg | gtg | gcc | atg | gcc | tat | gag | ggg | cag | aat | cag | 1296 |
| Asn | Leu | Ile | Leu | Ala | Val | Val | Ala | Met | Ala | Tyr | Glu | Gly | Gln | Asn | Gln | |
| | | | 420 | | | | | 425 | | | | | 430 | | | |

| | |
|---|---|
| gcc acc ttg gaa gaa gca gaa caa aaa gag gcc gaa ttt cag cag atg<br>Ala Thr Leu Glu Glu Ala Glu Gln Lys Glu Ala Glu Phe Gln Gln Met<br>435     440     445 | 1344 |
| ctc gaa cag ctt aaa aag caa cag gaa gaa gct cag gca gtt gcg gca<br>Leu Glu Gln Leu Lys Lys Gln Gln Glu Glu Ala Gln Ala Val Ala Ala<br>450     455     460 | 1392 |
| gca tca gct gct tca aga gat ttc agt gga ata ggt ggg tta gga gag<br>Ala Ser Ala Ala Ser Arg Asp Phe Ser Gly Ile Gly Gly Leu Gly Glu<br>465     470     475     480 | 1440 |
| ctg ttg gaa agt tct tca gaa gca tca aag ttg agt tcc aaa agt gct<br>Leu Leu Glu Ser Ser Ser Glu Ala Ser Lys Leu Ser Ser Lys Ser Ala<br>     485     490     495 | 1488 |
| aaa gaa tgg agg aac cga agg aag aaa aga aga cag aga gag cac ctt<br>Lys Glu Trp Arg Asn Arg Arg Lys Lys Arg Arg Gln Arg Glu His Leu<br>500     505     510 | 1536 |
| gaa gga aac aac aaa gga gag aga gac agc ttt ccc aaa tcc gaa tct<br>Glu Gly Asn Asn Lys Gly Glu Arg Asp Ser Phe Pro Lys Ser Glu Ser<br>515     520     525 | 1584 |
| gaa gac agc gtc aaa aga agc agc ttc ctt ttc tcc atg gat gga aac<br>Glu Asp Ser Val Lys Arg Ser Ser Phe Leu Phe Ser Met Asp Gly Asn<br>530     535     540 | 1632 |
| aga ctg acc agt gac aaa aaa ttc tgc tcc cct cat cag tct ctc ttg<br>Arg Leu Thr Ser Asp Lys Lys Phe Cys Ser Pro His Gln Ser Leu Leu<br>545     550     555     560 | 1680 |
| agt atc cgt ggc tcc ctg ttt tcc cca aga cgc aat agc aaa aca agc<br>Ser Ile Arg Gly Ser Leu Phe Ser Pro Arg Arg Asn Ser Lys Thr Ser<br>     565     570     575 | 1728 |
| att ttc agt ttc aga ggt cgg gca aag gat gtt gga tct gaa aat gac<br>Ile Phe Ser Phe Arg Gly Arg Ala Lys Asp Val Gly Ser Glu Asn Asp<br>580     585     590 | 1776 |
| ttt gct gat gat gaa cac agc aca ttt gaa gac agc gaa agc agg aga<br>Phe Ala Asp Asp Glu His Ser Thr Phe Glu Asp Ser Glu Ser Arg Arg<br>595     600     605 | 1824 |
| gac tca ctg ttt gtg ccg cac aga cat gga gag cga cgc aac agt aac<br>Asp Ser Leu Phe Val Pro His Arg His Gly Glu Arg Arg Asn Ser Asn<br>610     615     620 | 1872 |
| ggc acc acc act gaa acg gaa gtc aga aag aga agg tta agc tct tac<br>Gly Thr Thr Thr Glu Thr Glu Val Arg Lys Arg Arg Leu Ser Ser Tyr<br>625     630     635     640 | 1920 |
| cag att tca atg gag atg ctg gag gat tcc tct gga agg caa aga gcc<br>Gln Ile Ser Met Glu Met Leu Glu Asp Ser Ser Gly Arg Gln Arg Ala<br>     645     650     655 | 1968 |
| gtg agc ata gcc agc att ctg acc aac aca atg gaa gaa ctt gaa gaa<br>Val Ser Ile Ala Ser Ile Leu Thr Asn Thr Met Glu Glu Leu Glu Glu<br>660     665     670 | 2016 |
| tct aga cag aaa tgt ccg cca tgc tgg tat aga ttt gcc aat gtg ttc<br>Ser Arg Gln Lys Cys Pro Pro Cys Trp Tyr Arg Phe Ala Asn Val Phe<br>675     680     685 | 2064 |
| ttg atc tgg gac tgc tgt gat gca tgg tta aaa gta aaa cat ctt gtg<br>Leu Ile Trp Asp Cys Cys Asp Ala Trp Leu Lys Val Lys His Leu Val<br>690     695     700 | 2112 |
| aat tta att gtt atg gat cca ttt gtt gat ctt gcc atc act att tgc<br>Asn Leu Ile Val Met Asp Pro Phe Val Asp Leu Ala Ile Thr Ile Cys<br>705     710     715     720 | 2160 |
| att gtc tta aat acc ctc ttt atg gcc atg gag cac tac ccc atg act<br>Ile Val Leu Asn Thr Leu Phe Met Ala Met Glu His Tyr Pro Met Thr<br>     725     730     735 | 2208 |
| gag caa ttc agt agt gtg ttg act gta gga aac ctg gtc ttt act ggg<br>Glu Gln Phe Ser Ser Val Leu Thr Val Gly Asn Leu Val Phe Thr Gly<br>740     745     750 | 2256 |

```
att ttt aca gca gaa atg gtt ctc aag atc att gcc atg gat cct tat    2304
Ile Phe Thr Ala Glu Met Val Leu Lys Ile Ile Ala Met Asp Pro Tyr
    755                 760                 765 tac tat ttc caa gaa ggc tgg aat atc ttt gat gga att att gtc agc    2352
Tyr Tyr Phe Gln Glu Gly Trp Asn Ile Phe Asp Gly Ile Ile Val Ser
770                 775                 780 ctc agt tta atg gag ctt ggt ctg tca aat gtg gag gga ttg tct gta    2400
Leu Ser Leu Met Glu Leu Gly Leu Ser Asn Val Glu Gly Leu Ser Val
785                 790                 795                 800 ctg cga tca ttc aga ctg ctt aga gtt ttc aag ttg gca aaa tcc tgg    2448
Leu Arg Ser Phe Arg Leu Leu Arg Val Phe Lys Leu Ala Lys Ser Trp
                805                 810                 815 ccc aca cta aat atg cta att aag atc att ggc aat tct gtg ggg gct    2496
Pro Thr Leu Asn Met Leu Ile Lys Ile Ile Gly Asn Ser Val Gly Ala
                820                 825                 830 cta gga aac ctc acc ttg gtg ttg gcc atc atc gtc ttc att ttt gct    2544
Leu Gly Asn Leu Thr Leu Val Leu Ala Ile Ile Val Phe Ile Phe Ala
            835                 840                 845 gtg gtc ggc atg cag ctc ttt ggt aag agc tac aaa gaa tgt gtc tgc    2592
Val Val Gly Met Gln Leu Phe Gly Lys Ser Tyr Lys Glu Cys Val Cys
850                 855                 860 aag atc aat gat gac tgt acg ctc cca cgg tgg cac atg aac gac ttc    2640
Lys Ile Asn Asp Asp Cys Thr Leu Pro Arg Trp His Met Asn Asp Phe
865                 870                 875                 880 ttc cac tcc ttc ctg att gtg ttc cgc gtg ctg tgt gga gag tgg ata    2688
Phe His Ser Phe Leu Ile Val Phe Arg Val Leu Cys Gly Glu Trp Ile
                885                 890                 895 gag acc atg tgg gac tgt atg gag gtc gct ggc caa acc atg tgc ctt    2736
Glu Thr Met Trp Asp Cys Met Glu Val Ala Gly Gln Thr Met Cys Leu
                900                 905                 910 att gtt ttc atg ttg gtc atg gtc att gga aac ctt gtg gtt ctg aac    2784
Ile Val Phe Met Leu Val Met Val Ile Gly Asn Leu Val Val Leu Asn
            915                 920                 925 ctc ttt ctg gcc tta ttg ttg agt tca ttt agc tca gac aac ctt gct    2832
Leu Phe Leu Ala Leu Leu Leu Ser Ser Phe Ser Ser Asp Asn Leu Ala
930                 935                 940 gct act gat gat gac aat gaa atg aat aat ctg cag att gca gta gga    2880
Ala Thr Asp Asp Asp Asn Glu Met Asn Asn Leu Gln Ile Ala Val Gly
945                 950                 955                 960 aga atg caa aag gga att gat tat gtg aaa aat aag atg cgg gag tgt    2928
Arg Met Gln Lys Gly Ile Asp Tyr Val Lys Asn Lys Met Arg Glu Cys
                965                 970                 975 ttc caa aaa gcc ttt ttt aga aag cca aaa gtt ata gaa atc cat gaa    2976
Phe Gln Lys Ala Phe Phe Arg Lys Pro Lys Val Ile Glu Ile His Glu
                980                 985                 990 ggc aat aag ata gac agc tgc atg tcc aat aat act gga att gaa ata    3024
Gly Asn Lys Ile Asp Ser Cys Met Ser Asn Asn Thr Gly Ile Glu Ile
            995                 1000                1005 agc aaa gag ctt aat tat ctt aga gat ggg aat gga acc acc agt       3069
Ser Lys Glu Leu Asn Tyr Leu Arg Asp Gly Asn Gly Thr Thr Ser
1010                1015                1020 ggt gta ggt act gga agc agt gtt gaa aaa tac ata atc gat gaa       3114
Gly Val Gly Thr Gly Ser Ser Val Glu Lys Tyr Ile Ile Asp Glu
    1025                1030                1035 aat gat tat atg tca ttc ata aac aac ccc agc ctc acc gtc aca       3159
Asn Asp Tyr Met Ser Phe Ile Asn Asn Pro Ser Leu Thr Val Thr
        1040                1045                1050 gtg cca att gct gtt gga gag tct gac ttt gaa aac tta aat act       3204
Val Pro Ile Ala Val Gly Glu Ser Asp Phe Glu Asn Leu Asn Thr
    1055                1060                1065
```

| | | | | | | | | | | | | |
|---|---|---|---|---|---|---|---|---|---|---|---|---|
| gaa | gag | ttc | agc | agt | gag | tca | gaa | cta | gaa | gaa | agc | aag | gag | aaa | 3249 |
| Glu | Glu | Phe | Ser | Ser | Glu | Ser | Glu | Leu | Glu | Glu | Ser | Lys | Glu | Lys | |
| 1070 | | | | | 1075 | | | | | 1080 | | | | | |
| tta | aat | gca | acc | agc | tca | tct | gaa | gga | agc | aca | gtt | gat | gtt | gtt | 3294 |
| Leu | Asn | Ala | Thr | Ser | Ser | Ser | Glu | Gly | Ser | Thr | Val | Asp | Val | Val | |
| 1085 | | | | | 1090 | | | | | 1095 | | | | | |
| cta | ccc | cga | gaa | ggt | gaa | caa | gct | gaa | act | gaa | ccc | gaa | gaa | gac | 3339 |
| Leu | Pro | Arg | Glu | Gly | Glu | Gln | Ala | Glu | Thr | Glu | Pro | Glu | Glu | Asp | |
| 1100 | | | | | 1105 | | | | | 1110 | | | | | |
| ctt | aaa | ccg | gaa | gct | tgt | ttt | act | gaa | gga | tgt | att | aaa | aag | ttt | 3384 |
| Leu | Lys | Pro | Glu | Ala | Cys | Phe | Thr | Glu | Gly | Cys | Ile | Lys | Lys | Phe | |
| 1115 | | | | | 1120 | | | | | 1125 | | | | | |
| cca | ttc | tgt | caa | gta | agt | aca | gaa | gaa | ggc | aaa | ggg | aag | atc | tgg | 3429 |
| Pro | Phe | Cys | Gln | Val | Ser | Thr | Glu | Glu | Gly | Lys | Gly | Lys | Ile | Trp | |
| 1130 | | | | | 1135 | | | | | 1140 | | | | | |
| tgg | aat | ctt | cga | aaa | acc | tgc | tac | agt | att | gtt | gag | cac | aac | tgg | 3474 |
| Trp | Asn | Leu | Arg | Lys | Thr | Cys | Tyr | Ser | Ile | Val | Glu | His | Asn | Trp | |
| 1145 | | | | | 1150 | | | | | 1155 | | | | | |
| ttt | gag | act | ttc | att | gtg | ttc | atg | atc | ctt | ctc | agt | agt | ggt | gca | 3519 |
| Phe | Glu | Thr | Phe | Ile | Val | Phe | Met | Ile | Leu | Leu | Ser | Ser | Gly | Ala | |
| 1160 | | | | | 1165 | | | | | 1170 | | | | | |
| ttg | gcc | ttt | gaa | gat | ata | tac | att | gaa | cag | cga | aag | act | atc | aaa | 3564 |
| Leu | Ala | Phe | Glu | Asp | Ile | Tyr | Ile | Glu | Gln | Arg | Lys | Thr | Ile | Lys | |
| 1175 | | | | | 1180 | | | | | 1185 | | | | | |
| acc | atg | cta | gaa | tat | gct | gac | aaa | gtc | ttt | acc | tat | ata | ttc | att | 3609 |
| Thr | Met | Leu | Glu | Tyr | Ala | Asp | Lys | Val | Phe | Thr | Tyr | Ile | Phe | Ile | |
| 1190 | | | | | 1195 | | | | | 1200 | | | | | |
| ctg | gaa | atg | ctt | ctc | aaa | tgg | gtt | gct | tat | gga | ttt | caa | aca | tat | 3654 |
| Leu | Glu | Met | Leu | Leu | Lys | Trp | Val | Ala | Tyr | Gly | Phe | Gln | Thr | Tyr | |
| 1205 | | | | | 1210 | | | | | 1215 | | | | | |
| ttc | act | aat | gcc | tgg | tgc | tgg | cta | gat | ttc | ttg | atc | gtt | gat | gtt | 3699 |
| Phe | Thr | Asn | Ala | Trp | Cys | Trp | Leu | Asp | Phe | Leu | Ile | Val | Asp | Val | |
| 1220 | | | | | 1225 | | | | | 1230 | | | | | |
| tct | ttg | gtt | agc | ctg | gta | gcc | aat | gct | ctt | ggc | tac | tca | gaa | ctc | 3744 |
| Ser | Leu | Val | Ser | Leu | Val | Ala | Asn | Ala | Leu | Gly | Tyr | Ser | Glu | Leu | |
| 1235 | | | | | 1240 | | | | | 1245 | | | | | |
| ggt | gcc | atc | aaa | tca | tta | cgg | aca | tta | aga | gct | tta | aga | cct | cta | 3789 |
| Gly | Ala | Ile | Lys | Ser | Leu | Arg | Thr | Leu | Arg | Ala | Leu | Arg | Pro | Leu | |
| 1250 | | | | | 1255 | | | | | 1260 | | | | | |
| aga | gcc | tta | tcc | cgg | ttt | gaa | ggc | atg | agg | gtg | gtt | gtg | aat | gct | 3834 |
| Arg | Ala | Leu | Ser | Arg | Phe | Glu | Gly | Met | Arg | Val | Val | Val | Asn | Ala | |
| 1265 | | | | | 1270 | | | | | 1275 | | | | | |
| ctt | gtt | gga | gca | att | ccc | tct | atc | atg | aat | gtg | ctg | ttg | gtc | tgt | 3879 |
| Leu | Val | Gly | Ala | Ile | Pro | Ser | Ile | Met | Asn | Val | Leu | Leu | Val | Cys | |
| 1280 | | | | | 1285 | | | | | 1290 | | | | | |
| ctc | atc | ttc | tgg | ttg | atc | ttt | agc | atc | atg | ggt | gtg | aat | ttg | ttt | 3924 |
| Leu | Ile | Phe | Trp | Leu | Ile | Phe | Ser | Ile | Met | Gly | Val | Asn | Leu | Phe | |
| 1295 | | | | | 1300 | | | | | 1305 | | | | | |
| gct | ggc | aag | ttc | tac | cac | tgt | gtt | aac | atg | aca | acg | ggt | aac | atg | 3969 |
| Ala | Gly | Lys | Phe | Tyr | His | Cys | Val | Asn | Met | Thr | Thr | Gly | Asn | Met | |
| 1310 | | | | | 1315 | | | | | 1320 | | | | | |
| ttt | gac | att | agt | gat | gtt | aac | aat | ttg | agt | gac | tgt | cag | gct | ctt | 4014 |
| Phe | Asp | Ile | Ser | Asp | Val | Asn | Asn | Leu | Ser | Asp | Cys | Gln | Ala | Leu | |
| 1325 | | | | | 1330 | | | | | 1335 | | | | | |
| ggc | aag | caa | gct | cgg | tgg | aaa | aac | gtg | aaa | gta | aac | ttt | gat | aat | 4059 |
| Gly | Lys | Gln | Ala | Arg | Trp | Lys | Asn | Val | Lys | Val | Asn | Phe | Asp | Asn | |
| 1340 | | | | | 1345 | | | | | 1350 | | | | | |
| gtt | ggc | gct | ggc | tat | ctt | gca | ctg | ctt | caa | gtg | gcc | aca | ttt | aaa | 4104 |
| Val | Gly | Ala | Gly | Tyr | Leu | Ala | Leu | Leu | Gln | Val | Ala | Thr | Phe | Lys | |
| 1355 | | | | | 1360 | | | | | 1365 | | | | | |

-continued

| | | |
|---|---|---|
| ggc tgg atg gat att atg tat gca gct gtt gat tca cga gat gtt<br>Gly Trp Met Asp Ile Met Tyr Ala Ala Val Asp Ser Arg Asp Val<br>1370                   1375                 1380 | 4149 |
| aaa ctt cag cct gta tat gaa gaa aat ctg tac atg tat tta tac<br>Lys Leu Gln Pro Val Tyr Glu Glu Asn Leu Tyr Met Tyr Leu Tyr<br>1385                   1390                 1395 | 4194 |
| ttt gtc atc ttt atc atc ttt ggg tca ttc ttc act ctg aat cta<br>Phe Val Ile Phe Ile Ile Phe Gly Ser Phe Phe Thr Leu Asn Leu<br>1400                   1405                 1410 | 4239 |
| ttc att ggt gtc atc ata gat aac ttc aac cag cag aaa aag aag<br>Phe Ile Gly Val Ile Ile Asp Asn Phe Asn Gln Gln Lys Lys Lys<br>1415                   1420                 1425 | 4284 |
| ttt gga ggt caa gac atc ttt atg aca gag gaa cag aaa aaa tat<br>Phe Gly Gly Gln Asp Ile Phe Met Thr Glu Glu Gln Lys Lys Tyr<br>1430                   1435                 1440 | 4329 |
| tac aat gca atg aag aaa ctt gga tcc aag aaa cct cag aaa ccc<br>Tyr Asn Ala Met Lys Lys Leu Gly Ser Lys Lys Pro Gln Lys Pro<br>1445                   1450                 1455 | 4374 |
| ata cct cgc cca gca aac aaa ttc caa gga atg gtc ttt gat ttt<br>Ile Pro Arg Pro Ala Asn Lys Phe Gln Gly Met Val Phe Asp Phe<br>1460                   1465                 1470 | 4419 |
| gta acc aga caa gtc ttt gat atc agc atc atg atc ctc atc tgc<br>Val Thr Arg Gln Val Phe Asp Ile Ser Ile Met Ile Leu Ile Cys<br>1475                   1480                 1485 | 4464 |
| ctc aac atg gtc acc atg atg gtg gaa acg gat gac cag ggc aaa<br>Leu Asn Met Val Thr Met Met Val Glu Thr Asp Asp Gln Gly Lys<br>1490                   1495                 1500 | 4509 |
| tac atg acc cta gtt ttg tcc cgg atc aac cta gtg ttc att gtt<br>Tyr Met Thr Leu Val Leu Ser Arg Ile Asn Leu Val Phe Ile Val<br>1505                   1510                 1515 | 4554 |
| ctg ttc act gga gaa ttt gtg ctg aag ctc gtc tcc ctc aga cac<br>Leu Phe Thr Gly Glu Phe Val Leu Lys Leu Val Ser Leu Arg His<br>1520                   1525                 1530 | 4599 |
| tac tac ttc act ata ggc tgg aac atc ttt gac ttt gtg gtg gtg<br>Tyr Tyr Phe Thr Ile Gly Trp Asn Ile Phe Asp Phe Val Val Val<br>1535                   1540                 1545 | 4644 |
| att ctc tcc att gta ggt atg ttt ctg gct gag atg ata gaa aag<br>Ile Leu Ser Ile Val Gly Met Phe Leu Ala Glu Met Ile Glu Lys<br>1550                   1555                 1560 | 4689 |
| tat ttt gtg tcc cct acc ttg ttc cga gtg atc cgt ctt gcc agg<br>Tyr Phe Val Ser Pro Thr Leu Phe Arg Val Ile Arg Leu Ala Arg<br>1565                   1570                 1575 | 4734 |
| att ggc cga atc cta cgt ctg atc aaa gga gca aag ggg atc cgc<br>Ile Gly Arg Ile Leu Arg Leu Ile Lys Gly Ala Lys Gly Ile Arg<br>1580                   1585                 1590 | 4779 |
| acg ctg ctc ttt gct ttg atg atg tcc ctt cct gcg ttg ttt aac<br>Thr Leu Leu Phe Ala Leu Met Met Ser Leu Pro Ala Leu Phe Asn<br>1595                   1600                 1605 | 4824 |
| atc ggc ctc ctg ctc ttc ctg gtc atg ttt atc tat gcc atc ttt<br>Ile Gly Leu Leu Leu Phe Leu Val Met Phe Ile Tyr Ala Ile Phe<br>1610                   1615                 1620 | 4869 |
| ggg atg tcc aac ttt gcc tat gtt aaa aag gaa gct gga att gat<br>Gly Met Ser Asn Phe Ala Tyr Val Lys Lys Glu Ala Gly Ile Asp<br>1625                   1630                 1635 | 4914 |
| gac atg ttc aac ttt gag acc ttt ggc aac agc atg atc tgc ttg<br>Asp Met Phe Asn Phe Glu Thr Phe Gly Asn Ser Met Ile Cys Leu<br>1640                   1645                 1650 | 4959 |
| ttc caa att aca acc tct gct gga tgg gat gga ttg cta gca cct<br>Phe Gln Ile Thr Thr Ser Ala Gly Trp Asp Gly Leu Leu Ala Pro<br>1655                   1660                 1665 | 5004 |

| | | | | | | | | | | | | |
|---|---|---|---|---|---|---|---|---|---|---|---|---|
| att | ctt | aat | agt | gca | cca | ccc | gac | tgt | gac | cct | gac | aca att cac | 5049 |
| Ile | Leu | Asn | Ser | Ala | Pro | Pro | Asp | Cys | Asp | Pro | Asp | Thr Ile His |
| | 1670 | | | | 1675 | | | | 1680 | | | |
| cct | ggc | agc | tca | gtt | aag | gga | gac | tgt | ggg | aac | cca | tct gtt ggg | 5094 |
| Pro | Gly | Ser | Ser | Val | Lys | Gly | Asp | Cys | Gly | Asn | Pro | Ser Val Gly |
| | 1685 | | | | 1690 | | | | 1695 | | | |
| att | ttc | ttt | ttt | gtc | agt | tac | atc | atc | ata | tcc | ttc | ctg gtg gtg | 5139 |
| Ile | Phe | Phe | Phe | Val | Ser | Tyr | Ile | Ile | Ile | Ser | Phe | Leu Val Val |
| | 1700 | | | | 1705 | | | | 1710 | | | |
| gtg | aac | agt | tac | atc | gcg | gtc | atc | ctg | gag | aac | ttc | agt gtt gct | 5184 |
| Val | Asn | Ser | Tyr | Ile | Ala | Val | Ile | Leu | Glu | Asn | Phe | Ser Val Ala |
| | 1715 | | | | 1720 | | | | 1725 | | | |
| act | gaa | gaa | agt | gca | gag | ccc | ctg | agt | gag | gat | gac | ttt gag atg | 5229 |
| Thr | Glu | Glu | Ser | Ala | Glu | Pro | Leu | Ser | Glu | Asp | Asp | Phe Glu Met |
| | 1730 | | | | 1735 | | | | 1740 | | | |
| ttc | tat | gag | gtt | tgg | gaa | aag | ttt | gat | ccc | gat | gcg | acc cag ttt | 5274 |
| Phe | Tyr | Glu | Val | Trp | Glu | Lys | Phe | Asp | Pro | Asp | Ala | Thr Gln Phe |
| | 1745 | | | | 1750 | | | | 1755 | | | |
| ata | gag | ttc | tct | aaa | ctc | tct | gat | ttt | gca | gct | gcc | ctg gat cct | 5319 |
| Ile | Glu | Phe | Ser | Lys | Leu | Ser | Asp | Phe | Ala | Ala | Ala | Leu Asp Pro |
| | 1760 | | | | 1765 | | | | 1770 | | | |
| cct | ctt | ctc | ata | gca | aaa | ccc | aac | aaa | gtc | cag | ctt | att gcc atg | 5364 |
| Pro | Leu | Leu | Ile | Ala | Lys | Pro | Asn | Lys | Val | Gln | Leu | Ile Ala Met |
| | 1775 | | | | 1780 | | | | 1785 | | | |
| gat | ctg | ccc | atg | gtc | agt | ggt | gac | cgg | atc | cac | tgt | ctt gat att | 5409 |
| Asp | Leu | Pro | Met | Val | Ser | Gly | Asp | Arg | Ile | His | Cys | Leu Asp Ile |
| | 1790 | | | | 1795 | | | | 1800 | | | |
| tta | ttt | gcc | ttt | aca | aag | cgt | gtt | ttg | ggt | gag | agt | gga gag atg | 5454 |
| Leu | Phe | Ala | Phe | Thr | Lys | Arg | Val | Leu | Gly | Glu | Ser | Gly Glu Met |
| | 1805 | | | | 1810 | | | | 1815 | | | |
| gat | gcc | ctt | cga | ata | cag | atg | gaa | gac | agg | ttt | atg | gca tca aac | 5499 |
| Asp | Ala | Leu | Arg | Ile | Gln | Met | Glu | Asp | Arg | Phe | Met | Ala Ser Asn |
| | 1820 | | | | 1825 | | | | 1830 | | | |
| ccc | tcc | aaa | gtc | tct | tat | gag | cct | att | aca | acc | act | ttg aaa cgt | 5544 |
| Pro | Ser | Lys | Val | Ser | Tyr | Glu | Pro | Ile | Thr | Thr | Thr | Leu Lys Arg |
| | 1835 | | | | 1840 | | | | 1845 | | | |
| aaa | caa | gag | gag | gtg | tct | gcc | gct | atc | att | cag | cgt | aat ttc aga | 5589 |
| Lys | Gln | Glu | Glu | Val | Ser | Ala | Ala | Ile | Ile | Gln | Arg | Asn Phe Arg |
| | 1850 | | | | 1855 | | | | 1860 | | | |
| tgt | tat | ctt | tta | aag | caa | agg | tta | aaa | aat | ata | tca | agt aac tat | 5634 |
| Cys | Tyr | Leu | Leu | Lys | Gln | Arg | Leu | Lys | Asn | Ile | Ser | Ser Asn Tyr |
| | 1865 | | | | 1870 | | | | 1875 | | | |
| aac | aaa | gag | gca | ata | aag | ggg | agg | att | gac | tta | cct | ata aaa caa | 5679 |
| Asn | Lys | Glu | Ala | Ile | Lys | Gly | Arg | Ile | Asp | Leu | Pro | Ile Lys Gln |
| | 1880 | | | | 1885 | | | | 1890 | | | |
| gac | atg | att | att | gac | aaa | ctg | aat | ggg | aac | tcc | act | cca gaa aaa | 5724 |
| Asp | Met | Ile | Ile | Asp | Lys | Leu | Asn | Gly | Asn | Ser | Thr | Pro Glu Lys |
| | 1895 | | | | 1900 | | | | 1905 | | | |
| aca | gat | ggg | agt | tcc | tct | acc | acc | tct | cct | cct | tcc | tat gat agt | 5769 |
| Thr | Asp | Gly | Ser | Ser | Ser | Thr | Thr | Ser | Pro | Pro | Ser | Tyr Asp Ser |
| | 1910 | | | | 1915 | | | | 1920 | | | |
| gta | aca | aaa | cca | gac | aag | gaa | aag | ttt | gag | aaa | gac | aaa cca gaa | 5814 |
| Val | Thr | Lys | Pro | Asp | Lys | Glu | Lys | Phe | Glu | Lys | Asp | Lys Pro Glu |
| | 1925 | | | | 1930 | | | | 1935 | | | |
| aaa | gaa | agc | aaa | gga | aaa | gag | gtc | aga | gaa | aat | caa | aag taa | 5856 |
| Lys | Glu | Ser | Lys | Gly | Lys | Glu | Val | Arg | Glu | Asn | Gln | Lys |
| | 1940 | | | | 1945 | | | | 1950 | | | |